US012473370B2

(12) United States Patent
Biasci et al.

(10) Patent No.: US 12,473,370 B2
(45) Date of Patent: Nov. 18, 2025

(54) TL1A ASSOCIATED ANTIBODY COMPOSITIONS AND METHODS OF USE

(71) Applicant: ABSCI CORPORATION, Vancouver, WA (US)

(72) Inventors: Daniele Biasci, Athens (GR); Sharrol Bachas, Vancouver, WA (US); Amir Shanehsazzadeh, Vancouver, WA (US); Vincent Blay, Vancouver, WA (US); Matthew Waugh, Vancouver, WA (US); Simon Levine-Gottreich, Vancouver, WA (US); Anand Sastry, Vancouver, WA (US); Douglas Ganini Da Silva, Vancouver, WA (US); Matthew McPartlon, Vancouver, WA (US); Emily Gage, Vancouver, WA (US); David Spencer, Vancouver, WA (US)

(73) Assignee: ABSCI CORPORATION, Vancouver, WA (US)

( * ) Notice: Subject to any disclaimer, the term of this patent is extended or adjusted under 35 U.S.C. 154(b) by 0 days.

(21) Appl. No.: 18/905,034

(22) Filed: Oct. 2, 2024

(65) Prior Publication Data

US 2025/0109210 A1 Apr. 3, 2025

Related U.S. Application Data

(60) Provisional application No. 63/682,593, filed on Aug. 13, 2024, provisional application No. 63/675,403, filed on Jul. 25, 2024, provisional application No. 63/554,832, filed on Feb. 16, 2024, provisional application No. 63/542,186, filed on Oct. 3, 2023.

(51) Int. Cl.

| | |
|---|---|
| ***C07K 16/28*** | (2006.01) |
| ***G16B 15/30*** | (2019.01) |
| ***G16B 40/00*** | (2019.01) |

(52) U.S. Cl.

CPC .......... *C07K 16/2875* (2013.01); *G16B 15/30* (2019.02); *G16B 40/00* (2019.02); *C07K 2317/24* (2013.01); *C07K 2317/34* (2013.01); *C07K 2317/732* (2013.01); *C07K 2317/76* (2013.01); *C07K 2317/92* (2013.01); *C07K 2317/94* (2013.01)

(58) Field of Classification Search

None

See application file for complete search history.

(56) References Cited

U.S. PATENT DOCUMENTS

| | | | |
|---|---|---|---|
| 5,677,425 | A | 10/1997 | Bodmer et al. |
| 5,869,046 | A | 2/1999 | Presta et al. |
| 6,121,022 | A | 9/2000 | Presta et al. |
| 6,165,745 | A | 12/2000 | Ward et al. |
| 8,642,741 | B2 | 2/2014 | Classon et al. |
| 9,068,003 | B2 | 6/2015 | Siegel et al. |
| 9,290,576 | B2 | 3/2016 | Attinger et al. |
| 9,556,277 | B2 | 1/2017 | Classon et al. |
| 9,617,335 | B2 | 4/2017 | McClain et al. |
| 9,683,998 | B2 | 6/2017 | Arch et al. |
| 10,138,296 | B2 | 11/2018 | Poulton et al. |
| 10,316,083 | B2 | 6/2019 | Michelsen et al. |
| 10,322,174 | B2 | 6/2019 | Bilsborough et al. |
| 10,689,439 | B2 | 6/2020 | Watkins et al. |
| 10,822,422 | B2 | 11/2020 | Poulton et al. |
| 10,968,279 | B2 | 4/2021 | Pashine et al. |
| 11,136,386 | B2 | 10/2021 | Kruidenier et al. |
| 11,292,848 | B2 | 4/2022 | Watkins et al. |
| 11,371,048 | B2 | 6/2022 | McClain et al. |
| 11,474,112 | B2 | 10/2022 | Arch et al. |
| 11,584,785 | B2 | 2/2023 | Doerner et al. |
| 2018/0052175 | A1 | 2/2018 | Arch et al. |
| 2018/0282405 | A1 | 10/2018 | McClain et al. |
| 2019/0247498 | A1 | 8/2019 | Bilsborough et al. |
| 2020/0362025 | A1 | 11/2020 | Kruidenier et al. |
| 2021/0037193 | A1 | 2/2021 | Lin et al. |

(Continued)

FOREIGN PATENT DOCUMENTS

| | | | |
|---|---|---|---|
| WO | 2009/089154 | A2 | 7/2009 |
| WO | 2014/025663 | A1 | 2/2014 |
| WO | 2014/106602 | A1 | 7/2014 |

(Continued)

OTHER PUBLICATIONS

Aiba et al., The role of TL1A and DR3 in autoimmune and inflammatory diseases, Mediators Inflamm, 2013:258164 (Dec. 21, 2013).

(Continued)

*Primary Examiner* — Meera Natarajan

(74) *Attorney, Agent, or Firm* — MARSHALL, GERSTEIN & BORUN LLP

(57) ABSTRACT

The disclosure herein relates to the development and production of novel antibodies and antigen binding fragments thereof that bind TL1A and that are useful in the treatment, prevention and diagnosis of a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis. Some of the elements of final antibody structure being designed de novo by a computer system and its data training set without reference to a specific reference molecule.

23 Claims, 35 Drawing Sheets

Specification includes a Sequence Listing.

(56) References Cited

U.S. PATENT DOCUMENTS

| | | | |
|---|---|---|---|
| 2021/0395824 | A1 | 12/2021 | Gonsky et al. |
| 2022/0029024 | A1 | 1/2022 | More et al. |

FOREIGN PATENT DOCUMENTS

| | | | |
|---|---|---|---|
| WO | 2016/205570 | A1 | 12/2016 |
| WO | 2017/106583 | A1 | 6/2017 |
| WO | 2021/146626 | A1 | 7/2021 |
| WO | 2021/163349 | A1 | 8/2021 |
| WO | 2022/103961 | A1 | 5/2022 |
| WO | 2022/119842 | A1 | 6/2022 |
| WO | 2022/178158 | A1 | 8/2022 |
| WO | 2022/178159 | A1 | 8/2022 |
| WO | 2022/232253 | A1 | 11/2022 |
| WO | 2023/009545 | A1 | 2/2023 |
| WO | 2023/129881 | A1 | 7/2023 |
| WO | 2023/133462 | A1 | 7/2023 |
| WO | 2024/040020 | A1 | 2/2024 |

OTHER PUBLICATIONS

Angal et al., A single amino acid substitution abolishes the heterogeneity of chimeric mouse/human (IgG4) antibody, Molecular Immunology, 30(1):105-108 (Jan. 1993).

Banfield et al., First-in-human, randomized dose-escalation study of the safety, tolerability, pharmacokinetics, pharmacodynamics and immunogenicity of PF-06480605 in healthy subjects, British Journal of Clinical Pharmacology, 86(4):812-24 (Jan. 28, 2020).

Cox et al., A directory of human germ-line VX segments reveals a strong bias in their usage, European Journal of Immunology, 24(4):827-836 (Apr. 1994).

Danese et al., Anti-TL1A Antibody PF-06480605 Safety and Efficacy for Ulcerative Colitis: A Phase 2a Single-Arm Study, Clin Gastroenterol Hepatol 19(11):2324-32.e6 (Nov. 2021).

Fang et al., Essential role of TNF receptor superfamily 25 (TNFRSF25) in the development of allergic lung inflammation, J Exp Med, 205(5):1037-48 (May 12, 2008).

Feagan et al., Abstract citation ID: jjac190.0127DOP87 The Anti-TL1A Antibody PRA023 Demonstrated Proof-of-Concept in Crohn's Disease: Phase 2a APOLLO-CD Study Results, Journal of Crohn's, and Colitis 17: i162-i164 (2023).

Kokkotis and Bamias, TL1A as a therapeutic target in inflammatory bowel disease, Expert Rev. Clin. Immunol., 18(6):551-55 (2022).

Micheau et al., Induction of TNF receptor I-mediated apoptosis via two sequential signaling complexes, Cell, 114 (2):181-90 (Jul. 25, 2003).

Migone et al., TL1A is a TNF-like ligand for DR3 and TR6/DcR3 and functions as a T cell costimulator, Immunity, 16(3):479-92 (Mar. 2020).

Picornell et al, TNFSF15 is an ethnic-specific IBD gene, Inflamm Bowel Dis., 13(11):1333-8 (Nov. 2007).

Prehn et al., The T cell costimulator TL1A is induced by FcgammaR signaling in human monocytes and dendritic cells, J Immunol, 178(7):4033-8 (Apr. 1, 2007).

Sands et al., OP40 PRA023 Demonstrated Efficacy and Favorable Safety as Induction Therapy for Moderately to Severely Active UC: Phase 2 ARTEMIS-UC Study Results, Journal of Crohn's and Colitis, 17 (Supplement_1): i56-i59 (Feb. 2023).

Schreiber et al., Immunobiology of TNFSF15 and TNFRSF25, Immunol Res, 57(1-3):3-11 (Dec. 2013).

Schuurman et al., The inter-heavy chain disulfide bonds of IgG4 are in equilibrium with intra-chain disulfide bonds, Molecular Immunology, 38(1):1-8 (Jan. 2001).

Tomlinson et al., The repertoire of human germline vH sequences reveals about fifty groups of VH segments with different hypervariable loops, Journal of Molecular Biology, 227(3):776-798 (Oct. 1992).

Wen et al., TL1A-induced NF-kappaB activation and c-IAP2 production prevent DR3-mediated apoptosis in TF-1 cells, J Biol Chem, 278(40):39251-8 (Oct. 3, 2003).

Xu et al., Role of TL1A in Inflammatory Autoimmune Diseases: A Comprehensive Review, Front Immunol., 13:913-28 (Jul. 14, 2022).

Yamazaki et al., Single nucleotide polymorphisms in TNFSF15 confer susceptibility to Crohn's disease, Hum Mol Genet. 14(22):3499-506 (Nov. 2005).

Zhan et al., Biochemical and structural characterization of the human TL1A ectodomain, Biochemistry 48(32):7636-45 (Aug. 2009).

Clarke et al., An anti-TL1A antibody for the treatment of asthma and inflammatory bowel disease, MABS, 10(4): 664-677, (Mar. 2018).

Lippow et al., Computational design of antibody-affinity improvement beyond in vivo maturation, Nat. Biotechnol., 25(10: 1171-1176, (Oct. 2007).

Dose dependent antibody inhibition of IFNg in whole blood

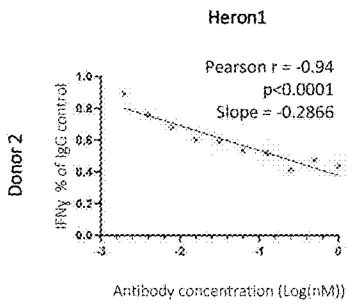

FIG. 1A

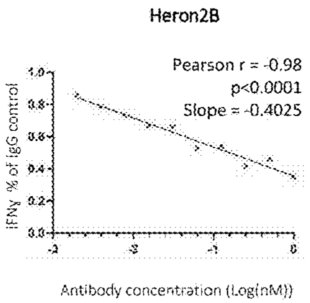

FIG. 1B

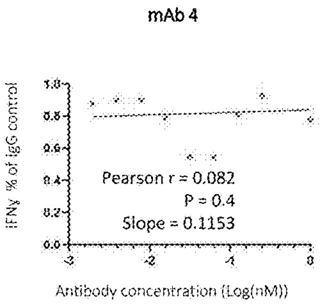

FIG. 1C

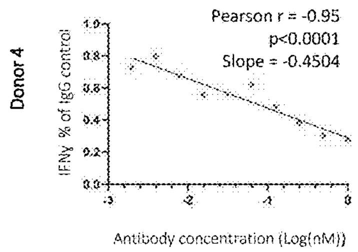

FIG. 1D

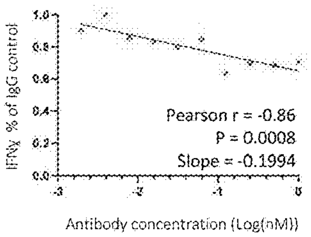

FIG. 1E

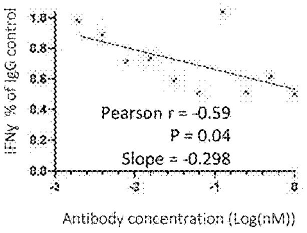

FIG. 1F

- Data for the two responsive donors shown.
- Assay entry criteria: One out of 53 mAbs show SPR $K_D$ < 2 nM. All other mAbs had affinities above the limit of detection.
- Trend between Pearson correlation*slope[†] and $K_D$.

| IFNγ Assay Avg Rank Order | Average Pearson r * slope[†] | Antibody | BLI Avg $K_D$ (pM) |
|---|---|---|---|
| 1 | 0.4847 | Heron1 | 21.8 |
| 2 | 0.3912 | Heron2B | 30.1 |
| 3 | 0.1976 | mAb 4 | 630 |

[†] Pearson Correlation (r)*slope = [abs(r) * abs(slope)] ^ (1/2)

FIG. 1G

AI-model predicts high diversity variants with tighter binding than parental Heron2B

- ACE scores predicted by model strongly correlate with measured ACE scores in the library.
- AI-predicted novel variants with edit distances up to 10 in HCDRs and high probability of affinities ≥Heron2B.

SPR confirms AI-optimized high diversity variants with tighter binding than Heron2B

- 22 variants from tracks 1 & 2 identified with higher affinity than Heron2B by up to an order of magnitude and up to 7 edit distance across all 3 HCDRs.
- Of these, 6 variants are sub-nM binders in Fab format.

| Control | SPR affinity capture Fab Avg $K_D$ (nM) |
|---|---|
| Heron2B | 2.50 (±0.16) |
| Heron2B-Toci | 5.71 (±3.1) |

Summary of 20 high priority AI-optimized leads

| Lead # | Sample Name | Human TL1A Fab Avg SPR KD (nM) | Cyno TL1A Fab Avg SPR KD (nM) | Ratio of Human:Cyno binding | HCDR3 edit distance from Heron2B | Total edit distance from Heron2B |
|---|---|---|---|---|---|---|
| 1 | ASN1447 | 0.17 | 0.17 | 1.00 | 3 | 10 |
| 2 | ASN1448 | 0.20 | 0.94 | 0.22 | 2 | 7 |
| 3 | ASN1449 | 0.31 | 0.62 | 0.51 | 2 | 9 |
| 4 | ASN1450 | 0.33 | 0.16 | 2.09 | 2 | 8 |
| 5 | ASN1451 | 0.33 | 0.79 | 0.42 | 1 | 8 |
| 6 | ASN1452 | 0.41 | 0.26 | 1.58 | 2 | 11 |
| 7 | ASN1453 | 0.43 | 1.63 | 0.27 | 2 | 11 |
| 8 | ASN1454 | 0.38 | 3.26 | 0.12 | 1 | 7 |
| 9 | ASN1455 | 0.43 | 1.99 | 0.21 | 2 | 9 |
| 10 | ASN1456 | 0.48 | 1.83 | 0.26 | 2 | 12 |
| 11 | ASN1457 | 0.48 | 0.38 | 1.27 | 2 | 11 |
| 12 | ASN1458 | 0.43 | 1.29 | 0.34 | 1 | 9 |
| 13 | ASN1459 | 0.43 | 0.34 | 1.27 | 2 | 6 |
| 14 | ASN1460 | 0.70 | 4.25 | 0.16 | 2 | 13 |
| 15 | ASN1461 | 0.50 | 1.81 | 0.28 | 2 | 10 |
| 16 | ASN1462 | 0.51 | 0.32 | 1.58 | 1 | 10 |
| 17 | ASN1463 | 0.57 | 0.33 | 1.74 | 1 | 10 |
| 18 | ASN1464 | 0.67 | 1.28 | 0.52 | 2 | 8 |
| 19 | ASN1465 | 0.72 | 5.14 | 0.14 | 1 | 9 |
| 20 | ASN1466 | 0.76 | 1.28 | 0.59 | 2 | 8 |

FIG. 4

Most candidates had no red-flags in early developability assessment

| Lead # | Sample Name | SEC, Main% | NR-CGE, Main% | icIEF, Main% | AC-SINS (shift nm) | Polyspecificity anti-DNA (score) | Polyspecificity anti-insulin (score) | HIC, RRT | HIC, # peaks | FcRn, RRT |
|---|---|---|---|---|---|---|---|---|---|---|
| 1 | ASN1447 | 100.0 | 88.0 | 64.7 | -1.1 | 0.24 | 0.15 | 0.95 | 1 | 1.22 |
| 2 | ASN1448 | 100.0 | 89.8 | 57.8 | -0.4 | 0.27 | 0.16 | 0.93 | 1 | 1.22 |
| 3 | ASN1449 | 100.0 | 83.4 | 63.0 | -0.4 | 0.27 | 0.18 | 0.93 | 1 | 1.28 |
| 4 | ASN1450 | 100.0 | 80.2 | 50.5 | -0.4 | 0.28 | 0.17 | 0.94 | 1 | 1.25 |
| 5 | ASN1451 | 100.0 | 84.3 | 48.0 | 0.0 | 0.32 | 0.19 | 0.97 | 1 | 1.25 |
| 6 | ASN1452 | 100.0 | 81.7 | 52.1 | -1.3 | 0.32 | 0.19 | 0.91 | 1 | 1.23 |
| 7 | ASN1453 | 99.6 | 84.4 | 53.5 | -0.4 | 0.32 | 0.18 | 0.94 | 1 | 1.22 |
| 8 | ASN1454 | 100.0 | 83.0 | 58.3 | -0.4 | 0.32 | 0.20 | 0.98 | 1 | 1.26 |
| 9 | ASN1455 | 100.0 | 82.1 | 50.3 | -0.4 | 0.28 | 0.19 | 0.97 | 1 | 1.24 |
| 10 | ASN1456 | 100.0 | 88.1 | 56.5 | -0.4 | 0.29 | 0.16 | 0.91 | 1 | 1.21 |
| 11 | ASN1457 | 98.8 | 79.5 | 47.5 | -0.4 | 0.27 | 0.17 | 0.94 | 1 | 1.22 |
| 12 | ASN1458 | 98.5 | 81.7 | 63.2 | 0.3 | 0.30 | 0.18 | 0.93 | 1 | 1.23 |
| 13 | ASN1459 | 78.7 | 80.1 | 57.1 | -0.4 | 0.31 | 0.18 | 0.94 | 2 | 1.23 |
| 14 | ASN1460 | 100.0 | 86.3 | 55.8 | 2.7 | 0.30 | 0.18 | 1.07 | 1 | 1.25 |
| 15 | ASN1461 | 97.8 | 80.1 | 49.0 | -0.4 | 0.28 | 0.28 | 1.12 | 1 | 1.28 |
| 16 | ASN1462 | 100.0 | 83.0 | 49.3 | -0.4 | 0.29 | 0.19 | 0.94 | 1 | 1.24 |
| 17 | ASN1463 | 100.0 | 86.4 | 63.1 | -0.4 | 0.26 | 0.17 | 0.93 | 1 | 1.22 |
| 18 | ASN1464 | 100.0 | 83.5 | 53.5 | 0.7 | 0.24 | 0.16 | 1.06 | 1 | 1.25 |
| 19 | ASN1465 | 100.0 | 81.1 | 62.8 | -0.4 | 0.24 | 0.16 | 0.98 | 1 | 1.23 |
| 20 | ASN1466 | 100.0 | 79.5 | 55.6 | 0.7 | 0.28 | 0.17 | 0.97 | 1 | 1.25 |

FIG. 5

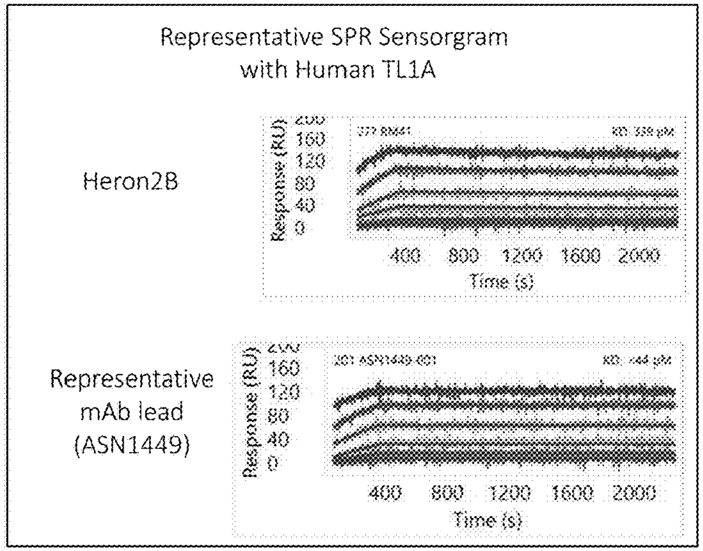

FIG. 6A

- 17/20 high priority lead mAbs have higher binding affinity to Human TL1A than Heron2B.
- 8/20 leads achieve TPP parameter of $K_D \leq 100$pM to human TL1A

| Lead # | Sample Name | Total edit distance from Heron2B | SPR Fab lysate, Human TL1A Avg $K_D$ (pM) | SPR mAb, Human TL1A Avg $K_D$ (pM) |
|---|---|---|---|---|
| | Heron1 | N/A | 170±270 | 49±2 |
| | Heron2B | 0 | 2500±160 | 365±76 |
| | Heron3A | N/A | Not measured | 19±1 |
| 1 | ASN1447 | 10 | 170 | 151±110 |
| 2 | ASN1448 | 7 | 200 | 195±142 |
| 3 | ASN1449 | 9 | 310 | 44±2 |
| 4 | ASN1450 | 8 | 330 | 51±2 |
| 5 | ASN1451 | 8 | 330 | 73±43 |
| 6 | ASN1452 | 11 | 410 | 101±14 |
| 7 | ASN1453 | 11 | 430 | 179±20 |
| 8 | ASN1454 | 7 | 380 | 91±35 |
| 9 | ASN1455 | 9 | 430 | 96±27 |
| 10 | ASN1456 | 12 | 480 | 482±477 |
| 11 | ASN1457 | 11 | 480 | 200±24 |
| 12 | ASN1458 | 9 | 430 | 170±56 |
| 13 | ASN1459 | 6 | 430 | 385±156 |
| 14 | ASN1460 | 13 | 700 | 286±162 |
| 15 | ASN1461 | 10 | 500 | 67±18 |
| 16 | ASN1462 | 10 | 510 | 339±239 |
| 17 | ASN1463 | 10 | 570 | 172±10 |
| 18 | ASN1464 | 8 | 670 | 252±144 |
| 19 | ASN1465 | 9 | 720 | 380±342 |
| 20 | ASN1466 | 8 | 760 | 79±48 |

▒ High affinity leads

FIG. 6B

All 20 high priority lead mAbs have cyno cross-reactivity and lack mouse cross-reactivity

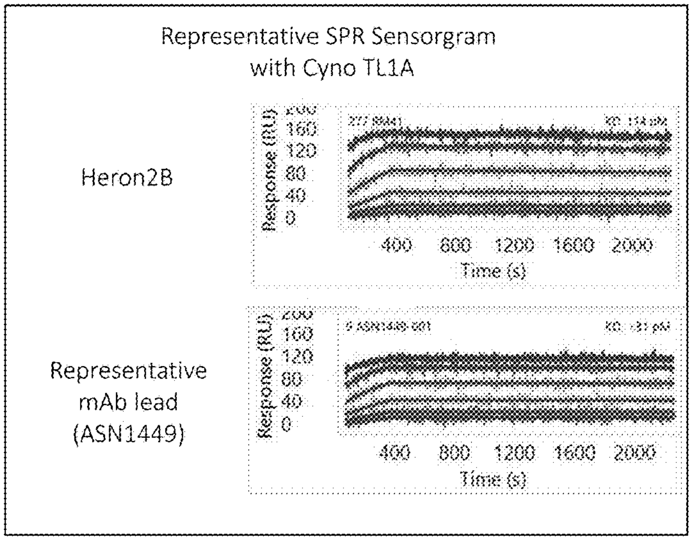

FIG. 7A

- All 20 high priority leads have cross-reactivity to cyno TL1A (defined as ratio < 10-fold)
- All 20 high priority leads lack cross-reactivity to mouse TL1A (defined as ratio > 100-fold).

| Lead # | Sample Name | SPR mAb, Human TL1A Avg $K_D$ (pM) | SPR mAb, Cyno TL1A Avg $K_D$ (pM) | Fold change Cyno:Human | SPR mAb, Mouse TL1A Avg $K_D$ (nM) | Fold Change Mouse:Human |
|---|---|---|---|---|---|---|
| | Heron1 | 49±2 | 54±1 | 1.1 | 0.070±0.005 | 1 |
| | Heron2B | 365±76 | 90±37 | 0.3 | 81,900±94,000 | 220,000 |
| | Heron3A | 19±1 | 36±14 | 1.9 | 0.355±0.039 | 19 |
| 1 | ASN1447 | 151±110 | 139±88 | 0.9 | 74,500±101,000 | 490,000 |
| 2 | ASN1448 | 195±142 | 408±170 | 2.0 | No binding | N/A |
| 3 | ASN1449 | 44±2 | 32±1 | 0.7 | 117±15 | 2,600 |
| 4 | ASN1450 | 51±2 | 34±6 | 0.7 | 290±61 | 5,600 |
| 5 | ASN1451 | 73±43 | 38±10 | 0.5 | 727±156 | 9,900 |
| 6 | ASN1452 | 101±14 | 85±65 | 0.8 | 1,720±927 | 17,000 |
| 7 | ASN1453 | 179±20 | 125±94 | 0.7 | 1,270±528 | 7,100 |
| 8 | ASN1454 | 91±35 | 85±48 | 0.9 | 418±102 | 4,600 |
| 9 | ASN1455 | 96±27 | 64±24 | 0.7 | 739±185 | 7,700 |
| 10 | ASN1456 | 482±477 | 253±235 | 0.5 | No binding | N/A |
| 11 | ASN1457 | 200±24 | 135±117 | 0.7 | 842±275 | 4,200 |
| 12 | ASN1458 | 170±56 | 118±59 | 0.4 | 13,100±17,500 | 7,7000 |
| 13 | ASN1459 | 385±156 | 154±60 | 0.8 | No binding | N/A |
| 14 | ASN1460 | 296±162 | 224±98 | 0.7 | 3,810±4,620 | 13,000 |
| 15 | ASN1461 | 67±18 | 46±12 | 0.3 | 162±11 | 2,400 |
| 16 | ASN1462 | 339±239 | 90±26 | 0.6 | 955±310 | 2,800 |
| 17 | ASN1463 | 172±10 | 99±37 | 0.3 | 452±146 | 2,600 |
| 18 | ASN1464 | 252±144 | 87±6 | 0.3 | 397±85 | 1,600 |
| 19 | ASN1465 | 380±342 | 123±44 | 0.6 | 691±453 | 1,800 |
| 20 | ASN1466 | 79±48 | 46±25 | 1.1 | 391±97 | 5,000 |

FIG. 7B

$T_{1/2}$ extension mutations increase FcRn affinity at pH 6.0 by ~10-fold relative to Herons

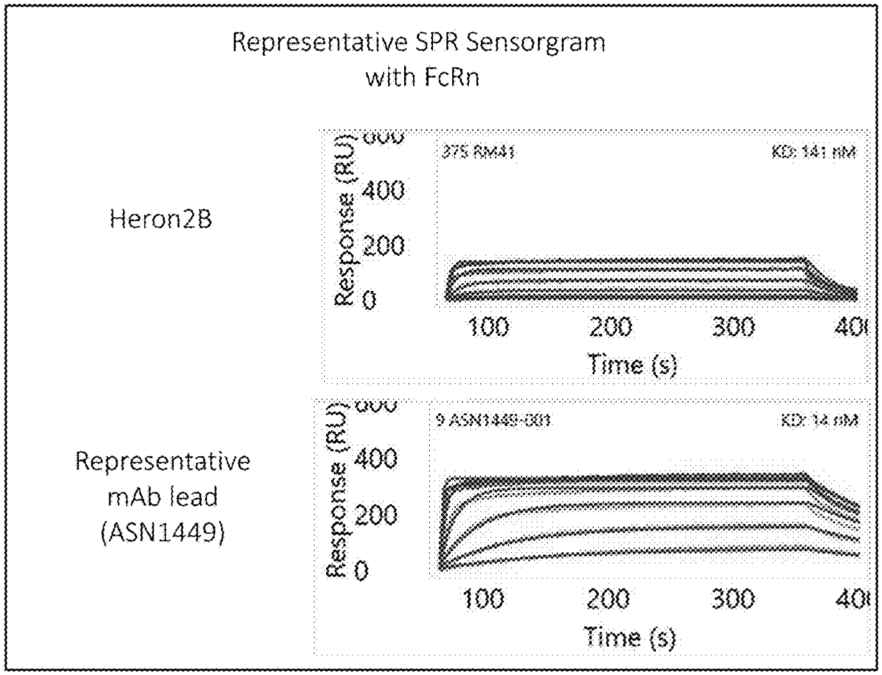

FIG. 8A $T_{1/2}$ extension mutations increase FcRn affinity by ~10-fold at pH 6.0

| Lead # | Sample Name | SPR mAb, Human TL1A Avg $K_D$ (pM) | SPR mAb, FcRn Avg $K_D$ (nM) |
|---|---|---|---|
| | Heron1 | 49±2 | 140±15 |
| | Heron2B | 365±78 | 145±27 |
| | Heron3A | 19±1 | 191±18 |
| 1 | ASN1447 | 151±110 | 17.5±2.3 |
| 2 | ASN1448 | 195±142 | 17.1±1.2 |
| 3 | ASN1449 | 44±2 | 16.0±1.3 |
| 4 | ASN1450 | 51±2 | 16.9±1.7 |
| 5 | ASN1451 | 73±43 | 17.2±1.4 |
| 6 | ASN1452 | 101±14 | 20.9±3.2 |
| 7 | ASN1453 | 179±20 | 19.0±2.0 |
| 8 | ASN1454 | 91±35 | 17.6±1.7 |
| 9 | ASN1455 | 96±27 | 18.2±1.3 |
| 10 | ASN1456 | 482±477 | 22.1±3.2 |
| 11 | ASN1457 | 200±24 | 20.4±2.5 |
| 12 | ASN1458 | 170±56 | 19.7±3.4 |
| 13 | ASN1459 | 385±156 | 18.8±2.0 |
| 14 | ASN1460 | 296±162 | 19.8±2.0 |
| 15 | ASN1461 | 67±18 | 17.4±1.4 |
| 16 | ASN1462 | 339±239 | 17.7±1.8 |
| 17 | ASN1463 | 172±10 | 17.4±1.0 |
| 18 | ASN1464 | 252±144 | 16.2±3.2 |
| 19 | ASN1465 | 380±342 | 16.5±1.4 |
| 20 | ASN1466 | 79±48 | 16.4±1.1 |

FIG. 8B

Correlation of TL1A binding by cell-surface staining Avg gMFI vs SPR KD (pM) for top 20 high priority leads. Heron2B reference antibody is indicated by arrow

| SPR $K_D$ rank order | Sample Name | SPR mAb, Human TL1A Avg $K_D$ (pM) | NFKb Assay $IC_{50}$ | NFkb Assay rank order |
|---|---|---|---|---|
| | Heron1 | 49±2 | N/A | |
| | Heron2B | 365±78 | 0.967 | |
| | Heron3A | 19±1 | N/A | |
| 1 | ASN1449 | 44±2 | 0.2313 | 1 |
| 2 | ASN1450 | 51±2 | | |
| 3 | ASN1461 | 67±18 | 0.7897 | 12 |
| 4 | ASN1451 | 73±43 | 0.4293 | 5 |
| 5 | ASN1466 | 79±48 | 0.3015 | 2 |
| 6 | ASN1454 | 91±35 | 0.4055 | 3 |
| 7 | ASN1455 | 98±27 | 0.8793 | 15 |
| 8 | ASN1452 | 101±14 | 0.7369 | 10 |
| 9 | ASN1447 | 151±110 | 1.201 | 19 |
| 10 | ASN1458 | 170±56 | 0.6965 | 9 |
| 11 | ASN1463 | 172±10 | 0.9712 | 16 |
| 12 | ASN1453 | 179±20 | 0.8604 | 14 |
| 13 | ASN1448 | 195±142 | 0.4413 | 6 |
| 14 | ASN1457 | 200±24 | 0.5719 | 8 |
| 15 | ASN1464 | 252±144 | 0.9756 | 17 |
| 16 | ASN1460 | 296±162 | 0.7416 | 11 |
| 17 | ASN1465 | 380±342 | 0.811 | 13 |
| 18 | ASN1462 | 339±239 | 1.119 | 18 |
| 19 | ASN1459 | 385±156 | 0.4418 | 7 |
| 20 | ASN1456 | 482±477 | 0.4105 | 4 |

* Average of the 4PL curve fit values across 4 sets of plates (groups A through D).

FIG. 10G

Error bars indicate the standard deviation of triplicates

Error bars indicate the standard deviation of triplicates

| SPR $K_D$ rank order | Sample Name | SPR mAb, Human TL1A Avg $K_D$ (pM) | Apoptosis Assay $IC_{50}$ | Apoptosis Assay rank order |
|---|---|---|---|---|
| | Heron1 | 49±2 | N/A | |
| | Heron2B | 365±76 | 2.935* | |
| | Heron3A | 19±1 | N/A | |
| 1 | ASN1449 | 44±2 | 2.540 | 2 |
| 2 | ASN1450 | 51±2 | 2.907 | 3 |
| 3 | ASN1461 | 67±18 | **1.831** | 1 |
| 4 | ASN1451 | 73±43 | 3.017 | 4 |
| 5 | ASN1466 | 79±48 | 3.217 | 5 |
| 6 | ASN1454 | 91±35 | 3.241 | 6 |
| 7 | ASN1455 | 98±27 | 4.200 | 11 |
| 8 | ASN1452 | 101±14 | 4.047 | 10 |
| 9 | ASN1447 | 151±110 | 4.854 | 13 |
| 10 | ASN1458 | 170±56 | 6.492 | 15 |
| 11 | ASN1463 | 172±10 | 3.604 | 9 |
| 12 | ASN1453 | 179±20 | 5.710 | 14 |
| 13 | ASN1448 | 195±142 | 9.313 | 18 |
| 14 | ASN1457 | 200±24 | 4.554 | 12 |
| 15 | ASN1464 | 252±144 | 3.496 | 8 |
| 16 | ASN1460 | 296±162 | 6.865 | 17 |
| 17 | ASN1465 | 380±342 | 8.762 | 16 |
| 18 | ASN1462 | 339±239 | 3.291 | 7 |
| 19 | ASN1459 | 385±156 | 10.92 | 19 |
| 20 | ASN1456 | 482±477 | 24.03 | 20 |

* Average of the 4PL curve fit values across 4 sets of plates (groups A through D).

FIG. 11E

New *de novo* LCDR modeling generated high affinity variants for LCDR1 and LCDR2

- LCDR1 and LCDR2 variants with equivalent or better affinity than Heron2B-toci parent identified
- A subset of the most promising LCDR variants were combined with HCDR variants from tracks 1 & 2.

Binding affinity vs. edit distance for
*de novo* AI modeling generated LCDR variants

High affinity and high diversity obtained by combining AI-optimized HCDRs with *de novo* AI-generated LCDRs

- **Top HCs from tracks 1 & 2 were combined with LCs from additional *de novo* modeling.**
- 143 variants identified with higher affinity than Heron2B by up to an order of magnitude and up to 12 edit distance across 5 CDRs.
- 59 variants with sub-nM affinity in Fab format.

All 20 high priority AI-optimized leads selected for stage 3 have sub-nM affinity to Human TL1A

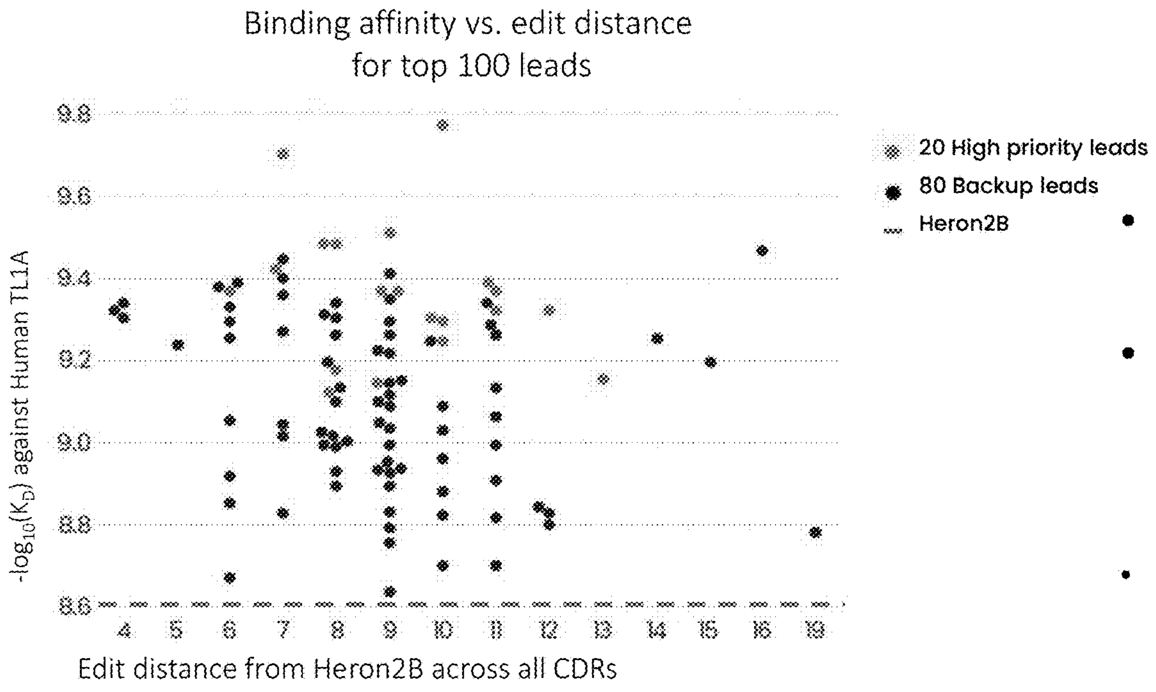

FIG. 14

- All 100 AI-optimized leads have affinity higher than Heron2B.
- 20 high-priority leads were risk adjusted to maximize sequence diversity and minimize sequence liabilities.
- 80 backup leads include 4 high edit distance variants identified from Track 4 with affinities higher than Heron2B but with lower confidence.
    - Subset of Track 4 library tested directly by SPR.

AI-guided lead optimization for improved therapeutics

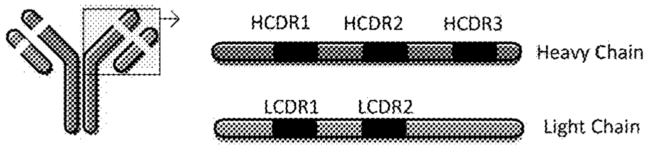

- AI predicted Heavy Chain variants (HCDR123) with improved affinity over parental binder.
- **Combined AI-optimized Heavy Chain (HCDR123) with *de novo* designed Light Chain (LCDR12) achieves high affinity and high diversity.**

FIG. 16A

AI-GUIDED OPTIMIZATION

> 50 novel AI-optimized variants with sub-nanomolar affinity[1] and no *in silico* developability flags.

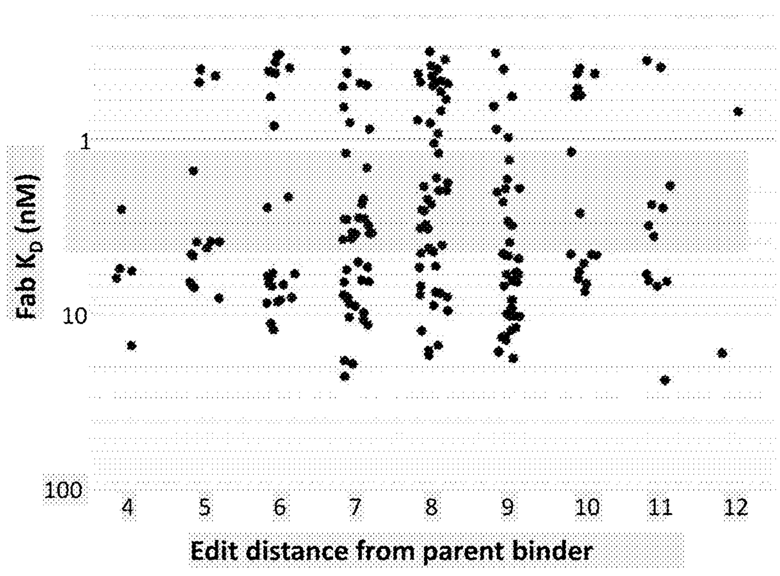

[1]Affinity by surface plasmon resonance (SPR)
[2]Parental binder is the Heavy Chain AI de novo designed variant.

FIG. 16B

Lead candidates bind to both monomeric and trimeric TL1A

LEAD mAb CANDIDATES BIND TO MONOMERIC AND TRIMERIC TL1A WITH HIGH AFFINITY

* Estimated performance of clinical competitor reagent generated for in house comparison.

AI-optimized lead candidates inhibit TL1A:DR3-driven apoptosis

#Estimated performance of a putative clinical competitor molecule generated for in house comparison.

AI-optimized lead candidates inhibit TL1A:DR3-driven NF-kB activation

#Estimated Performance Of A Putative Clinical Competitor Molecule Generated For In House Comparison.

AI-optimized lead candidates inhibit TL1A:DR3-driven INFγ release

CONFIRMATION OF EFFECTOR FUNCTION KNOCKOUT IN ADCC ACTIVATION ASSAY

All ABS-101 lead variants designed with effector function knockout mutations (LALADS).

Lack of antibody-dependent cellular cytotoxicity (ADCC) demonstrated (right panel)

Lack of binding to a panel of FcγR receptors: FcγRI, FcγRIIA (H167), FcγRIIA (R167), FcγRIIB/C, FcγRIIIA (F176), FcγRIIA (V176), FcγRIIIB (NA1)

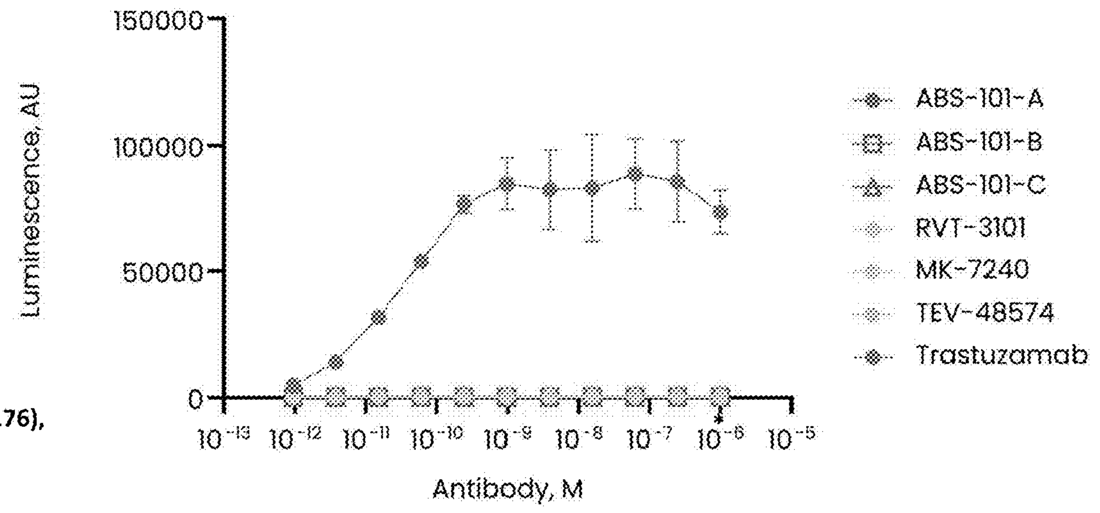

Trastuzumab used as an assay positive control in HER2 +ve cell line SKOV3.
* Isotype negative control

FIG. 22

- AI-designed and optimized leads span multiple epitopes on TL1A.
  - Further differentiation from clinical competitors for ABS-101 lead candidates.
  - Epitopes are contained within oneTL1A subunit to bind to both monomer AND trimer.
- The epitope for RVT-3101 was excluded during design due to high ADA observed for that clinical molecule.

Epitope bins on TL1A*

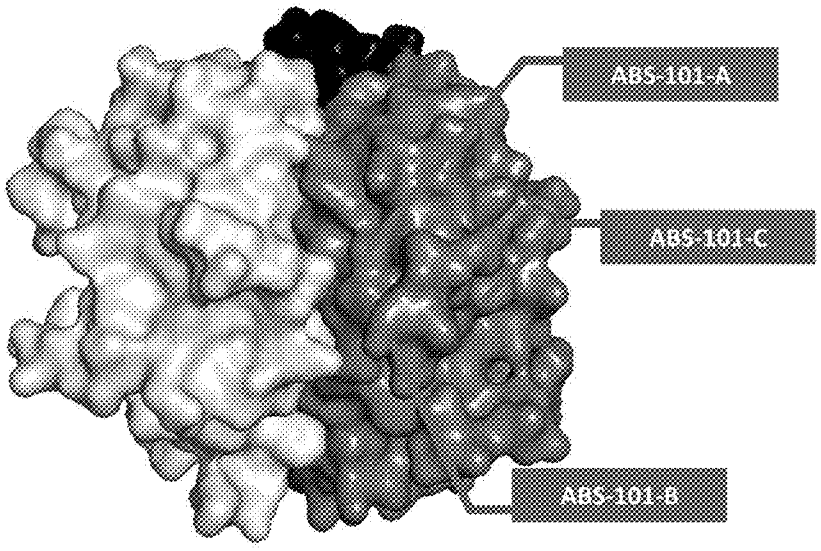

* Epitope binning for lead candidates by BLI competition experiment. RVT-3101 and TEV-48574 epitopes were inferred from publicly available information. MK-7240 epitope placement based on internal epitope binning, biophysical, and functional data.

* Estimated performance of clinical competitor reagent generated for in house comparison.

FIG. 23

Low immunogenicity of lead candidates to enable sub-Q formulation and longer dosing intervals

**Low *ex vivo* T-cell activation overserved for lead candidates**

T-cell activation scores do not correlate with clinically observed ADA for TL1A antibodies. ADAs most likely driven by biology and epitope selection.

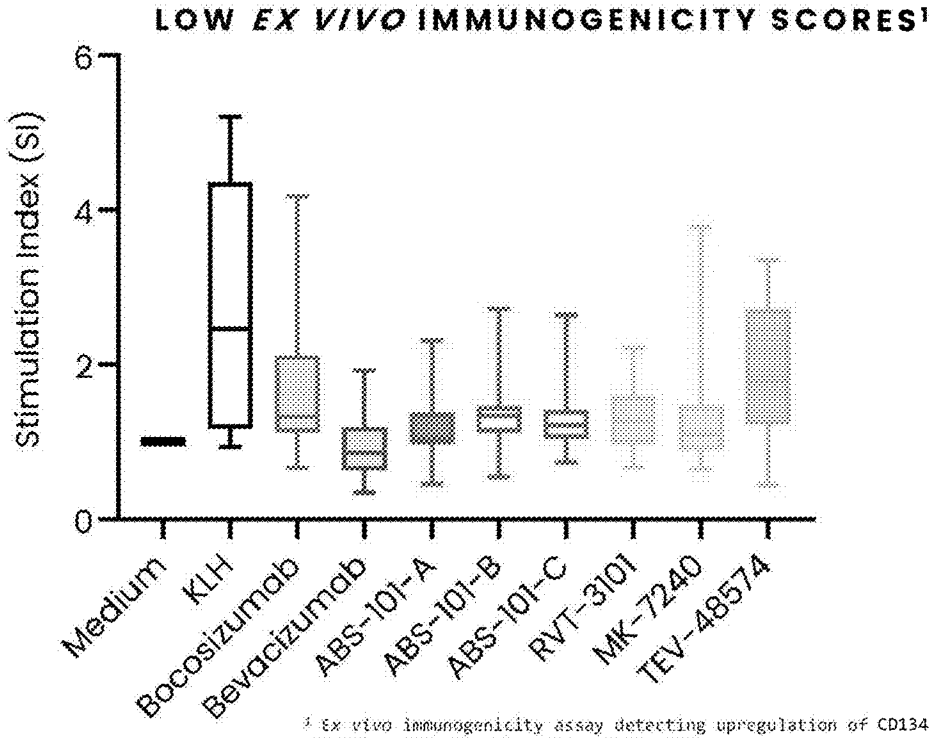

[1] Ex vivo immunogenicity assay detecting upregulation of CD134 and CD137 on CD4+ T cells. Cohen 2020. DOI: 10.1080/19420862.2021.1898831.

[#] Estimated performance of a putative clinical competitor molecule generated for in house comparison

FIG. 24

CDR Length: Sum Of The Length Of All Six CDRs
PSH: Patches Of Surface Hydrophobicity
PPC: Patches Of Positive charge
PNC: Patches Of Negative Charge
SFvCSP: Structural Fv Charge Symmetry Parameter

#Estimated Performance Of A Putative Clinical Competitor Molecule Generated For In House Comparison.

Half-life extension mutation
to improve antibody pharmacokinetics
pharmacokinetics

Half-life extension mutations introduced on lead candidates to improve antibody recycling.

- Increased affinity for FcRn at pH 6.0 to promote antibody recycling from endosomes.
- Preserved low affinity at pH 7.4 to promote antibody release in the extracellular environment

Successful development of drug substance at 200 mg/mL

ABS-101-A FORMULATION AND STABILITY ASSESSMENT

| Formulation[1] | Target concentration (mg/mL) | Measured concentration (mg/mL) | Viscosity (cP @ 20°C) | HIAC sub-visible particles | | Stability Assessment SEC (Δ Main%)[2] | | | | |
|---|---|---|---|---|---|---|---|---|---|---|
| | | | | ≥ 10 µm | ≥25 µm | 5 FT (per cycle) | 3-day AG (per day)* | -70°C (per week) | -20°C (per week) | 40°C (per week) |
| 20 mM His, 140 mM Arg.HCl, pH 6.0, 0.04% PS80 (w/v) | 200 | 194.9 | 21.4 | 2 | 0 | -0.01 | -0.13 | 0.10 | -0.22 | -1.28 |
| | 150 | 155.7 | 9.1 | 102 | 14 | -0.01 | -0.04 | 0.00 | -0.22 | -1.28 |

HIAC = high accuracy liquid particle counter
SEC = size exclusion chromatography
CGE = capillary gel electrophoresis
icIEF = imagining capillary isoelectric focusing
FT = freeze-and-thaw
AG = agitation

FIG. 27

#Estimated Performance Of A Putative Clinical Competitor Molecule Generated For In House Comparison

*Linear Regression Analysis Only For Interims Visualization - Final Plot To Be Delivered By ABM

Preliminary PK analysis in NHP confirmation pending by in silico modelling CRO ABM

| Analysis | PK Parameters | ABS-101-A | MK-7420# | RVT-3101# |
|---|---|---|---|---|
| In house | $t_{1/2}$ (d) | 10.7 | 2.5 | 6.6 |
| | CL (mL/hr/kg) | 0.37 | 0.26 | 0.24 |
| | $AUC_{0\text{-}\infty}$ (μg.d/mL) | 177602 | 234401 | 245297 |
| | Vss (mL/kg) | 124.0 | 22.7 | 55.8 |
| | Cmax (μg/ml) | 462 | 909 | 767 |
| WuXi | $t_{1/2}$ (d) | 7.6 | 3.7 | 4.8 |
| | CL (mL/hr/kg) | 0.39 | 0.26 | 0.26 |
| | $AUC_{0\text{-}672h}$ (μg.d/mL) | 145000 | 232000 | 223000 |
| | Vz (mL/kg) | 91.3 | 34.8 | 43.2 |
| | Cmax (μg/ml) | 462 | 909 | 767 |

FIG. 28B

TL1A ASSOCIATED ANTIBODY COMPOSITIONS AND METHODS OF USE

CROSS REFERENCE TO RELATED APPLICATIONS

This application claims benefit of and priority to U.S. Provisional Application No. 63/542,186 filed on Oct. 3, 2023, U.S. Provisional Application No. 63/554,832 filed on Feb. 16, 2024, U.S. Provisional Application No. 63/675,403, filed on Jul. 25, 2024, and 63/682,593 filed on Aug. 13, 2024, the disclosure of which are each hereby incorporated by reference in its entirety herein.

INCORPORATION OF SEQUENCE LISTING

The instant application contains a Sequence Listing XML, which has been submitted electronically and is hereby incorporated by reference in its entirety. Said XML copy, created on: Oct. 2, 2024, is named 59413_SeqListing.xml and is 132,207 bytes in size.

BACKGROUND OF THE INVENTION

TL1A, also called TNFSF15, is a member of tumor necrosis factor family. It is expressed in different immune cells, such as monocyte, macrophage, dendritic cell, T cell and non-immune cell, for example, synovial fibroblast, endothelial cell. TL1A competitively binds to death receptor 3 (DR3) or decoy receptor 3 ("DcR3"), providing stimulatory signal for downstream signaling pathways, and then regulates proliferation, activation, apoptosis of and cytokine, chemokine production in effector cells. Recent findings showed that TL1A was abnormally expressed in autoimmune diseases, including rheumatoid arthritis, inflammatory bowel disease, psoriasis, primary biliary cirrhosis, systemic lupus erythematosus and ankylosing spondylitis. In vivo and in vitro studies further demonstrated that TL1A was involved in development and pathogenesis of these diseases. These accumulating data have raised the possibility that TL1A pathways may represent a significant therapeutic target for chronic immunological diseases.

SUMMARY OF THE INVENTION

As described herein, the present disclosure provides TL1A antibodies and related host cells, expression vectors, compositions, as well methods of treating and methods of producing the same.

In one embodiment, an antibody or antigen-binding fragment thereof is provided comprising an antibody or antigen-binding fragment thereof comprising at least one of: a variable heavy chain complementarity-determining region CDR-H1, CDR-H2, and CDR-H3, wherein: CDR-H1 comprises a polypeptide sequence selected from any one of the sequences provided in Sequence Table 1, CDR-H2 comprises a polypeptide sequence selected from any one of the sequences provided in Sequence Table 1, and CDR-H3 comprises a polypeptide sequence selected from any one of the sequences provided in Sequence Table 1; and a variable light chain complementarity-determining region CDR-L1, CDR-L2 and CDR-L3, wherein: CDR-L1 comprises a polypeptide sequence selected from any one of the sequences provided in Sequence Table 1, CDR-L2 comprises a polypeptide sequence selected from any one of the sequences provided in Sequence Table 1, and CDR-L3 comprises a polypeptide sequence selected from any one of the sequences provided in Sequence Table 1.

In another embodiment, an antibody or antigen-binding fragment thereof is provided comprising at least one of: a variable heavy chain, wherein the variable heavy chain comprises a polypeptide sequence having at least 90% sequence identity to an amino acid sequence selected from any one of the sequences provided in Sequence Table 1 including any sequence from the sequences of SEQ ID NOS: 9, 18, 22, 26, 32, 38, 40, 45, 47, 52, 55, 60, 68, 75, 82, 91, 96, 101, 103, 106, 108, 111, 114, 119, 121, 124, 126, 129, 132, 134, 136, or 138; and a variable light chain, wherein the variable light chain comprises a polypeptide sequence having at least 90% sequence identity to an amino acid sequence selected from any one of the sequences provided in Sequence Table 1 including any sequence from the sequences of SEQ ID NOS: 7, 17, 21, 25, 31, 34, 42, 51, 54, 57, 58, 67, 71, 74, 76, 81, 83, 85, 86, 90, 92, 93, or 97.

In still another embodiment, the present disclosure provides antibody or antigen-binding fragment thereof that comprises: a variable heavy chain complementarity-determining region CDR-H1, CDR-H2, and CDR-H3, wherein CDR-H1 comprises a polypeptide sequence selected from any one of the sequences provided in Sequence Table 1 including any sequence from SEQ ID NOS: 4, 14, 23, 28, 35, 39, 43, 46, 48, 64, 78, 84, 88, 94, 98, 109, 112, 115, 118, 120, 122, 125, 127, 130, or 137, CDR-H2 comprises a polypeptide sequence selected from any one of the sequences provided in Sequence Table 1 including any sequence from SEQ ID NOS: 5, 15, 29, 36, 49, 65, 79, 89, 99, 104, 131, or 133, and CDR-H3 comprises a polypeptide sequence selected from any one of the sequences provided in Sequence Table 1 including any sequence from SEQ ID NOS: 6, 16, 20, 24, 30, 37, 44, 50, 59, 66, 73, 80, 95, 100, 102, 105, 107, 110, 113, 123, 128, or 135; and a variable light chain complementarity-determining region CDR-L1, CDR-L2, and CDR-L3, wherein CDR-L1 comprises a polypeptide sequence selected from any one of the sequences provided in Sequence Table 1 including any sequence of SEQ ID NOS: 1, 12, 19, 27, 41, 53, 61, or 69, CDR-L2 comprises a polypeptide sequence selected from any one of the sequences provided in Sequence Table 1 including any sequence of GAS, ATS, SAS, YAS, or a sequence of SEQ ID NOS: 62, 70, 72, 77, or 87, and CDR-L3 comprises a polypeptide sequence selected from any one of the sequences provided in Sequence Table 1 including any sequence of SEQ ID NOS: 3, or 63.

In yet another embodiment, the present disclosure provides an antibody or antigen-binding fragment thereof that comprises a variable heavy chain, wherein the variable heavy chain comprises a polypeptide sequence selected from any one of the sequences provided in Sequence Table 1 including any sequence of SEQ ID NOS: 9, 18, 22, 26, 32, 38, 40, 45, 47, 52, 55, 60, 68, 75, 82, 91, 96, 101, 103, 106, 108, 111, 114, 119, 121, 124, 126, 129, 132, 134, 136, or 138; and a variable light chain, wherein the variable light chain comprises a polypeptide sequence selected from any one of the sequences provided in Sequence Table 1 including any sequence of SEQ ID NOS: 7, 17, 21, 25, 31, 34, 42, 51, 54, 57, 58, 67, 71, 74, 76, 81, 83, 85, 86, 90, 92, 93, or 97. In another embodiment, an antibody or antigen-binding fragment thereof is provided that comprises a variable heavy chain complementarity-determining region CDR-H1, CDR-H2, and CDR-H3, wherein CDR-H1 comprises a polypeptide sequence selected from any one of the sequences provided in Sequence Table 1 including any sequence of SEQ ID NOS: 4, 14, 23, 28, 35, 39, 43, 46, 48, 64, 78, 84, 88, 94, 98, 109, 112, 115, 118, 120, 122, 125, 127, 130, or 137, CDR-H2 comprises a polypeptide sequence selected from any one of the sequences provided in Sequence Table 1 including any sequence of SEQ ID NOS: 5, 15, 29, 36, 49, 65, 79, 89, 99, 104, 131, or 133, and CDR-H3 comprises a polypeptide sequence selected from any one of the sequences provided in Sequence Table 1 including any sequence of SEQ ID NOS: 6, 16, 20, 24, 30, 37, 44, 50, 59, 66, 73, 80, 95, 100, 102, 105, 107, 110, 113, 123, 128, or 135. The present disclosure also provides, in one embodiment, an antibody or antigen-binding fragment thereof that comprises a variable light chain complementarity-determining region CDR-L1, CDR-L2, and CDR-L3, wherein CDR-L1 comprises a polypeptide sequence selected from any one of the sequences provided in Sequence Table 1 including any sequence of SEQ ID NOS: 1, 12, 19, 27, 41, 53, 61, or 69, CDR-L2 comprises a polypeptide sequence selected from any one of the sequences provided in Sequence Table 1 including any sequence comprising GAS, ATS, SAS, or YAS a sequence of SEQ ID NOS: 62, 70, 72, 77, or 87, and CDR-L3 comprises a polypeptide sequence selected from any one of the sequences provided in Sequence Table 1 including any sequence of SEQ ID NOS: 3 or 63. In still another embodiment, an antibody or antigen-binding fragment thereof is provided that comprises: a variable heavy chain complementarity-determining region CDR-H1, CDR-H2, and CDR-H3, wherein CDR-H1 comprises a polypeptide sequence selected from any one of the sequences provided in Sequence Table 1 including any sequence of SEQ ID NOS: 4, 14, 23, 28, 35, 39, 43, 46, 48, 64, 78, 84, 88, 94, 98, 109, 112, 115, 118, 120, 122, 125, 127, 130, or 137, CDR-H2 comprises a polypeptide sequence selected from any one of the sequences provided in Sequence Table 1 including any sequence of SEQ ID NOS: 5, 15, 29, 36, 49, 65, 79, 89, 99, 104, 131, or 133, and CDR-H3 comprises a polypeptide sequence selected from any one of the sequences provided in Sequence Table 1 including any sequence of SEQ ID NOS: 6, 16, 20, 24, 30, 37, 44, 50, 59, 66, 73, 80, 95, 100, 102, 105, 107, 110, 113, 123, 128, or 135; and a variable light chain complementarity-determining region CDR-L1, CDR-L2, and CDR-L3, wherein CDR-L1 comprises a polypeptide sequence selected from any one of the sequences provided in Sequence Table 1 including any sequence of SEQ ID NOS: 1, 12, 19, 27, 41, 53, 61, or 69, CDR-L2 comprises a polypeptide sequence selected from any one of the sequences provided in Sequence Table 1 including any sequence comprising GAS, ATS, SAS, YAS or any sequence of SEQ ID NOS: 62, 70, 72, 77, or 87, and CDR-L3 comprises a polypeptide sequence selected from any one of the sequences provided in Sequence Table 1 including any sequence of SEQ ID NOS: 3 or 63.

In one embodiment, the present disclosure provides an antibody or antigen-binding fragment thereof that comprises a variable heavy chain, wherein the variable heavy chain comprises a polypeptide sequence selected from any one of the sequences provided in Sequence Table 1 including any sequence of SEQ ID NOS: 9, 18, 22, 26, 32, 38, 40, 45, 47, 52, 55, 60, 68, 75, 82, 91, 96, 101, 103, 106, 108, 111, 114, 119, 121, 124, 126, 129, 132, 134, 136, or 138. In one embodiment, the present disclosure provides an antibody or antigen-binding fragment thereof that comprises a variable light chain, wherein the variable light chain comprises a polypeptide sequence selected from any of the sequences provided in Sequence Table 1 including any sequence of SEQ ID NOS: 7, 17, 21, 25, 31, 34, 42, 51, 54, 57, 58, 67, 71, 74, 76, 81, 83, 85, 86, 90, 92, 93, or 97. In another embodiment, the present disclosure provides an antibody or antigen-binding fragment thereof that comprises: a variable heavy chain, wherein the variable heavy chain comprises a polypeptide sequence selected from any one of the sequences provided in Sequence Table 1 including any sequence of SEQ ID NOS: 9, 18, 22, 26, 32, 38, 40, 45, 47, 52, 55, 60, 68, 75, 82, 91, 96, 101, 103, 106, 108, 111, 114, 119, 121, 124, 126, 129, 132, 134, 136, or 138; and an antibody or antigen-binding fragment thereof that comprises a variable light chain, wherein the variable light chain comprises a polypeptide sequence selected from any of the sequences provided in Sequence Table 1 including any sequence of SEQ ID NOS: 7, 17, 21, 25, 31, 34, 42, 51, 54, 57, 58, 67, 71, 74, 76, 81, 83, 85, 86, 90, 92, 93, or 97.

In one embodiment, the present disclosure provides an antibody or antigen-binding fragment thereof that comprises: (i) a variable heavy chain complementarity-determining region CDR-H1, CDR-H2 and CDR-H3, wherein (a) the CDR-H1 comprises the amino acid sequence of antibody 1 as set out in the Sequence Table 1 (SEQ ID NO: 4), (b) the CDR-H2 comprises the amino acid sequence of antibody 1 as set out in the Sequence Table 1 (SEQ ID NO: 5), and (c) the CDR-H3 comprises the amino acid sequence of antibody 1 as set out in the Sequence Table 1 (SEQ ID NO: 6); (ii) a variable light chain complementarity-determining region CDR-L1, CDR-L2 and CDR-L3, wherein: (a) CDR-L1 comprises the amino acid sequence of antibody 1 as set out in the Sequence Table 1 (SEQ ID NO: 1), (b) CDR-L2 comprises the amino acid sequence of antibody 1 as set out in the Sequence Table 1 (GAS), and (c) CDR-L3 comprises the amino acid sequence of lead antibody 1 as set out in the Sequence Table 1 (SEQ ID NO: 3); or (iii) the variable heavy chain complementarity-determining region CDR-H1, CDR-H2 and CDR-H3 of (i) (SEQ ID NO: 9), and the variable light chain complementarity-determining region CDR-L1, CDR-L2 and CDR-L3 of (ii) (SEQ ID NO: 7). In one embodiment, the present disclosure provides an aforementioned antibody that is capable of binding human TL1A.

In still another embodiment, embodiment, the present disclosure provides an antibody or antigen binding fragment thereof that comprises: (a) a variable heavy chain that comprises a polypeptide sequence having at least 90% sequence identity to an amino acid sequence of lead antibody 1 as set out in the Sequence Table 1 (SEQ ID NO: 9); (b) a variable light chain that comprises a polypeptide sequence having at least 90% sequence identity to an amino acid sequence of lead antibody 1 as set out in the Sequence Table 1 (SEQ ID NO: 7); or (c) the variable heavy chain of (a), and the variable light chain of (b).

In one embodiment, the present disclosure provides a pharmaceutical composition or a medicament that comprises an aforementioned antibody or antigen-binding fragment thereof and a pharmaceutically acceptable carrier, excipient, or diluent.

A method for preventing a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis in a subject in need thereof, the method comprising administering to the subject a therapeutically effective amount of either an aforementioned antibody or antigen binding fragment or an aforementioned pharmaceutical composition.

The present disclosure also provides, in one embodiment, a method for treating a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis a subject in need thereof, the method comprising administering to the subject, (a) an aforementioned antibody or antigen-binding fragment thereof; or and aforementioned pharmaceutical composition.

In one embodiment, the present disclosure provides a hybridoma that produces an aforementioned antibody or antigen-binding fragment thereof. In one embodiment, the present disclosure provides a fusion protein or an immunoconjugate that comprises an aforementioned antibody or antigen-binding fragment thereof.

The present disclosure further provides, in one embodiment, an isolated nucleic acid that encodes one or more or all the CDRs of an aforementioned antibody. In yet another embodiment, an expression vector is provided comprising an aforementioned isolated nucleic acid molecule. In still another embodiment, a host cell is provided comprising an aforementioned expression vector, or an aforementioned isolated nucleic acid molecule.

In still another embodiment, the present disclosure provides a method of inhibiting binding of TL1A to a host cell expressing DR3, the method comprising contacting the host cell with an aforementioned antibody or antigen binding fragment thereof.

The present disclosure also provides, in one embodiment, a method of producing an antibody or an antigen binding fragment thereof, the method comprising: culturing a host cell, in a medium under conditions permitting expression of a polypeptide encoded by the isolated nucleic acid and assembling of the antibody or an antigen binding fragment thereof; and purifying the antibody or antigen binding fragment thereof from the cultured cell or the cell culturing medium.

In one embodiment, a method of preparing an antibody or antigen-binding fragment thereof capable of binding to TL1A with higher affinity compared to a reference antibody is provided, said method comprising: identifying a reference antibody or fragment thereof comprising one or more CDR sequences associated with TL1A-binding activity; optionally identifying a framework sequence; modifying one or more amino acids in one or more of said CDR sequences thereby generating a variant antibody, wherein one or more of the amino acid modifications is predicted to improve affinity of the variant antibody to TL1A as compared to the reference antibody and wherein said prediction is produced from a computing system. In one embodiment, the computing system comprises: one or more processors; and one or more non-transitory computer-readable media having stored thereon: a machine-learned model trained using training data, wherein the training data includes one or more training antibody sequence variants, each having a respective measured binding characteristic representing an ability of each to bind to a corresponding respective binding partner, and wherein the machine-learned model is configured to output a predicted antibody binding characteristic of an input antibody sequence variant; and instructions that, when executed by the one or more processors, cause the computing system to: process one or more antibody sequence variants with the machine-learned model to generate one or more predicted binding characteristics, each corresponding to a respective one of the one or more antibody sequence variants; analyze the one or more predicted binding characteristics to identify one or more antibody sequence variants of interest from among the one or more antibody sequence variants, each of the one or more antibody sequence variants of interest having a respective one or more desired properties; and provide the one or more antibody sequence variants of interest as an output. In another embodiment, computing system comprises: one or more processors; and one or more non-transitory computer-readable media having stored thereon: a machine-learned antibody prediction model trained to predict structural information of antibodies based on an input; and instructions that, when executed by the one or more processors, cause the computing system to: (1) receive a target input including one or more of a target binding partner primary sequence, three-dimensional coordinates of a target binding partner, a target binding partner epitope primary sequence, or three-dimensional coordinates of a target binding partner epitope primary sequence, or a fragment or portion of any of the foregoing; and (2) predict the structural information of the target antibody by processing the target input with the machine-learned antibody prediction model. In another embodiment, the computing system comprises: one or more processors; and one or more non-transitory computer-readable media having stored thereon: a machine-learned affinity prediction artificial neural network, including: (i) one or more antibody prediction layers trained to predict antibody structural information from target inputs; (ii) one or more docking layers trained to generate docked complexes from two or more input three-dimensional antibody; and (iii) one or more affinity prediction layers trained to predict affinity from input docked complexes; wherein the one or more antibody prediction layers, the one or more docking layers, and the one or more affinity prediction layers are connected; and instructions that, when executed by the one or more processors, cause the computing system to: receive a target input comprising one or more of a target binding partner sequence, a target binding partner, or a target epitope; and process the target input using the affinity prediction artificial neural network to generate a docked complex corresponding to the target input and a corresponding structural affinity value. In yet another embodiment, the computing system performs antigen-aware antibody folding and comprises: one or more processors; and one or more memories having stored thereon: a machine-learned model trained to predict an output antibody digital representation corresponding to an output antibody using one or more training inputs including one or more training antibody digital representations each corresponding to a respective one of a plurality of training antibodies; and a set of computer-executable instructions that, when executed by the one or more processors, cause the computing system to: receive a plurality of input antibody digital representations each corresponding to a respective one of a plurality of input antibodies; and process one or more of the pluralities of input antibody digital representations using the machine-learned model to generate one or more predicted output antibody digital representations.

The present disclosure also provides, in one embodiment, an antibody or antigen-binding fragment thereof capable of binding to TL1A with higher affinity compared to a reference antibody, comprising one or more of: at least one HCDR sequence comprising one or more amino acid modifications compared to the reference antibody, and wherein the one or more amino acid modifications is predicted to improve affinity of the antibody to TL1A as compared to the reference antibody and wherein said prediction is produced from a computing system; and/or at least one LCDR sequence comprising one or more amino acid modifications compared to the reference antibody, and wherein the one or more amino acid modifications is predicted to improve affinity of the antibody to TL1A as compared to the reference antibody and wherein said prediction is produced from a computing system; wherein at least one LCDR is unmodified compared to the reference antibody. In one embodiment, the antibody or antigen-binding fragment thereof comprises amino acid modifications in HCDR1, HCDR2 and HCDR3 compared to the reference antibody. In another embodiment, the antibody or antigen-binding fragment thereof comprises amino acid modifications in LCDR1, LCDR2 compared to the reference antibody. In still another embodiment, the antibody or antigen-binding fragment thereof comprises a framework region that is different than the framework region of the reference antibody. In still another embodiment, the antibody or antigen-binding fragment thereof is produced by an aforementioned method.

In still other embodiments, the antibodies or fragments thereof provided herein, including for example ABS-101-A, ABS-101-B or ABS-101-C, have superior properties relative to a reference antibody, including binding affinity, stability at high concentrations and half-life properties.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIGS. 1A-1G shows dose-dependent antibody inhibition of IFN-γ in whole blood by Heron1, Heron2B, or a novel antibody (mAb 4).

FIG. 4 depicts a summary of 20 high priority AI-optimized leads.

FIG. 5 shows a summary of quality and developability metrics of 20 high priority AI-optimized leads.

FIGS. 6A-6B shows a binding assessment of 20 high priority AI-optimized leads in mAb format against TL1A.

FIG. 7A-7B shows an assessment of cross-reactivity of 20 high priority AI-optimized leads in mAb format.

FIG. 8A-8B shows that $T_{1/2}$ extension mutations increase FcRn affinity at pH 6.0 by ~10-fold relative to Herons by SPR

FIGS. 10A-10G shows the results of a NFKb affinity assay.

FIGS. 11A-11E shows the results of an apoptosis assay.

FIG. 14 shows that all 20 high priority AI-optimized leads have sub-nM affinity to Human TL1A.

FIGS. 16A-16B shows AI-guided lead optimization for improved therapeutics.

FIG. 22 shows lead variants designed to prevent effector function activation.

FIG. 23 shows the epitope chosen during AI design to manage immunogenicity.

FIG. 24 shows low immunogenicity of lead candidates to enable sub-Q formulation and longer dosing intervals.

FIG. 27 shows the results of a formulation and stability assessment for ABS-101.

FIGS. 28A-28B shows a prolonged half-life profile of ABS-101-A.

DETAILED DESCRIPTION OF THE INVENTION

Figure 2A:
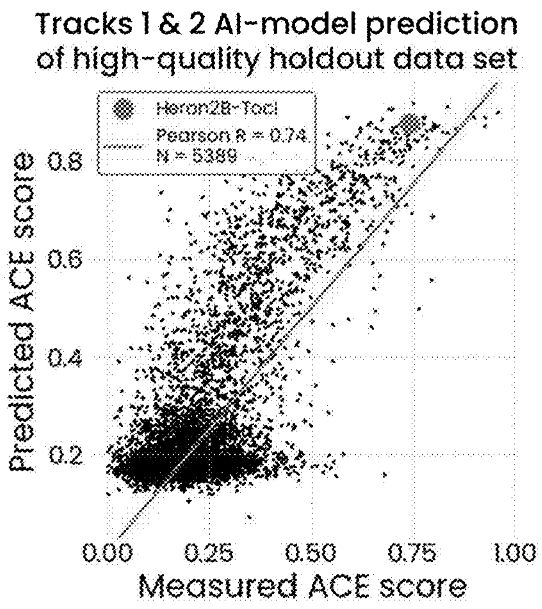
FIGS. 2A-2B shows AI-model prediction of ACE score based on a high-quality holdout data set and subsequent ACE score prediction for novel, AI predicted HCDR sequences.

The instant disclosure provides antibodies and/or antigen-binding fragments thereof that specifically bind to TL1A (e.g., human TL1A) and antagonize TL1A function, e.g., TL1A-mediated inflammation suppression. Also provided are pharmaceutical compositions comprising these antibodies and/or antigen-binding fragments thereof, nucleic acids encoding these antibodies and/or antigen-binding fragments thereof, expression vectors and host cells for making these antibodies and/or antigen-binding fragments thereof, and methods of treating a subject using these antibodies and/or antigen-binding fragments thereof. The antibodies and/or antigen-binding fragments thereof disclosed herein are particularly useful for inhibiting the binding of TL1A to death receptor 3 (DR3) and/or blocks DR3 and decoy receptor 3 (DcR3) on a host cell. The antibodies and/or antigen-binding fragments thereof are useful for treating and/or preventing a disease, disorder, or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis in a subject. All instances of "isolated antibodies" described herein are additionally contemplated as antibodies that may be, but need not be, isolated. All instances of "isolated polynucleotides" described herein are additionally contemplated as polynucleotides that may be, but need not be, isolated. All instances of "antibodies" described herein are additionally contemplated as antibodies that may be, but need not be, isolated. All instances of "polynucleotides" described herein are additionally contemplated as polynucleotides that may be, but need not be, isolated. In other aspects, the instant disclosure provides a method of preparing an antibody or antigen-binding fragment thereof capable of binding to TL1A with higher affinity compared to a reference antibody, said method comprising: identifying a reference antibody or fragment thereof comprising one or more CDR sequences associated with TL1A-binding activity; optionally identifying a framework sequence; modifying one or more amino acids in one or more of said CDR sequences thereby generating a variant antibody, wherein one or more of the amino acid modifications is predicted to improve affinity of the variant antibody to TL1A as compared to the reference antibody and wherein said prediction is produced from a computing system.

As used herein, the term "antibody" refers to an immunoglobulin (Ig) whether natural or partly or wholly synthetically produced. The term also covers any polypeptide or protein having a binding domain which is, or is homologous to, an antigen-binding domain. The term further includes "antigen-binding fragments" and other interchangeable terms for similar binding fragments such as described herein.

An antibody includes, but is not to be limited to, any specific binding member, immunoglobulin class and/or isotype (e.g., IgG1, IgG2, IgG3, IgG4, IgM, IgA, IgD, IgE, and IgM), and biologically relevant fragment or specific binding member thereof. Thus, an antibody includes, for example, monoclonal antibodies, chimeric antibodies, humanized antibodies, human antibodies, recombinant antibodies, chemically engineered antibodies, deimmunized antibodies, affinity-matured antibodies, multispecific antibodies (for example, bispecific antibodies and polyreactive antibodies), heteroconjugate antibodies, antibody fragments, and combinations thereof (e.g., a monoclonal antibody that is also deimmunized, a humanized antibody that is also deimmunized, etc.).

The term "TL1A associated antibody" as used herein refers to an antibody specific for an TL1A associated antigen or epitope.

Native antibodies and native immunoglobulins are usually heterotetrametric glycoproteins of about 150,000 Daltons, composed of two identical light (L) chains and two identical heavy (H) chains. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ("$V_H$") followed by a number of constant domains ("$C_H$"). Each light chain has a variable domain at one end ("$V_L$") and a constant domain ("$C_L$") at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The antibodies or antigen-binding fragment thereof of the present disclosure can comprise a deletion at an end of a light chain. The antibodies or antigen-binding fragment thereof of the disclosure can comprise a deletion of 3 or more amino acids at an end of the light chain. The antibodies or antigen-binding fragment thereof of the disclosure can comprise a deletion of 7 or less amino acids at an end of the light chain. The antibodies or antigen-binding fragment thereof of the disclosure can comprise a deletion of 3, 4, 5, 6, or 7 amino acids at an end of the light chain.

The antibodies or antigen-binding fragments thereof of the present disclosure can comprise an insertion in a light chain. The antibodies or antigen-binding fragment thereof of the disclosure can comprise an insertion of 1, 2, 3, 4, 5, 6, 7, 8, 9, or 10, or more amino acids in the light chain. The antibodies or antigen-binding fragment thereof of the disclosure can comprise an insertion of 3 amino acids in the light chain.

A "variable region" of an antibody refers to the variable region of the antibody light chain or the variable region of the antibody heavy chain, either alone or in combination. The variable regions of the heavy and light chain each consist of four framework regions (FR) connected by three complementarity-determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (e.g., Kabat et al. Sequences of Proteins of Immunological Interest, (5th ed., 1991, National Institutes of Health, Bethesda Md.)); and (2) an approach based on crystallographic studies of antigen-antibody complexes (Allazikani et al. (1997) *J. Moles. Biol.* 273:927-48)). A CDR may refer to CDRs defined by either approach or by a combination of both approaches.

A "constant region" of an antibody refers to the constant region of the antibody light chain or the constant region of the antibody heavy chain, either alone or in combination. The constant region does not vary with respect to antigen specificity.

As used herein, the term "heavy chain region" includes amino acid sequences derived from the constant domains of an immunoglobulin heavy chain. A polypeptide comprising a heavy chain region comprises at least one of: a $C_H1$ domain, a hinge (e.g., upper, middle, and/or lower hinge region) domain, a $C_H2$ domain, a $C_H3$ domain, or a variant or fragment thereof. In an embodiment, an antibody or an antigen-binding fragment thereof may comprise the Fc region of an immunoglobulin heavy chain (e.g., a hinge portion, a $C_H2$ domain, and a $C_H3$ domain). In another embodiment, an antibody or an antigen-binding fragment thereof lacks at least a region of a constant domain (e.g., all or part of a $C_H2$ domain). In certain embodiments, at least one, and preferably all, of the constant domains are derived from a human immunoglobulin heavy chain. For example, in one preferred embodiment, the heavy chain region comprises a fully human hinge domain. In other preferred embodiments, the heavy chain region comprising a fully human Fc region (e.g., hinge, $C_H2$ and $C_H3$ domain sequences from a human immunoglobulin). In certain embodiments, the constituent constant domains of the heavy chain region are from different immunoglobulin molecules. For example, a heavy chain region of a polypeptide may comprise a domain derived from an IgG1 molecule, and a hinge region derived from an IgG3 or IgG4 molecule. In other embodiments, the constant domains are chimeric domains comprising regions of different immunoglobulin molecules. For example, a hinge may comprise a first region from an IgG1 molecule and a second region from an IgG3 or IgG4 molecule. It will be understood by one of ordinary skill in the art that the constant domains of the heavy chain region may be modified such that they vary in amino acid sequence from the naturally occurring (wild type) immunoglobulin molecule. That is, the polypeptides of the disclosure disclosed herein may comprise alterations or modifications to one or more of the heavy chain constant domains ($C_H1$, hinge, $C_H2$, or $C_H3$) and/or to the light chain constant domain ($C_L$). Exemplary modifications include additions, deletions, or substitutions of one or more amino acids in one or more domains.

As used herein, the term "hinge region" includes the region of a heavy chain molecule that joins the $C_H1$ domain to the $C_H2$ domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al. *J. Immunol.* 1998 161:4083).

As used herein, the term "Fv" is the minimum antibody fragment that contains a complete antigen-recognition and -binding site. This fragment consists of a dimer of one heavy- and one light-chain variable region domain in tight, non-covalent association.

"Heavy chain variable region" or "$V_H$" with regard to an antibody refers to the fragment of the heavy chain that contains three CDRs interposed between flanking stretches known as framework regions, these framework regions are generally more highly conserved than the CDRs and form a scaffold to support the CDRs.

Six hypervariable loops (three loops each from the H and L chain) contribute the amino acid residues for antigen-binding and confer antigen-binding specificity to the antibody. However, even a single variable domain (or half of an Fv comprising only three CDRs specific for an antigen) has the ability to recognize and bind antigen, although at a lower affinity than the entire binding site.

"Framework" or FR residues are those variable domain residues other than the hypervariable region residues.

It is understood in the art that an antibody is a glycoprotein having at least two heavy (H) chains and two light (L) chains interconnected by disulfide bonds, or an antigen-binding portion thereof. A heavy chain is comprised of a heavy chain variable region ($V_H$) and a heavy chain constant region ($C_H1$, $C_H2$, and $C_H3$). A light chain is comprised of a light chain variable region ($V_L$) and a light chain constant region ($C_L$). The variable regions of both the heavy and light chains comprise framework regions (FRs or FWRs) and hypervariable regions (HVRs). The HVRs are the amino acid residues of an antibody that are responsible for antigen binding. The hypervariable region generally comprises amino acid residues from a complementarity determining region (CDR), which have the highest sequence variability and/or involved in antigen recognition. With the exception of CDR1 in $V_H$, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See, e.g., Fransson, *Front. Biosci.* 13:1619-1633 (2008).)

Unless otherwise indicated, HVR residues and other residues in the variable domain (e.g., FR residues) are numbered herein according to Kabat et al., supra. A variable region is a domain of an antibody heavy or light chain that is involved in binding the antibody to antigen. (See, e.g., Kindt et al. Kuby Immunology, 6th ed., W.H. Freeman and Co., p. 91 (2007)). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$or $V_H$ domains, respectively. (See, e.g., Portolano et al., *J. Immunol.* 150:880-87 (1993); Clarkson et al., *Nature* 352:624-28 (1991)). The four FWR regions are typically more conserved while CDR regions (CDR1, CDR2 and CDR3) represent hypervariable regions and are arranged from NH2 terminus to the COOH terminus as follows: FWR1, CDR1, FWR2, CDR2, FWR3, CDR3, and FWR4. The variable regions of the heavy and light chains contain a binding domain that interacts with an antigen while, depending on the isotype, the constant region(s) may mediate the binding of the immunoglobulin to host tissues or factors. An antibody also includes chimeric antibodies, humanized antibodies, and recombinant antibodies, human antibodies generated from a transgenic non-human animal, as well as antibodies selected from libraries using enrichment technologies available to the artisan.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa ("K") and lambda ("X") light chains refer to the two major antibody light chain isotypes.

An antibody or antigen-binding fragment thereof "specifically binds" or "preferentially binds" to a target antigen if it binds with greater affinity and/or avidity than it binds to epitopes on unrelated polypeptides. The specificity of an antibody or antigen-binding fragment or portion thereof can be determined based on affinity and/or avidity. Methods to determine such specific binding are also well known in art. According to certain embodiments of the present disclosure, the antibodies or antigen-binding fragment thereof can bind to human TL1A but not to TL1A from other subjects. Instill other embodiments, the antibodies or antigen-binding fragment thereof can bind to human TL1A as well as TL1A from other subjects. In some embodiments, an antibody or antigen binding fragment thereof disclosed herein specifically binds to a target antigen disclosed herein.

The affinity, represented by the equilibrium constant for the dissociation ($K_D$) of an antigen with an antigen-binding protein, is a measure for the binding strength between an antigenic determinant and an antigen-binding site on the antigen-binding protein: the lesser the value of the $K_D$, the stronger the binding strength between an antigenic determinant and the antigen-binding molecule. Alternatively, the affinity can also be expressed as the affinity constant ($K_A$), which is $1/K_D$). As will be clear to the skilled person, affinity can be determined in a manner known per se, depending on the specific antigen of interest. Accordingly, an antibody or antigen-binding fragment thereof as defined herein is said to be "specific for" a first target or antigen compared to a second target or antigen when it binds to the first antigen with an affinity (suitably expressed, for example, as a $K_D$ value) that is at least 50 times, such as at least 100 times, and preferably at least 1000 times, and up to 10,000 times or more better than the affinity with which said amino acid sequence or polypeptide binds to another target or polypeptide. Preferably, when an antibody or antigen-binding fragment thereof is "specific for" a target or antigen, compared to another target or antigen, it can bind the target or antigen, but does not bind the other target or antigen. However, as understood by one of ordinary skill in the art, in some embodiments, where a binding site on a target is shared or partially shared by multiple, different ligands, an antibody or antigen-binding fragment thereof can specifically bind to a target, such as a TL1A, and have the functional effect of, for example, inhibiting/preventing diseases, disorders or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis.

$K_D$ can be measured by any suitable assay. For example, $K_D$ can be measured by a radiolabeled antigen-binding assay (RIA) (see, e.g., Chen et al., *J. Mol. Biol.* 293:865-881 (1999); Presta et al., *Cancer Res.* 57:4593-4599 (1997)). For example, $K_D$ can be measured using a surface plasmon resonance assay (e.g., using a BIACORE®-2000 or a BIACORE®-3000). For example, $K_D$ can be measured using a competitive ELISA.

Avidity is the measure of the strength of binding between an antigen-binding molecule and the pertinent antigen. Avidity is related to both the affinity between an antigenic determinant and its antigen-binding site on the antigen-binding molecule, and the number of pertinent binding sites present on the antigen-binding molecule. Typically, antigen-binding proteins will bind to their cognate or specific antigen with a dissociation constant ($K_D$ of $10^{-5}$ to $10^{-12}$ M or less, and preferably $10^{-7}$ to $10^{-12}$ M or less and more preferably $10^{-8}$ to $10^{-12}$ M (i.e., with an association constant ($K_A$) of $10^5$ to $10^{12}$ $M^{-1}$ or more, and preferably $10^7$ to $10^{12}$ $M^{-1}$ or more and more preferably $10^8$ to $10^{12}$ $M^{-1}$). Any $K_D$ value greater than $10^{-4}$ M (or any $K_A$ value lower than $10^4$ $M^{-1}$) is generally considered to indicate non-specific binding. The $K_D$ for biological interactions which are considered meaningful (e.g., specific) are typically in the range of $10^{-10}$ M (0.1 nM) to $10^{-5}$ M (10000 nM). The stronger an interaction is, the lower is its $K_D$. Preferably, a binding site on an anti-LAP antibody or antigen-binding fragment thereof described herein will bind with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassay's (RIA), enzyme immunoassays (EIA) and sandwich competition assays, and the different variants thereof known per se in the art; as well as other techniques as mentioned herein.

The term "$k_{on}$", as used herein, is intended to refer to the rate constant for association of an antibody or antigen-binding fragment thereof to an antigen.

The term "$k_{off}$", as used herein, is intended to refer to the rate constant for dissociation of an antibody or antigen-binding fragment thereof from the antibody/antigen complex.

It is to be understood that this application is not limited to particular formulations or process parameters, as these may, of course, vary. It is also to be understood that the terminology used herein is for the purpose of describing particular embodiments only and is not intended to be limiting. Further, it is understood that a number of methods and materials similar or equivalent to those described herein can be used in the practice of the present disclosure.

In accordance with the present application, there may be employed conventional molecular biology, microbiology, and recombinant DNA techniques as explained fully in the art. The definitions contained herein supplement those in the art and are directed to the current application and are not to be imputed to any related or unrelated case, e.g., to any commonly owned patent or application. Accordingly, the terminology used herein is for the purpose of describing particular embodiments only and is not intended to be limiting.

In this application, the use of the singular includes the plural unless specifically stated otherwise. It must be noted that, as used in the specification, the singular forms "a," "an," and "the" include plural referents unless the context clearly dictates otherwise. Furthermore, use of the term "including" as well as other forms, such as "include", "includes," and "included," is not limiting.

The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C."

The term "or" can be used conjunctively or disjunctively unless the context specifically refers to a disjunctive use.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the disclosure can be used to achieve methods of the disclosure.

As used herein the term "consisting essentially of" refers to those elements required for a given embodiment. The term permits the presence of elements that do not materially affect the basic and novel or functional characteristic(s) of that embodiment of the disclosure.

As used herein the term "consisting of" refers to compositions, methods, and respective components thereof as described herein, which are exclusive of any element not recited in that description of the embodiment.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosure.

TL1A and Anti-TL1A Antibodies

Provided herein are antibodies and antigen binding fragments thereof that bind TL1A, and are useful in treatment, and prevention of diseases, disorders or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis.

Tumor necrosis factor (TNF)-like cytokine 1A (TL1A), is a member of the TNF superfamily and was first identified in 2002 (Xu W D, et al., *Front Immunol.* 2022 Jul. 14; 13:913-28). The tnfsf15 gene encoding TL1A is located at chromosome 9q32 in human and chromosome 4 in mouse. TL1A is a type 2 transmembrane protein that self-assembles into stable trimers by interacting with TNF homology domain (THD). It is mainly expressed as the membrane-bound form, and it forms stable trimers. The soluble TL1A (sTL1A) was produced by alternative splicing or TNF-α-converting enzyme (TACE) cleavage (Migone T S, et al., *Immunity* (2002) 16(3):479-92; Zhan C, et al., *Biochemistry* (2009) 48(32):7636-45). TL1A is constitutively expressed in endothelial cells, and it is up-regulated in response to tumor necrosis factor-α (TNF-α) stimulation. Expression of TL1A in dendritic cell (DC) and macrophage is increased when the cells were triggered by toll-like receptors 4 (TLR4), TLR11 or Fc region of IgG (FcγR) (Schreiber T H, et al., *Immunol Res* (2013) 57(1-3):3-11; Fang L, et al., *J Exp Med* (2008) 205(5):1037-48; and Prehn J L, et al., *J Immunol* (2007) 178(7):4033-8). Mitogen-activated protein kinases (MAPKs), nuclear factor kappa-light-chain enhancer of activated B cells (NF-κB), caspase-8 signaling pathways regulate immune response, ranging from apoptosis to autoimmunity (Wen L, et al., *J Biol Chem* (2003) 278(40):39251-8; and Micheau O, et al., *Cell* (2003) 114(2):181-90). TL1A binds to its receptor, death receptor 3 (DR3), and thereafter activates downstream signaling, and then participates in innate and adaptive immune homeostasis. Binding of APC-derived TL1A to lymphocytic DR3 provides co-stimulatory signals for activated lymphocytes. DR3 signaling affects the proliferative activity of and cytokine production by effector lymphocytes, but also critically influences the development and suppressive function of regulatory T-cells. DR3 was also found to be highly expressed by innate lymphoid cells (ILCS), which respond to stimulation by TL1A. Several recent studies with transgenic and knockout mice as well as neutralizing or agonistic antibodies for these two proteins, have clearly shown that TL1A/DR3 are important mediators of several chronic immunological disorders, including Inflammatory Bowel Disease (IBD). TL1A and DR3 are abundantly localized at inflamed intestinal areas of patients with IBD and mice with experimental ileitis or colitis and actively participate in the immunological pathways that underlie mucosal homeostasis and intestinal inflammation.

It has been shown that soluble TL1A (sTL1A) can be detected in serum and body fluids of patients with T cell-mediated inflammatory autoimmune diseases, such as rheumatoid arthritis (RA), psoriatic arthritis (PsA), and ankylosing spondylitis (AS). TL1A also plays important roles in the pathogenesis of these diseases (Aiba Y, et al., *Mediators Inflamm* (2013) 2013:258164). In recent years, TL1A, as an important mediator of inflammation, has attracted much attention because anti-TL1A antibody treatment may be a promising therapeutic approach in inflammatory disorders (Danese S, et al., *Clin Gastroenterol Hepatol* (2021) 19(11): 2324-32.e6).

The relationship between TL1A and inflammatory bowel disease (IBD) has also been described by Kokkotis and Bamias (Kokkotis, G., and Bamias, G., *Expert Rev. Clin. Immunol.,* 2022, 18(6): 551-55). TL1A was first reported in 2002 (Migone et al., *Immunity* (2002) 16 p 479-92). It was found to be a member of the TNF superfamily of proteins (TNFSF), and it is encoded by the Tnfsf15 gene that is located on chromosome 9q32 in humans and chromosome 4 in mice. In 2005, Yamazaki et al. were the first to report that a specific genetic variant of Tnfsf15, tnfsf15_28, was strongly associated with susceptibility to IBD in Japanese patients, whereas the gene was monomorphic in a Caucasian population from the UK (Yamazaki K et al., "Single nucleotide polymorphisms in TNFSF15 confer susceptibility to Crohn's disease", *Hum Mol Genet.* 14 (3400-506) (2005). Further investigation of these two ethnic groups revealed 5 different SNPs, tnfsf15_26, 31, 35, 36, and 41, that were polymorphic in both groups, forming three different haplotypes which affected susceptibility to IBD. In both ethnic groups, haplotype A was identified as a high-risk marker for susceptibility to IBD, whereas haplotype B was found to be a low-risk genetic factor. Haplotype C was not significantly associated with IBD risk in either population, despite its frequent detection. Two years later, Picornell et al. investigated the aforementioned three haplotypes in Jewish and non-Jewish IBD and control populations in Los Angeles, USA. In the non-Jewish population, similar to the previous study, haplotype B was less frequent in both CD and UC patients compared to controls, highlighting a possible protective role (Picornell Y. et al, "TNFSF15 is an ethnic-specific IBD gene". *Inflamm Bowel Dis.* (2007) 13:1333-8.20). On the other hand, no association of haplotype A with IBD was seen in either population, suggesting that Tnfsf15 polymorphisms are ethnic-specific. These findings were further supported by independent studies from Asia and Europe.

Pfizer developed a fully human anti-TL1A antibody (PF-06480605) that binds the trimeric forms of TL1A (Banfield, Christopher, et al., *British Journal of Clinical Pharmacology* 86.4 (2020): 812-24; Danese S, et. al., *Clinical Gastroenterology and Hepatology,* 2021. 19: 2324-2332.e6). Prometheus Bioscience developed a humanized anti-TL1A murine IgG1 mAb (PRA023) that binds both the trimeric and monomeric forms of TL1A (Sands, B., et al., *Journal of Crohn's and Colitis* 17. Supplement_1 (2023): i56-i59; Feagan, B G, et. al., Journal of Crohn's, and Colitis 2023 17: 162-164). Glenmark Pharmaceuticals developed a humanized anti-TL1A mAb (WO 2014/106602; U.S. Pat. No. 9,290,576). Pelican Therapeutics developed a human TL1A-Ig fusion protein agonist of TNFRSF25/DR3 (PTX-45).

Additional antibodies and related methods have been described, for example, in U.S. Pat. Nos. 9,068,003, 8,642,741, 9,556,277, 10,822,422, 2021/037193, 10,316,083, 11,474,112, 9,683,998, 10,138,296, 10,968,279, 10,322,174, 10,689,439, 11,136,386, 2020/0362025, 11,292,848, 2022/029024, 2021/0395824, WO 2022/103961, WO 2022/119842, WO2022/178158, WO 2022/178159, WO 2022/232253, and WO 2023/009545.

In some aspects, the present disclosure provides nucleic acid and polypeptide sequences for TL1A associated antibodies.

As used herein, the terms "protein," "peptide," and "polypeptide" are used interchangeably to designate a series of amino acid residues connected to each other by peptide bonds between the alpha-amino and carboxy groups of adjacent residues. The terms "protein," "peptide," and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein", "peptide" and "polypeptide" are used interchangeably herein when referring to a gene product and fragments thereof. The term "fusion protein" as used herein refers to a polypeptide that comprises an amino acid sequence of an antibody or fragment thereof and an amino acid sequence of a heterologous polypeptide (i.e., an unrelated polypeptide).

As used herein, an "isolated" nucleic acid molecule or "isolated" nucleic acid sequence is a nucleic acid molecule that is either: (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined, is considered isolated. An isolated nucleic acid molecule is other than in the form or setting in which it is found in nature. Isolated nucleic acid molecules therefore are distinguished from the nucleic acid molecule as they exist in natural cells. However, an isolated nucleic acid molecule includes a nucleic acid molecule contained in cells that ordinarily express the antibody where, for example, the nucleic acid molecule is in a chromosomal location different from that of natural cells.

The terms "synthetic polynucleotide," "synthetic gene," or "synthetic polypeptide," as used herein, mean that the corresponding polynucleotide sequence or portion thereof, or amino acid sequence or portion thereof, is derived, from a sequence that has been designed, or synthesized de novo, or modified, compared to an equivalent naturally occurring sequence. Synthetic polynucleotides (antibodies or antigen-binding fragments) or synthetic genes can be prepared by methods known in the art, including but not limited to, the chemical synthesis of nucleic acid or amino acid sequences. Synthetic genes are typically different from naturally occurring genes, either at the amino acid, or polynucleotide level, (or both) and are typically located within the context of synthetic expression control sequences. Synthetic gene polynucleotide sequences, may not necessarily encode proteins with different amino acids, compared to the natural gene; for example, they can also encompass synthetic polynucleotide sequences that incorporate different codons, but which encode the same amino acid (i.e., the nucleotide changes represent silent mutations at the amino acid level).

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in several ways that are within the skill in the art, for instance, using publicly available computer software such as BLAST, BLAST-2, ALIGN, or MegAlign (DNASTAR®) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration NO: TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In some embodiments, the present disclosure further provides complete nucleic acid sequences and complete polypeptide sequences of the variable heavy chain ($V_H$) and variable light chain ($V_L$) of antibodies according to numerous embodiments of the present disclosure. The nucleic acid and polypeptide sequences of the three complementarity-determining regions (CDRs) of the $V_H$ and the $V_L$ are also provided.

One aspect of the present disclosure pertains to nucleic acid sequences that encode an antibody polypeptide as described herein or antigen-binding fragment thereof. In some embodiments, the nucleic acid sequence encoding a heavy chain polypeptide is selected from any one of the sequences provided in Sequence Table 1 herein. In some embodiments, the nucleic acid sequence encoding a light chain polypeptide is selected from any one of the sequences provided in Sequence Table 1 herein. In some embodiments, the nucleic acid sequence encodes a CDR1, CDR2, or CDR3 polypeptide of a variable heavy chain, such that:

(a) the nucleic acid sequence encoding the CDR1 polypeptide of a variable heavy chain is selected from any one of the sequences provided in Sequence Table 1 herein including any sequence of SEQ ID NOS: 4, 14, 23, 28, 35, 39, 43, 46, 48, 64, 78, 84, 88, 94, 98, 109, 112, 115, 118, 120, 122, 125, 127, 130, or 137, (b) the nucleic acid sequence encoding the CDR2 polypeptide of a variable heavy chain is selected from any one of the sequences provided in Sequence Table 1 herein including any sequence of SEQ ID NOS: 5, 15, 29, 36, 49, 65, 79, 89, 99, 104, 131, or 133, or (c) the nucleic acid sequence encoding the CDR3 polypeptide of a variable heavy chain is selected from any one of the sequences provided in Sequence Table 1 herein including any sequence of SEQ ID NOS: 6, 16, 20, 24, 30, 37, 44, 50, 59, 66, 73, 80, 95, 100, 102, 105, 107, 110, 113, 123, 128, or 135.

In some embodiments, the nucleic acid sequence encodes a CDR1, CDR2, or CDR3 polypeptide of a variable light chain, such that:

(a) the nucleic acid sequence encoding the CDR1 region of a variable light chain polypeptide is selected from any one of the sequences provided in Sequence Table 1 herein including any sequence of SEQ ID NOS: 1, 12, 19, 27, 41, 53, 61, or 69, (b) the nucleic acid sequence encoding the CDR2 region of a variable light chain polypeptide is selected from any one of the sequences provided in Sequence Table 1 herein including any sequence comprising GAS, ATS, SAS, or YAS, or any sequence of SEQ ID NOS: 62, 70, 72, 77, or 87 or (c) the nucleic acid sequence encoding the CDR3 region of a variable light chain polypeptide is selected from any one of the sequences provided in Sequence Table 1 herein including any sequence of SEQ ID NOS: 3, or 63.

In some embodiments, the nucleic acid sequence encodes a HCDR1 (SEQ ID NO: 4), HCDR2 (SEQ ID NO: 5), HCDR3 (SEQ ID NO: 20), LCDR1 (SEQ ID NO: 19), LCDR2 (GAS), LCDR3 (SEQ ID NO: 3), VL (SEQ ID NO: 21), CL (SEQ ID NO: 8), VH (SEQ ID NO: 22), CH (SEQ ID NO: 10) and or Fc region (SEQ ID NO: 139) of ABS-101-A, a HCDR1 (SEQ ID NO: 28), HCDR2 (SEQ ID NO: 29), HCDR3 (SEQ ID NO: 30), LCDR1 (SEQ ID NO: 27), LCDR2 (GAS), LCDR3 (SEQ ID NO: 3), VL (SEQ ID NO: 31), CL (SEQ ID NO: 8), VH (SEQ ID NO: 32), CH (SEQ ID NO: 10) and or Fc region (SEQ ID NO: 139) of ABS-101-B or a HCDR1 (SEQ ID NO: 4), HCDR2 (SEQ ID NO: 5), HCDR3 (SEQ ID NO: 20), LCDR1 (SEQ ID NO: 41), LCDR2 (SAS), LCDR3 (SEQ ID NO: 3), VL (SEQ ID NO: 42), CL (SEQ ID NO: 8), VH (SEQ ID NO: 22), CH (SEQ ID NO: 10) and or Fc region (SEQ ID NO: 139) of ABS-101-C.

Another aspect of the present disclosure pertains to nucleic acid comprising nucleic acid sequences that encode the antibody polypeptide, described herein or antigen-binding fragment thereof. In some embodiments, the isolated nucleic acid comprises a nucleic acid sequence encoding a heavy chain polypeptide of an antibody. In some embodiments, the nucleic acid sequence encoding a heavy chain polypeptide is selected from the sequences provided in Sequence Table 1 herein. In some embodiments, the isolated nucleic acid comprises a nucleic acid sequence encoding a light chain polypeptide of an antibody. In some embodiments, the nucleic acid sequence encoding a light chain polypeptide is selected from the sequences provided in Sequence Table 1 herein.

In some embodiments, the isolated nucleic acid comprises a nucleic acid sequence encoding a CDR1 polypeptide of a variable heavy chain. In some embodiments, the isolated nucleic acid molecule comprises a nucleic acid sequence encoding a CDR2 polypeptide of a variable heavy chain. In some embodiments, the isolated nucleic molecule comprises a nucleic acid sequence encoding a CDR3 polypeptide of a variable heavy chain. In some embodiments, the nucleic acid sequence encoding the CDR1 polypeptide of a variable heavy chain (CDR-H1) comprises a sequence selected from the sequences provided in Sequence Table 1 herein including any sequence of SEQ ID NOS: 4, 14, 23, 28, 35, 39, 43, 46, 48, 64, 78, 84, 88, 94, 98, 109, 112, 115, 118, 120, 122, 125, 127, 130, or 137. In some embodiments, the nucleic acid sequence encoding the CDR2 polypeptide of a variable heavy chain (CDR-H2) comprises a sequence selected from the sequences provided in Sequence Table 1 herein including any sequence of SEQ ID NOS: 5, 15, 29, 36, 49, 65, 79, 89, 99, 104, 131, or 133. In some embodiments, the nucleic acid sequence encoding the CDR3 polypeptide of a variable heavy chain (CDR-H3) comprises a sequence selected from the sequences provided in Sequence Table 1 herein including any sequence of SEQ ID NOS: 6, 16, 20, 24, 30, 37, 44, 50, 59, 66, 73, 80, 95, 100, 102, 105, 107, 110, 113, 123, 128, or 135. In some embodiments, the isolated nucleic acid comprises a nucleic acid sequence encoding a CDR1 polypeptide of a variable light chain. In some embodiments, the isolated nucleic acid molecule comprises a nucleic acid sequence encoding a CDR2 polypeptide of a variable light chain. In some embodiments, the isolated nucleic acid comprises a nucleic acid sequence encoding a CDR3 polypeptide of a variable light chain. In some, embodiments, the nucleic acid sequence encoding the CDR1 region of a variable light chain polypeptide (CDR-L1) comprises a sequence selected from the sequences provided in Sequence Table 1 herein including any sequence of SEQ ID NOS: 1, 12, 19, 27, 41, 53, 61, or 69. In some embodiments, the nucleic acid sequence encoding the CDR2 region of a variable light chain polypeptide (CDR-L2) comprises a sequence selected from the sequences provided in Sequence Table 1 herein including a sequence comprising GAS, ATS, SAS, or YAS, or a sequence of SEQ ID NOS: 62, 70, 72, 77, or 87. In some, embodiments, the nucleic acid sequence encoding the CDR3 region of a variable light chain polypeptide (CDR-L3) comprises a sequence selected from the sequences provided in Sequence Table 1 herein including any sequence of SEQ ID NOS: 3 or 63.

Nucleic acids according to at least some embodiments of the present disclosure can be obtained using standard molecular biology techniques. For antibodies expressed by hybridomas (e.g., hybridomas prepared from transgenic mice carrying human immunoglobulin genes), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library. Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame. The isolated DNA encoding the VH region can be converted to a full-length heavy chain gene by operatively linking the VH-encoding DNA to another DNA molecule encoding heavy chain constant regions ($C_H1$, $C_H2$ and $C_H3$). The sequences of human heavy chain constant region genes are known in the art (see, e.g., Kabat, E. A., et al. (1991) Sequences of Proteins of Immunological Interest, Fifth Edition, U.S. Department of Health and Human Services, NIH Publication NO: 91-3242) and DNA fragments encompassing these regions can be obtained by standard PCR amplification. The heavy chain constant region can be an IgG1, IgG2, IgG3, IgG4, IgA, IgE, IgM, or IgD constant region, but most preferably is an IgG1 or IgG4 constant region. For a Fab fragment heavy chain gene, the VH-encoding DNA can be operatively linked to another DNA molecule encoding only the heavy chain CHI constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see, e.g., Kabat, E. A., et al. (1991) Sequences of Proteins of Immunological Interest, Fifth Edition, U.S. Department of Health and Human Services, NIH Publication NO: 91-3242) and DNA fragments encompassing these regions can be obtained by standard PCR amplification. The light chain constant region can be a kappa or lambda constant region, but most preferably is a kappa constant region. To create a scFv gene, the VH- and VL-encoding DNA fragments are operatively linked to another fragment encoding a flexible linker, e.g., encoding the amino acid sequence (Gly-4-Ser)3, such that the VH and VL sequences can be expressed as a contiguous single-chain protein, with the VL and VH regions joined by the flexible linker (see, e.g., Bird et al. (1988) *Science* 242:423-26; Huston et al. (1988) *Proc. Natl. Acad. Sci. USA* 85:5879-5883; and McCafferty et al., (1990) *Nature* 348:552-554).

Nucleic acids comprising a nucleotide sequence substantially different from those described but which, due to the degeneracy of the genetic code, still encode at least an antibody or an antigen binding fragment thereof as described herein and/or as it is known in the art are also contemplated. Of course, the genetic code is well known in the art. Therefore, it would be routine for one skilled in the art to generate such degenerate nucleic acid variants encoding specific antibodies of the present disclosure. See, e.g., Ausubel et al., supra, and such nucleic acid variants are included in the present disclosure.

In some embodiments, the nucleic acid is one that encodes for any of the amino acid sequences for the antibodies in Sequence Table 1 herein. In some embodiments, the nucleic acid sequence is one that is at least 80% identical to a nucleic acid encoding any of the amino acid sequences for the antibodies in the in the Sequence Table 1 herein including any sequence of SEQ ID NOS: 1-139, for example, at least 80, 85, 90, 91, 92, 93, 94, 95, 96, 97, 98, or 99% identical. In some embodiments, the nucleic acid is one that hybridizes to any one or more of the nucleic acid sequences provided herein. In some of the embodiments, hybridization is under moderate conditions. In some embodiments, the hybridization is under highly stringent conditions, such as: at least about 6×SSC and 1% SDS at 65° C., with a first wash for 10 minutes at about 42° C. with about 20% (v/v) formamide in 0.1×SSC, and with a subsequent wash with 0.2×SSC and 0.1% SDS at 65° C.

Nucleic acids can be constructed using recombinant DNA techniques conventional in the art. In some embodiments, a nucleic acid disclosed herein is placed in an expression vector that is suitable for expression in a selected host cell. Vectors comprising nucleic acids that encode the antibodies or antigen binding fragments herein are provided. Vectors comprising nucleic acids that encode a heavy chain and/or a light chain are also provided. Such vectors include, but are not limited to, DNA vectors, phage vectors, viral vectors, retroviral vectors, etc. In one embodiment, the nucleic acid coding for the light chain and that coding for the heavy chain are isolated separately by the procedures outlined above. In one embodiment, the isolated nucleic acid encoding the light chain and that coding for the heavy chain may be inserted into separate expression plasmids, or together in the same plasmid, so long as each is under suitable promoter and translation control. In some embodiments, the suitable promoter is an inducible promoter. In some embodiments a suitable promoter is a constitutive promoter. In some embodiments, the heavy chain and light chain are expressed as part of a single polypeptide, such as, for example, when the antibody is an scFv.

In some embodiments, a first vector comprises a nucleic acid that encodes a heavy chain and a second vector comprises a nucleic acid that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used. In some embodiments, a vector is selected that is optimized for expression of polypeptides in CHO or CHO-derived cells, or in NSO cells. Exemplary such vectors are described, for example, in Running Deer et al., *Biotechnol. Prog.* 20:880-889 (2004).

Additional vectors contemplated for use in antibody expression and purification are described in U.S. Pat. Nos. 9,617,335, 11,371,048, US Pub. NO: 2018/0282405, U.S. Pat. No. 11,584,785, and PCT/US22/82294.

Exemplary TL1A Associated Antibodies or Antigen-Binding Fragments Thereof

The present disclosure provides TL1A associated antibodies or antigen-binding fragments thereof. In some embodiments, the antibodies or antigen-binding fragments thereof block or otherwise inhibit the binding of TL1A to death receptor 3 (DR3; TNFRSF25) and/or block DR3 and DcR3. In some embodiments, the TL1A associated antibodies or antigen-binding fragments thereof comprise one or more of the HCDR1 (SEQ ID NO: 4), HCDR2 (SEQ ID NO: 5), HCDR3 (SEQ ID NO: 20), LCDR1 (SEQ ID NO: 19), LCDR2 (GAS), LCDR3 (SEQ ID NO: 3), VL (SEQ ID NO: 21), CL (SEQ ID NO: 8), VH (SEQ ID NO: 22), CH (SEQ ID NO: 10) and/or Fc region (SEQ ID NO: 139) of ABS-101-A, one or more of the HCDR1, HCDR2, HCDR3, LCDR1 (SEQ ID NO: 27), LCDR2 (GAS), LCDR3 (SEQ ID NO: 3), VL (SEQ ID NO: 31), CL (SEQ ID NO: 8), VH (SEQ ID NO: 32), CH (SEQ ID NO: 10) and/or Fc region (SEQ ID NO: 139) ABS-101-B or one or more of the HCDR1 (SEQ ID NO: 4), HCDR2 (SEQ ID NO: 5), HCDR3 (SEQ ID NO: 20), LCDR1 (SEQ ID NO: 41), LCDR2 (SAS), LCDR3 (SEQ ID NO: 3), VL (SEQ ID NO: 42), CL (SEQ ID NO: 8), VH (SEQ ID NO: 32), CH (SEQ ID NO: 10) and/or Fc region (SEQ ID NO: 139) ABS-101-C as set out in Sequence Table 1 herein.

In one aspect, an antibody or antigen-binding fragment thereof is provided, wherein the antibody or antigen-binding fragment thereof comprises a heavy chain variable domain ($V_H$) having at least 90%, 91%, 92%, 93%, 94%, 95%, 96%, 97%, 98%, 99%, or 100% sequence identity to the amino acid sequence of any one of SEQ ID NO:1 or any sequence provided in a Table herein including any sequence of SEQ ID NOS: 9, 18, 22, 26, 32, 38, 40, 45, 47, 52, 55, 60, 68, 75, 82, 91, 96, 101, 103, 106, 108, 111, 114, 119, 121, 124, 126, 129, 132, 134, 136, or 138. In some embodiments, a $V_H$ sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to TL1A as of the parent. In some embodiments, a total of 1 to 10 amino acids have been substituted, inserted and/or deleted in the amino acid sequence of any one of the sequences provided in Sequence Table 1 herein including any sequence of SEQ ID NOS: 9, 18, 22, 26, 32, 38, 40, 45, 47, 52, 55, 60, 68, 75, 82, 91, 96, 101, 103, 106, 108, 111, 114, 119, 121, 124, 126, 129, 132, 134, 136, or 138. In some embodiments, substitutions, insertions, or deletions occur in regions outside the CDRs (e.g., in the FRs). Optionally, the antibody or antigen-binding fragment thereof comprises the $V_H$ sequence of any one of the sequences provided in Sequence Table 1 herein including any sequence of SEQ ID NOS: 9, 18, 22, 26, 32, 38, 40, 45, 47, 52, 55, 60, 68, 75, 82, 91, 96, 101, 103, 106, 108, 111, 114, 119, 121, 124, 126, 129, 132, 134, 136, or 138, including one or more post-translational modifications of that sequence.

In some embodiments, the $V_H$ comprises one, two or three CDRs selected from: (a) CDR-H1, comprising the amino acid sequence of any one of the sequences provided in Sequence Table 1 herein including any sequence of SEQ ID NOS: 4, 14, 23, 28, 35, 39, 43, 46, 48, 64, 78, 84, 88, 94, 98, 109, 112, 115, 118, 120, 122, 125, 127, 130, or 137, (b) CDR-H2, comprising the amino acid sequence of any one of the sequences provided in Sequence Table 1 herein including any sequence of SEQ ID NOS: 5, 15, 29, 36, 49, 65, 79, 89, 99, 104, 131, or 133, and (c) CDR-H3, comprising the amino acid sequence of any one of the sequences provided in Sequence Table 1 herein including any sequence of SEQ ID NOS: 6, 16, 20, 24, 30, 37, 44, 50, 59, 66, 73, 80, 95, 100, 102, 105, 107, 110, 113, 123, 128, or 135.

In some embodiments, the $V_H$ comprises one, two or three CDRs selected from: (a) CDR-H1, comprising the amino acid sequence of any one of the sequences provided in Sequence Table 1 herein including any sequence of SEQ ID NOS: 4, 14, 23, 28, 35, 39, 43, 46, 48, 64, 78, 84, 88, 94, 98, 109, 112, 115, 118, 120, 122, 125, 127, 130, or 137, (b) CDR-H2, comprising the amino acid sequence of any one of the sequences provided in Sequence Table 1 herein including any sequence of SEQ ID NOS: 5, 15, 29, 36, 49, 65, 79, 89, 99, 104, 131, or 133, and (c) CDR-H3, comprising the amino acid sequence of any one of the sequences provided in Sequence Table 1 herein 6, 16, 20, 24, 30, 37, 44, 50, 59, 66, 73, 80, 95, 100, 102, 105, 107, 110, 113, 123, 128, or 135, wherein the selected CDR-H1, CDR-H2, and CDR-H3 are paired according to Sequence Table 1.

In one aspect, an antibody or antigen-binding fragment thereof is provided, wherein the antibody or antigen-binding fragment thereof comprises a light chain variable domain ($V_L$) having at least 90%, 91%, 92%, 93%, 94%, 95%, 96%, 97%, 98%, 99%, or 100% sequence identity to the amino acid sequence of any one of the sequences provided in Sequence Table 1 herein including any sequence of SEQ ID NOS: 7, 17, 21, 25, 31, 34, 42, 51, 54, 57, 58, 67, 71, 74, 76, 81, 83, 85, 86, 90, 92, 93, or 97. In some embodiments, a $V_L$ sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to TL1A as the parent. In some embodiments, a total of 1 to 10 amino acids have been substituted, inserted and/or deleted in the amino acid sequence of any one of the sequences provided in Sequence Table 1 herein including any sequence of SEQ ID NOS: 7, 17, 21, 25, 31, 34, 42, 51, 54, 57, 58, 67, 71, 74, 76, 81, 83, 85, 86, 90, 92, 93, or 97. In some embodiments, the substitutions, insertions, or deletions occur in regions outside the CDRs (e.g., in the FRs). Optionally, the antibody or antigen-binding fragment thereof comprises the $V_L$ sequence of any one of the sequences provided in Sequence Table 1 herein including any sequence of SEQ ID NOS: 7, 17, 21, 25, 31, 34, 42, 51, 54, 57, 58, 67, 71, 74, 76, 81, 83, 85, 86, 90, 92, 93, or 97, including one or more post-translational modifications of that sequence.

In some embodiments, the $V_L$ comprises one, two or three CDRs selected from: (a) CDR-L1, comprising the amino acid sequence of any one of the sequences provided in Sequence Table 1 herein including any sequence of SEQ ID NOS: 1, 12, 19, 27, 41, 53, 61, or 69, (b) CDR-L2, comprising the amino acid sequence of any one of the sequences provided in Sequence Table 1 herein including any sequence comprising GAS, ATS, SAS, or YAS, or any sequence of SEQ ID NOS: 62, 70, 72, 77, or 87, and (c) CDR-L3, comprising the amino acid sequence of any one of the sequences provided in Sequence Table 1 herein including any sequence of SEQ ID NO: 3 or 63.

In some embodiments, the $V_L$ comprises one, two or three CDRs selected from: (a) CDR-L1, comprising the amino acid sequence of any one of the sequences provided in Sequence Table 1 herein including any sequence of SEQ ID NOS: 1, 12, 19, 27, 41, 53, 61, or 69, (b) CDR-L2, comprising the amino acid sequence of any one of the sequences provided in Sequence Table 1 herein including any sequence comprising GAS, ATS, SAS, or YAS, or any sequence of SEQ ID NOS: 62, 70, 72, 77, or 87, and (c) CDR-L3, comprising the amino acid sequence of any one of the sequences provided in Sequence Table 1 herein including any sequence of SEQ ID NO: 3 or 63, wherein the selected CDR-L1, CDR-L2, and CDR-L3 are paired according to Sequence Table 1.

In one aspect, an antibody or antigen-binding fragment thereof is provided, wherein the antibody or antigen-binding fragment thereof comprises: (a) a $V_H$ comprising the amino acid sequence of any one of the sequences provided in Sequence Table 1 herein including any sequence of SEQ ID NOS: 9, 18, 22, 26, 32, 38, 40, 45, 47, 52, 55, 60, 68, 75, 82, 91, 96, 101, 103, 106, 108, 111, 114, 119, 121, 124, 126, 129, 132, 134, 136, or 138, and (b) a $V_L$, comprising the amino acid sequence of any one of the sequences provided in Sequence Table 1 herein including any sequence of SEQ ID NOS: 7, 17, 21, 25, 31, 34, 42, 51, 54, 57, 58, 67, 71, 74, 76, 81, 83, 85, 86, 90, 92, 93, or 97, and optionally including post-translational modifications of those sequences.

In one aspect, an antibody or antigen-binding fragment thereof is provided, wherein the antibody or antigen-binding fragment thereof comprises: (a) a $V_H$ comprising the amino acid sequence of any one of the sequences provided in Sequence Table 1 herein including any sequence of SEQ ID NOS: 9, 18, 22, 26, 32, 38, 40, 45, 47, 52, 55, 60, 68, 75, 82, 91, 96, 101, 103, 106, 108, 111, 114, 119, 121, 124, 126, 129, 132, 134, 136, or 138, and (b) a $V_L$, comprising the amino acid sequence of any one of the sequences provided in Sequence Table 1 herein including any sequence of SEQ ID NOS: 7, 17, 21, 25, 31, 34, 42, 51, 54, 57, 58, 67, 71, 74, 76, 81, 83, 85, 86, 90, 92, 93, or 97, wherein the selected $V_H$ and $V_L$ are paired according to Sequence Table 1.

In one aspect, an antibody or antigen-binding fragment thereof is provided, wherein the antibody or antigen-binding fragment thereof comprises: (a) a CDR-H1 selected from any one of the sequences provided in Sequence Table 1 herein including any sequence of SEQ ID NOS: 4, 14, 23, 28, 35, 39, 43, 46, 48, 64, 78, 84, 88, 94, 98, 109, 112, 115, 118, 120, 122, 125, 127, 130, or 137, and (b) a CDR-L1 selected from any one of the sequences provided in Sequence Table 1 herein including any sequence of SEQ ID NOS: 1, 12, 19, 27, 41, 53, 61, or 69, wherein the selected CDR-H1 and CDR-L1 are paired according to Sequence Table 1.

In one aspect, an antibody or antigen-binding fragment thereof is provided, wherein the antibody or antigen-binding fragment thereof comprises: (a) a CDR-H2 selected from any one of the sequences provided in Sequence Table 1 herein including any sequence of SEQ ID NOS: 5, 15, 29, 36, 49, 65, 79, 89, 99, 104, 131, or 133, and (b) a CDR-L2 selected from any one of the sequences provided in Sequence Table 1 herein including a sequence comprising GAS, ATS, SAS, or YAS, or a sequence of SEQ ID NOS: 62, 70, 72, 77, or 87, wherein the selected CDR-H2 and CDR-L2 are paired according to Sequence Table 1.

In one aspect, an antibody or antigen-binding fragment thereof is provided, wherein the antibody or antigen-binding fragment thereof comprises: (a) a CDR-H3 selected from any one of the sequences provided in Sequence Table 1 herein including any sequence of SEQ ID NOS: 6, 16, 20, 24, 30, 37, 44, 50, 59, 66, 73, 80, 95, 100, 102, 105, 107, 110, 113, 123, 128, or 135, and (b) a CDR-L3 selected from any one of the sequences provided in Sequence Table 1 herein including any sequence of SEQ ID NOS: 3 or 63, wherein the selected CDR-H3 and CDR-L3 are paired according to Sequence Table 1.

In one aspect, an antibody or antigen-binding fragment thereof is provided, wherein the antibody or antigen-binding fragment thereof comprises: (a) a CDR-H1 selected from any one of the sequences provided in Sequence Table 1 herein including any sequence of SEQ ID NOS: 4, 14, 23, 28, 35, 39, 43, 46, 48, 64, 78, 84, 88, 94, 98, 109, 112, 115, 118, 120, 122, 125, 127, 130, or 137, a CDR-H2 selected from any one of the sequences provided in Sequence Table 1 herein including any sequence of SEQ ID NOS: 5, 15, 29, 36, 49, 65, 79, 89, 99, 104, 131, or 133, and a CDR-H3 selected from any one of the sequences provided in Sequence Table 1 herein including any sequence of SEQ ID NOS: 6, 16, 20, 24, 30, 37, 44, 50, 59, 66, 73, 80, 95, 100, 102, 105, 107, 110, 113, 123, 128, or 135, and (b) a CDR-L1 selected from any one of the sequences provided in Sequence Table 1 herein including any sequence of SEQ ID NOS: 1, 12, 19, 27, 41, 53, 61, or 69, a CDR-L2 selected from any one of the sequences provided in Sequence Table 1 herein including a sequence comprising GAS, ATS, SAS, or YAS, or a sequence of SEQ ID NOS: 62, 70, 72, 77, or 87, and a CDR-L3 selected from any one of the sequences provided in Sequence Table 1 herein including any sequence of SEQ ID NOS: 3 or 63, wherein the selected CDR-H1, CDR-H2, CDR-H3, CDR-L1, CDR-L2, and CDR-L3 are paired according to Sequence Table 1.

Lead Antibody and High Priority Antibodies

Antibodies, described herein as numbered 1-20, as well as additional variant antibodies, described herein as numbered 21-100, are described herein and in Sequence Table 1. In one aspect, the present disclosure provides an antibody or antigen-binding fragment thereof comprises one or more variable regions selected from the group consisting of (a) $V_H$ comprising the amino acid sequence of antibody 1 as set out in the Sequence Table 1, (b) $V_L$ comprising the amino acid sequence of antibody 1 as set out in the Sequence Table 1, and (c) a combination thereof.

In one aspect, the present disclosure provides an antibody or antigen-binding fragment thereof comprising at least one, two, three, four, five, or six CDRs selected from (a) CDR-H1 comprising the amino acid sequence of antibody 1 as set out in the Sequence Table 1 (SEQ ID NO: 4); (b) CDR-H2 comprising the amino acid sequence of antibody 1 as set out in the Sequence Table 1 (SEQ ID NO: 5); (c) CDR-H3 comprising the amino acid sequence of antibody 1 as set out in the Sequence Table 1 (SEQ ID NO: 6); (d) CDR-L1 comprising the amino acid sequence of antibody 1 as set out in the Sequence Table 1 (SEQ ID NO: 1); (e) CDR-L2 comprising the amino acid sequence of antibody 1 as set out in the Sequence Table 1 comprising GAS; and (f) CDR-L3 comprising the amino acid sequence of antibody 1 as set out in the Sequence Table 1 (SEQ ID NO:3).

In one aspect, the present disclosure provides an antibody or antigen-binding fragment thereof comprising at least one, at least two, or all three $V_H$ CDR sequences selected from (a) CDR-H1 comprising the amino acid sequence of lead antibody 1 as set out in the Sequence Table 1 (SEQ ID NO: 4); (b) CDR-H2 comprising the amino acid sequence of lead antibody 1 as set out in the Sequence Table 1 (SEQ ID NO: 5); and (c) CDR-H3 comprising the amino acid sequence of lead antibody 1 as set out in the Sequence Table 1 (SEQ ID NO: 6); and (d) a $V_L$ comprising the amino acid sequence of lead antibody 1 as set out in the Sequence Table 1 (SEQ ID NO: 7).

In one aspect, the present disclosure provides an antibody or antigen-binding fragment thereof comprising at least one, at least two, or all three $V_L$ CDR sequences selected from (a) CDR-L1 comprising the amino acid sequence of antibody 1 as set out in the Sequence Table 1 (SEQ ID NO: 1); (b) CDR-L2 comprising the amino acid sequence of antibody 1 as set out in the Sequence Table 1 (GAS); and (c) CDR-L3 comprising the amino acid sequence of antibody 1 as set out in the Sequence Table 1 (SEQ ID NO: 3); and a $V_H$ comprising the amino acid sequence of antibody 1 as set out in the Sequence Table 1 (SEQ ID NO: 9).

In one aspect, the present disclosure provides an antibody or antigen-binding fragment thereof comprising the CDRs: CDR-H3 comprising the amino acid sequence of antibody 1 as set out in the Sequence Table 1 (SEQ ID NO: 6); and CDR-L3 comprising the amino acid sequence of antibody 1 as set out in the Sequence Table 1 (SEQ ID NO: 3).

In one aspect, the disclosure herein provides an antibody or antigen-binding fragment thereof comprising at least one, at least two, or all three $V_L$ CDR sequences selected from (a) CDR-L1 comprising the amino acid sequence of antibody 1 as set out in the Sequence Table 1 (SEQ ID NO: 1); (b) CDR-L2 comprising the amino acid sequence of antibody 1 as set out in the Sequence Table 1 (GAS) and (c) CDR-L3 comprising the amino acid sequence of antibody 1 as set out in the Sequence Table 1 (SEQ ID NO: 3). In one aspect, the disclosure provides an antibody or antigen-binding fragment thereof comprising at least one, at least two, or all three $V_H$ CDR sequences selected from (a) CDR-H1 comprising the amino acid sequence of antibody 1 as set out in the Sequence Table 1 (SEQ ID NO: 4); (b) CDR-H2 comprising the amino acid sequence of antibody 1 as set out in the Sequence Table 1 (SEQ ID NO: 5) and (c) CDR-H3 comprising the amino acid sequence of antibody 1 as set out in the Sequence Table 1 (SEQ ID NO: 6).

In one aspect, the disclosure provides an antibody or antigen-binding fragment thereof comprising the CDRs: (a) CDR-H1 comprising the amino acid sequence of antibody 1 as set out in the Sequence Table 1 (SEQ ID NO: 4); (b) CDR-H2 comprising the amino acid sequence of antibody 1 as set out in the Sequence Table 1 (SEQ ID NO: 5); (c) CDR-H3 comprising the amino acid sequence of antibody 1 as set out in the Sequence Table 1 (SEQ ID NO: 6); (d) CDR-L1 comprising the amino acid sequence of antibody 1 as set out in the Sequence Table 1 (SEQ ID NO: 1); (e) CDR-L2 comprising the amino acid sequence of antibody 1 as set out in the Sequence Table 1 (GAS); and (f) CDR-L3 comprising the amino acid sequence of antibody 1 as set out in the Sequence Table 1 (SEQ ID NO: 3).

In one aspect, an antibody or antigen-binding fragment thereof comprises a $V_H$ sequence having at least 90%, 91%, 92%, 93%, 94%, 95%, 96%, 97%, 98%, 99%, or 100% sequence identity to the amino acid sequence of antibody 1 as set out in the Sequence Table 1 including SEQ ID NO: 9. In some embodiments, a $V_H$ sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of antibody 1 as set out in the Sequence Table 1 including SEQ ID NO: 9. In some embodiments, substitutions, insertions, or deletions occur in regions outside the CDRs (e.g., in the FRs). Optionally, the antibody or antigen-binding fragment thereof comprises the $V_H$sequence of the amino acid sequence of antibody 1 as set out in the Sequence Table 1 including SEQ ID NO: 9, including post-translational modifications of that sequence. In a particular embodiment, the VH comprises one, two or three CDRs selected from: (a) CDR-H1 comprising the amino acid sequence of antibody 1 as set out in the Sequence Table 1 (SEQ ID NO: 4), (b) CDR-H2 comprising the amino acid sequence of antibody 1 as set out in the Sequence Table 1 (SEQ ID NO: 5), and (c) CDR-H3 comprising the amino acid sequence of antibody 1 as set out in the Sequence Table 1 (SEQ ID NO: 6).

In one aspect, an antibody or antigen-binding fragment thereof is provided, wherein the antibody or antigen-binding fragment thereof comprises a light chain variable domain ($V_L$) having at least 90%, 91%, 92%, 93%, 94%, 95%, 96%, 97%, 98%, 99%, or 100% sequence identity to the amino acid sequence of lead antibody 1 as set out in the Sequence Table 1 including SEQ ID NO: 7). In some embodiments, a $V_L$ sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequences of antibody 1 as set out in the Sequence Table 1 including SEQ ID NO: 7. In some embodiments, the substitutions, insertions, or deletions occur in regions outside the CDRs (e.g., in the FRs). Optionally, the antibody or antigen-binding fragment thereof comprises the $V_L$ sequence of antibody 1 as set out in the Sequence Table 1 including SEQ ID NO: 7, including post-translational modifications of that sequence. In a particular embodiment, the $V_L$ comprises one, two or three CDRs selected from (a) CDR-L1 comprising the amino acid sequence of antibody 1 as set out in the Sequence Table 1 including SEQ ID NO: 1; (b) CDR-L2 comprising the amino acid sequence of antibody 1 as set out in the Sequence Table 1 comprising the sequence of GAS; and (c) CDR-L3 comprising the amino acid sequence of antibody 1 as set out in the Sequence Table 1 including SEQ ID NO:3.

In one aspect, an antibody or antigen-binding fragment thereof is provided, wherein the antibody or antigen-binding fragment thereof comprises a $V_H$ as in any of the embodiments provided above, and a $V_L$ as in any of the embodiments provided above. In some embodiments, the antibody comprises a $V_H$ comprising the amino acid sequence of antibody 1 as set out in the Sequence Table 1 including SEQ ID NO: 9, and a $V_L$ sequence in antibody 1 as set out in the Sequence Table 1 including SEQ ID NO: 7, including post-translational modifications of those sequences.

In still other embodiments, the above aspects are repeated and contemplated for lead antibodies numbered 3, 4, 5, 6, 7, 8, 9, 15, and 20 as described herein and provided in Sequence Table 1.

The antibodies or antigen-binding fragment thereof of the present disclosure can comprise a CDR3 region that is a length of at least about 10, 11, 12, 13, 14, 15, 16, 17, 18, 19, 20, 21, 22, 23, 24, 25, 26, 27, 28, 29, or 30 amino acids in length. The antibodies or antigen-binding fragment thereof of the present disclosure can comprise a CDR3 region that is at least about 18 amino acids in length.

In some embodiments, an antibody provided herein has a dissociation constant ($K_D$) of about 1 μM, 100 nM, 10 nM, 5 nM, 2 nM, 1 nM, 0.5 nM, 0.1 nM, 0.05 nM, 0.01 nM, or 0.001 nM or less (e.g., $10^{-8}$ M or less, e.g., from $10^{-8}$ M to $10^{-13}$ M, e.g., from $10^{-9}$ M to $10^{-13}$ M). Another aspect of the disclosure provides for an antibody or antigen-binding fragment thereof with an increased affinity for its target, for example, an affinity matured antibody. An affinity matured antibody is an antibody with one or more alterations in one or more hypervariable regions (HVRs), compared to a parent antibody which does not possess such alterations, such alterations resulting in an improvement in the affinity of the antibody for antigen. These antibodies can bind to antigen with a $K_D$ of about $5\times10^{-9}$ M, $2\times10^{-9}$ M, $1\times10^{-9}$ M, $5\times10^{-10}$ M, $2\times10^{-9}$ M, $1\times10^{-10}$ M, $5\times10^{-11}$ M, $1\times10^{-11}$ M, $5\times10^{-12}$ M, $1\times10^{-12}$ M, or less. In some embodiments, the present disclosure provides an antibody or antigen-binding fragment thereof which has an increased affinity of at least 1.5-fold, 2-fold, 2.5-fold, 3-fold, 4-fold, 5-fold, 10-fold, 20-fold, or greater as compared to a germline antibody containing the heavy chain sequence and light chain sequence, or both. In other embodiments, an antibody is provided that competes for binding to the same epitope as an antibody as described herein. In some embodiments, the antibody or antigen-binding fragment thereof that binds to the same epitope, and/or competes for binding to the same epitope as an antibody exhibits effector function activities, such as, for example, Fc-mediated cellular cytotoxicity, including ADCC activity.

Methods of Producing Anti-TL1A Antibodies

Antibody Synthesis and Purification

Starting from in silico nucleic acid sequences, antibody polypeptides may be synthesized and purified using conventional procedures. In one embodiment, an artificial gene construct encoding an antibody or antibody fragment thereof is synthesized (see, e.g., Khorana, H. G. et al., *J. Mol. Biol.* 72(2):209-217 (1972); Itakura, K. et al., *Science* 198(4321): 1056-1063 (1977); and Edge, M. D. et al. *Nature* 292(5825): 756-762 (1981)). The DNA template for the synthetic gene construct may then be cloned into a suitable expression vector and operably linked to a regulatory control sequence, transformed into an appropriate host for amplification, and the resulting amplified quantities of expression vector purified and transfected into an appropriate host for transient expression of the final resulting polypeptide encoding an antibody or antibody fragment thereof (see, e.g., Vazquez-Lombardi, R. et al., *Nat. Protoc.* 13(1):99-117 (2018)).

Using the information provided herein, for example, the nucleic acid and amino acid sequences of the antibodies; a nucleic acid encoding the antibodies or antigen-binding fragment thereof can be obtained. Such a nucleic acid can be obtained, for example, using conventional methods disclosed in the art. Nucleic acids of the present disclosure may be in the form of RNA, such as mRNA, hnRNA, tRNA or any other form, or in the form of DNA, including but not limited to, cDNA and genomic DNA obtained by cloning or produced synthetically, or any combinations thereof. The DNA may be triplex, duplex, single-stranded, or any combination thereof. Any portion of at least one strand of the DNA or RNA may be the coding strand, also known as the sense strand, or it can be the antisense strand, also known as the antisense strand.

"Polynucleotide" or "nucleic acid" as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A nucleic acid can comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or $CH_2$ ("formacetal"), in which each R or R' is independently H or substituted or unsubstituted alkyl (1-20 C) optionally containing an ether (—O—) linkage, aryl, alkenyl, cycloalkyl, cycloalkenyl, or araldyl. Not all linkages in a polynucleotide need be identical. The preceding description applies to all polynucleotides referred to herein, including isolated nucleic acid, RNA and DNA.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine. In some embodiments, the nucleic acid molecule comprises an isolated nucleic acid.

The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including, but not limited to alkaline/SDS treatment, CsCl banding, column chromatography, agarose gel electrophoresis and others well known in the art. See F. Ausubel, et al., ed. (1987) Current Protocols in Molecular Biology, Greene Publishing and Wiley Interscience, New York. A nucleic acid according to at least some embodiments of the disclosure can be, for example, DNA or RNA and may or may not contain intronic sequences. In a preferred embodiment, the nucleic acid is a cDNA molecule.

Artificial Gene Synthesis

A variety of standard recombinant DNA techniques may be used for manipulating domains or functional segments within an antibody nucleic acid sequence. Once DNA fragments encoding $V_H$ and $V_L$ segments are obtained, these DNA fragments can be further manipulated, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame. The isolated DNA encoding the $V_H$ region can be converted to a full-length heavy chain gene by operatively linking the $V_H$-encoding DNA to another DNA molecule encoding heavy chain constant regions ($C_H1$, $C_H2$, and $C_H3$). The sequences of human heavy chain constant region genes are known in the art (see, e.g., Kabat, E. A. et al. (1991) Sequences of Proteins of Immunological Interest, Fifth Edition, U.S. Department of Health and Human Services, NIH Publication NO: 91-3242) and DNA fragments encompassing these regions can be obtained by standard PCR amplification. The heavy chain constant region can be IgG1, IgG2, IgG3, IgG4, IgA, IgE, IgM, or IgD constant region, but most preferably is an IgG1 or IgG4 constant region. For a Fab fragment heavy chain gene, the $V_H$-encoding DNA can be operatively linked to another DNA molecule encoding only the heavy chain $C_H1$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art (see, e.g., Kabat, E. A. et al. (1991) Sequences of Proteins of Immunological Interest, Fifth Edition, U.S. Department of Health and Human Services, NIH Publication NO: 91-3242) and DNA fragments encompassing these regions can be obtained by standard PCR amplification. The light chain constant region can be a kappa or lambda constant region, but most preferably is a kappa constant region.

To create a scFv gene, the $V_H$- and $V_L$-encoding DNA fragments are operatively linked to another fragment encoding a flexible linker, e.g., encoding the amino acid sequence $(Gly-Gly-Gly-Gly-Ser)_3$, such that the $V_H$ and $V_L$ sequences can be expressed as a contiguous single-chain protein, with the $V_L$ and $V_H$ regions joined by the flexible linker (see, e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Selection and Transformation of Host Cells

In one aspect, provided herein is a host cell that comprises the isolated nucleic acids described above or a vector comprising said isolated nucleic acids described above. The vector can be a cloning vector or an expression vector. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescens*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1 776 (ATCC 31,537), and *E. coli* W3110 (ATCC 27,325) are suitable. These examples are illustrative rather than limiting. Additional embodiments are described below.

Purification

In one aspect, disclosed herein is a purified antibody or antigen-binding fragment as provided herein. Once expressed, the whole antibodies, their dimers, individual light and heavy chains, or other immunoglobulin forms of the present disclosure can be recovered and purified by known techniques, e.g., immunoadsorption or immunoaffinity chromatography, chromatographic methods such as HPLC (high performance liquid chromatography), ammonium sulfate precipitation, gel electrophoresis, or any combination of these. See generally, Scopes, Protein Purif. (Springer-Verlag, NY, 1982).

Substantially pure immunoglobulins of at least about 90% to 95% homogeneity are advantageous, as are those with 98% to 99% or more homogeneity, particularly for pharmaceutical uses. When using recombinant techniques, the antibody can be produced intracellularly, in the periplasmic space, or directly secreted into the medium, including from microbial cultures. If the antibody is produced intracellularly, as a first step, the particulate debris, either host cells or lysed fragments, is removed, for example, by centrifugation or ultrafiltration. Better et al. *Science* 240: 1041-1043 (1988); *ICSU Short Reports* 10: 105 (1990); and *Proc. Natl. Acad. Sci. USA* 90: 457-461 (1993) describe a procedure for isolating antibodies which are secreted to the periplasmic space of *E. coli*. (See also Carter et al., *Bio/Technology* 10: 163-167 (1992).

The antibody composition prepared from microbial, or mammalian cells can be purified using, for example, hydroxyapatite chromatography cation or avian exchange chromatography, and affinity chromatography, with affinity chromatography being the preferred purification technique. The suitability of protein A as an affinity ligand depends on the species and isotype of any immunoglobulin Fe domain that is present in the antibody. Protein A can be used to purify antibodies that are based on human γ1, γ2, or γ4 heavy chains (Lindmark et al., *J. Immunol. Meth.* 62: 1-13 (1983)). Protein G is recommended for all mouse isotypes and for human γ3 (Guss et al., *EMBO J.* 5: 15671575 (1986)). The matrix to which the affinity ligand is attached is most often agarose, but other matrices are available. Mechanically stable matrices such as controlled pore glass or poly(styrene divinyl) benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered. Once purified, partially or to homogeneity as desired, a humanized or composite human antibody can then be used therapeutically or in developing and performing assay procedures, immunofluorescent staining, and the like. See generally, Vols. I & II Immunol. Meth. (Lefkovits & Pernis, eds., Acad. Press, NY, 1979 and 1981).

Antibody Compositions and Structural Conformations

In various embodiments of the disclosure, the resulting antibody polypeptides may take on a range of compositions or structural conformations. Included herein are bispecific antibodies, multispecific antibodies, multivalent antibodies, chimeric antibodies, human antibodies, humanized antibodies, monoclonal antibodies, deimmunized antibodies, or a combination thereof.

The multiple variants described herein are known in the art and are common knowledge in the art for one of ordinary skill to produce anti-TL1A antibodies and/or antigen-binding fragments thereof comprising one or more of such variants.

Bispecific and Multispecific Antibodies

In some embodiments, it may be desirable to generate multispecific (e.g., bispecific) monoclonal antibody including monoclonal, human, humanized, or variant antibodies having binding specificities for at least two different epitopes. In some embodiments, the antibodies disclosed herein are multispecific. Exemplary bispecific antibodies may bind to two different epitopes of an antigen (e.g., SARS-CoV-2 associated antigen). Alternatively, an antigen-binding region may be combined with a region which binds to a triggering molecule on a leukocyte such as a T-cell receptor molecule (e.g., CD2 or CD3), or Fe receptors for IgG (FcγR), such as FcγRI (CD64), FcγRII (CD32), and FcγRIII (CD16) so as to focus cellular defense mechanisms to the antigen-expressing cell. Bispecific antibodies can be prepared as full-length antibodies or antibody fragments (e.g., $F(ab')_2$ bispecific antibodies).

According to another approach for making bispecific antibodies, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or comparable size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are contemplated, along with a number of cross-linking techniques.

Techniques for generating bispecific antibodies from antibody fragments have also been described in the literature. For example, bispecific antibodies can be prepared using chemical linkage. Brennan et al., *Science* 229: 81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. In yet a further embodiment, Fab'-SH fragments directly recovered from *E. coli* can be chemically coupled in vitro to form bispecific antibodies. (Shalaby et al., *J. Exp. Med.* 175:217-225 (1992)).

Exemplary techniques for making multispecific antibodies include recombinant co-expression of two immunoglobulin heavy chain-light chain pairs having different specificities, engineering electrostatic steering effects for making antibody Fc-heterodimeric molecules, cross-linking two or more antibodies or fragments, using leucine zippers to produce bi-specific antibodies, using "diabody" technology for making bispecific antibody fragments, using single-chain Fv (sFv) dimers, preparing trispecific antibodies, and "knob-in-hole" engineering (see, e.g., Milstein and Cuello, *Nature* 305: 537 (1983); Traunecker et al., *EMBO J.* 10: 3655 (1991); U.S. Pat. Nos. 4,676,980 and 5,731,168; Brennan et al., *Science,* 229: 81 (1985); Kostelny et al., *J. Immunol.* 148(5):1547-1553 (1992); Hollinger et al., *Proc. Natl. Acad. Sci. USA* 90:6444-48 (1993); Gruber et al., *J. Immunol.* 152:5368 (1994)); and Tutt et al. *J. Immunol.* 147: 60 (1991)). Engineered antibodies with three or more functional antigen-binding sites are also contemplated.

Chimeric Antibodies

In some embodiments, an antibody provided herein is chimeric. A chimeric antibody is an antibody in which a portion of the heavy and/or light chain is derived from a particular source or species, while the remainder of the heavy and/or light chain is derived from a different source or species. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof. For details, see, for example, Jones et al., *Nature* 321: 522-525 (1986); Reichmann et al., *Nature* 332: 323-329 (1988); *Presta, Curr. Op. Struct. Biol.* 2: 593-596 (1992); and Morrison et al., *Proc. Natl. Acad. Sci. USA* 81:6851-6855 (1984).

Human Antibodies

In some embodiments, an antibody provided herein is a human antibody. Human antibodies can be produced using various techniques known in the art (see, e.g., van Dijk and van de Winkel, *Curr. Opin. Pharmacol.* 5: 368-74 (2001); and Lonberg, *Curr. Opin. Immunol.* 20:450-459 (2008)). A human antibody is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Human antibodies may be prepared by administering an immunogen (e.g., TL1A) to a transgenic animal that has been modified to produce intact human antibodies or intact antibodies with human variable regions in response to antigenic challenge. (See, e.g., Lonberg, *Nat. Biotech.* 23:1117-1125 (2005)). Human variable regions from intact antibodies generated by such animals may be further modified, e.g., by combining with a different human constant region.

In one embodiment, the antibodies described herein are fully human antibodies.

Human antibodies can also be made by hybridoma-based methods. For example, human antibodies can be produced from human myeloma and mouse-human heteromyeloma cell lines, using human B-cell hybridoma technology, and other methods (see, e.g., Kozbor *J. Immunol.* 133: 3001 (1984); Brodeur et al., Monoclonal Antibody Production Techniques and Applications, pp. 51-63 (1987); Boerner et al., *J. Immunol.* 147: 86 (1991); Li et al., *Proc. Natl. Acad. USA* 103:3557-3562 (2006); *Ni, Xiandai Mianyixue,* 26(4): 265-268 (2006); Vollmers and Brandlein, *Histology and Histopathology* 20(3):927-937 (2005); and Vollmers and Brandlein, Methods and Findings in Experimental and Clinical *Pharmacology* 27(3):185-91 (2005)). Human antibodies may also be generated by isolating Fv clone variable domain sequences selected from human-derived phage display libraries. Such variable domain sequences may then be combined with a desired human constant domain.

Recombinant Human Antibodies

The term "recombinant human antibody," as used herein, includes all human antibodies that are prepared, expressed, created or isolated by recombinant means, such as: (a) antibodies isolated from an animal (e.g., a mouse) that is transgenic or transchromosomal for human immunoglobulin genes or a hybridoma prepared therefrom; (b) antibodies isolated from a host cell transformed to express the human antibody, e.g., from a transfectoma; (c) antibodies isolated from a recombinant, combinatorial human antibody library; and (d) antibodies prepared, expressed, created or isolated by any other means that involve splicing of human immunoglobulin gene sequences to other DNA sequences. Such recombinant human antibodies have variable regions in which the framework and CDR regions are derived from immunoglobulin sequences, disclosed herein. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human immunoglobulin $V_H$ and $V_L$ sequences, may not naturally exist within the human antibody germline repertoire in vivo.

Humanized Antibodies

In some embodiments, an antibody provided herein is a humanized antibody. In one embodiment, a humanized antibody is an antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. See, e.g., Almagro and Fransson, *Front. Biosci.* 13:1619-1633 (2008); Riechmann et al., *Nature* 332:323-329 (1988); Queen et al., *Proc. Nat'l Acad. Sci. USA* 86:10029-10033 (1989); Kashmiri et al., *Methods* 36:25-34 (2005); *Padlan, Mol. Immunol.* 28:489-498 (1991); Dall'Acqua et al., *Methods* 36:43-60 (2005); Osbourn et al., *Methods* 36:61-68 (2005); and Klimka et al., *Br. J. Cancer* 83:252-260 (2000).

A non-human antibody can be humanized to reduce immunogenicity to humans, while retaining the specificity and affinity of the parental non-human antibody. A humanized antibody can comprise one or more variable domains comprising one or more CDRs, or portions thereof, derived from a non-human antibody. A humanized antibody can comprise one or more variable domains comprising one or more FRs, or portions thereof, derived from human antibody sequences. A humanized antibody can optionally comprise at least a portion of a human constant region. In some embodiments, one or more FR residues in a humanized antibody are substituted with corresponding residues from a non-human antibody (e.g., the antibody from which the CDR residues are derived), e.g., to restore or improve antibody specificity or affinity.

Human framework regions that may be used for humanization include but are not limited to: framework regions selected using a "best-fit" method; framework regions derived from the sequence of human antibodies of a particular subgroup of light or heavy chain variable regions; human mature (somatically mutated) framework regions or human germline framework regions; and framework regions derived from screening FR libraries (see, e.g., Sims et al. *J. Immunol.* 151:2296 (1993); Carter et al. *Proc. Natl. Acad. Sci. USA* 89:4285 (1992); Presta et al. *J. Immunol.* 151:2623 (1993); Baca et al. *J. Biol. Chem.* 272:10678-10684 (1997); and Rosok et al. *J. Biol. Chem.* 271:22611-22618 (1996)).

Monoclonal Antibodies

A monoclonal antibody is obtained from a population of substantially homogeneous antibodies, i.e., the individual antibodies comprising the population are identical except for possible naturally occurring mutations that may be present in minor amounts. In some embodiments, the antibodies of the present disclosure are monoclonal. In a preferred embodiment, monoclonal antibodies may be made using recombinant DNA methods, or in an alternative embodiment, by the hybridoma method first described by Kohler et al., *Nature,* 256:495 (1975).

Deimmunized Antibodies

An antibody or an antigen-binding fragment thereof described herein can be optionally assessed for immunogenicity and, as needed, be deimmunized (i.e., the antibody is made less immunoreactive by altering one or more T cell epitopes). As used herein, a "deimmunized antibody" means that one or more T cell epitopes in an antibody sequence have been modified such that a T cell response after administration of the antibody to a subject is reduced compared to an antibody that has not been deimmunized, yet the antibody retains its binding activity. Analysis of immunogenicity and T-cell epitopes present in the antibodies and antigen-binding fragments described herein can be carried out via the use of software and specific databases known in the art. Exemplary software and databases include iTope™ developed by Antitope of Cambridge, England. iTope™, is an in-silico technology for analysis of peptide binding to human MHC class II alleles. The iTope™ software predicts peptide binding to human MHC class II alleles and thereby provides an initial screen for the location of such "potential T cell epitopes." iTope™ software predicts favorable interactions between amino acid side chains of a peptide and specific binding pockets within the binding grooves of 34 human MHC class II alleles. The location of key binding residues is achieved by the in-silico generation of 9mer peptides that overlap by one amino acid spanning the test antibody variable region sequence. Each 9mer peptide can be tested against each of the 34 MHC class II allotypes and scored based on their potential "fit" and interactions with the MHC class II binding groove. Peptides that produce a high mean binding score (>0.55 in the iTope™ scoring function) against >50% of the MHC class II alleles are considered as potential T cell epitopes. In such regions, the core 9 amino acid sequence for peptide binding within the MHC class II groove is analyzed to determine the MHC class II pocket residues (P1, P4, P6, P7 and P9) and the possible T cell receptor (TCR) contact residues (P-1, P2, P3, P5, P8). After identification of any T-cell epitopes, amino acid residue changes, substitutions, additions, and/or deletions can be introduced to remove the identified T-cell epitope. Such changes can be made so as to preserve antibody structure and function while still removing the identified epitope. Exemplary changes can include, but are not limited to, conservative amino acid changes.

Engineered and Modified Antibodies

An antibody according to at least some embodiments of the disclosure further can be prepared using an antibody having one or more of the $V_H$ and/or $V_L$ sequences derived from an antibody or antigen-binding fragment thereof, disclosed herein, starting material to engineer a modified antibody, which modified antibody may have altered properties from the starting antibody. Provided herein are completely amino acid and nucleic acid sequences of $V_H$ and $V_L$ chain regions of antibodies disclosed herein. Also provided herein are the amino acid and nucleic acid sequences of the CDR3 regions of the $V_H$ and $V_L$ of the antibodies, described herein. An antibody can be engineered by modifying one or more residues within one or both variable regions (i.e., $V_H$ and/or $V_L$), for example within one or more CDR regions and/or within one or more framework regions. Additionally, or alternatively, an antibody can be engineered by modifying residues within the constant regions, for example to alter the effector functions of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific antibodies by constructing expression vectors that include CDR sequences from the specific antibody (e.g., antibodies disclosed herein) grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. Sci. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Suitable framework sequences can be obtained from public DNA databases or published references that include germline antibody gene sequences. For example, germline DNA sequences for human heavy and light chain variable region genes can be found in the "VBase" human germline sequence database (available on the Internet), as well as in Kabat, E. A., et al. (1991) *Sequences of Proteins of Immunological Interest*, Fifth Edition, U.S. Department of Health and Human Services, NIH Publication NO: 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference.

Another type of variable region modification is to mutate amino acid residues within the $V_H$ and/or $V_L$ CDR 1, CDR2 and/or CDR3 regions to thereby improve one or more binding properties (e.g., affinity) of the antibody of interest. Site-directed mutagenesis or PCR-mediated mutagenesis can be performed to introduce the mutations and the effect on antibody binding, or other functional property of interest, can be evaluated in appropriate in vitro or in vivo assays. Preferably conservative modifications (as discussed above) are introduced. The mutations may be amino acid substitutions, additions, or deletions, but are preferably substitutions. Moreover, typically no more than one, two, three, four or five residues within a CDR region are altered.

Engineered antibodies according to at least some embodiments of the disclosure include those in which modifications have been made to framework residues within $V_H$ and/or $V_L$, e.g., to improve the properties of the antibody. Typically, such framework modifications are made to decrease the immunogenicity of the antibody. For example, one approach is to "back mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

In addition, or alternative to modifications made within the framework or CDR regions, antibodies according to at least some embodiments of the disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody according to at least some embodiments of the disclosure may be chemically modified (e.g., one or more chemical moieties can be attached to the antibody) or be modified to alter its glycosylation, again to alter one or more functional properties of the antibody. Such embodiments are described above. The numbering of residues in the Fc region is that of the EU index of Kabat.

In one embodiment, the hinge region of $C_H1$ is modified such that the number of cysteine residues in the hinge region is altered, e.g., increased or decreased. This approach is described further in U.S. Pat. No. 5,677,425 by Bodmer et al. The number of cysteine residues in the hinge region of $C_H1$ is altered to, for example, facilitate assembly of the light and heavy chains or to increase or decrease the stability of the antibody. In another embodiment, the Fc hinge region of an antibody is mutated to decrease the biological half-life of the antibody. More specifically, one or more amino acid mutations are introduced into the $C_H2$-$C_H3$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, to increase the biological half-life, the antibody can be altered within the $C_H1$ or $C_L$ region to contain a salvage receptor binding epitope taken from two loops of a $C_H2$ domain of an Fc region of an IgG, as described in U.S. Pat. Nos. 5,869,046 and 6,121,022 by Presta et al.

In another aspect, provided herein are variants of antibodies or antigen-binding fragments thereof.

Substitution, Insertion, and Deletion Variants

In some embodiments, amino acid sequence variants of the antibodies provided herein are contemplated. A variant typically differs from a polypeptide specifically disclosed herein in one or more substitutions, deletions, additions and/or insertions. Such variants can be naturally occurring or can be synthetically generated, for example, by modifying one or more of the above polypeptide sequences of the disclosure and evaluating one or more biological activities of the polypeptide as described herein and/or using any of a number of techniques well known in the art. For example, it may be desirable to improve the binding affinity and/or other biological properties of the antibody amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In some embodiments, antibody variants or antigen-binding fragments thereof having one or more amino acid substitutions are provided. Sites of interest for mutagenesis by substitution include the CDRs and FRs. Amino acid substitutions may be introduced into an antibody of interest and the products screened for a desired activity, e.g., retained/improved antigen binding, decreased immunogenicity, or improved ADCC or CDC function.

| Original Residue | Exemplary Conserved Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Hydrophobic amino acids include: Norleucine, Met, Ala, Val, Len, and Ile. Neutral hydrophilic amino acids include: Cys, Ser, Thr, Asn, and Gln. Acidic amino acids include Asp and Glu. Basic amino acids include: His, Lys, and Arg. Amino acids with residues that influence chain orientation include: Gly and Pro. Aromatic amino acids include: Trp, Tyr, and Phe.

In some embodiments, substitutions, insertions, or deletions may occur within one or more CDRs, wherein the substitutions, insertions, or deletions do not substantially reduce antibody binding to antigen. For example, conservative substitutions that do not substantially reduce binding affinity may be made in CDRs. Such alterations may be outside of CDR "hotspots" or SDRs. In some embodiments of the variant $V_H$ and $V_L$ sequences, each CDR either is unaltered, or contains no more than one, two or three amino acid substitutions.

Alterations (e.g., substitutions) may be made in CDRs, e.g., to improve antibody affinity. Such alterations may be made in CDR encoding codons with a high mutation rate during somatic maturation (see, e.g., Chowdhury, *Methods Mol. Biol.* 207:179-196 (2008)), and the resulting variant can be tested for binding affinity. Affinity maturation (e.g., using error-prone PCR, chain shuffling, randomization of CDRs, or oligonucleotide-directed mutagenesis) can be used to improve antibody affinity (see, e.g., Hoogenboom et al. in *Methods Mol. Biol.* 178:1-37 (2001)). CDR residues involved in antigen-binding may be specifically identified, e.g., using alanine scanning mutagenesis or modeling (see, e.g., Cunningham and Wells, *Science* 244:1081-1085 (1989)). CDR-H3 and CDR-L3 in particular are often targeted. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions and deletions include amino- and/or carboxyl-terminal fusions ranging in length from one residue to polypeptides containing a hundred or more residues, as well as intra-sequence insertions and deletions of single or multiple amino acid residues. Examples of terminal insertions include an antibody with an N-terminal methionyl residue. Other insertional variants of the antibody molecule include the fusion to a polypeptide which increases serum half-life of the antibody, for example, at the N-terminus or C-terminus. The term "epitope tagged" refers to the antibody fused to an epitope tag. The epitope tag polypeptide has enough residues to provide an epitope against which an antibody there against can be made yet is short enough such that it does not interfere with activity of the antibody. The epitope tag preferably is sufficiently unique so that the antibody there against does not substantially cross-react with other epitopes. Suitable tag polypeptides generally have at least 6 amino acid residues and usually between about 8-50 amino acid residues (preferably between about 9-30 residues). Examples include the flu HA tag polypeptide and its antibody 12CA5 (Field et al., *Mal. Cell. Biol.* 8:2159-2165 (1988)); the c-myc tag and the 8F9, 3C7, 6E10, G4, B7 and 9E10 antibodies thereto (Evan et al., *Mal. Cell. Biol.* 5(12):3610-16 (1985)); and the Herpes Simplex virus glycoprotein D (gD) tag and its antibody (Paborsky et al., *Protein Engineering* 3(6):547-553 (1990)). Other exemplary tags are a poly-histidine sequence, generally around six histidine residues, that permits isolation of a compound so labeled using nickel chelation. Other labels and tags, such as the FLAG® tag (Eastman Kodak, Rochester, N.Y.), well known and routinely used in the art, are embraced by the disclosure.

Other insertional variants of the antibody molecule include the fusion to the N- or C-terminus of the antibody to an enzyme (e.g., for ADEPT) or a polypeptide which increases the serum half-life of the antibody. Examples of intra-sequence insertion variants of the antibody molecules include an insertion of 3 amino acids in the light chain. Examples of terminal deletions include an antibody with a deletion of 7 or less amino acids at an end of the light chain.

Glycosylation Variants

In some embodiments, the antibodies are altered to increase or decrease their glycosylation (e.g., by altering the amino acid sequence such that one or more glycosylation sites are created or removed). A carbohydrate attached to an Fc region of an antibody may be altered. Native antibodies from mammalian cells typically comprise a branched, biantennary oligosaccharide attached by an N-linkage to Asn297 of the $C_H2$ domain of the Fc region (see, e.g., Wright et al. *TIBTECH* 15:26-32 (1997)). The oligosaccharide can be various carbohydrates, e.g., mannose, N-acetyl glucosamine (GlcNAc), galactose, sialic acid, fucose attached to a GlcNAc in the stem of the biantennary oligosaccharide structure. Modifications of the oligosaccharide in an antibody can be made, for example, to create antibody variants with certain improved properties. Antibody glycosylation variants can have improved ADCC and/or CDC function.

In some embodiments, antibody variants are provided having a carbohydrate structure that lacks fucose attached (directly or indirectly) to an Fc region. For example, the amount of fucose in such an antibody may be from 1% to 80%, from 1% to 65%, from 5% to 65%, or from 20% to 40%. The amount of fucose is determined by calculating the average amount of fucose within the sugar chain at Asn297, relative to the sum of all glycostructures attached to Asn297 (see, e.g., WO 08/077546). Asn297 refers to the asparagine residue located at about position 297 in the Fc region (Eu numbering of Fc region residues); however, Asn297 may also be located about 3 amino acids upstream or downstream of position 297, i.e., between positions 294 and 300, due to minor sequence variations in antibodies. Such fucosylation variants can have improved ADCC function (see, e.g., Okazaki et al. *J. Mol. Biol.* 336:1239-1249 (2004); and Yamane-Ohnuki et al. *Biotech. Bioeng.* 87: 614 (2004)). Cell lines, e.g., knockout cell lines and methods of their use can be used to produce defucosylated antibodies, e.g., Lec13 CHO cells deficient in protein fucosylation and alpha-1,6-fucosyltransferase gene (FUT8) knockout CHO cells (see, e.g., Ripka et al. *Arch. Biochem. Biophys.* 249:533-545 (1986); Yamane-Ohnuki et al. *Biotech. Bioeng.* 87: 614 (2004); Kanda, Y. et al., *Biotechnol. Bioeng.* 94(4):680-688 (2006). Other antibody glycosylation variants are also contemplated.

In still another embodiment, the glycosylation of an antibody is modified. For example, an aglycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al. Conservative substitutions involve replacing an amino acid with another member of its class. Non-conservative substitutions involve replacing a member of one of these classes with a member of another class.

Accordingly, an antibody or antigen-binding fragment thereof in the present disclosure can be produced by a host cell with one or more of exogenous and/or high endogenous glycosyltransferase activities. Genes with glycosyltransferase activity include β(1,4)-N-acetylglucosaminyltransferase III (GnTII), α-mannosidase II (ManII), β(1,4)-galactosyltransferase (GalT), β(1,2)-N-acetylglucosaminyltransferase I (GnTI), and β(1,2)-N-acetylglucosaminyltransferase II (GnTII). The glycotranferases can comprise a fusion comprising a Golgi localization domain (see, e.g., Lifely et al., *Glycobiology* 318:813-22 (1995); Schachter, *Biochem. Cell Biol.* 64:163-81 (1986)). In some embodiments, an antibody can be expressed in a host cell comprising a disrupted or deactivated glycosyltransferase gene. Accordingly, in some embodiments, the present disclosure is directed to a host cell comprising (a) an isolated nucleic acid comprising a sequence encoding a polypeptide having a glycosyltransferase activity; and (b) an isolated polynucleotide encoding an antibody or antigen-binding fragment thereof of the present disclosure. In a particular embodiment, the modified antibody produced by the host cell has an IgG constant region or a fragment thereof comprising the Fc region. In another embodiment the antibody is a humanized antibody or a fragment thereof comprising an Fc region.

Antibodies with altered glycosylation produced by the host cells of the disclosure can exhibit increased Fc receptor binding affinity (e.g., increased binding to a Fcγ activating receptor, such as the FcγRIIIa receptor) and/or increased effector function. The increased effector function can be an increase in one or more of the following: increased antibody-dependent cellular cytotoxicity, increased antibody-dependent cellular phagocytosis (ADCP), increased cytokine secretion, increased immune-complex-mediated antigen uptake by antigen-presenting cells, increased Fc-mediated cellular cytotoxicity, increased binding to NK cells, increased binding to macrophages, increased binding to polymorphonuclear cells (PMNs), increased binding to monocytes, increased crosslinking of target-bound antibodies, increased direct signaling inducing apoptosis, increased dendritic cell maturation, and increased T cell priming. Accordingly, in one aspect, the present disclosure provides glycoforms of an antibody having increased effector function as compared to the antibody that has not been glycoengineered. (See, e.g., Tang et al., *J. Immunol.* 179: 2815-2823 (2007)).

The present disclosure is also directed to a method for producing an antibody or antigen-binding fragment thereof, described herein having modified oligosaccharides, comprising (a) culturing a host cell engineered to express at least one nucleic acid encoding a polypeptide having glycosyltransferase activity under conditions which permit the production of an antibody according to the present disclosure, wherein said polypeptide having glycosyltransferase activity is expressed in an amount sufficient to modify the oligosaccharides in the Fc region of said antibody produced by said host cell; and (b) isolating said antibody. In another embodiment, there are two polypeptides having glycosyltransferase activity. The antibodies or antigen-binding fragment thereof produced by the methods of the present disclosure can have increased Fc receptor binding affinity and/or increased effector function.

In some embodiments, the percentage of bisected N-linked oligosaccharides in the Fc region of the antibody is at least about 10% to about 100%, specifically at least about 50%, more specifically, at least about 60%, at least about 70%, at least about 80%, or at least about 90-95% of the total oligosaccharides. In yet another embodiment, the antibody produced by the methods of the disclosure has an increased proportion of nonfucosylated oligosaccharides in the Fc region as a result of the modification of its oligosaccharides by the methods of the present disclosure. In some embodiments, the percentage of nonfucosylated oligosaccharides is at least about 20% to about 100%, specifically at least about 50%, at least about 60% to about 70%, and more specifically, at least about 75%. The nonfucosylated oligosaccharides may be of the hybrid or complex type. In yet another embodiment, the antibody or antigen-binding fragment thereof produced by the methods of the disclosure has an increased proportion of bisected oligosaccharides in the Fc region as a result of the modification of its oligosaccharides by the methods of the present disclosure. In some embodiments, the percentage of bisected oligosaccharides is at least about 20% to about 100%, specifically at least about 50%, at least about 60% to about 70%, and more specifically, at least about 75%.

In another embodiment, the present disclosure is directed to an antibody or antigen-binding fragment thereof engineered to have increased effector function and/or increased Fc receptor binding affinity, produced by the methods of the disclosure. In some embodiments, the antibody is an intact antibody. In some embodiments, the antibody is an antibody fragment containing the Fc region, or a fusion protein that includes a region equivalent to the Fc region of an immunoglobulin.

In one aspect, the present disclosure provides host cell expression systems for the generation of the antibodies or antigen-binding fragment thereof of the present disclosure having modified glycosylation patterns. In particular, the present disclosure provides host cell systems for the generation of glycoforms of the antibodies or antigen-binding fragment thereof, disclosed herein, having an improved therapeutic value. Therefore, the present disclosure provides host cell expression systems selected or engineered to express a polypeptide having a glycosyltransferase activity. Any type of cultured cell line, including the cell lines discussed above, can be used as a background to engineer the host cell lines of the present disclosure. In some embodiments, CHO cells, BHK cells, NSO cells, SP2/0 cells, YO myeloma cells, P3X63 mouse myeloma cells, PER cells, PER.C6 cells, or hybridoma cells, other mammalian cells, yeast cells, insect cells, or plant cells are used as the background cell line to generate the engineered host cells of the disclosure.

The host cells which contain the coding sequence of an antibody or antigen-binding fragment thereof of the disclosure and which express the biologically active gene products may be identified by at least four general approaches: (a) DNA-DNA or DNA-RNA hybridization; (b) the presence or absence of "marker" gene functions; (c) assessing the level of transcription as measured by the expression of the respective mRNA transcripts in the host cell; and (d) detection of the gene product as measured by immunoassay or by its biological activity.

Cysteine Engineered Antibody Variants

In some embodiments, it may be desirable to create cysteine engineered antibodies or antigen-binding fragments thereof, e.g., "thioMAbs," in which one or more residues of an antibody are substituted with cysteine residues. In some embodiments, the substituted residues occur at accessible sites of the antibody. Reactive thiol groups can be positioned at sites for conjugation to other moieties, such as drug moieties or linker-drug moieties, to create an immunoconjugate. In some embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described.

Any cysteine residue not involved in maintaining the proper conformation of the monoclonal, human, humanized, or variant antibody also may be substituted with serine to improve the oxidative stability of the molecule and prevent aberrant crosslinking. Conversely, cysteine bond(s) may be added to the antibody to improve its stability (particularly where the antibody is an antibody fragment such as an Fv fragment).

Fc Region Variants

Mutation of residues within Fc receptor binding sites can result in altered effector function, such as altered ADCC, CDC activity, and/or altered half-life. Mutations include, for example, insertion, deletion, and/or substitution of one or more residues as described in more detail above, including substitution with alanine, a conservative substitution, a non-conservative substitution, and/or replacement with a corresponding amino acid residue at the same position from a different IgG subclass (e.g., replacing an IgG1 residue with a corresponding IgG2 residue at that position).

An Fc region herein is a C-terminal region of an immunoglobulin heavy chain that contains at least a portion of the constant region. An Fc region includes native sequence Fc regions and variant Fc regions. The Fc region variant may comprise a human Fc region sequence (e.g., a human IgG1, IgG2, IgG3 or IgG4 Fc region) comprising an amino acid modification (e.g., a substitution) at one or more amino acid positions.

Previous studies mapped the binding site on human and murine IgG for FcγR primarily to the lower hinge region composed of IgG residues 233-239. Other studies proposed additional broad segments, e.g., Gly316-Lys338 for human Fc gamma receptor I, Lys274-Arg301 and Tyr407Arg416 for human Fc gamma receptor III, or found a few specific residues outside the lower hinge, e.g., Asn297 and Glu318 for murine IgG2b interacting with murine Fc gamma receptor II. The report of the 3.2-A crystal structure of the human IgG Fc fragment with human Fc gamma receptor IIIA delineated IgG1 residues Leu234-Ser239, Asp265-Glu269, Asn297-Thr299, and Ala327-Ile332 as involved in binding to Fc receptor yIIIA. It has been suggested based on crystal structure that in addition to the lower hinge (Leu234-Gly237), residues in IgG $C_H2$ domain loops FG (residues 326-330) and BC (residues 265-271) might play a role in binding to Fc gamma receptor IIA. See Shields et al., *J. Biol. Chem.* 276(9):6591-6604 (2001). Shields et al. reported that IgG1 residues involved in binding to all human Fc receptors are located in the $C_H2$ domain proximal to the hinge and fall into two categories as follows: 1) positions that may interact directly with all FcR include Leu234-Pro238, Ala327, and Pro329 (and possibly Asp265); 2) positions that influence carbohydrate nature or position include Asp265 and Asn297.

In some embodiments, the disclosure contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the effect of one or more Fc amino acid modifications on CDC and/or ADCC activities. For example, Fc receptor (FcR) binding assays can be conducted to ensure that the antibody lacks FcγR binding (hence likely lacking ADCC activity) but retains FcRn binding ability.

Fc Variants with Altered Binding to an Fc Gamma Receptor

In some instances, an Fc variant exhibits altered affinity for one or more Fc gamma receptors (FcγR). For example, an Fc variant exhibits increased affinity for one or more Fc gamma receptors (FcγR), decreased affinity for one or more Fc gamma receptors (FcγR), or a combination thereof. In one instance, an Fc variant exhibits increased ADCC activity. In yet another example, the Fc region is modified to increase the ability of the antibody to mediate antibody dependent cellular cytotoxicity (ADCC). The binding sites on human IgG1 for Fc gamma RI (FcγRI), Fc gamma RII (FcγRII), Fc gamma RIII (FcγRIIII), and FcRn have been mapped and variants with altered binding have been described. Non-limiting examples of such modifications are described in, for example, U.S. Pat. No. 6,737,056; PCT Publication WO 00/42072 by Presta; Shields, R. L. et al. (2001) *J. Biol. Chem.* 276:6591-6604; U.S. Pat. No. 7,332,581, etc. In some embodiments, the constant region of the antibodies disclosed herein is replaced with an IGHG1.

Armour et al. (*Mol Immunol.* 2003; 40(9):585-93) identified IgG1 variants which react with the activating receptor, FcγRIIa, at least 10-fold less efficiently than wildtype IgG1, but whose binding to the inhibitory receptor, FcγRIIb, is only four-fold reduced. Mutations were made in the region of amino acids 233-236 and/or at amino acid positions 327, 330, and 331. See also WO 99/58572.

Non-limiting examples of in vitro assays to assess ADCC activity of a molecule of interest are described, for example, in U.S. Pat. Nos. 5,500,362 and 5,821,337. Alternatively, non-radioactive assays methods may be employed (e.g., ACTI™ and CYTOTOX 96® non-radioactive cytotoxicity assays). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model (see, e.g., Clynes et al., *Proc. Nat'l Acad. Sci. USA* 95:652-656 (1998)).

Fc Variants with Decreased C1q Binding

In another instance, an Fc variant exhibits reduced C1q binding. C1q binding assays may also be carried out to confirm that the antibody is able or unable to bind C1q and, hence, contains or lacks CDC activity (Idusogie et al., *J. Immunol.* 164: 4178-84 (2000)). To assess complement activation, a CDC assay may be performed (see, e.g., Gazzano-Santoro et al., *J. Immunol. Methods* 202:163 (1996); Cragg, M. S. et al., *Blood* 101:1045-52 (2003); and Cragg et al., *Blood* 103:2738-43 (2004)).

In another example, one or more amino acids can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al. In another example, one or more amino acid residues are altered to thereby alter the ability of the antibody to fix complement. This approach is described further in PCT Publication WO 94/2935 1 by Bodmer et al. In one instance, an Fc variant provided herein can contain a mutation at amino acid position 329, 331, and/or 322 (using Kabat numbering), and exhibits reduced C1q binding and/or CDC activity. In some instances, C1q binding activity and/or CDC activity of an antibody can be reduced by mutating amino acid residue 318, 320, and/or 322 (using Kabat numbering) of a heavy chain; replacing residue 297 (Asn) may result in removal of lytic activity of an antibody.

Cytophilic activity of IgG1 is a property of its heavy chain $C_H2$ domain. In one instance, where an Fc variant is an IgG, amino acid residues 234-237 are maintained as wild type to preserve cytophilic activity of the molecule. An IgG2 antibody containing the entire ELLGGP sequence (residues 233-238) may, in some instances, be more active than wild-type IgG1.

In some instances, C1q binding activity and/or lytic activity of an IgG1 antibody can be reduced by mutating amino acid residue Pro331 to Ser. In other instances, C1q binding activity and/or lytic activity of an IgG4 antibody can be reduced by mutating amino acid residue Pro for Ser331 (Xu et al., *J Biol Chem.* 1994; 269(5):3469-74).

Fc Variants with Interchain Disulfide Bonds or Dual Fc Regions

In yet another embodiment, it may be desirable to modify the antibody of the disclosure with respect to effector function, so as to enhance the therapeutic effectiveness of the antibody. For example, one or more cysteine residue(s) may be introduced in the Fc region, thereby allowing interchain disulfide bond formation in this region. The homodimeric antibody thus generated may have improved internalization capability, increased complement-mediated cell killing, and/or antibody-dependent cellular cytotoxicity (ADCC). See Caron et al., *J. Exp Med.* 176:1191-95 (1992) and Shapes, B. *J. Immunol.* 148:2918-22 (1992). Alternatively, an antibody can be engineered which has dual Fc regions and may thereby have enhanced complement lysis and/or ADCC capabilities. See, Stevenson et al., *Anti-Cancer Drug Design* 3: 219-30 (1989).

Fc Variants with Increased FcRn Binding and In Vivo Half-Life

Fc region variants with altered binding affinity for the neonatal receptor (FcRn) are also contemplated herein. Fc region variants with improved affinity for FcRn are anticipated to have longer serum half-lives, and such variants are useful in methods of treating subjects where long half-life of the administered polypeptide is desired, e.g., to treat a chronic infection. Fc region variants with decreased FcRn binding affinity, on the contrary, are expected to have shorter half-lives, and such variants may be administered to a subject where a shortened circulation time may be preferred, e.g., for in vivo diagnostic imaging or for antibodies which have toxic side effects when left circulating in the blood stream for extended periods, etc. Determination of FcRn binding and in vivo clearance/half-life can be performed using methods known in the art (see, e.g., Petkova, S. B. et al., *Int'l. Immunol.* 18(12):1759-1769 (2006)).

Schuurman et al., *Mol Immunol.* 2001; 38(1):1-8, incorporated by reference herein in its entirety, report that mutating one of the hinge cysteines involved in the inter-heavy chain bond formation, Cys226, to serine resulted in a more stable inter-heavy chain linkage. Mutating the IgG4 hinge sequence Cys-Pro-Ser-Cys to the IgG1 hinge sequence Cys-Pro-Pro-Cys also markedly stabilizes the covalent interaction between the heavy chains. Angal et al., *Mol Immunol.* 1993; 30(1):105-8, incorporated by reference herein in its entirety, report that mutating the serine at amino acid position 241 in IgG4 to praline (found at that position in IgG1 and IgG2) led to the production of a homogeneous antibody, as well as extending serum half-life and improving tissue distribution compared to the original chimeric IgG4. Other such examples of Fc region variants are also contemplated (see, e.g., Duncan & Winter, *Nature* 322:738-40 (1988); Chan C A and Carter P J (2010) *Nature Rev. Immunol.* 10:301-316); and Shields et al., *J. Biol. Chem.* 9(2): 6591-6604 (2001).

Antigen-Binding Fragments

The terms "antibody fragment," "antigen-binding fragment," or "antibody binding domain" refer to at least one portion of an antibody, or recombinant variants thereof, that contains the antigen-binding domain, i.e., an antigenic determining variable region of an intact antibody, that is sufficient to confer recognition and specific binding of the antibody fragment to a target, such as an antigen and its defined epitope. Examples of antigen-binding fragments include, but are not limited to, Fab, Fab', $F(ab')_2$, and Fv fragments, single-chain (sc)Fv ("scFv") antibody fragments, linear antibodies, single domain antibodies such as sdAb (either $V_L$ or $V_H$), camelid $V_HH$ domains, and multi-specific antibodies formed from antibody fragments.

Antibody fragments can be made by various techniques, including but not limited to proteolytic digestion of an intact antibody as well as production by recombinant host cells (e.g., *E. coli* or phage), as described herein.

An Fv is the minimum antibody fragment that contains a complete antigen-recognition and antigen-binding site. This fragment contains a dimer of one heavy- and one light-chain variable region domain in tight, non-covalent association. From the folding of these two domains emanate six hypervariable loops (three loops each from the H and L chain) that contribute the amino acid residues for antigen-binding and confer antigen-binding specificity to the antibody. However, even a single variable region (or half of an Fv comprising only three CDRs specific for an antigen) has the ability to recognize and bind antigen, although at a lower affinity than the entire binding site.

The term "scFv" refers to a fusion protein comprising at least one antibody fragment comprising a variable region of a light chain and at least one antibody fragment comprising a variable region of a heavy chain, wherein the light and heavy chain variable regions are contiguously linked via short flexible polypeptide linker, and capable of being expressed as a single polypeptide chain, and wherein the scFv retains the specificity of the intact antibody from which it is derived. Unless specified, as used herein a scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

A diabody is a small antibody fragment prepared by constructing a scFv fragment with a short linker (about 5-10 residues) between the $V_H$ and $V_L$ domains such that interchain but not intra-chain pairing of the V domains is achieved, resulting in a bivalent fragment. Bispecific diabodies are heterodimers of two crossover scFv fragments in which the $V_H$ and $V_L$ domains of the two antibodies are present on different polypeptide chains. (See, e.g., Hollinger et al. *Proc. Natl. Acad. Sci. USA* 90:6444-6448 (1993)).

Domain antibodies (dAbs), which can be produced in fully human form, are the smallest known antigen-binding fragments of antibodies, ranging from about 11 kDa to about 15 kDa. DAbs are the robust variable regions of the heavy and light chains of immunoglobulins ($V_H$ and $V_L$, respectively). They are highly expressed in microbial cell culture, show favorable biophysical properties including, for example, but not limited to, solubility and temperature stability, and are well suited to selection and affinity maturation by in vitro selection systems such as, for example, phage display. DAbs are bioactive as monomers and, owing to their small size and inherent stability can be formatted into larger molecules to create drugs with prolonged serum half-lives or other pharmacological activities.

Fv and scFv are the only species with intact combining sites that are devoid of constant regions. Thus, they are suitable for reduced nonspecific binding during in vivo use. scFv fusion proteins can be constructed to yield fusion of an effector protein at either the amino or the carboxy terminus of an scFv. The antibody fragment also can be a "linear antibody". Such linear antibody fragments can be monospecific or bispecific.

In an alternative embodiment of the disclosure, an antigen-binding fragment may be produced in a variety of forms where the antigen-binding domain is expressed as part of a contiguous polypeptide chain including, for example, a single domain antibody fragment (sdAb), a single chain antibody (scFv) derived from a human antibody (Harlow et al., 1999, In: Using Antibodies: a Laboratory Manual, Cold Spring Harbor Laboratory Press, N.Y.; Harlow et al., 1989, In: Antibodies: a Laboratory Manual, Cold Spring Harbor, N.Y.; Houston et al., 1988, *Proc. Natl. Acad. Sci. USA* 85:5879-5883; Bird et al., 1988, *Science* 242:423-426). In such an embodiment, the antigen-binding domain comprises:

(a) one or more (e.g., one, two, or all three) of:
  (i) heavy chain complementary determining region 1 (CDR-H1), wherein the CDR-H1 comprises a sequence selected from any one of the sequences provided in Sequence Table 1 herein including any sequence of SEQ ID NOS: 4, 14, 23, 28, 35, 39, 43, 46, 48, 64, 78, 84, 88, 94, 98, 109, 112, 115, 118, 120, 122, 125, 127, 130, or 137,
  (ii) heavy chain complementary determining region 2 (CDR-H2), wherein the CDR-H2 comprises a sequence selected from any one of the sequences provided in Sequence Table 1 herein including any sequence of SEQ ID NOS: 5, 15, 29, 36, 49, 65, 79, 89, 99, 104, 131, or 133,
  (iii) heavy chain complementary determining region 3 (CDR-H3), wherein the CDR-H3 comprises a sequence selected from any one of the sequences provided in Sequence Table 1 herein including any sequence of SEQ ID NOS: 6, 16, 20, 24, 30, 37, 44, 50, 59, 66, 73, 80, 95, 100, 102, 105, 107, 110, 113, 123, 128, or 135, and/or
(b) one or more (e.g., one, two, or all three) of:
  (i) light chain complementary determining region 1 (CDR-L1), wherein the CDR-L1 comprises a sequence selected from any one of the sequences provided in Sequence Table 1 herein including any sequence of SEQ ID NOS: 1, 12, 19, 27, 41, 53, 61, or 69,
  (ii) light chain complementary determining region 2 (CDR-L2), wherein the CDR-L2 comprises a sequence selected from any one of the sequences provided in Sequence Table 1 herein including any sequence comprising a sequence of GAS, ATS, SAS, or YAS or a sequence of SEQ ID NOS: 62, 70, 72, 77, or 87,
  (iii) light chain complementary determining region 3 (CDR-L3), wherein the CDR-L3 comprises a sequence selected from any one of the sequences provided in Sequence Table 1 herein including any sequence of SEQ ID NOS: 3, or 63.

In one embodiment, the antigen-binding domain comprises a heavy chain variable region described herein and/or a light chain variable region described herein. In some embodiments:

(a) the heavy chain variable region comprises a sequence selected from any one of the sequences provided in Sequence Table 1 herein including any sequence of SEQ ID NOS: 9, 18, 22, 26, 32, 38, 40, 45, 47, 52, 55, 60, 68, 75, 82, 91, 96, 101, 103, 106, 108, 111, 114, 119, 121, 124, 126, 129, 132, 134, 136, or 138, and/or
(b) the light chain variable region comprises a sequence selected from any one of the sequences provided in Sequence Table 1 herein including any sequence of SEQ ID NOS: 7, 17, 21, 25, 31, 34, 42, 51, 54, 57, 58, 67, 71, 74, 76, 81, 83, 85, 86, 90, 92, 93, or 97.

In one embodiment, the antigen-binding domain is a scFv comprising a heavy chain variable region and a light chain variable region of an amino acid sequence, e.g., a heavy chain variable region and light chain variable region described herein. In an embodiment, the antigen-binding domain (e.g., an scFv) comprises:

(a) a heavy chain variable region comprising:
  (i) an amino acid sequence having at least one, two or three modifications (e.g., substitutions) but not more than 30, 20 or 10 modifications (e.g., substitutions) of an amino acid sequence of a heavy chain variable region provided herein, or
  (ii) a sequence with 85-99% (e.g., 90-99%, or 95-99%) identity to an amino acid sequence provided herein including any sequence of SEQ ID NOS: 9, 18, 22, 26, 32, 38, 40, 45, 47, 52, 55, 60, 68, 75, 82, 91, 96, 101, 103, 106, 108, 111, 114, 119, 121, 124, 126, 129, 132, 134, 136, or 138; and/or
(b) a light chain variable region comprising:
  (i) an amino acid sequence having at least one, two or three modifications (e.g., substitutions) but not more than 30, 20 or 10 modifications (e.g., substitutions) of an amino acid sequence of a light chain variable region provided herein, or
  (ii) a sequence with 85-99% (e.g., 90-99%, or 95-99%) identity to an amino acid sequence provided herein including any sequence of SEQ ID NOS: 7, 17, 21, 25, 31, 34, 42, 51, 54, 57, 58, 67, 71, 74, 76, 81, 83, 85, 86, 90, 92, 93, or 97.

In some embodiments, the above aspects are contemplated for antibodies numbered 1, 3, 4, 5, 6, 7, 8, 9, 15, and 20 as described herein and provided in Sequence Table 1.

In some embodiments, the above aspects are contemplated for antibodies ABS-101-A, ABS-101-B and ABS-101-C as described herein and provided in Sequence Table 1.

Synthesis of Antigen Binding Fragments

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame. The isolated DNA encoding the $V_H$ region can be converted to a full-length heavy chain gene by operatively linking the $V_H$-encoding DNA to another DNA molecule encoding heavy chain constant regions ($C_H1$, $C_H2$ and $C_H3$). The sequences of human heavy chain constant region genes are known in the art (see, e.g., Kabat, E. A., et al. (1991) *Sequences of Proteins of Immunological Interest*, Fifth Edition, U.S. Department of Health and Human Services, NIH Publication NO: 91-3242) and DNA fragments encompassing these regions can be obtained by standard PCR amplification. The heavy chain constant region can be IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_H1$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art (see, e.g., Kabat, E. A., et al. (1991) *Sequences of Proteins of Immunological Interest*, Fifth Edition, U.S. Department of Health and Human Services, NIH Publication NO: 91-3242) and DNA fragments encompassing these regions can be obtained by standard PCR amplification. The light chain constant region can be a kappa or lambda constant region, but most preferably is a kappa constant region.

To create a scFv gene, the $V_H$- and $V_L$-encoding DNA fragments are operatively linked to another fragment encoding a flexible linker, e.g., encoding the amino acid sequence $(Gly-Gly-Gly-Gly-Ser)_3$, such that the $V_H$ and $V_L$ sequences can be expressed as a contiguous single-chain protein, with the $V_L$ and $V_H$ regions joined by the flexible linker (see, e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Alternative Paths to Antibody Production

As an alternative to direct synthesis using recombinant DNA methods, the antibodies or antigen binding fragments described in this disclosure may be produced via hybridoma. In the hybridoma method, a mouse or other appropriate host animal, such as a hamster or macaque monkey, is immunized as herein described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferred myeloma cells are those that fuse efficiently, support stable high-level production of antibody by the selected antibody-producing cells, and are sensitive to a medium. Human myeloma and mouse-human heteromyeloma cell lines also have been described for the production of human monoclonal antibodies (Kozbor, *J. Immunol.*, 133: 3001 (1984); Brodeur et al., Monoclonal Antibody Production Techniques and Applications, pp. 51-63 (Marcel Dekker, Inc., New York, 1987)). Exemplary murine myeloma lines include those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA. Culture medium in which hybridoma cells are growing is assayed for production of monoclonal antibodies directed against the antigen. Accordingly, in one aspect the present disclosure provides a hybridoma producing the antibody or antigen-binding fragment thereof, described herein. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by Scatchard analysis (Munson et al., *Anal. Biochem.* 107:220 (1980)).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxyapatite chromatography, gel electrophoresis, dialysis, or affinity chromatography.

Screening Methods for Identification of Target Antigens Binding Affinity

Antibodies may be screened for binding affinity by methods known in the art. For example, gel-shift assays, Western blots, radiolabeled competition assay, co-fractionation by chromatography, co-precipitation, cross linking, ELISA, and the like may be used, which are described in, for example, Current Protocols in Molecular Biology (1999) John Wiley & Sons, NY, which is incorporated herein by reference in its entirety.

To initially screen for antibodies which bind to the desired epitope on an antigen, a routine cross-blocking assay such as that described in Antibodies, a Laboratory Manual, Cold Spring Harbor Laboratory, Ed Harlow, and David Lane (1988), can be performed. Routine competitive binding assays may also be used, in which the unknown antibody is characterized by its ability to inhibit binding of antigen to an antigen specific antibody of the disclosure. Intact antigen, fragments thereof, or linear epitopes can be used. Epitope mapping is described in Champe et al., *J. Biol. Chem.* 270: 1388-94 (1995).

In one variation of an in vitro assay, the present disclosure provides a method comprising the steps of (a) contacting an immobilized antigen with a candidate antibody and (b) detecting binding of the candidate antibody to the antigen. In an alternative embodiment, the candidate antibody is immobilized, and binding of antigen is detected. Immobilization is accomplished using any of the methods well known in the art, including covalent bonding to a support, a bead, or a chromatographic resin, as well as non-covalent, high affinity interaction such as antibody binding, or use of streptavidin/biotin binding wherein the immobilized compound includes a biotin moiety. Detection of binding can be accomplished (a) using a radioactive label on the compound that is not immobilized, (b) using a fluorescent label on the non-immobilized compound, (c) using an antibody immunospecific for the non-immobilized compound, (d) using a label on the non-immobilized compound that excites a fluorescent support to which the immobilized compound is attached, as well as other techniques well known and routinely practiced in the art.

In some embodiments, an antibody or antigen-binding fragment thereof is provided herein wherein the antibody or antigen-binding fragment is capable of binding to human TL1A with an affinity at least up to 1, 2, 3, 4, 5, 6, 7, 8, 9, or 10-fold higher compared to a reference antibody. In one embodiment, the antibody or antigen-binding fragment is capable of binding to human TL1A with an affinity at least up to 8.30-fold higher compared to a reference antibody. In still other embodiments, an antibody or antigen-binding fragment is provided herein wherein the antibody or antigen-binding fragment is capable of binding to human FcRn with an affinity at least 1, 2, 3, 4, 5, 6, 7, 8, 9, or 10-fold higher compared to a reference antibody. In one embodiment, the antibody or antigen-binding fragment is capable of binding to human FcRn with an affinity at least 6.6-9.1-fold higher compared to a reference antibody. In still other embodiments, the antibody or antigen-binding fragment binds human TL1A with an affinity of approximately 0.05 nM, 0.10 nM, 0.15 nM, 0.20 nM, 0.25 nM, 0.3 nM, 0.25 nM, 0.40 nM, 0.45 nM, 0.50 nM, 0.55 nM, 0.60 nM, 0.65 nM, 0.70 nM, 0.75 nM, 0.80 nM, 0.85 nM, 0.90 nM, 0.95 nM, 1.00 nM, 1.10 nM, 1.20 nM, 1.30 nM, 1.40 nM, 1.50 nM, 1.60 nM, 1.70 nM, 1.80 nM, 1.90 nM, 2.0 nM, 3.0 nM, 4.0 nM, 5.0 nM, 6.0 nM, 7.0 nM, 8.0 nM, 9.0 nM, or 10.0 nM.

Modulator Activity

Another aspect of the present disclosure is directed to methods of identifying antibodies which modulate (i.e., decrease) activity of a target antigen comprising contacting a target antigen with an antibody, and determining whether the antibody modifies activity of the antigen. The activity in the presence of the test antibody is compared to the activity in the absence of the test antibody. Where the activity of the sample containing the test antibody is lower than the activity in the sample lacking the test antibody, the antibody will have inhibited activity.

Antibodies that modulate (i.e., increase, decrease, or block) the activity or expression of desired target may be identified by incubating a putative modulator with a cell expressing the desired target and determining the effect of the putative modulator on the activity or expression of the target. The selectivity of an antibody that modulates the activity of a target polypeptide or polynucleotide can be evaluated by comparing its effects on the target polypeptide or polynucleotide to its effect on other related compounds. Selective modulators may include, for example, antibodies and other proteins, peptides, or organic molecules which specifically bind to target polypeptides or to a nucleic acid encoding a target polypeptide. Modulators of target activity will be therapeutically useful in treatment of diseases and physiological conditions in which normal or aberrant activity of target polypeptide is involved. The target can be a for example, TL1A.

In one embodiment of the disclosure, methods of screening for antibodies which modulate the activity of target antigen comprise contacting antibodies with a target antigen polypeptide and assaying for the presence of a complex between the antibody and the target antigen. In such assays, the ligand is typically labeled. After suitable incubation, free ligand is separated from that present in bound form, and the amount of free or uncomplexed label is a measure of the ability of the particular antibody to bind to the target antigen.

High Throughput Screening

As described herein, the AI-based de novo design, optimization/affinity maturation, and/or folding methods contemplated by the present disclosure employ a variety of experimental "wet lab" techniques including, for example, ACE and gaACE as described herein.

The disclosure also contemplates high throughput screening (HTS) assays to identify antibodies that interact with or inhibit biological activity (i.e., inhibit enzymatic activity, binding activity, etc.) of an antigen. HTS assays permit screening of large numbers of compounds in an efficient manner. Cell-based HTS systems are contemplated to investigate the interaction between antibodies and their target antigen and their binding partners. HTS assays are designed to identify "hits" or "lead compounds" having the desired property, from which modifications can be designed to improve the desired property. Chemical modification of the "hit" or "lead compound" is often based on an identifiable structure/activity relationship between the "hit" and target antigen.

An HTS array may consist of one or more protein arrays (e.g., antibody arrays, antibody microarrays, protein microarray). The array can comprise one or more antibodies or antigen-binding fragment thereof, disclosed herein, immobilized on a solid support. Methods of production and use of such arrays are well known in art (e.g., (Buessow et al., *Nucleic Acids Res.* 1998, Lueking et al., *Mol Cell Proteomics.,* 2003; Angenendt et al., *Mol Cell* Proteomics., 2006) In some embodiments, very small amounts (e.g., 1 to 500 μg) of antibody or antigen-binding fragment thereof is immobilized. In some embodiments, there will be from 1 μg to 100 g, from 1 μg to 50 g, from 1 μg to 20 g, from 3 μg to 100 g, from 3 μg to 50 g, from 3 μg to 20, from 5 μg to 100 g, from 5 μg to 50 g, from 5 μg to 20 g of antibody present in a single sample. In one aspect, at least one of the samples in a plurality of samples will have from 1 μg to 100 g, from 1 μg to 50 g, from 1 μg to 20 g, from 3 μg to 100 g, from 3 μg to 50 g, from 3 μg to 20, from 5 μg to 100 g, from 5 μg to 50 g, from 5 μg to 20 g of antibody present. A solid support refers to an insoluble, functionalized material to which the antibodies can be reversibly attached, either directly or indirectly, allowing them to be separated from unwanted materials, for example, excess reagents, contaminants, and solvents. Examples of solid supports include, for example, functionalized polymeric materials, e.g., agarose, or its bead form Sepharose®, dextran, polystyrene and polypropylene, or mixtures thereof; compact discs comprising microfluidic channel structures; protein array chips; pipet tips; membranes, e.g., nitrocellulose or PVDF membranes; and microparticles, e.g., paramagnetic, or non-paramagnetic beads. In some embodiments, an affinity medium will be bound to the solid support and the antibody will be indirectly attached to solid support via the affinity medium. In one aspect, the solid support comprises a protein A affinity medium or protein G affinity medium. A "protein A affinity medium" and a "protein G affinity medium" each refer to a solid phase onto which is bound a natural or synthetic protein comprising an Fc-binding domain of protein A or protein G, respectively, or a mutated variant or fragment of an Fc-binding domain of protein A or protein G, respectively, which variant or fragment retains the affinity for an Fc-portion of an antibody. Antibody arrays can be fabricated by the transfer of antibodies onto the solid surface in an organized high-density format followed by chemical immobilization. Representative techniques for fabrication of an array include photolithography, ink jet and contact printing, liquid dispensing and piezoelectrics. The patterns and dimensions of antibody arrays are to be determined by each specific application. The sizes of each antibody spot may be easily controlled by the users. Antibodies may be attached to various kinds of surfaces via diffusion, adsorption/absorption, or covalent cross-linking and affinity. Antibodies may be directly spotted onto a plain glass surface. To keep antibodies in a wet environment during the printing process, high percent glycerol (e.g., 30-40%) may be used in sample buffer and the spotting is carried out in a humidity-controlled environment.

ADCC and CDC Assays

In one aspect, the antibodies or antigen-binding fragment thereof, disclosed herein, are contemplated as therapeutic antibodies for treatment of a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis, and an infection. Accordingly, the antibodies or antigen-binding fragment thereof, can be further screened in an antibody-dependent cell-mediated cytotoxicity (ADCC) assay and/or Complement-dependent cytotoxicity (CDC) assay. "ADCC activity" refers to the ability of an antibody to elicit an ADCC reaction. ADCC is a cell-mediated reaction in which antigen-nonspecific cytotoxic cells that express FcRs (e.g., natural killer (NK) cells, neutrophils, and macrophages) recognize antibody bound to the surface of a target cell and subsequently cause lysis of (i.e., "kill") the target cell. The primary mediator cells are natural killer (NK) cells. NK cells express FcγRIII only, with FcγRIIIA being an activating receptor and FcγRIIIB an inhibiting one; monocytes express FcγRI, FcγRII, and FcγRIII (Ravetch et al. (1991) *Annu. Rev. Immunol.* 9:457-92). ADCC activity can be assessed directly using an in vitro assay, e.g., a $^{51}$Cr release assay using peripheral blood mononuclear cells (PBMC) and/or NK effector cells as described in the Examples and Shields et al. (2001) *J. Biol. Chem.* 276:6591-6604, or another suitable method known in the art. ADCC activity may be expressed as a concentration of antibody at which the lysis of target cells is half-maximal. Accordingly, in some embodiments, the concentration of an antibody or antigen-binding fragment thereof of the disclosure, at which the lysis level is the same as the half-maximal lysis level by the wild-type control, is at least 2-, 3-, 5-, 10-, 20-, 50-, 100-fold lower than the concentration of the wild-type control itself.

Additionally, in some embodiments, the antibody or antigen-binding fragment thereof of the present disclosure may exhibit a higher maximal target cell lysis as compared to the wild-type control. For example, the maximal target cell lysis of an antibody or Fc fusion protein of the disclosure may be 10%, 15%, 20%, 25%, or more higher than that of the wild-type control. "Complement dependent cytotoxicity" or "CDC" refers to the ability of a molecule to lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santoro et al. *J. Immunol. Methods* 202:163 (1996), may be performed.

Target Antigen

In some embodiments, an antibody or antigen binding fragment thereof disclosed herein binds TL1A. In some embodiments, the anti-TL1A antibody or fragment thereof binds the same or similar or overlapping or partial epitope as the reference molecule as described herein.

In some embodiments, an antibody or antigen binding fragment thereof of the present disclosure binds an epitope on the target antigen (e.g., TL1A). In some embodiments, an antibody or antigen binding fragment thereof of the present disclosure binds multiple (e.g., 1, 2, 3, 4, 5, 6, 7, 8, 9, 10, or more epitopes on TL1A.

The binding affinity and dissociation rate of an antibody or an antigen binding fragment thereof disclosed herein to an epitope on TL1A can be determined by methods known in art. The binding affinity can be measured by ELISAs, RIAs, flow cytometry, surface plasmon resonance, such as BIACORE™. The dissociate rate can be measured by surface plasmon resonance. Preferably, the binding affinity and dissociation rate is measured by surface plasmon resonance. More preferably, the binding affinity and dissociation rate are measured using BIACORE™.

Epitope Mapping

The term "epitope," as used herein, refers to an antigenic determinant that interacts with a specific antigen-binding site in the variable region of an antibody molecule known as a paratope. A single antigen can have more than one epitope. Thus, different antibodies may bind to different areas on an antigen and can have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstances, an epitope may include moieties of saccharides, phosphoryl groups, or sulfonyl groups on the antigen.

Various techniques known to people of ordinary skill in the art can be used to determine whether an antigen-binding domain of an antibody "interacts with one or more amino acids" within a polypeptide or protein. Exemplary techniques include, e.g., routine cross-blocking assay such as that described Antibodies, Harlow, and Lane (Cold Spring Harbor Press, Cold Spring Harb., NY), alanine scanning mutational analysis, peptide blots analysis (Reineke, 2004, *Methods Mol. Biol.* 248:443-463), and peptide cleavage analysis. In addition, methods such as epitope excision, epitope extraction and chemical modification of antigens can be employed (Tomer, 2000, *Protein Science* 9:487-96). Another method that can be used to identify the amino acids within a polypeptide with which an antigen-binding domain of an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues, which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystallography of the antigen/antibody complex may also be used for epitope mapping purposes.

The epitope on a target antigen to which the antibody or antigen-binding fragment, disclosed herein, bind may consist of a single contiguous sequence of 3 or more (e.g., 3, 4, 5, 6, 7, 8, 9, 10, 11, 12, 13, 14, 15, 16, 17, 18, 19, 20 or more) amino acids of the target antigen. Alternatively, the epitope may consist of a plurality of non-contiguous amino acids (or amino acid sequences) of antigen (e.g., TL1A). Additional epitope mapping, including contemplated epitope(s), are provided in the Examples herein.

Additional host cells contemplated for use in antibody expression and purification are described in U.S. Pat. Nos. 9,617,335, 11,371,048, US Pub. NO: 2018/0282405, U.S. Pat. No. 11,584,785, and PCT/US22/82294.

Production of Antibodies from Prokaryotic Host Cells

In one aspect, provided herein is a host cell that comprises the isolated nucleic acids described above or a vector comprising said isolated nucleic acids described above. The vector can be a cloning vector or an expression vector. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescens*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1 776 (ATCC 31,537), and *E. coli* W3110 (ATCC 27,325) are suitable. These examples are illustrative rather than limiting.

Additional host cells contemplated for use in antibody expression and purification are described in U.S. Pat. Nos. 9,617,335, 11,371,048, US Pub. No. 2018/0282405, U.S. Pat. No. 11,584,785, and PCT/US22/82294.

As described herein, in another embodiment the SoluPro *E. coli* stain is contemplated (See, e.g., WO/2014/025663 and WO/2017/106583). As described in International Publication No. WO 2017/106583, incorporated by reference in its entirety herein, producing an antigen binding protein at commercial scale and in soluble form is addressed by providing suitable host cells capable of growth at high cell density in fermentation culture, and which can produce soluble gene products in the oxidizing host cell cytoplasm through highly controlled inducible gene expression. Prokaryotic cells with these qualities are produced by combining some or all the following characteristics: (1) The host cells are genetically modified to have an oxidizing cytoplasm, through increasing the expression or function of oxidizing polypeptides in the cytoplasm, and/or by decreasing the expression or function of reducing polypeptides in the cytoplasm. Specific examples of such genetic alterations are provided herein. Optionally, host cells can also be genetically modified to express chaperones and/or cofactors that assist in the production of the desired gene product(s), and/or to glycosylate polypeptide gene products. (2) The host cells comprise one or more expression constructs designed for the expression of one or more gene products of interest; in certain embodiments, at least one expression construct comprises an inducible promoter and a polynucleotide encoding a gene product to be expressed from the inducible promoter. (3) The host cells contain additional genetic modifications designed to improve certain aspects of gene product expression from the expression construct(s). In particular embodiments, the host cells (A) have an alteration of gene function of at least one gene encoding a transporter protein for an inducer of at least one inducible promoter, and as another example, wherein the gene encoding the transporter protein is selected from the group consisting of araE, araE, araG, araH, rhaT, xylF, xylG, and xylH, or particularly is araE, or wherein the alteration of gene function more particularly is expression of araE from a constitutive promoter; and/or (B) have a reduced level of gene function of at least one gene encoding a protein that metabolizes an inducer of at least one inducible promoter, and as further examples, wherein the gene encoding a protein that metabolizes an inducer of at least one said inducible promoter is selected from the group consisting of araA, araB, araD, prpB, prpD, rhaA, rhaB, rhaD, xylA, and xylB; and/or (C) have a reduced level of gene function of at least one gene encoding a protein involved in biosynthesis of an inducer of at least one inducible promoter, which gene in further embodiments is selected from the group consisting of scpA/sbm, argK/ygfD, scpB/ygfG, scpC/ygfH, rmlA, rmlB, rmlC, and rmlD.

Prokaryotic Cells with Oxidizing Cytoplasm

Examples of host cells are provided that allow for the efficient and cost-effective expression of gene products, including components of multimeric products. Host cells can include, in addition to isolated cells in culture, cells that are part of a multicellular organism, or cells grown within a different organism or system of organisms. In certain embodiments of the disclosure, the host cells are microbial cells such as yeasts (*Saccharomyces, Schizosaccharomyces*, etc.) or bacterial cells, or are gram-positive bacteria or gram-negative bacteria, or are *E. coli*, or are an *E. coli* B strain, or are *E. coli* (B strain) EB0001 cells (also called *E. coli* ASE (DGH) cells) or are *E. coli* (B strain) EB0002 cells. In growth experiments with *E. coli* host cells having oxidizing cytoplasm, specifically the *E. coli* B strains Shuffle® Express (NEB Catalog No. C3028H) and Shuffle® T7 Express (NEB Catalog No. C3029H) and the *E. coli* K strain Shuffle® T7 (NEB Catalog No. C3026H), these *E. coli* B strains with oxidizing cytoplasm are able to grow to much higher cell densities than the most closely corresponding *E. coli* K strain (International Publication No. WO 2017/106583).

Certain alterations can be made to the gene functions of host cells comprising inducible expression constructs, to promote efficient and homogeneous induction of the host cell population by an inducer. In some embodiments, the combination of expression constructs, host cell genotype, and induction conditions results in at least 75% (more preferably at least 85%, and most preferably, at least 95%) of the cells in the culture expressing gene product from each induced promoter, as measured by the method of Khlebnikov et al. described in Example 9 of International Publication No. WO 2017/106583. For host cells other than *E. coli*, these alterations can involve the function of genes that are structurally similar to an *E. coli* gene, or genes that carry out a function within the host cell similar to that of the *E. coli* gene. Alterations to host cell gene functions include eliminating or reducing gene function by deleting the gene protein-coding sequence in its entirety, or deleting a large enough portion of the gene, inserting sequence into the gene, or otherwise altering the gene sequence so that a reduced level of functional gene product is made from that gene. Alterations to host cell gene functions also include increasing gene function by, for example, altering the native promoter to create a stronger promoter that directs a higher level of transcription of the gene, or introducing a missense mutation into the protein-coding sequence that results in a more highly active gene product. Alterations to host cell gene functions include altering gene function in any way, including for example, altering a native inducible promoter to create a promoter that is constitutively activated. In addition to alterations in gene functions for the transport and metabolism of inducers, as described herein with relation to inducible promoters, and/or an altered expression of chaperone proteins, it is also possible to alter the reduction-oxidation environment of the host cell.

Host Cell Reduction-Oxidation Environment

In bacterial cells such as *E. coli*, proteins that need disulfide bonds are typically exported into the periplasm where disulfide bond formation and isomerization is catalyzed by the Dsb. system, comprising DsbABCD and DsbG. Increased expression of the cysteine oxidase DsbA, the disulfide isomerase DsbC, or combinations of the Dsb proteins, which are all normally transported into the periplasm, has been utilized in the expression of heterologous proteins that require disulfide bonds (Makino et al., *Microb Cell Fact* 2011 May 14; 10: 32). It is also possible to express cytoplasmic forms of these Dsb proteins, such as a cytoplasmic version of DsbA and/or of DsbC ('cDsbA or 'cDsbC'), that lacks a signal peptide and therefore is not transported into the periplasm. Cytoplasmic Dsb proteins such as cDsbA and/or cDsbC are useful for making the cytoplasm of the host cell more oxidizing and thus more conducive to the formation of disulfide bonds in heterologous proteins produced in the cytoplasm. The host cell cytoplasm can also be made less reducing and thus more oxidizing by altering the thioredoxin and the glutaredoxin/glutathione enzyme systems directly: mutant strains defective in glutathione reductase (gor) or glutathione synthetase (gshB), together with thioredoxin reductase (trxB), render the cytoplasm oxidizing. These strains are unable to reduce ribonucleotides and therefore cannot grow in the absence of exogenous reductants, such as dithiothreitol (DTT). Suppressor mutations (such as ahpC* and ahpCA, Lobstein et al., *Microb Cell Fact* 2012 May 8; 11: 56) in the gene ahpC, which encodes the peroxiredoxin AhpC, convert it to a disulfide reductase that generates reduced glutathione, allowing the channeling of electrons onto the enzyme ribonucleotide reductase and enabling the cells defective in gor and trxB, or defective in gshB and trxB, to grow in the absence of DTT. A different class of mutated forms of AhpC can allow strains, defective in the activity of gamma-glutamyl cysteine synthetase (gshA) and defective in trxB, to grow in the absence of DTT; these include AhpC V164G, AhpC S71F, AhpC E173/S71F, AhpC E171Ter, and AhpC dupl62-169 (Faulkner et al., *Proc Natl Acad Sci USA* 2008 May 6; 105(18): 6735-6740, Epub 2008 May 2). In such strains with oxidizing cytoplasm, exposed protein cysteines become readily oxidized in a process that is catalyzed by thioredoxins, in a reversal of their physiological function, resulting in the formation of disulfide bonds. Other proteins that may be helpful to reduce the oxidative stress effects in host cells of an oxidizing cytoplasm are HPI (hydroperoxidase I) catalase-peroxidase encoded by *E. coli* katG and HPII (hydroperoxidase II) catalase-peroxidase encoded by *E. coli* katE, which disproportionate peroxide into water and 02 (Farr and Kogoma, *Microbiol Rev.* 1991 December; 55(4): 561-85; Review). Increasing levels of KatG and/or KatE protein in host cells through induced co-expression or through elevated levels of constitutive expression is an aspect of some embodiments of the disclosure.

Another alteration that can be made to host cells is to express the sulfhydryl oxidase Ervlp from the inner membrane space of yeast mitochondria in the host cell cytoplasm, which has been shown to increase the production of a variety of complex, disulfide-bonded proteins of eukaryotic origin in the cytoplasm of *E. coli*, even in the absence of mutations in gor or trxB (Nguyen et al, *Microb Cell Fact* 2011 Jan. 7; 10: 1).

Host cells comprising expression constructs preferably also express cDsbA and/or cDsbC and/or Ervlp; are deficient in trxB gene function; are also deficient in the gene function of either gor, gshB, or gshA; optionally have increased levels of katG and/or katE gene function; and express an appropriate mutant form of AhpC so that the host cells can be grown in the absence of DTT.

Cellular Transport of Cofactors

When using the expression systems of the disclosure to produce enzymes that require cofactors for function, it is helpful to use a host cell either capable of synthesizing the cofactor from available precursors, or capable of taking it up from the environment. Common cofactors include ATP, coenzyme A, flavin adenine dinucleotide (FAD), NAD+/NADH, and heme. Polynucleotides encoding cofactor transport polypeptides and/or cofactor synthesizing polypeptides can be introduced into host cells, and such polypeptides can be constitutively expressed, or inducibly co-expressed with the active gene products to be produced by methods of the disclosure.

Proteases

Host cells can have alterations in their ability to degrade expressed protein products because of the lack of or lowering of the activity of one or more proteases. Exemplary protease include, but are not limited to, Clp, ClpP, OmpT, Lon, FtsH, ClpX, ClpY, ClpA, ClpQ, ClpAP, ClpXP, ClpAXP, ClpYQ, ClpY, and the proteases encoded by yaeL, sppA, tldD, sprT, yhbU, ptrA, frvX, hyaD, hybD, hycH, envC, ddpX, degP, degQ, degS, hslV, hslU, pepB, pepP, sohB, yggG, pepE, pepN, pepQ, abgA, pepT, iadA, pepA, pepD, ptrB, ycaL, ycbZ, yegQ, ygeY, ypdF, hycI, sgcX, and htpX (Gottesman, Annu Rev Genet, 30: 465-506, 1996).

Glycosylation of Polypeptide Gene Products

Host cells can have alterations in their ability to glycosylate polypeptides. For example, eukaryotic host cells can have eliminated or reduced gene function of the glycosyltransferase and/or oligo-saccharyltransferase genes, impairing the normal eukaryotic glycosylation of polypeptides to form glycoproteins. Prokaryotic host cells such as *E. coli*, which do not normally glycosylate polypeptides, can be altered to express a set of eukaryotic and prokaryotic genes that provide a glycosylation function (DeLisa et al., WO 2009/089154A2).

Other technologies related to host cell engineering include Rosano et al. (Front Microbiol, 5, 2014), Jensen et al. (Sci Rep, 5: 17874, 2015), Gu et al. (Biotech, 9(3): 77, 2019), Meyer et al. (Nat Chem Biol, 15: 169-204, 2019), and Euler et al. (PLoS ONE, 11: e0146408, 2016).

Chaperones

In some embodiments, an active gene product may be co-expressed with another gene product, such as a chaperone, that facilitates formation of the active form of the gene product of interest within a host cell. Chaperones are proteins that assist the non-covalent folding or unfolding, and/or the assembly or disassembly, of other gene products, but do not occur in the resulting monomeric or multimeric gene product structures when the structures are performing their normal biological functions (having completed the processes of folding and/or assembly). Chaperones can be expressed from an inducible promoter or a constitutive promoter within an expression construct or can be expressed from the host cell chromosome. Exemplary chaperones present in *E. coli* host cells are the folding factors DnaK/DnaJ/GrpE, DsbC/DsbG, GroEL/GroES, IbpA/IbpB, Skp, Tig (trigger factor), and FkpA, which have been used to prevent protein aggregation of cytoplasmic or periplasmic proteins. DnaK/DnaJ/GrpE, GroEL/GroES, and ClpB can function synergistically in assisting protein folding, and expression of these chaperones in various combinations has been shown to facilitate expression of properly folded gene product. When expressing eukaryotic proteins in prokaryotic host cells, a eukaryotic chaperone protein, such as protein disulfide isomerase (PDI) from the same or a related eukaryotic species, can be co-expressed, e.g., inducibly co-expressed, with the gene product of interest.

In one embodiment, the accessory protein PnlP-1 as described in WO2023/122448 is provided in a modified cell line.

In one embodiment, the materials and assays described herein do not require a chaperone.

Deleting Chromosomal Proteases and Metabolic Engineering

During the development of SoluPro (see, e.g., WO 2017/106583), single gene knockout studies were performed to produce hosts capable of generating higher titers of the protein of interest. clpA and ptsP were discovered throughout different cell line development programs. Subsequently, the individual gene deletions were combined into one host to achieve even higher titers.

clpA is a native host protein that directs the ClpAP protease towards the degradation of unfolded or abnormal proteins. SoluPro (see, e.g., WO 2017/106583), built from the parental B strain, specifically BL21 is deficient in Lon protease, which degrades many foreign proteins. This follows a general methodology of knocking out proteases to increase the titer of heterologous protein. Clp proteins, like chaperones, are highly conserved, present in all organisms, and contain ATP and polypeptide binding sites. ClpA, the ATPase component of ATP-dependent ClpAP protease, also functions as a molecular chaperone. ClpA is a class I Hsp100 family member, which forms a homohexameric ring-like structure in the presence of ATP to perform its chaperone activity. ClpA catalyzes the ATP-dependent unfolding of substrate proteins and mediates their translocation into the proteolytic cavity of ClpP (Reid et al., PNAS, 98(7): 3768-72, 2001). ClpA hexamers interact with ClpP through a considered IGL/F motif nestled in a helix-loop-helix region near the C-terminal end of ClpP's nucleotide binding domain 2 (NBD2) (Kim et al. Nat Struct Biol, 8: 230-33, 200). In the absence of the proteolytic component ClpP. ClpA catalyzes protein remodeling reactions, such as the remodeling of an inactive dimer of RepA into two active monomers. (Walker et al., EMBO J, 1: 945-51, 1994).

ptsP is a native host protein that encodes for Enzyme I (EI) of the nitrogen-related phosphotransferase system (PTS). As part of the initial step of the phosphorylation cascade, this gene is involved in the transport and phosphorylation of glucose and other sugars. Literature suggests that a potential reason for increased titer is that ptsP knockouts can achieve faster acetate assimilation through both upregulating actP (acetate permease) and increasing the cAMP/CRP level, thus increasing transcription of acetyl CoA synthetase Acs. In other words, this phenotype of increased acetate tolerance is particularly relevant for high cell density fermentations where acetate accumulation can be alleviated through ptsP deletion to utilize another carbon source other than glucose more efficiently.

Integrating Regulators to Reduce Plasmid Size

Typically, plasmids encode four different components; an origin of replication, an antibiotic resistance marker, a gene of interest, and a regulatory protein used to control the expression of the gene of interest. There are several regulatory proteins commonly used to control gene expression. These regulatory proteins, or genetic sensors, and all their associated genetic elements add significantly to the size of a plasmid; often more than 1000 base pairs per sensor. This increased size adds to the burden the cell carries from maintaining a plasmid and increases the chances for the plasmid to recombine or mutate in a way that may deactivate the protein of interest or some other necessary plasmid encoded element. Altogether, these larger plasmid sizes result in formation and unintended selection of deactivated plasmids during protein production, reducing yield of the target protein.

Lowering Prophage Reactivation Potential

Prophages are typically present in at least 50% of bacterial genomes. Specifically, for the SoluPro strain, the presence of prophage regions has been detected and were re-activated during a testing of the RCB using mitomycin C to induce viable phage production. The phage was subsequently sequenced, which revealed regions of interest that targeted our approach to selectively knockout certain regions of the genome to prevent that region from producing a fully functional bacteriophage capable of lytic infection and lysogeny.

Suppressing Post-Translational Gluconylation of Heterologous Proteins

The SoluPro (see, e.g., WO 2017/106583) strain produces heterologously expressed proteins which are subject to gluconoylation, an undesired posttranslational modification. It has been shown that the formation of gluconylated/phosphogluconoylated could be caused by accumulation of 6-phosphogluconolactone due to the lack of phosphogluconolactonase (PGL). This is inherent to *E. coli* B strain lineages as a mutation can be traced back to a UV-induced deletion of galM-ybhJ locus found in the parental strain *E. coli* B707. PGL catalyzes hydrolysis of 6-phosphoglucono-lactone to 6-phosphogluconate. Non-specific protein protein gluconoylation can be suppressed by overexpression of heterologous PGL in the SoluPro host.

Cellular Transport of Cofactors

Common cofactors include ATP, coenzyme A, flavin adenine dinucleotide (FAD), NAD+/NADH, and heme. Polynucleotides encoding cofactor transport polypeptides and/or cofactor synthesizing polypeptides can be introduced into host cells, and such polypeptides can be constitutively expressed, or inducibly co-expressed with the gene products to be produced by methods of the disclosure.

Glycosylation of Polypeptide Gene Products

Host cells can have alterations in their ability to glycosylate polypeptides. For example, eukaryotic host cells can have eliminated or reduced gene function in glycosyltransferase and/or oligo saccharyltransferase genes, impairing the normal eukaryotic glycosylation of polypeptides to form glycoproteins. Prokaryotic host cells such as *E. coli*, which do not normally glycosylate polypeptides, can be altered to express a set of eukaryotic and prokaryotic genes that provide a glycosylation function (DeLisa et al., WO 2009/089154A2, 2009 Jul. 16).

Assays: Activity-Specific Cell-Enrichment (ACE) Assay and HiPrBind Assay

The activity-specific cell-enrichment (ACE) assay identifies host cells that express active gene product of interest rather than inactive material, as described in WO 2021/146626, incorporated herein in relevant part. Active gene product can be distinguished from inactive material by the ability of active gene product to specifically bind a binding partner molecule, or by the ability of gene product to participate in a chemical or enzymatic reaction, as examples. The presence of properly formed disulfide bonds in a polypeptide gene product is an indication that it is correctly folded and presumptively active. In the cell-enrichment methods, active gene product of interest is detected by utilizing an appropriate labeling complex that specifically binds to active gene product of interest, such as a labeled antigen if the gene product of interest is an antibody or Fab; or a labeled ligand if the gene product of interest is a receptor or a receptor fragment, where the ligand specifically binds to an active conformation of the receptor; or a labeled substrate or a labeled substrate analog if the gene product of interest is an enzyme, as examples. For any gene product of interest, if there is an available antibody or antibody fragment that specifically binds to the active gene product and not to inactive gene product, that antibody or antibody fragment can be used to label the active gene product of interest when attached to a detectable moiety.

The HiPrBind assay provides an efficient method for multiple interrogations of an active gene product, such as by providing at least two distinct interrogations of a characteristic property of the active gene product or simultaneously interrogating at least two characteristic properties of that active gene product. HiPrBind assays are described in WO 2021/163349, incorporated herein in relevant part. The assay is an advance on the principle underlying the yeast two hybrid assay in that a multi-component detection mechanism is brought into proximity, and thereby brought into an environment where the detection mechanism can be active in producing a signal capable of detection. One component of the multi-component (e.g., two component) detection system is stably associated with a first analyte-associating moiety (i.e., active gene product-associating moiety) and a second component of the detection system is stably associated with a distinct second analyte-associating moiety. A detectable signal is generated when the two components of the detection system are brought into proximity by the analyte-associating moieties binding to the analyte. Because each of the analyte-associating moieties is specific for an active gene product as analyte, a signal is only generated when a characteristic property of an active gene product is detected using two distinct mechanisms, or when two distinct characteristic properties of an active gene product are simultaneously detected. The HiPrBind assay is versatile in detecting a variety of characteristic properties, but a simple example involves a gene product that is active in homodimeric form wherein each monomer requires disulfide bonds to properly fold. One active gene product-associating moiety can be a binding agent that specifically binds to the properly folded and therefore active monomer, and a second active gene product-associating moiety can be a distinct second binding agent that specifically binds to the dimeric form of the gene product. Thus, the HiPrBind assay in this embodiment simultaneously detects a gene product that is properly folded and in dimeric form.

Available host cell strains with altered gene functions. To create preferred strains of host cells to be used in the expression systems and methods of the disclosure, it is useful to start with a strain that already comprises desired genetic alterations (Table A; International Publication No. WO 2017/106583).

TABLE A

Exemplary host cell strains

| Strain | Genotype | Source |
|---|---|---|
| *E, coli* TOP10 | F-mcrA Δ(mrr-hsdRMS-mcrBC) Φ80lacZ ΔM15 Δlacx74 recA1 araD139 Δ(ara-leu)7697 galU galK rpsL ($Str^R$) endA1 nupG λ | Invitrogen Life Technologies Catalog Nos. C404-10, C4040-03, C4040-06, C4040-50, and C4040-52 |

TABLE A-continued

Exemplary host cell strains

| Strain | Genotype | Source |
|---|---|---|
| *E, coli* Origami ™ 2 | Δ(ara-leu)7697 Δlacx74 ΔphoA PvuII phoR araD139 ahpC gale galK rpsL F'[$lac^+$ $lacI^q$ pro] gor522::Tn10 trxB ($Str^R$, $Tet^R$) | Merck (EMD Millipore Chemicals) Catalog NO: 71344 |
| *E, coli* SHuffle ® Express | fhuA2 [lon] ompT ahpC gal λatt::pNEB3-r1-cDsbc (Spec, lacI) ΔtrxB sulA11 R(mcr-73::miniTn10-$Tet^S$)2 [dcm] R(zgb-210::Tn10-$Tet^S$) endA1 Δgor Δ(mcrC-mrr)114::IS10 | New England Biolabs Catalog NO: C3028H |

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastors* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruit fly), and *Bombyx mori* have been identified. A variety of viral strains for transfection are publicly available, e.g., the L-1 variant of *Autographa californica* NPV and the Bin-5 strain of *Bombyx mori* NP\7, and such viruses may be used as the virus herein according to the present disclosure, particularly for transfection of *Spodoptera frugiperda* cells.

Plant cell cultures of cotton, corn, potato, soybean, *petunia*, tomato, tobacco, *lemna*, and other plant cells can also be utilized as hosts. However, interest has been greatest in vertebrate cells, and propagation of vertebrate cells in culture (tissue culture) has become routine procedure. Examples of useful mammalian host cell lines are Chinese hamster ovary cells, including CHOK1 cells (ATCC CCL61), DXB-11, DG-44, and Chinese hamster ovary cells/-DHFR (CHO, Urlaub et al., *Proc. Natl. Acad. Sci. USA* 77: 4216 (1980)); monkey kidney CV1 line transformed by SV40 (COS-7, ATCC CRL 1651); human embryonic kidney line (293 or 293 cells subcloned for growth in suspension culture, [Graham et al., *J. Gen Viral.* 36: 59 (1977)]; baby hamster kidney cells (BHK, ATCC CCL 10); mouse sertoli cells (TM4, Mather, *Biol. Reprod.* 23: 243-251 (1980)); monkey kidney cells (CV1 ATCC CCL 70); African green monkey kidney cells (VERO-76, ATCC CRL-1587); human cervical carcinoma cells (HELA, ATCC CCL 2);

canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y Acad. Sci.* 383: 44-68 (1982)); MRC 5 cells; FS4 cells; and a human hepatoma line (Hep G2).

Host cells are transformed or transfected with the above-described expression or cloning vectors for antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of antibodies, described herein.

For transfection of the expression vectors and production of the chimeric, humanized, or composite human antibodies described herein, the recipient cell line can be a myeloma cell. Myeloma cells can synthesize, assemble and secrete immunoglobulins encoded by transfected immunoglobulin nucleic acid sequences and possess the mechanism for glycosylation of the immunoglobulin. For example, in some embodiments, the recipient cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies hetero-hybridoma cells. An expression vector carrying a chimeric, humanized, or composite human antibody construct or antibody polypeptide described herein can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 *Science* 1538 (1988), as known to one of ordinary skill in the art.

Yeast provides certain advantages over bacteria to produce immunoglobulin H and L chains. Yeasts carry out post-translational peptide modifications including glycosylation. Several recombinant DNA strategies exist that utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11TH INTL. CONF. YEAST, GENETICS & MOLEC. BIOL. (Montpelier, France, 1982). Yeast gene expression systems can be routinely evaluated for the levels of production, secretion and the stability of antibody polypeptide or antigen-binding fragment peptide thereof, and assembled chimeric, humanized, or composite human antibodies, fragments and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. Several approaches can be taken for evaluating optimal expression plasmids for the expression of cloned immunoglobulin cDNAs in yeast.

Bacterial strains can also be utilized as hosts to produce the antibody molecules or fragments thereof described herein, *E. coli* K12 strains such as *E. coli* W3110 (ATCC 27325), *Bacillus* species, *enterobacteria* such as *Salmonella typhimurium* or *Serratia marcescens*, and various *Pseudomonas* species can be used. Plasmid vectors containing replicon and control sequences which are derived from species compatible with a host cell are used in connection with these bacterial hosts. The vector carries a replication site, as well as specific genes which can provide phenotypic selection in transformed cells. Several approaches can be taken for evaluating the expression plasmids for the production of chimeric, humanized, or composite humanized antibodies and fragments thereof encoded by the cloned immunoglobulin cDNAs or CDRs in bacteria (see Glover, 1985; Ausubel, 1987, 1993; Sambrook, 1989; Colligan, 1992-1996).

Host mammalian cells can be grown in vitro or in vivo. Mammalian cells provide post-translational modifications to immunoglobulin protein molecules including leader peptide removal, folding and assembly of H and L chains, glycosylation of the antibody molecules, and secretion of functional antibody protein. Mammalian cells which can be useful as hosts to produce antibody proteins, in addition to the cells of lymphoid origin described above, include cells of fibroblast origin, such as Vero (ATCC CRL 81) or CHO-K1 (ATCC CRL 61) cells. Exemplary eukaryotic cells that can be used to express polypeptides include, but are not limited to, COS cells, including COS 7 cells; 293 cells, including 293-6E cells; CHO cells, including CHO-S and DG44 cells; PER.C6® cells (Crucell); and NSO cells. In some embodiments, a particular eukaryotic host cell is selected based on its ability to make desired post-translational modifications to the variable heavy chains and/or variable light chains. For example, in some embodiments, CHO cells produce polypeptides that have a higher level of sialylation than the same polypeptide produced in 293 cells.

Expression Constructs

In some embodiments of the disclosure, inducible promoters are contemplated for use with the expression constructs to be introduced into the host cells according to the disclosure in order to achieve elevated expression of desired active gene products. Exemplary promoters are described herein and are also described in WO/2016/205570, incorporated herein by reference in relevant part. As described herein, the cells comprising one or more expression constructs may optionally include one or more inducible promoters to express a gene product of interest. In one embodiment, the gene product is a fusion protein. In other embodiments, the gene product is a protein, for example a therapeutic protein.

Expression constructs are polynucleotides designed for the expression of one or more gene products of interest, and thus are not naturally occurring molecules. Any expression construct known in the art is contemplated for use in the cells and methods of the disclosure, including expression constructs that can be integrated into a host cell chromosome or maintained within the host cell as extra-chromosomal, independently replicating polynucleotide molecules, i.e., episomes having origins of replication independent of the host cell chromosome, such as plasmids or artificial chromosomes. Expression constructs according to the disclosure also may have one or more selectable markers to enable selection of those cells harboring the expression construct.

Exemplary selectable markers confer resistance to antibiotics lethal to the host cell lacking that selectable marker or encode enzymes required to produce essential nutrients. Any selectable marker known in the art is contemplated for use in the expression constructs of the disclosure. Expression markers may also contain an inducible promoter to provide the ability to induce the expression of a coding region operably linked to that inducible promoter. Exemplary inducible promoters contemplated by the disclosure include the arabinose promoter (ParaBAD), ParaC, ParaE, the propionate promoter (PprpBCDE), the rhamnose promoter (PrhaSR), the xylose promoter (PxylA), the lactose promoter, and the alkaline phosphatase promoter. Additional information on contemplated inducible promoters, including the sequences thereof, is provided in WO 2016/205570, incorporated herein by reference in relevant part. In addition to inducible promoters, the disclosure comprehends expression constructs comprising constitutive promoters. To ensure that RNA transcribed from the expression construct is efficiently translated, the construct may also include a ribosome binding site (RBS). In prokaryotes in general (archaea and bacteria), the RBS consensus sequence is GGAGG or GGAGGU, and in bacteria such as *E. coli*, the RBS consensus sequence is further defined as AGGAGG or AGGAGGU. To facilitate incorporation of a coding region or gene of interest, the expression construct may include a multiple cloning site in which a variety of restriction endonuclease cleavage sites are clustered to provide flexibility in incorporating exogenous polynucleotides, as is known in the art. Some embodiments of the expression construct of the disclosure further include a coding region for a signal peptide or leader peptide, wherein the coding region is oriented to result in expression of fusion protein comprising the signal peptide and the active gene product of interest.

The term "expression construct" as used herein refers to polynucleotides designed for the expression of one or more antigen binding proteins of interest, and thus are not naturally occurring molecules. Expression constructs can be integrated into a host cell chromosome or maintained within the host cell as polynucleotide molecules replicating independently of the host cell chromosome, such as plasmids or artificial chromosomes. An example of an expression construct is a polynucleotide resulting from the insertion of one or more polynucleotide sequences into a host cell chromosome, where the inserted polynucleotide sequences alter the expression of chromosomal coding sequences. An expression vector is a plasmid expression construct specifically used for the expression of one or more antigen binding proteins. One or more expression constructs can be integrated into a host cell chromosome or be maintained on an extrachromosomal polynucleotide such as a plasmid or artificial chromosome. The following are descriptions of particular types of polynucleotide sequences that can be used in expression constructs for the expression or co-expression of gene products, including fusion proteins as described herein.

Origins of Replication

Expression constructs must comprise an origin of replication, also called a replicon, in order to be maintained within the host cell as independently replicating polynucleotides. Different replicons that use the same mechanism for replication cannot be maintained together in a single host cell through repeated cell divisions. As a result, plasmids can be categorized into incompatibility groups depending on the origin of replication that they contain, as shown in Table 2 of International Publication No. WO 2016/205570. Origins of replication can be selected for use in expression constructs on the basis of incompatibility group, copy number, and/or host range, among other criteria. As described above, if two or more different expression constructs are to be used in the same host cell for the co-expression of multiple gene products, it is best if the different expression constructs contain origins of replication from different incompatibility groups: a pMBl replicon in one expression construct and a pl5A replicon in another, for example. The average number of copies of an expression construct in the cell, relative to the number of host chromosome molecules, is determined by the origin of replication contained in that expression construct. Copy number can range from a few copies per cell to several hundred (Table 2 of WO/2016/205570). In some embodiments, different expression constructs are used which comprise inducible promoters that are activated by the same inducer, but which have different origins of replication. By selecting origins of replication that maintain each different expression construct at a certain approximate copy number in the cell, it is possible to adjust the levels of overall production of a gene product expressed from one expression construct, relative to another gene product expressed from a different expression construct. As an example, to co-express subunits A and B of a multimeric protein, an expression construct is created which comprises the colEl replicon, the am promoter, and a coding sequence for subunit A expressed from the am promoter: 'collet-Para-A.

Another expression construct is created comprising the pl 5A replicon, the am promoter, and a coding sequence for subunit B: 'pl5A-Para-B'. These two expression constructs can be maintained together in the same host cells, and expression of both subunits A and B is induced by the addition of one inducer, arabinose, to the growth medium. If the expression level of subunit A needed to be significantly increased relative to the expression level of subunit B, in order to bring the stoichiometric ratio of the expressed amounts of the two subunits closer to a desired ratio, for example, a new expression construct for subunit A could be created, having a modified pMB 1 replicon as is found in the origin of replication of the pUC9 plasmid ('pUC9ori'): pUC9ori-Para-A. Expressing subunit A from a high-copy-number expression construct such as pUC9ori-Para-A should increase the amount of subunit A produced relative to expression of subunit B from pl5A-Para-B. In a similar fashion, use of an origin of replication that maintains expression constructs at a lower copy number, such as pSOOl (WO/2016/205570), could reduce the overall level of a gene product expressed from that construct. Selection of an origin of replication can also determine which host cells can maintain an expression construct comprising that replicon. For example, expression constructs comprising the colEl origin of replication have a relatively narrow range of available hosts, species within the Enterobacteriaceae family, while expression constructs comprising the RK2 replicon can be maintained in *E. coli, Pseudomonas aeruginosa, Pseudomonas putida, Azotobacter vinelandii*, and *Alcaligenes eutrophus*, and if an expression construct comprises the RK2 replicon and some regulator genes from the RK2 plasmid, it can be maintained in host cells as diverse as *Sinorhizobium meliloti, Agrobacterium tumefaciens, Caulobacter crescentus, Acinetobacter calcoaceticus*, and *Rhodobacter sphaeroides* (Kiies and Stahl, Microbiol Rev 1989 December; 53(4): 491-516).

Similar considerations can be employed to create expression constructs for inducible expression or co-expression in eukaryotic cells. For example, the 2-micron circle plasmid of *Saccharomyces cerevisiae* is compatible with plasmids from other yeast strains, such as pSRl (ATCC Deposit Nos.

48233 and 66069; Araki et al., *JMol Biol* 1985 Mar. 20; 182(2): 191-203) and pKDl (ATCC Deposit No. 37519; Chen et al, *Nucleic Acids Res* 1986 Jun. 11; 14(11): 4471-81).

In some embodiments, the expression construct comprises a selection gene. A "selection gene," also termed a selectable marker, encodes a protein necessary for the survival or growth of a host cell in a selective culture medium. Host cells not containing the expression construct comprising the selection gene will not survive in the culture medium. Typical selection genes encode proteins that confer resistance to antibiotics or other toxins, or that complement auxotrophic deficiencies of the host cell. One example of a selection scheme utilizes a drug such as an antibiotic to arrest growth of a host cell. Those cells that contain an expression construct comprising the selectable marker produce a protein conferring drug resistance and survive the selection regimen. Some examples of antibiotics that are commonly used for the selection of selectable markers (and abbreviations indicating genes that provide antibiotic resistance phenotypes) are: ampicillin (AmpR), chloramphenicol (CmlR or CmR), kanamycin (KanR), spectinomycin (SpcR), streptomycin (StrR), and tetracycline (TetR). Many of the plasmids in Table 2 of WO/2016/205570 comprise selectable markers, such as pBR322 (AmpR, TetR); pMOB45 (CmR, TetR); pACYClW (AmpR, KanR); and pGBMl (SpcR, StrR). The native promoter region for a selection gene is usually included, along with the coding sequence for its gene product, as part of a selectable marker portion of an expression construct. Alternatively, the coding sequence for the selection gene can be expressed from a constitutive promoter.

Exemplary selectable markers include, but are not limited to, neomycin phosphotransferase (npt II), hygromycin phosphotransferase (hpt), dihydrofolate reductase (dhfr), zeocin, phleomycin, bleomycin resistance gene (ble), gentamicin acetyltransferase, streptomycin phosphotransferase, mutant form of acetolactate synthase (als), bromoxynil nitrilase, phosphinothricin acetyltransferase (bar), enolpyruvylshikimate-3-phosphate (EPSP) synthase (aro A), muscle specific tyrosine kinase receptor molecule (MuSK-R), copper-zinc superoxide dismutase (sod1), metallothioneins (cup1, MT1), beta-lactamase (BLA), puromycin N-acetyl-transferase (pac), blasticidin acetyl transferase (bls), blasticidin deaminase (bsr), histidinol dehydrogenase (HDH), N-succinyl-5-aminoimidazole-4-carboxamide ribotide (SAICAR) synthetase (adel), arginosuccinate lyase (arg4), beta-isopropylmalate dehydrogenase (leu2), invertase (suc2), orotidine-5'-phosphate (OMP) decarboxylase (ura3), and orthologs of any of the foregoing.

Inducible Promoter

As described herein, there are several different inducible promoters that can be included in expression constructs as part of the inducible coexpression systems of the disclosure. In some embodiments, inducible promoters share at least 80% polynucleotide sequence identity (more preferably, at least 90% identity, and most preferably, at least 95% identity) to at least 30 (more preferably, at least 40, and most preferably, at least 50) contiguous bases of a promoter polynucleotide sequence as defined in Table 1 of International Publication No. WO 2016/205570 by reference to the *E. coli* K-12 substrain MG1655 genomic sequence, where percent polynucleotide sequence identity is determined using the methods of Example 11 of WO/2016/205570. Under 'standard' inducing conditions (see Example 5 of International Publication No. WO 2016/205570), preferred inducible promoters have at least 75% (more preferably, at least 100%, and most preferably, at least 110%) of the strength of the corresponding 'wild-type' inducible promoter of *E. coli* K-12 substrain MG1655, as determined using the quantitative PCR method of De Mey et al. (Example 6 of International Publication No. WO 2016/205570). Within the expression construct, an inducible promoter is placed 5' to (or 'upstream of) the coding sequence for the gene product that is to be inducibly expressed, so that the presence of the inducible promoter will direct transcription of the gene product coding sequence in a 5' to 3' direction relative to the coding strand of the polynucleotide encoding the gene product.

Ribosome Binding Site

For polypeptide gene products, the nucleotide sequence of the region between the transcription initiation site and the initiation codon of the coding sequence of the gene product that is to be inducibly expressed corresponds to the 5' untranslated region ('UTR') of the mRNA for the polypeptide gene product. Preferably, the region of the expression construct that corresponds to the 5' UT comprises a polynucleotide sequence like the consensus ribosome binding site (RBS, also called the Shine-Dalgarno sequence) that is found in the species of the host cell. In prokaryotes (archaea and bacteria), the RBS consensus sequence is GGAGG or GGAGGU, and in bacteria such as *E. coli*, the RBS consensus sequence is AGGAGG or AGGAGGU. The RBS is typically separated from the initiation codon by 5 to 10 intervening nucleotides. In expression constructs, the RBS sequence is preferably at least 55% identical to the AGGAGGU consensus sequence, more preferably at least 70% identical, and most preferably at least 85% identical, and is separated from the initiation codon by 5 to 10 intervening nucleotides, more preferably by 6 to 9 intervening nucleotides, and most preferably by 6 or 7 intervening nucleotides. The ability of a given RBS to produce a desirable translation initiation rate can be calculated at the website salis.psu.edu/software/RBSLibraryCalculatorSearchMode, using the RBS Calculator; the same tool can be used to optimize a synthetic RBS for a translation rate across a 100,000+ fold range (Salis, *Methods Enzymol* 2011; 498: 49-42).

Multiple Cloning Site

A multiple cloning site (MCS), also called a polylinker, is a polynucleotide that contains multiple restriction sites in close proximity to or overlapping with each other. The restriction sites in the MCS typically occur once within the MCS sequence, and preferably do not occur within the rest of the plasmid or other polynucleotide construct, allowing restriction enzymes to cut the plasmid or other polynucleotide construct only within the MCS. Examples of MCS sequences are those in the pBAD series of expression vectors, including pBAD18, pBAD18-Cm, pBAD18-Kan, pBAD24, pBAD28, pBAD30, and pBAD33 (Guzman et al., *J Bacteriol* 1995 July; 177(14): 4121-30); or those in the pPRO series of expression vectors derived from the pBAD vectors, such as pPR018, pPR018-Cm, pPR018-Kan, pPR024, pPRO30, and pPR033 (U.S. Pat. No. 8,178,338 B2; May 15 2012; Keasling, Jay). A multiple cloning site can be used in the creation of an expression construct: by placing a multiple cloning site 3' to (or downstream of) a promoter sequence, the MCS can be used to insert the coding sequence for a gene product to be expressed or co-expressed into the construct, in the proper location relative to the promoter so that transcription of the coding sequence will occur. Depending on which restriction enzymes are used to cut within the MCS, there may be some part of the MCS sequence remaining within the expression construct after the coding sequence or other polynucleotide sequence is inserted into the expression construct. Any remaining MCS sequence can be upstream or, or downstream of, or on both sides of the inserted sequence. A ribosome binding site can be placed upstream of the MCS, preferably immediately adjacent to or separated from the MCS by only a few nucleotides, in which case the RBS would be upstream of any coding sequence inserted into the MCS. Another alternative is to include a ribosome binding site within the MCS, in which case the choice of restriction enzymes used to cut within the MCS will determine whether the RBS is retained, and in what relation to, the inserted sequences. A further alternative is to include an RBS within the polynucleotide sequence that is to be inserted into the expression construct at the MCS, preferably in the proper relation to any coding sequences to stimulate initiation of translation from the transcribed messenger RNA.

Expression from Constitutive Promoters

Expression constructs of the disclosure can also comprise coding sequences that are expressed from constitutive promoters. Unlike inducible promoters, constitutive promoters initiate continual gene product production under most growth conditions. One example of a constitutive promoter is that of the Tn3 bla gene, which encodes beta-lactamase and is responsible for the ampicillin-resistance (AmpR) phenotype conferred on the host cell by many plasmids, including pBR322 (ATCC 31344), pACYClW (ATCC 37031), and pBAD24 (ATCC 87399). Another constitutive promoter that can be used in expression constructs is the promoter for the *E. coli* lipoprotein gene, Ipp, which is located at positions 1755731-1755406 (plus strand) in *E. coli* K-12 substrain MG1655 (Inouye and Inouye, *Nucleic Acids Res* 1985 May 10; 13(9): 3101-10). A further example of a constitutive promoter that has been used for heterologous gene expression in *E. coli* is the trpLEDCBA promoter, located at positions 1321169-1321133 (minus strand) in *E. coli* K-12 substrain MG1655 (Windass et al., *Nucleic Acids Res* 1982 Nov. 11; 10(21): 6639-57). Constitutive promoters can be used in expression constructs for the expression of selectable markers, as described herein, and also for the constitutive expression of other gene products useful for the coexpression of the desired product. For example, transcriptional regulators of the inducible promoters, such as AraC, PrpR, RhaR, and XylR, if not expressed from a bidirectional inducible promoter, can alternatively be expressed from a constitutive promoter, on either the same expression construct as the inducible promoter they regulate, or a different expression construct. Similarly, gene products useful for the production or transport of the inducer, such as PrpEC, AraE, or Rha, or proteins that modify the reduction-oxidation environment of the cell, as a few examples, can be expressed from a constitutive promoter within an expression construct. Gene products are useful to produce co-expressed gene products, and the resulting desired product, also include chaperone proteins, cofactor transporters, etc.

Integrating regulators cymR, luxR, vanR, and AraC

VanR is a negative transcriptional regulator of bacteria that belongs to the PadR family, and regulates expression of the vanABK operon in response to vanillate. In the absence of vanillate, VanR represses the transcription of the vanABK genes by binding operator DNA located in the promoter region of vanABK genes (Merkens et al., Curr Microbiol, 51: 59-65, 2005). Upon exposure to vanillate, VanR releases from operator DNA, allowing RNA polymerase to initiate vanABK gene transcription. Among the roles of VanR is transcriptionally regulating the catabolism of vanillate, a phenolic acid, to utilize vanillate as a carbon or energy source (Morabbi et al., J Bacteriol, 197: 959-72, 2015).

CymR is a TetR-type regulator. Members of the TetR family exhibit high conservation of sequences for their DNA binding domain. These regulators mostly serve as repressors that bind their operator to repress the target genes, and are released from the DNA when bound to their cognate ligands (Ramos et al., Microbiol Mol Biol Rev, 69: 326-56, 2005). CymR is responsive to the inducer coumarate. CymR is a transcriptional repressor involved in the control of the gene expression for p-cymene (cym) and p-cumate (cmt) degradation (Eaton et al., J Bacteriol, 179: 3171-80, 1997). The CymR protein is a dimer in solution.

LuxI and LuxR are quorum-sensing regulatory genes. LuxI is the synthase of the autoinducer N-3-oxohexanoyl-L homoserine Lactone (OC6), which interacts with its cognate receptor LuxR to form a transcriptional activator for the lux operon (Perez et al., BMC Syst Biol, 5: 153, 2011; Hao et al., J Bacteriol, 188: 2173-83, 2006).

AraC is responsive to inducer arabinose; it is a positive-acting gene regulator that induces synthesis of other ara proteins in *E. coli*. The AraC cognate $P_{BAD}$ promoter also responds to the presence of arabinose; it is stimulated by CAP, and repressed by the AraC protein itself via DNA looping or direct binding to the Pc polymerase binding region (Casadaban et al., J Mol Biol, 104: 557-66, 1971).

In some embodiments, one or more of the aforementioned sensors are combined into a single sensor operon. In some embodiments, all four sensors are combined into a single sensor operon. In some embodiments, the sensor operon comprises cymR, luxR, vanR, and ara C, in that order. In some embodiments, the sensor operon further comprises a J23100 constitutive promoter. In some embodiments, the sensor operon is inserted into the genome of an *E. coli* strain at the yciA locus.

Δ(cusS-argU) Δ(cdsbC-galM)

Bacterial genomes can contain a significant proportion (>20%) of functional and non-functional bacteriophage genes. These phage or phage-like clusters of genes in a bacterial genome are referred to as "prophage regions" (Casjens et al., Mol. Microbiol., 49: 277-300, 2003). Prophage regions can be identified in a bacterial strain of interest either by (i) experimental methods, or (ii) computational methods. The experimental approach involves inducing host bacteria to release phage particles via exposure to UV light or other DNA-damaging conditions, although this approach will not reveal defective prophages or certain prophages induced by other conditions. Computational methods involve sequence comparisons to known phage or prophage genes, comparisons to known bacterial genes, tRNA and dinucleotide analysis and hidden Markov scanning for attachment site recognition. Programs that can conduct such an analysis include Phage_Finder, Prophinder, Prophage Finder, and PHASTER (Lima-Mendez et al., Bioinformatics, 24: 863-865, 2008).

In some embodiments, prophage regions are identified in the *E. coli* genome and removed, to minimize change of prophage reactivation and induction. In some embodiments, the prophage regions are replaced with a resistance marker-containing cassette. In some embodiments, the resistance marker-containing cassette is a kanamycin resistance marker.

Recombineering is an efficient method of in vivo genetic engineering applicable to *E. coli* replicons, enabling the insertion or deletion of DNA sequences without the need for restriction sites. Recombineering is the preferred method for inserting large DNA molecules, as opposed to classical techniques utilizing restriction enzymes and DNA ligases, as these large DNA molecules are more likely to possess restriction sites within their sequence that can be cleaved by the restriction enzymes. Recombineering allows DNA cloned in *E. coli* to be modified via homologous recombination. With recombineering, it is now possible to introduce virtually any type of nutation into a bacterial artificial chromosome (BAC) using PCR-amplified, linear, double-stranded DNA targeting cassettes that have short regions of homology at their ends, or single-stranded oligonucleotides.

In one embodiment, the prophage region replaced is the ~18,000 bp region located between the cusS CDS and argU tRNA gene. In another embodiment, the ~44,000 bp region located between the cytosolic dsbC CDS and the remnants of the galM CDS. In some embodiments, both the ~18,000 bp region located between the cusS CDS and argU tRNA and the ~44,000 bp region located between the cytosolic dsbC CDS and the remnants of the galM CDS are replaced.

6-phosphogluconolactonase (pgl)

Minimizing posttranslational modifications made to heterologously expressed proteins, especially when the protein is manufactured for pharmaceutical and medical applications, is a key goal of bacterial engineering. Gluconylation of heterologously expressed protein is commonly observed in *E. coli*, possibly due to the accumulation of 6-phosphogluconolactone due to the absence of phosphogluconolactonase (pgl) in the pentose phosphate pathway (Aon et al., Appl Environ Microbiol, 74(4): 950-58, 2008). In some embodiments, pgl is added into the *E. coli* genome. In other embodiments, heterologous pgl is added into the *E. coli* genome.

clpB

ClpB is an ATP-dependent molecular chaperon, belonging to the Hsp100 family of ATPases associated with diverse cellular activities. ClpB is a key protein mediating the heat-shock response, with the capacity to rescue stress-damaged proteins from an aggregated state (Vale et al., *J Cell Biol,* 150: F13-F19, 2000). Unlike other Hsp100 protein ClpA, ClpB does not associate with the structurally and functionally unrelated ClpP protease, and does not direct the degradation of its substrate proteins (Wickner et al., Science, 286: 1888-93, 1999). Instead, ClpB rescues proteins from an aggregated state by mediating the disaggregation of stress-damaged proteins, with full recovery of the proteins requiring additional participation from the DnaK/Hsp70 chaperone system (Parsell et al., Nature, 372 (b): 475-78, 1994; Zolkiewski et al., Protein Sci, 8: 1899-1903, 1999). In some embodiments, the engineered *E. coli* is further engineered with a plasmid to express clpB.

PDI (Protein Disulfide Isomerase)

Secreted and cell-surface proteins are often stabilized by disulfide bonds. Early in protein folding, disulfide formation is error-prone; the wrong cysteines are connected, or the correct cysteines are paired but in a temporal order that inhibits folding. Cells correct for this with a specialized redox environment in the endoplasmic reticulum (ER), equipped with catalysts of disulfide formation and isomerization (Wilkinson et al., Biochim Biophys Acta, 1699(1-2): 35-44, 2004). Protein Disulfide Isomerase (PDI) is one such essential folding catalyst as well as a chaperone of the ER, which functions by introducing disulfides into proteins (oxidase activity), catalyzes the rearrangement of incorrect disulfides (isomerase activity), and stabilizes misfolded proteins (redox-dependent chaperone activity). In some embodiments, the engineered *E. coli* is further engineered with a plasmid to express PDI. In other embodiments, the engineered *E. coli* is further engineered with two plasmids, one to express clpB and one to express PDI.

Signal Peptides

Polypeptide gene products expressed or co-expressed by the methods of the disclosure can contain signal peptides or lack them, depending on whether it is desirable for such gene products to be exported from the host cell cytoplasm into the periplasm, or to be retained in the cytoplasm, respectively. Signal peptides (also termed signal sequences, leader sequences, or leader peptides) are characterized structurally by a stretch of hydrophobic amino acids, approximately five to twenty amino acids long and often around ten to fifteen amino acids in length, that tend to form a single alpha-helix. This hydrophobic stretch is often immediately preceded by a shorter stretch enriched in positively charged amino acids (particularly lysine). Signal peptides that are to be cleaved from the mature polypeptide typically end in a stretch of amino acids that are recognized and cleaved by signal peptidase. Signal peptides can be characterized functionally by the ability to direct transport of a polypeptide, either co-translationally or post-translationally, through the plasma membrane of prokaryotes (or the inner membrane of gram-negative bacteria like *E. coli*), or into the endoplasmic reticulum of eukaryotic cells. The degree to which a signal peptide enables a polypeptide to be transported into the periplasmic space of a host cell like *E. coli*, for example, can be determined by separating periplasmic proteins from proteins retained in the cytoplasm, using a method such as described in Example 12 of International Publication No. WO 2016/205570.

Examples of inducible promoters and related genes are, unless otherwise specified, from *Escherichia coli* ("*E. coli*") strain MG1655 (American Type Culture Collection deposit ATCC 700926), which is a substrain of *E. coli* K-12 (American Type Culture Collection deposit ATCC 10798). Table 1 of International Publication No. WO 2016/205570 lists the genomic locations, in *E. coli* MG1655, of the nucleotide sequences for these examples of inducible promoters and related genes. Nucleotide and other genetic sequences, referenced by genomic location as in Table 1 of International Publication No. WO 2016/205570, are expressly incorporated by reference herein. Additional information about *E. coli* promoters, genes, and strains described herein can be found in many public sources, including the online *E. coli* Wiki resource, located at ecoliwiki.net.

Arabinose Promoter (As used herein, 'arabinose' means L-arabinose.) Several *E. coli* operons involved in arabinose utilization are inducible by arabinose—araBAD, araC, arciE, and araFGH—but the terms 'arabinose promoter' and 'ara promoter' are typically used to designate the araBAD promoter. Several additional terms have been used to indicate the *E. coli* araBAD promoter, such as Para, ParaB, ParaBAD, and PBAD—The use herein of 'ara promoter' or any of the alternative terms given above, means the *E. coli* araBAD promoter. As can be seen from the use of another term, 'araC-araBAD promoter', the araBAD promoter is considered to be part of a bidirectional promoter, with the araBAD promoter controlling expression of the araBAD operon in one direction, and the araC promoter, in close proximity to and on the opposite strand from the araBAD promoter, controlling expression of the araC coding sequence in the other direction. The AraC protein is both a positive and a negative transcriptional regulator of the araBAD promoter. In the absence of arabinose, the AraC protein represses transcription from PBAD, but in the presence of arabinose, the AraC protein, which alters its conformation upon binding arabinose, becomes a positive regulatory element that allows transcription from PBAD—The araBAD operon encodes proteins that metabolize L-arabinose by converting it, through the intermediates L-ribulose and L-ribulose-phosphate, to D-xylulose-5-phosphate. For the purpose of maximizing induction of expression from an arabinose-inducible promoter, it is useful to eliminate or reduce the function of AraA, which catalyzes the conversion of L-arabinose to L-ribulose, and optionally to eliminate or reduce the function of at least one of AraB and AraD, as well. Eliminating or reducing the ability of host cells to decrease the effective concentration of arabinose in the cell, by eliminating or reducing the cell's ability to convert arabinose to other sugars, allows more arabinose to be available for induction of the arabinose-inducible promoter. The genes encoding the transporters which move arabinose into the host cell are araE, which encodes the low-affinity L-arabinose proton symporter, and the araFGH operon, which encodes the subunits of an ABC superfamily high-affinity L-arabinose transporter. Other proteins which can transport L-arabinose into the cell are certain mutants of the LacY lactose permease: the LacY (AlWC) and the LacY(AlWV) proteins, having a cysteine or a valine amino acid instead of alanine at position 177, respectively (Morgan-Kiss et al., *Proc Natd Acad Sci* USA 2002 May 28; 99(11): 7373-77). In order to achieve homogeneous induction of an arabinose-inducible promoter, it is useful to make transport of arabinose into the cell independent of regulation by arabinose. This can be accomplished by eliminating or reducing the activity of the AraFGH transporter proteins and altering the expression of araE so that it is only transcribed from a constitutive promoter. Constitutive expression of araE can be accomplished by eliminating or reducing the function of the native araE gene, and introducing into the cell an expression construct which includes a coding sequence for the AraE protein expressed from a constitutive promoter. Alternatively, in a cell lacking AraFGH function, the promoter controlling expression of the host cell's chromosomal araE gene can be changed from an arabinose-inducible promoter to a constitutive promoter. In a analogous manner, as additional alternatives for homogenous induction of an arabinose-inducible promoter, a host cell that lacks AraE function can have any functional AraFGH coding sequence present in the cell expressed from a constitutive promoter. As another alternative, it is possible to express both the araE gene and the araFGH operon from constitutive promoters, by replacing the native araE and araFGH promoters with constitutive promoters in the host chromosome. It is also possible to eliminate or reduce the activity of both the AraE and the AraFGH arabinose transporters, and in that situation to use a mutation in the LacY lactose permease that allows this protein to transport arabinose. Since expression of the lacY gene is not normally regulated by arabinose, use of a LacY mutant such as LacY(A177C) or LacY(A177V), will not lead to the 'all or none' induction phenomenon when the arabinose-inducible promoter is induced by the presence of arabinose. Because the LacY(A177C) protein appears to be more effective in transporting arabinose into the cell, use of polynucleotides encoding the LacY(A177C) protein is preferred to the use of polynucleotides encoding the LacY (A177V) protein.

Propionate Promoter

The 'propionate promoter' or 'prp promoter' is the promoter for the *E. coli* prpBCDE operon. Like the ara promoter, the prp promoter is part of a bidirectional promoter, controlling expression of the prpBCDE operon in one direction, and with the prpR promoter controlling expression of the prpR coding sequence in the other direction. The PrpR protein is the transcriptional regulator of the prp promoter and activates transcription from the prp promoter when the PrpR protein binds 2-methylcitrate ('2-MC'). Propionate (also called propanoate) is the ion, CH3CH2COO—, of propionic acid (or 'propanoic acid') and is the smallest of the 'fatty' acids having the general formula H(CH2)"COOH that shares certain properties of this class of molecules: producing an oily layer when salted out of water and having a soapy potassium salt. Commercially available propionate is generally sold as a monovalent cation salt of propionic acid, such as sodium propionate (CH3CH2COONa), or as a divalent cation salt, such as calcium propionate (Ca (CH3CH2COO)2). Propionate is membrane-permeable and is metabolized to 2-MC by conversion of propionate to propionyl-CoA by PrpE (propionyl-CoA synthetase), and then conversion of propionyl-CoA to 2-MC by PrpC (2-methylcitrate synthase). The other proteins encoded by the prpBCDE operon, PrpD (2-methylcitrate dehydratase) and PrpB (2-methylisocitrate lyase), are involved in further catabolism of 2-MC into smaller products such as pyruvate and succinate. In order to maximize induction of a propionate-inducible promoter by propionate added to the cell growth medium, it is therefore desirable to have a host cell with PrpC and PrpE activity, to convert propionate into 2-MC, but also having eliminated or reduced PrpD activity, and optionally eliminated or reduced PrpB activity as well, to prevent 2-MC from being metabolized. Another operon encoding proteins involved in 2-MC biosynthesis is the scpA-argK-scpBC operon, also called the sbm-yg/DGH operon. These genes encode proteins required for the conversion of succinate to propionyl-CoA, which can then be converted to 2-MC by PrpC. Elimination or reduction of the function of these proteins would remove a parallel pathway to produce the 2-MC inducer, and thus might reduce background levels of expression of a propionate-inducible promoter and increase sensitivity of the propionate-inducible promoter to exogenously supplied propionate. It has been found that a deletion of sbm-ygfD-ygfG-ygfH-ygfl, introduced into *E. coli* BL21(DE3) to create strain JSB (Lee and Keasling, "A propionate-inducible expression system for enteric bacteria", *Appl Environ Microbiol* 2005 November; 71(11): 6856-62), was helpful in reducing background expression in the absence of exogenously supplied inducer, but this deletion also reduced overall expression from the prp promoter in strain JSB. It should be noted, however, that the deletion sbm-ygfD-ygfG-ygfH-ygfl also apparently affects ygfl, which encodes a putative LysR-family transcriptional regulator of unknown function. The genes sbm-gyn/DGH are transcribed as one operon, and gulf is transcribed from the opposite strand. The 3' ends of the ygfti and ygfl coding sequences overlap by a few base pairs, so a deletion that takes out all of the sbm-yg/DGH operon apparently takes out ygfl coding function as well. Eliminating or reducing the function of a subset of the sbm-ygfDGH gene products, such as YgfG (also called ScpB, methylmalonyl-CoA decarboxylase), or deleting the majority of the sbm-yg/DGH (or scpA-argK-scpBC) operon while leaving enough of the 3' end of the ygfli (or scpC) gene so that the expression of ygfl is not affected, could be sufficient to reduce background expression from a propionate-inducible promoter without reducing the maximal level of induced expression.

Rhamnose Promoter

As used herein, 'rhamnose' means L-rhamnose. The 'rhamnose promoter' or 'rha promoter,' or PrhaSR, is the promoter for the *E. coli* rhaSR operon. Like the ara and prp promoters, the rha promoter is part of a bidirectional promoter, controlling expression of the rhaSR operon in one direction, and with the rhaBAD promoter controlling expression of the rhaBAD operon in the other direction. The rha promoter, however, has two transcriptional regulators involved in modulating expression: RhaR and RhaS. The RhaR protein activates expression of the rhaSR operon in the presence of rhamnose, while RhaS protein activates expression of the L-rhamnose catabolic and transport operons, rhaBAD and rhaT, respectively (Wickstrum et al, *J Bacteriol* 2010 January; 192(1): 225-32). Although the RhaS protein can also activate expression of the rhaSR operon, in effect RhaS negatively autoregulates this expression by interfering with the ability of the cyclic AMP receptor protein (CRP) to coactivate expression with RhaR to a much greater level. The rhaBAD operon encodes the rhamnose catabolic proteins RhaA (L-rhamnose isomerase), which converts L-rhamnose to L-rhamnulose; RhaB (rhamnulokinase), which phosphorylates L-rhamnulose to form L-rhamnulose-1-P; and RhaD (rhamnulose-1-phosphate aldolase), which converts L-rhamnulose-1-P to L-lactaldehyde and DHAP (dihydroxy acetone phosphate). To maximize the amount of rhamnose in the cell available for induction of expression from a rhamnose-inducible promoter, it is desirable to reduce the amount of rhamnose that is broken down by catalysis, by eliminating or reducing the function of RhaA, or optionally of RhaA and at least one of RhaB and RhaD. *E. coli* cells can also synthesize L-rhamnose from alpha-D-glucose-1-P through the activities of the proteins RmlA, RmlB, RmlC, and RmlD (also called RfbA, RfbB, RfbC, and RfbD, respectively) encoded by the rmlBDACX (or rfbBDACX) operon. To reduce background expression from a rhamnose-inducible promoter, and to enhance the sensitivity of induction of the rhamnose-inducible promoter by exogenously supplied rhamnose, it could be useful to eliminate or reduce the function of one or more of the RmlA, RmlB, RmlC, and RmlD.

RmlD Proteins

L-rhamnose is transported into the cell by RhaT, the rhamnose permease or L-rhamnose:proton symporter. As noted above, the expression of RhaT is activated by the transcriptional regulator RhaS. To make expression of RhaT independent of induction by rhamnose (which induces expression of RhaS), the host cell can be altered so that all functional RhaT coding sequences in the cell are expressed from constitutive promoters. Additionally, the coding sequences for RhaS can be deleted or inactivated, so that no functional RhaS is produced. By eliminating or reducing the function of RhaS in the cell, the level of expression from the rhaSR promoter is increased due to the absence of negative autoregulation by RhaS, and the level of expression of the rhamnose catalytic operon rhaBAD is decreased, further increasing the ability of rhamnose to induce expression from the rha promoter.

Xylose Promoter

As used herein, 'xylose' means D-xylose. The xylose promoter, or 'xyl promoter,' or PxyiA, means the promoter for the *E. coli* xylAB operon. The xylose promoter region is similar in organization to other inducible promoters in that the xylAB operon and the xylFGHR operon are both expressed from adjacent xylose-inducible promoters in opposite directions on the *E. coli* chromosome (Song and Park, *J Bacteriol.* 1997 November; 179(22): 7025-7032). The transcriptional regulator of both the PxyiA and PxyiF promoters is XylR, which activates expression of these promoters in the presence of xylose. The xylR gene is expressed either as part of the xylFGHR operon or from its own weak promoter, which is not inducible by xylose, located between the xylH and xylR protein-coding sequences. D-xylose is catabolized by XylA (D-xylose isomerase), which converts D-xylose to D-xylulose, which is then phosphorylated by XylB (xylulokinase) to form D-xylulose-5-P. To maximize the amount of xylose in the cell available for induction of expression from a xylose-inducible promoter, it is desirable to reduce the amount of xylose that is broken down by catalysis, by eliminating or reducing the function of at least XylA, or optionally of both XylA and XylB. The xylFGHR operon encodes XylF, XylG, and XylH, the subunits of an ABC super-family high-affinity D-xylose transporter. The xylE gene, which encodes the *E. coli* low-affinity xylose-proton symporter, represents a separate operon, the expression of which is also inducible by xylose. To make expression of a xylose transporter independent of induction by xylose, the host cell can be altered so that all functional xylose transporters are expressed from constitutive promoters. For example, the xylFGHR operon could be altered so that the xylFGH coding sequences are deleted, leaving XylR as the only active protein expressed from the xylose inducible PxyiF promoter, and with the xylE coding sequence expressed from a constitutive promoter rather than its native promoter. As another example, the xylR coding sequence is expressed from the PxyiA or the promoter in an expression construct, while either the xylFGHR operon is deleted and xylE is constitutively expressed, or alternatively an xylFGH operon (lacking the xylR coding sequence since that is present in an expression construct) is expressed from a constitutive promoter and the xylE coding sequence is deleted or altered so that it does not produce an active protein.

Lactose Promoter

The term 'lactose promoter' refers to the lactose-inducible promoter for the lacZYA operon, a promoter which is also called lacZpl; this lactose promoter is located at ca. 365603-365568 (minus strand, with the NA polymerase binding ('−35') site at ca. 365603-365598, the Pribnow box ('−10') at 365579-365573, and a transcription initiation site at 365567) in the genomic sequence of the *E. coli* K-12 substrain MG1655 (NCBI Reference Sequence NC 000913.2, 11 Jan. 2012). In some embodiments, inducible coexpression systems of the disclosure can comprise a lactose-inducible promoter such as the lacZYA promoter. In other embodiments, the inducible coexpression systems of the disclosure comprise one or more inducible promoters that are not lactose-inducible promoters.

Alkaline Phosphatase Promoter

The terms 'alkaline phosphatase promoter' and 'phoA promoter' refer to the promoter for the phoApsiF operon, a promoter which is induced under conditions of phosphate starvation. The phoA promoter region is located at ca. 401647-401746 (plus strand, with the Pribnow box ('−10') at 401695-401701 (Kikuchi et al., *Nucleic Acids Res* 1981 Nov. 11; 9(21): 5671-78)) in the genomic sequence of the *E. coli* K-12 substrain MG1655 (*NCBI Reference Sequence* NC 000913.3, 16 Dec. 2014). The transcriptional activator for the phoA promoter is PhoB, a transcriptional regulator that, along with the sensor protein PhoR, forms a two-component signal transduction system in *E. coli*. PhoB and PhoR are transcribed from the phoBR operon, located at ca. 417050-419300 (plus strand, with the PhoB coding sequence at 417,142-417,831 and the PhoR coding sequence at 417,889-419,184) in the genomic sequence of the *E. coli* K-12 substrain MG1655 (NCBI Reference Sequence NC 000913.3, 16 Dec. 2014). The phoA promoter differs from the inducible promoters described above in that it is induced by the lack of a substance—intracellular phosphate—rather than by the addition of an inducer. For this reason, the phoA promoter is generally used to direct transcription of gene products that are to be produced at a stage when the host cells are depleted for phosphate, such as the later stages of fermentation. In some embodiments, inducible coexpression systems of the disclosure can comprise a phoA promoter. In other embodiments, the inducible coexpression systems of the disclosure comprise one or more inducible promoters that are not phoA promoters.

As described herein, it may be advantageous or desirable to remove (e.g., by way of an inducible or constitutive "curing" mechanism) an expression construct described herein, e.g., if the cell line harboring the expression construct is or will be used for commercial purposes. Thus, in some embodiments, the expression construct may comprise a "kill switch." For example, in embodiment, the expression construct includes a temperature-sensitive origin of replication. Additional curing methods are known in the art and include using detergents and intercalating agents, drugs, and antibiotics (Buckner, M. M. C., et al., *FEMS Microbiology Reviews*, fuy031, 42, 2018, 781-804).

In some embodiments, polypeptides of the antibodies or antigen-binding fragment thereof, disclosed herein can be produced in vivo in an animal that has been engineered or transfected with one or more nucleic acid molecules encoding the polypeptides, according to any suitable method.

In some embodiments, an antibody or antigen-binding fragment thereof is produced in a cell-free system. Non-limiting exemplary cell-free systems are described, e.g., in Sitaraman et al., *Methods Mol. Biol.* 498: 229-44 (2009); *Spirin, Trends Biotechnol.* 22: 538-45 (2004); and Endo et al., *Biotechnol. Adv.* 21: 695-713 (2003).

Many vector systems are available for the expression of H and L chain nucleic acid sequence in mammalian cells (see Glover, 1985). Different approaches can be followed to obtain complete $H_2L_2$ antibodies. As discussed above, it is possible to co-express H and L chains in the same cells to achieve intracellular association and linkage of H and L chains into complete tetrameric $H_2L_2$ antibodies and/or antigen-binding fragment peptides. The co-expression can occur by using either the same or different plasmids in the same host. Genes for both H and L chains and/or CDR3 regions peptides can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing antigen-binding peptide fragments and/or $H_2L2$ molecules via either route could be transfected with plasmids encoding additional copies of peptides, H, L, or H plus L chains in conjunction with additional selectable markers to generate cell lines with enhanced properties, such as higher production of assembled $H_2L_2$ antibody molecules or enhanced stability of the transfected cell lines.

Additionally, plants have emerged as a convenient, safe, and economical alternative main-stream expression systems for recombinant antibody production, which are based on large scale culture of microbes or animal cells. Antibodies can be expressed in plant cell culture, or plants grown conventionally. The expression in plants may be systemic, limited to sub-cellular plastids, or limited to seeds (endosperms). Several plant-derived antibodies have reached advanced stages of development (see, e.g., Biolex, NC). In some aspects, provided herein are methods and systems for the production of a humanized antibody, which is prepared by a process which comprises maintaining a host transformed with a first expression vector which encodes the light chain of the humanized antibody and with a second expression vector which encodes the heavy chain of the humanized antibody under such conditions that each chain is expressed and isolating the humanized antibody formed by assembly of the thus-expressed chains. The first and second expression vectors can be the same vector. Also provided herein are DNA sequences encoding the light chain or the heavy chain of the humanized antibody; an expression vector which incorporates a said DNA sequence; and a host transformed with a said expression vector. Generating a humanized antibody from the sequences and information provided herein can be practiced by those of ordinary skill in the art without undue experimentation. In one approach, there are four general steps employed to humanize a monoclonal antibody. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Generation of Antibodies Using AT Methods

Provided herein are polypeptide and nucleic acid sequences for TL1A antibodies that have been generated using AI and machine learning techniques.

As used herein, "de novo design" (e.g., AI-based de novo design of individual antibody CDRs) refers to structure-based design of antigen-targeted antibodies. In one embodiment, for de novo design, the region of the antibody being designed is not provided as a sequence input and an experimental structure of the antibody in complex with the antigen is not provided as a structure input. The methods are generally described in WO 2023/154829, incorporated by reference in its entirety herein. Briefly, this method addresses the need for artificial intelligence (AI) and machine learning (ML) models trained to predict improved biomolecule (e.g., antibody or antibody fragment) sequences or properties using known biomolecule/binding partner complexes, as provided herein, in some embodiments, for several light chain elements portions of the overall completed antibody. In particular, the techniques include using de novo generative deep learning models to de novo design antibodies against three distinct targets in a zero-shot fashion, where all designs are the result of a single round of model generations with no follow-up optimization. The described techniques demonstrate zero-shot antibody design with extensive wet lab experimentation. As a first step towards fully de novo antibody design, the described techniques show that HCDR3 can be designed with generative AI methods using a model system of trastuzumab and its target antigen, human epidermal growth factor receptor 2 (HER2), as a model system. The present techniques may include de novo design of many (e.g., approximately 440,000 or more) unique HCDR3 variants of trastuzumab and screened for binding to HER2 using an Activity-specific Cell-Enrichment ("ACE") assay. As used herein, the term "quantitative affinity Activity-specific Cell-Enrichment" or "qaACE assay" refers to a high throughput assay for obtaining affinity and sequence data of biomolecule variants (U.S. Provisional Application No. 63/371,474, filed Aug. 15, 2022, and PCT/US23/60167, filed on Jan. 5, 2023, as well as PCT/US23/72153, each incorporated by reference in its entirety).

For example, quantitative affinity ACE ("qaACE") and the ACE analyses described further herein and known as "de novo ACE" or "dnACE," are methods for sampling the binding of antibody variants at high throughput using flow cytometry and next generation sequencing. The main goal of this method is to generate high throughput binding information and/or training data for an AI model to perform sequence-based binding predictions. This method can be applied to any antibody formats, including but not limited to mabs, Fabs, scFv, scFab, VHHs, nanobodies, etc. and could conceivably be applied to other binding drug formats as well.

As used herein, "inverse folding" (e.g., AI-based design of individual antibody CDRs based on inverse folding) refers to designing antibody sequences by using either an experimental crystal structure of an antibody-antigen complex or a predicted antibody-antigen complex structure with the prediction relying on the sequences of both antibody and antigen as input. Briefly, and similar to the above, this method addresses the need for artificial intelligence (AI) and machine learning (ML) models trained to predict biomolecules (e.g., antibody or antibody fragment) using known biomolecule/binding partner complexes. In particular, the techniques may include predicting the sequence of a biomolecule from a crystal structure of the biomolecule, a sequence of a binding-partner biomolecule which binds to the biomolecule, and/or a structure of the binding-partner biomolecule.

By predicting biomolecule sequences that may fold into a biomolecule structure, the described techniques can be applied downstream and upstream of drug discovery as biomolecule design and/or biomolecule validation. For example, an optimized model may output sequences by determining how a sequence may fold based on desired specifications of the resultant structure e.g., for the structure to be nonimmunogenic, robust to varying pH, more compact, and/or be a particular size, etc.

Similarly, the sequence or structure of an efficacious and proprietary biomolecule may not be available to the public. Biomolecule (e.g., antibody or antibody fragment) sequence folding techniques may allow for diversification and further discovery of drugs (biomolecules) sharing a similar structure but a different and non-proprietary sequence. Additionally, or alternatively, downstream drug discovery may utilize biomolecule structure prediction to perform in-silico validation of an AI-designed biomolecule sequence, for example, by comparing a reference structure for the sequence to a biomolecule structure predicted by the present techniques.

As used herein, "AI-guided affinity optimization" refers to designing biomolecule (e.g., antibody) sequence variants with pre-specified attributes. The methods are generally described in WO 2023/133462 and PCT Application NO: PCT/US23/72153, incorporated by reference in its entirety herein. Briefly, this method addresses the need for an artificial intelligence (AI) and machine learning (ML) model that is trained using the mapping between antibody sequence variants and experimental measurements (e.g., binding affinities, pH sensitivities, and other data types.). Once trained, the model is able to predict the binding affinities of unseen sequence variants. The described techniques include deep contextual language models which, combined with high-throughput and low-throughput binding affinity data, may predict binding affinities of unseen antibody sequence variants spanning a KD range of several (e.g., four) orders of magnitude. The techniques also enable measuring the "naturalness" of biomolecule (e.g., antibody) sequence variants, a widely applicable metric shown herein to be associated with downstream issues related to drug developability and immunogenicity. The techniques thus accelerate and improve biomolecule (e.g., antibody) engineering, and increase the success rate of practical applications (e.g., developing antibody drug candidates).

The aforementioned methods use or otherwise require experimental measurements such as binding affinities. An activity-specific cell-enrichment (ACE) assay that identifies host cells that express active gene product of interest (e.g., antibody or fragments thereof, as used herein) rather than inactive material, has been described in WO 2021/146626, incorporated herein in relevant part. Active gene products can be distinguished from inactive material by the ability of active gene product to specifically bind a binding partner molecule, or by the ability of gene product to participate in a chemical or enzymatic reaction, as examples. The presence of properly formed disulfide bonds in a polypeptide gene product is an indication that it is correctly folded and presumptively active. In the cell-enrichment methods, active gene product of interest is detected by utilizing an appropriate labeling complex that specifically binds to active gene product of interest, such as a labeled antigen if the gene product of interest is an antibody or Fab; or a labeled ligand if the gene product of interest is a receptor or a receptor fragment, where the ligand specifically binds to an active conformation of the receptor; or a labeled substrate or a labeled substrate analog if the gene product of interest is an enzyme, as examples. For any gene product of interest, if there is an available antibody or antibody fragment that specifically binds to the active gene product and not to inactive gene product, that antibody or antibody fragment can be used to label the active gene product of interest when attached to a detectable moiety.

A key strength of ACE is its ability to screen tens of thousands of "units of variation" in a single run. However, ongoing AI efforts applied to drug discovery add additional requirements to wet lab-only screenings, which impose additional optimization of ACE to generate datasets suitable for AI. Wet lab-only screenings aimed at selecting top performing variants do not require stringent quantitative analysis from an assay. Indeed, the iterative nature of such screenings is such that hits from the n−1 step are rescreened in step n, effectively weeding out n−1 false positives. Moreover, wet lab screenings are often tuned to selecting only a desired population of interest (for example, higher affinity variants), and as such the assay does not have to be quantitative over a large dynamic range of the parameter of interest (for example, antibody affinity). However, AI models for predicting quantitative predictions benefit from quantitative sequence variant training data. As such, quantitative sequence variant training data need to be accurate for the model to produce meaningful predictions down the line. The present disclosure addresses these needs and shortcomings.

As described herein, the aforementioned methods thus may use an augmentation of the ACE assay—quantitative affinity gaACE ("qaACE"), as a method for sampling the affinity of antibody variants at high throughput using flow cytometry and next generation sequencing to generate a gaACE score that correlates with KD. The main goal of this method is to generate highly quantitative high throughput training data for an AI model to perform sequence-based affinity predictions. This method can be applied to any antibody formats, including but not limited to mabs, Fabs, scFv, scFab, VHHs, nanobodies, etc. and could conceivably be applied to other binding drug formats as well.

In one embodiment described in WO 2023/133462 and thus provided herein, the first step in the gaACE process is to generate a mutationally diverse antibody library, that evenly sample the sequence space around the starting point antibody molecule. This library contains variants that span a range in mutational distance from the original sequence. In some embodiments including the Examples herein, the method provides a flow cytometry read out of an antibody, expressed in SoluPro *E. coli*, binding to a fluorescently labeled antigen probe. In the gaACE assay, setting expression of the antibody molecule is normalized such that a change in fluorescent signal in a cell will be due to different affinities of the expressed antibody variants in the cells binding to the fluorescent antigen probe. This normalization is accomplished via a generic target molecule probe that will bind to all variants and whose signal will be in an orthogonal fluorescent channel to the antigen probe. In this setting we show that the fluorescent signal of a variant is proportional to the measured KD of an antibody variant within a range. Given this proportionality, using FACS, cells containing antibody variants can be sorted that span a range (e.g., a distribution) of affinities.

After sorting across a range of affinity values with gating across the library population distribution, the cell material is sequenced and quantified for the prevalence of observed variants across the affinity gates (bins, tubes). Using the quantifications, an enrichment score is calculated for each variant. The enrichment scores generated via gaACE are an ideal data type for AI modeling purposes because of the accuracy and throughput.

In one exemplary workflow, the present disclosure provides a gaACE assay that comprises some or all of the following general steps:

1) Generation of an antibody or other drug molecule library for screening through gaACE expressed in a host cell such as SoluPro *E. coli.*
2) Identification of an antigen or binding partner probe that is fluorescently labeled for use in, for example, FACS via initial cytometry development process.
3) Use of generic probe to the target molecule variants that will allow for detection of expression level within a cell. This expression signal is used to gate a uniformly expression population to disambiguate affinity and expression signal related to epitope binding signal.
4) Sorting of cells across the affinity distribution.
5) Sequencing of cells sorted across the affinity distribution.
6) During the sequencing DNA barcodes or UMIs may be added via PCR amplification of the region of interest. These UMIs will enable absolute quantification of variants retrieved from the gates.
7) Generation of affinity correlated enrichment scores for each observed variant.
8) AI model training using enrichment score and antibody variant sequence.

Pharmaceutical Compositions and Medicaments

In one aspect, the present disclosure provides a composition comprising an antibody or antigen binding fragment thereof disclosed herein and/or a nucleic acid encoding the antibody or antigen binding fragment thereof disclosed herein. The nucleic acids encoding the antibodies or antigen binding fragments are described above including their sequences. For the clinical use of the methods described herein, administration of the antibodies or antigen binding fragments thereof, and/or nucleic acids encoding the antibodies or antigen binding fragments thereof of the present disclosure can include formulation into pharmaceutical compositions, pharmaceutical formulations, or medicaments, for administration, e.g., subcutaneous, intravenous, intradermal, intraperitoneal, oral, intramuscular, intracranial, or other routs of administration. In some embodiments, the antibodies or antigen binding fragments thereof, described herein, or nucleic acids encoding the antibodies or antigen binding fragments thereof can be administered along with any pharmaceutically acceptable carrier, excipient, or diluent, which results in an effective treatment and/or effective prophylaxis in the subject. Thus, in one aspect, the present disclosure provides pharmaceutical compositions comprising one or more antibodies or antigen binding fragments thereof, and/or nucleic acids encoding the one or more antibodies or antigen binding fragments thereof described herein, in combination with one or more pharmaceutically acceptable carrier, excipient, or diluent.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, an antibody or an antigen binding fragment thereof of the present disclosure. Examples include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like. Each carrier must be "acceptable" in the sense of being compatible with the other ingredients of the formulation and not injurious to the patient. The terms "excipient", "carrier", "pharmaceutically acceptable carrier", or the like are used interchangeably herein. The compositions of the present disclosure may further comprise one or more pharmaceutically acceptable carriers, excipients, and other agents that are incorporated into formulations to provide improved transfer, delivery, tolerance, and the like (herein collectively referred to as "pharmaceutically acceptable carriers or diluents"). A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA, 1998*, J. Pharm. Sci. Technol.* 52:238-311.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyl dimethyl benzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS®, or polyethylene glycol (PEG).

Optionally, the formulations comprising the compositions described herein contain a pharmaceutically acceptable salt, typically, e.g., sodium chloride, and preferably at about physiological concentrations. Optionally, the formulations of the disclosure can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are examples of preservatives. Optionally, the formulations of the disclosure can include a pharmaceutically acceptable surfactant at a concentration of 0.005 to 0.02%.

The compositions described herein can be specially formulated for administration of the antibody or antigen binding fragment thereof to a subject in solid, liquid or gel form, including those adapted for the following: (a) parenteral administration, for example, by subcutaneous, intramuscular, intravenous or epidural injection as, for example, a sterile solution or suspension, or sustained-release formulation; (b) topical application, for example, as a cream, ointment, or a controlled-release patch or spray applied to the skin; (c) intravaginally or intrarectally, for example, as a pessary, cream or foam; (d) ocularly; (e) transdermally; (f) transmucosally; or (g) nasally. Additionally, an antibody or antigen binding fragment thereof, or compositions of the present disclosure can be implanted into a patient or injected using a drug delivery system. See, e.g., Urquhart et al., 24 *Ann. Rev. Pharmacol. Toxicol.* 199 (1984); Controlled Release of Pesticides & Pharmaceuticals (Lewis, ed., Plenum Press, New York, 1981); U.S. Pat. Nos. 3,773,919, 3,270,960.

In some embodiments, sustained-release preparations can be used. Suitable examples of sustained-release preparations include semipermeable matrices of solid hydrophobic polymers containing an antibody or antigen binding fragment of the present disclosure, in which the matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they can denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions. In certain situations, the pharmaceutical composition can be delivered in a controlled release system. In one embodiment, a pump may be used (see Langer R. *Science* 249(4976):1527-33 (1990); Sefton 1987 *CRC Crit. Ref Biomed. Eng.* 14:201). In another embodiment, polymeric materials can be used. In yet another embodiment, a controlled release system can be placed in proximity of the composition's target, thus requiring only a fraction of the systemic dose (see, e.g., Goodson, in R. S. Langer and D. L. Wise (eds.), Medical Applications of Controlled Release, vol. 2, pp. 115-38 (CRC Press, Boca Raton, 1984)).

A pharmaceutical composition of the present disclosure can be delivered, e.g., subcutaneously, or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded. Numerous reusable pens and autoinjector delivery devices have applications in the subcutaneous delivery of a pharmaceutical composition of the present disclosure. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN70130™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition include, but certainly are not limited to the SOLOSTAR™ pen (Sanofi-Aventis), the FLEXPEN™ (Novo Nordisk), and the KWIKPEN™ (Eli Lilly).

The injectable preparations may include dosage forms for intravenous, subcutaneous, intracutaneous, and intramuscular injections, drip infusions, etc. These injectable preparations may be prepared by methods publicly known. For example, the injectable preparations may be prepared, e.g., by dissolving, suspending, or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Compositions of the present disclosure can be in the form of, for example, granules, powders, tablets, capsules, syrup, suppositories, injections, emulsions, elixirs, suspensions, or solutions. The amount of the previously mentioned antibody contained can be about 5 to about 500 mg per dosage form in a unit dose; especially in the form of injection, it is preferred that the aforesaid antibody is contained in about 5 to about 100 mg and in about 10 to about 250 mg for the other dosage forms.

For oral, buccal, and sublingual administration, powders, suspensions, granules, tablets, pills, capsules, gelcaps, and caplets are acceptable as solid dosage forms. These can be prepared, for example, by mixing one or more compounds of the instant disclosure, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or antioxidants such as ascorbic acid, tocopherol or cysteine, a disintegrating agent, binders, thickeners, buffers, sweeteners, flavoring agents, or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or par-enteral administration. In some embodiments, pharmaceutical compositions can be prepared in a lyophilized form. The lyophilized preparations can comprise a cryoprotectant known in the art. The term "cryoprotectants" as used herein generally includes agents, which provide stability to the protein from freezing-induced stresses. Examples of cryoprotectants include polyols such as, for example, mannitol, and include saccharides such as, for example, sucrose, as well as including surfactants such as, for example, polysorbate, poloxamer or polyethylene glycol, and the like. Cryoprotectants also contribute to the tonicity of the formulations. Pharmaceutically suitable surfactants, suspending agents, emulsifying agents, may be added for oral or par-enteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, iso-propyl alcohol, hexadecyl alcohol, glycerol, and propylene glycol. Ethers, such as but not limited to, poly(ethyleneglycol), petroleum hydrocarbons such as mineral oil and petrolatum; and water may also be used in suspension formulations.

For nasal administration, the pharmaceutical formulations and medicaments may be a spray or aerosol containing an appropriate solvent(s) and optionally other compounds such as, but not limited to, stabilizers, antimicrobial agents, antioxidants, pH modifiers, surfactants, bio-availability modifiers and combinations of these. A propellant for an aerosol formulation may include compressed air, nitrogen, carbon dioxide, or a hydrocarbon based low boiling solvent.

Injectable dosage forms include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is non-volatile, including natural or synthetic oils, fatty acids, mono-, di-, or triglycerides.

For injections, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

For rectal administration, the pharmaceutical formulations and medicaments may be in the form of a suppository, an ointment, an enema, a tablet, or a cream for release of compound in the intestines, sigmoid flexure and/or rectum. Rectal suppositories are prepared by mixing one or more compounds of the instant disclosure, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose, and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

The concentration of an antibody or an antigen binding fragment thereof in these compositions can vary widely, i.e., from less than about 10%, usually at least about 25% to as much as 75% or 90% by weight and will be selected primarily by fluid volumes, viscosities, etc., in accordance with the mode of administration selected. Actual methods for preparing orally, topically, and parenterally administrable compositions will be known or apparent to those skilled in the art and are described in detail in, for example, REMINGTON'S PHARMACEUTICAL SCIENCE, 19th ed., Mack Publishing Co., Easton, Pa. (1995), which is incorporated herein by reference.

In another embodiment of the disclosure, an article of manufacture containing materials useful for prophylaxis against or treatment of a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody of the disclosure. The label on or associated with, the container indicates that the composition is used for treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user stand-point, including other buffers, diluents, filters, needles, syringes, and package inserts with instructions for use.

The present disclosure provides, in some embodiments, a formulation buffer comprising histidine and arginine hydrochloride and optionally an emulsifier such as polysorbate (e.g., PS20, PS40, PS60 or PS80). In some embodiments, the pH of the formulation is approximately 5.0, 5.5, 6.0, 6.5, 7.0, or 7.5. As described herein, formulations are designed to allow stable drug product at high concentrations (e.g., 100, 150, 200, 250 mg/ml, or greater).

In one embodiment, the present disclosure provides the following formulation: 20 mM His, 140 mM Arg HCl, pH 6.0, and 0.04% PS80 (w/v).

Methods of Treatment and Prevention

The present disclosure provides methods for treating a subject with a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis. The methods comprise administering to the subject an effective amount of an antibody or antigen binding fragment thereof disclosed herein.

In one aspect, the disclosure provides methods for treatment or prevention of a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis, by the administration of an antibody or antigen-binding fragment thereof disclosed herein, to a patient in an amount effective to treat the patient.

In some embodiments, the subject has one or more co-morbidities or has an increased risk of infection. Non-limiting exemplary co-morbidities or an underlying condition that the subject can have include high blood pressure, cardiac disease, diabetes, lung disease, cancer, clots, thrombosis, autoimmune disease, an inflammatory disease, or a combination thereof. In some embodiments, the subject is immunocompromised. In some embodiments, the subject is pregnant. In some embodiments, the subject to be treated is symptomatic prior to the administration. In other embodiments, the subject to be treated is asymptomatic prior to the administration.

In one aspect, the present disclosure provides methods for treatment or prevention of a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis, comprising administering a nucleic acid, wherein the nucleic acid encodes for a VH, VL, CDR3 region of VH, or CDR3 region of VL, or antigen binding fragment thereof, wherein the nucleic acid comprises a sequence disclosed herein by way of gene therapy. Gene therapy refers to therapy performed by the administration to a subject of an expressed or expressible nucleic acid. In this embodiment of the disclosure, the nucleic acids produce their encoded protein that mediates a prophylactic or therapeutic effect. Any of the methods for gene therapy available in the art can be used according to the embodiments herein.

For general reviews of the methods of gene therapy, see Goldspiel et al., 1993, *Clinical Pharmacy* 12:488-505; Wu and Wu, 1991, *Biotherapy* 3:87-95; Tolstoshev, 1993, *Ann. Rev. Pharmacol. Toxicol.* 32:573-96; Mulligan, 1993, *Science* 260:926-32; and Morgan and Anderson, 1993, *Ann. Rev. Biochem.* 62:191-217; May 1993, TIBTECH 11(5): 155-215. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY. Delivery of a therapeutic antibody to appropriate cells can be affected via gene therapy ex vivo, in situ, or in vivo by use of any suitable approach known in the art, including by use of physical DNA transfer methods (e.g., liposomes or chemical treatments) or by use of viral vectors (e.g., adenovirus, adeno-associated virus, or a retrovirus). For example, for in vivo therapy, a nucleic acid encoding the desired antibody, either alone or in conjunction with a vector, liposome, or precipitate may be injected directly into the subject, and in some embodiments, may be injected at the site where the expression of the antibody compound is desired. For ex vivo treatment, the subject's cells are removed, the nucleic acid is introduced into these cells, and the modified cells are returned to the subject either directly or, for example, encapsulated within porous membranes which are implanted into the patient. See, e.g., U.S. Pat. Nos. 4,892,538 and 5,283,187. There are a variety of techniques available for introducing nucleic acids into viable cells. The techniques vary depending upon whether the nucleic acid is transferred into cultured cells in vitro or in vivo in the cells of the intended host. Techniques suitable for the transfer of nucleic acid into mammalian cells in vitro include the use of liposomes, electroporation, microinjection, cell fusion, DEAE-dextran, and calcium phosphate precipitation. A commonly used vector for ex vivo delivery of a nucleic acid is a retrovirus.

Other in vivo nucleic acid transfer techniques include transfection with viral vectors (such as adenovirus, Herpes simplex I virus, or adeno-associated virus) and lipid-based systems. Nucleic acid and transfection agents are optionally associated with microparticles. Exemplary transfection agents include calcium phosphate or calcium chloride co-precipitation, DEAE-dextran-mediated transfection, quaternary ammonium amphiphile DOTMA ((dioleoyloxypropyl) trimethylammonium bromide, commercialized as Lipofectin by GIBCO-BRL)) (Felgner et al, (1987) *Proc. Natl. Acad. Sci. USA* 84, 7413-17; Malone et al. (1989) *Proc. Natd Acad.*

*Sci. USA* 86 6077-6081); lipophilic glutamate diesters with pendent trimethylammonium heads (Ito et al. (1990) *Biochem. Biophys. Acta* 1023, 124-32); the metabolizable parent lipids such as the cationic lipid dioctadecylamido glycylspermine (DOGS, Transfect am, Promega) and dipalmitoyl phosphatidyl ethanolamylspermine (DPPES) (J. P. Behr (1986) *Tetrahedron Lett.* 27, 5861-64; J. P. Behr et al. (1989) *Proc. Natl. Acad. Sci. USA* 86, 6982-86); metabolizable quaternary ammonium salts (DOTB, N-(1-[2,3-dioleoyloxy]propyl)-N,N,N-trimethylammonium methyl sulfate (DOTAP) (Boehringer Mannheim), polyethyleneimine (PEI), dioleoyl esters, ChoTB, ChoSC, DOSC) (Leventis et al. (1990) *Biochim. Inter.* 22, 235-41); 3beta[N-(N',N'-dimethylaminoethane)-carbamoyl]cholesterol (DC-Chol), dioleoylphosphatidyl ethanolamine (DOPE)/3beta[N-(N',N' dimethylaminoethane)-carbamoyl]cholesterol DC-Chol in one-to-one mixtures (Gao et al., (1991) *Biochim. Biophys. Acta* 1065, 8-14), spermine, spermidine, lipopolyamines (Behr et al., *Bioconjugate Chem,* 1994, 5: 382-89), lipophilic polylysines (LPLL) (Zhou et al., (1991) *Biochim. Biophys. Acta* 939, 8-18), [[(1,1,3,3 tetramethyl butyl) cresoxy]ethoxy]ethyl]dimethylbenzylamine hydroxide (DEBDA hydroxide) with excess phosphatidylcholine/cholesterol (Ballas et al., (1988) *Biochim. Biophys. Acta* 939, 8-18), cetyltrimethylammonium bromide (CTAB)/DOPE mixtures (Pinnaduwage et al, (1989) *Biochim. Biophys. Acta* 985, 33-37), lipophilic diester of glutamic acid (TMAG) with DOPE, CTAB, DEBDA, didodecylammonium bromide (DDAB), and stearylamine in admixture with phosphatidylethanolamine (Rose et al., (1991) *Biotechnique* 10, 520-25), DDAB/DOPE (Transfect ACE, GIBCO BRL), and oligogalactose bearing lipids. Exemplary transfection enhancer agents that increase the efficiency of transfer include, for example, DEAE-dextran, polybrene, lysosome-disruptive peptide (Ohmori N I et al, *Biochem Biophys Res Commun* Jun. 27, 1997; 235(3):726-29), chondroitan-based proteoglycans, sulfated proteoglycans, polyethylenimine, polylysine (Pollard H et al. *J Biol Chem,* 1998 273 (13):7507-11), integrin-binding peptide CYGGRGDTP, linear dextran Nona saccharide, glycerol, cholesteryl groups tethered at the 3'-terminal internucleoside link of an oligonucleotide (Letsinger, R. L. 1989 *Proc Nat Acad Sci USA* 86: (17): 6553-56), lysophosphatide, Lys phosphatidylcholine, lysophosphatidylethanolamine, and 1-oleoyl Lys phosphatidylcholine.

In some situations, it may be desirable to deliver the nucleic acid with an agent that directs the nucleic acid containing vector to host cells. Such "targeting" molecules include antibodies specific for a cell-surface membrane protein on the target cell, or a ligand for a receptor on the target cell. Where liposomes are employed, proteins which bind to a cell-surface membrane protein associated with endocytosis may be used for targeting and/or to facilitate uptake. Examples of such proteins include capsid proteins and fragments thereof tropic for a particular cell type, antibodies for proteins which undergo internalization in cycling, and proteins that target intracellular localization and enhance intracellular half-life. In other embodiments, receptor-mediated endocytosis can be used. Such methods are described, for example, in Wu et al., 1987 or Wagner et al., 1990. For review of the currently known gene marking and gene therapy protocols, see Anderson 1992. See also WO 93/25673 and the references cited therein.

In some embodiments, the subject is exhibiting one or more symptoms associated with a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis.

As used herein, a "subject", "patient", "individual" and like terms are used interchangeably and refers to a vertebrate, a mammal, a primate, or a human. A subject can be male or female. A subject can be one who has been previously diagnosed with or identified as suffering from an infection with a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis. A subject can be one who is currently being treated for, or seeking treatment, monitoring, adjustment or modification of an existing therapeutic treatment, or is at a risk of developing an infection with a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis. Mammals include, without limitation, humans, primates, rodents, wild or domesticated animals, including feral animals, farm animals, sport animals, and pets. Primates include, for example, chimpanzees, cynomologous monkeys, spider monkeys, and macaques, e.g., Rhesus. Rodents include, for example, mice, rats, woodchucks, ferrets, rabbits, and hamsters. Domestic and game animals include, for example, cows, horses, pigs, deer, bison, buffalo, feline species, e.g., domestic cat, and canine species, e.g., dog, fox, wolf, avian species, e.g., chicken, emu, ostrich, and fish, e.g., trout, catfish, and salmon. Mammals other than humans can be advantageously used as subjects that represent animal models of conditions or disorders associated with infection with a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis. In addition, the compositions and methods described herein can be used to treat domesticated animals and/or pets. In some embodiments, the subject is a human.

The terms "disease," "disorder," or "condition" are used interchangeably herein, refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailment, malady, disorder, sickness, illness, complaint, or affectation.

The term "in need thereof" when used in the context of a therapeutic or prophylactic treatment, means having a disease, being diagnosed with a disease, or being in need of preventing a disease, e.g., for one at risk of developing the disease. Thus, a subject in need thereof can be a subject in need of treating or preventing a disease.

As used herein, the term "administering," refers to the placement of a compound (e.g., an antibody or antigen binding fragment thereof as disclosed herein) into a subject by a method or route that results in at least partial delivery of the agent at a desired site. Pharmaceutical compositions comprising an antibody or antigen binding fragment thereof, disclosed herein can be administered by any appropriate route which results in an effective treatment in the subject, including but not limited to intravenous, intraarterial, injection or infusion directly into a tissue parenchyma, etc. Where necessary or desired, administration can include, for example, intracerebroventricular ("ice") administration, intranasal administration, intracranial administration, intracelial administration, intracerebellar administration, or intrathecal administration.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of the antibody or antibody fragment other than directly into a target site, tissue, or organ, such as a tumor site, such that it enters the subject's circulatory system and, thus, is subject to metabolism and other like processes.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

The term "effective amount" as used herein refers to the amount of an antibody or antigen binding fragment thereof or composition comprising the same needed to alleviate at least one or more symptom of the disease or disorder and relates to a sufficient amount of pharmacological composition to provide the desired effect. The term "therapeutically effective amount" therefore refers to an amount of an antibody or antigen binding fragment thereof using the methods as disclosed herein, that is sufficient to affect a particular effect when administered to a typical subject. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". For any given case, however, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $LD_{50}/ED_{50}$-Compositions and methods that exhibit large therapeutic indices are preferred. A therapeutically effective dose can be estimated initially from cell culture assays. Also, a dose can be formulated in animal models to achieve a circulating plasma concentration range that includes the $IC_{50}$ (i.e., the concentration of the antibody or antigen binding fragment thereof), which achieves a half-maximal inhibition of symptoms as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

The terms "increased," "increase," or "enhance" are all used herein to generally mean an increase by a statically significant amount; for the avoidance of doubt, the terms "increased", "increase", or "enhance", mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The terms "decrease," "reduce," "reduction," "lower" or "lowering," or "inhibit" are all used herein generally to mean a decrease by a statistically significant amount. For example, "decrease", "reduce", "reduction", or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., tumor size after treatment as compared to a reference level prior to the treatment), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease. Reduce or inhibit can refer to, for example, the symptoms of the disorder being treated, or the viral titer measurable in a subject's blood or other bodily fluids.

The antibodies or antigen binding fragments thereof or the compositions described herein (e.g., comprising an antibody or antigen binding fragment thereof, or a nucleic acid encoding said antibody or antigen binding fragment thereof described herein) can be administered alone or in combination with an additional therapeutic agent or therapy. In some embodiments, the methods of the present disclosure further comprise administering an additional therapeutic agent or therapy (e.g., administering a combination of an antibody disclosed herein and an additional therapeutic agent or therapy. In some embodiments, a combination with an additional therapeutic agent or therapy induces a synergistic effect relative to an effect induced upon administering the antibody or antigen binding fragment thereof or the composition alone, or the additional therapeutic agent or therapy alone. In some embodiments, the synergistic effect is therapeutic or prophylactic. In some embodiments, a combination with an additional therapeutic agent or therapy induces an additive effect relative to an effect induced upon administering the antibody or antigen binding fragment thereof, or the composition alone, or the additional therapeutic agent or therapy alone. In some embodiments, the additive effect is therapeutic or prophylactic.

In some embodiments, an antibody or an antigen binding fragment thereof or a composition disclosed herein is administered, for the prevention or treatment of a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis, at least 1 minute, 15 minutes, 30 minutes, 45 minutes, 1 hour, 2 hours, 4 hours, 6 hours, 8 hours, 12 hours, 24 hours, 2 days, or 1 week before), subsequent to administering an additional therapeutic agent or therapy. In some embodiments, an antibody or antigen binding fragment thereof or a composition disclosed herein is administered, for the prevention or treatment of a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis, at least 1 minute, 15 minutes, 30 minutes, 45 minutes, 1 hour, 2 hours, 4 hours, 6 hours, 8 hours, 12 hours, 24 hours, 2 days, or 1 week before), prior to administering an additional therapeutic agent or therapy. In some embodiments, an antibody or an antigen binding fragment thereof, or a composition disclosed herein is administered, for the prevention or treatment of a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis concomitantly with an additional therapeutic agent or therapy.

In some embodiments, the additional therapeutic agent or therapy is useful for treating an infection of a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis. In some embodiments, the additional therapy is convalescent plasma therapy. In some embodiments, an additional therapeutic agent, can be a small molecule, an mRNA vaccine, a peptide, a peptide-body, a cytotoxic agent, a cytostatic agent, immunological modifier, interferon, interleukin, immunostimulatory growth hormone, cytokine, vitamin, mineral, aromatase inhibitor, RNAi, Histone Deacetylase Inhibitor, proteasome inhibitor, another antibody (for example, a TL1A neutralizing antibody), immunostimulatory antibody, a NSAID, a corticosteroid, a dietary supplement such as an antioxidant, cisplatin, ifosfamide, paclitaxel, taxanes, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, taxol, one or more antibiotics (e.g., doxycycline, Azithromycin, etc.); one or more decongestants (e.g., Mucinex, Sudafed, etc.); one or more anti-histamines and/or glucocorticoids (e.g., Zyrtec, Claritin, Allegra, fluticasone luroate, etc.); one or more pain relievers (e.g., acetominophen); one or more zinc-containing medications (e.g., Zycam, etc.); Azithromycin, hydroquinolone, or a combination thereof; one or more integrase inhibitors (e.g. Bictegravir, dolutegravir (Tivicay), elvitegravir, raltegravir, or a combination thereof); one or more nucleoside/nucleotide reverse transcriptase inhibitors (NRTIs; e.g., abacavir (Ziagen), emtricitabine (Emtriva), lamivudine (Epivir), tenofovir alafenamide fumarate (Vemlidy), tenofovir disoproxil fumarate (Viread), zidovudine (Retrovir), didanosine (Videx, Videx EC), stavudine (Zerit), or a combination thereof); a combination of NRTIs (e.g., (i) abacavir, lamivudine, and zidovudine (Trizivir), abacavir and lamivudine (Epzicom), (iii) emtricitabine and tenofovir alafenamide fumarate (Descovy), (iv) emtricitabine and tenofovir disoproxil fumarate (Truvada), (v) lamivudine and tenofovir disoproxil fumarate (Cimduo, Temixys), (vi) lamivudine and zidovudine (Combivir), etc.); a combination of Descovy and Truvada; one or more non-nucleoside reverse transcriptase inhibitors (NNRTIs; e.g., doravirine (Pifeltro), efavirenz (Sustiva), etravirine (Intelence), nevirapine (Viramune, Viramune rilpivirine (Edurant), delavirdine (Rescriptor), or a combination thereof); one or more Cytochrome P4503A (CYP3A) inhibitors (e.g., cobicistat (Tybost), ritonavir (Norvir), etc.); one or more protease inhibitors (PIs; e.g., atazanavir (Reyataz), darunavir (Prezista), fosamprenavir (Lexiva), lopinavir, ritonavir (Norvir), tipranavir (Aptivus), etc.); one or PIs in combination with cobicistat, ritonavir, Lopinavir, Tipranavir, Atazanavir, fosamprenavir, indinavir (Crixivan), nelfinavir (Viracept), saquinavir (Invirase), or a combination thereof; Atazanavir; fosamprenavir; a combination of Atazanavir, darunavir and cobicistat; one or more fusion inhibitors (e.g., enfuvirtide (Fuzeon); one or more post-attachment inhibitors (e.g., ibalizumab-uiyk (Trogarzo)); one or more Chemokine coreceptor antagonists (CCR5 antagonists; maraviroc (Selzentry)); and one or more viral entry inhibitors (e.g., enfuvirtide (Fuzeon), ibalizumab-uiyk (Trogarzo), maraviroc (Selzentry), etc.); or a combination thereof.

In some embodiments, the additional therapeutic agent can be an additional anti-TL1A antibody or an antigen binding fragment thereof.

In some embodiments, the additional therapeutic agent can be an anti-inflammatory therapy such as, for example, a NSAID including Diclofenac, Diflunisal, Etodolac, Fenoprofen, Flurbiprofen, Ibuprofen, Indomethacin, Ketoprofen, Ketorolac, Mefenamic acid, Meloxicam, Nabumetone, Naproxen, Oxaprozin, Piroxicam, Sulindac, Tolmetin, COX-2 Selective NSAIDs such as Celecoxib, Rofecoxib and/or Valdecoxib.

In some embodiments, the additional therapeutic agent can be an anti-cancer agent including, for example, radiotherapy, chemotherapy, surgery, small molecule inhibitors, and checkpoint inhibitors. In one embodiment, the therapeutic agent is cyclophosphamide. In other embodiments, the checkpoint inhibitor is selected from the group consisting of an inhibitor of CTLA-4, 4-1BB (CD137), 4-1BBL (CD137L), PDL1, PDL2, PD1, B7-H3, B7-H4, BTLA, HVEM, TIM3, GAL9, LAG3, TIM3, B7H3, B7H4, VISTA, KIR, BTLA, SIGLEC9, and 2B4. In some embodiments, the checkpoint inhibitor is pembrolizumab, avelumab, atezolizumab, cetrelimab, dostarlimab, cemiplimab, spartalizumab, camrelizumab, durvalumab, or nivolumab.

Examples of additional active agents contemplated for use in combination therapies include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and paclitaxel protein-bound particles (ABRAXANE®) and doxetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine, docetaxel, platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as TARGRETIN™ (bexarotene), PANRETIN™ (alitretinoin); and ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids, or derivatives of any of the above. Further cancer active agents include sorafenib and other protein kinase inhibitors such as afatinib, axitinib, bevacizumab, cetuximab, crizotinib, dasatinib, erlotinib, fostamatinib, gefitinib, imatinib, lapatinib, lenvatinib, mubritinib, nilotinib, panitumumab, pazopanib, pegaptanib, ranibizumab, ruxolitinib, trastuzumab, vandetanib, vemurafenib, and sunitinib; sirolimus (rapamycin), everolimus and other mTOR inhibitors.

In further embodiments, an antibody described herein is administered in combination with a TLR4 agonist, TLR8 agonist, or TLR9 agonist. Such an agonist may be selected from peptidoglycan, polyI:C, CpG, 3M003, flagellin, and *Leishmania* homolog of eukaryotic ribosomal elongation and initiation factor 4a (LeIF).

In some embodiments, an antibody described herein is administered in combination with a cytokine. In some embodiments, the compositions disclosed herein may be administered in conjunction with molecules targeting one or more of the following: Adhesion: MAdCAM1, ICAM1, VCAM1, CD103; Inhibitory Mediators: IDO, TDO; MDSCs/Tregs: NOS1, arginase, CSFR1, FOXP3, cyclophosphamide, PI3Kgamma, PI3Kdelta, tasquinimod; Immunosuppression: TGFβ, IL-10; Priming and Presenting: BATF3, XCR1/XCL1, STING, INFalpha; Apoptotic Recycling: IL-6, surviving, IAP, mTOR, MCL1, PI3K; T-Cell Trafficking: CXCL9/10/11, CXCL1/13, CCL2/5, anti-LIGHT, anti-CCR5; Oncogenic Activation: WNT-beta-cat, MEK, PPARgamma, FGFR3, TKIs, MET; Epigenetic Reprogramming: HDAC, HMA, BET; Angiogenesis immune modulation: VEGF(alpha, beta, gamma); Hypoxia: HIFlalpha, adenosine, anitADORA2A, anti-CD73, and anti-CD39.

In certain embodiments, an antibody disclosed herein may be administered in conjunction with a histone deacetylase (HDAC) inhibitor. HDAC inhibitors include hydroxamates, cyclic peptides, aliphatic acids and benzamides. Illustrative HDAC inhibitors contemplated for use herein include, but are not limited to, Suberoylanilide hydroxamic acid (SAHA/Vorinostat/Zolinza), Trichostatin A (TSA), PXD-101, Depsipeptide (FK228/romidepsin/ISTODAX®), panobinostat (LBH589), MS-275, Mocetinostat (MGCD0103), ACY-738, TMP195, Tucidinostat, valproic acid, sodium phenylbutyrate, 5-aza-2'-deoxycytidine (decitabine). See, e.g., Kim and Bae, *Am J Transl Res* 2011; 3(2):166-179; Odunsi et al., *Cancer Immunol Res.* 2014 Jan. 1; 2(1): 37-49. Other HDAC inhibitors include Vorinostat (SAHA, MK0683), Entinostat (MS-275), Panobinostat (LBH589), Trichostatin A (TSA), Mocetinostat (MGCD0103), ACY-738, Tucidinostat (Chidamide), TMP195, Citarinostat (ACY-241), Belinostat (PXD101), Romidepsin (FK228, Depsipeptide), MC1568, Tubastatin A HCl, Givinostat (ITF2357), Dacinostat (LAQ824), CUDC-101, Quisinostat (JNJ-26481585) 2HCl, Pracinostat (SB939), PCI-34051, Droxinostat, Abexinostat (PCI-24781), RGFP966, AR-42, Ricolinostat (ACY-1215), Valproic acid sodium salt (Sodium valproate), Tacedinaline (CI994), CUDC-907, Sodium butyrate, Curcumin, M344, Tubacin, RG2833 (RGFP109), Resminostat, Divalproex Sodium, Scriptaid, and Tubastatin A. In some embodiments, the compositions disclosed herein may be administered in conjunction with molecules targeting one or more of the following: Adhesion: MAdCAM1, ICAM1, VCAM1, CD103; Inhibitory Mediators: IDO, TDO; MDSCs/Tregs: NOS1, arginase, CSFR1, FOXP3, cyclophosphamide, PI3Kgamma, PI3Kdelta, tasquinimod; Immunosuppression: TGFβ, IL-10; Priming and Presenting: BATF3, XCR1/XCL1, STING, INFalpha; Apoptotic Recycling: IL-6, surviving, IAP, mTOR, MCL1, PI3K; T-Cell Trafficking: CXCL9/10/11, CXCL1/13, CCL2/5, anti-LIGHT, anti-CCR5; Oncogenic Activation: WNT-beta-cat, MEK, PPAR-gamma, FGFR3, TKIs, MET; Epigenetic Reprogramming: HDAC, HMA, BET; Angiogenesis immune modulation: VEGF(alpha, beta, gamma); Hypoxia: HIFlalpha, adenosine, anitADORA2A, anti-CD73, and anti-CD39.

In certain embodiments, an antibody disclosed herein may be administered in conjunction with a histone deacetylase (HDAC) inhibitor. HDAC inhibitors include hydroxamates, cyclic peptides, aliphatic acids and benzamides. Illustrative HDAC inhibitors contemplated for use herein include, but are not limited to, Suberoylanilide hydroxamic acid (SAHA/Vorinostat/Zolinza), Trichostatin A (TSA), PXD-101, Depsipeptide (FK228/romidepsin/ISTODAX®), panobinostat (LBH589), MS-275, Mocetinostat (MGCD0103), ACY-738, TMP195, Tucidinostat, valproic acid, sodium phenylbutyrate, 5-aza-2'-deoxycytidine (decitabine). See, e.g., Kim and Bae, Am J Transl Res 2011; 3(2):166-179; Odunsi et al., Cancer Immunol Res. 2014 Jan. 1; 2(1): 37-49. Other HDAC inhibitors include Vorinostat (SAHA, MK0683), Entinostat (MS-275), Panobinostat (LBH589), Trichostatin A (TSA), Mocetinostat (MGCD0103), ACY-738, Tucidinostat (Chidamide), TMP195, Citarinostat (ACY-241), Belinostat I1I (PXD101), Romidepsin (FK228, Depsipeptide), MC1568, Tubastatin A HCl, Givinostat (ITF2357), Dacinostat (LAQ824), CUDC-101, Quisinostat (JNJ-26481585) 2HCl, Pracinostat (SB939), PCI-34051, Droxinostat, Abexinostat (PCI-24781), RGFP966, AR-42, Ricolinostat (ACY-1215), Valproic acid sodium salt (Sodium valproate), Tacedinaline (CI994), CUDC-907, Sodium butyrate, Curcumin, M344, Tubacin, RG2833 (RGFP109), Resminostat, Divalproex Sodium, Scriptaid, and Tubastatin A.

In some embodiments, the additional therapeutic agent can be an agent for the treatment of rheumatoid arthritis including for example, non-steroidal anti-inflammatory agents (NSAIDs), corticosteroids, disease modifying anti-rheumatic drugs (DMARDs), methotrexate, sulfasalazine, leflunomide (Arava®), etanercept (Enbrel®), infliximab (Remicade®), adalimumab (Humira®), certolizumab pegol (Cimzia®), golimumab (Simponi®), abatacept (Orencia®), rituximab (Rituxan®), tocilizumab (Actemra®), anakinra (Kineret®), antimalarials (e.g. Plaquenil®), azathioprine (Imuran) and cyclosporine.

In some embodiments, the additional therapeutic agent can be an agent for the treatment of atopic dermatitis including for example, cyclosporine, azathioprine, methotrexate, and mycophenolate mofetil.

In some embodiments, the additional therapeutic agent can be an agent for the treatment of lupus erythematosus including for example, azathioprine, cyclophosphamide, mycophenolate mofetil, voclosporin, and methotrexate.

In some embodiments, the additional therapeutic agent can be an agent for the treatment of asthma including for example, prednisone, methylprednisolone, prednisolone, epinephrine, albuterol, levalbuterl, zafirlukast, fluticasone, salmeterol, ciclesonide, mometasone, vilanterol, reslizumab, formoterol, dupilimab, benralizumab, mepolizumab, budesonide, beclomethasone, montelukast, tiotropium, Tezepelumab, fluticasone furoate, umeclidinium, vilanterol, omalizumab.

In some embodiments, the additional therapeutic agent can be an agent for the treatment of psoriasis including for example, corticosteroids, cyclosporine, methotrexate, Adalimumab (Humira), Adalimumab-adbm (Cyltezo), Brodalumab (Siliq), Certolizumab pegol (Cimzia), Etanercept (Enbrel), Etanercept-szzs (Erelzi), Guselkumab (Tremfya), Infliximab (Remicade), Ixekizumab (Taltz), Risankizumab-rzaa (SKYRIZI), Secukinumab (Cosentyx), and Ustekinumab (Stelara).

In some embodiments, the additional therapeutic agent can be an agent for the treatment of intestinal fibrosis including for example, aminosalicylates such as mesalamine (Delzicol, Rowasa, others), balsalazide (Colazal) and olsalazine (Dipentum), steroids such as prednisone; Azathioprine (Imuran®), 6-Mercaptopurine (Purinethol®), and Methotrexate; Infliximab (Remicade®), Adalimumab (Humira®), and Certolizumab Pegol (Cimzia®); and Natalizumab (Tysabri®).

In some embodiments, the additional therapeutic agent can be an agent for the treatment of pulmonary fibrosis including for example, mycophenolate mofetil, and infliximab.

In some embodiments, the additional therapeutic agent can be an agent for the treatment of inflammatory bowel disease (IBD) including for example, aminosalicylates such as mesalamine (Delzicol, Rowasa, others), balsalazide (Colazal) and olsalazine (Dipentum), steroids such as prednisone; Azathioprine (Imuran®), 6-Mercaptopurine (Purinethol®), and Methotrexate; Infliximab (Remicade®), Adalimumab (Humira®), and Certolizumab Pegol (Cimzia®); and Natalizumab (Tysabri®).

In some embodiments, the additional therapeutic agent can be an agent for the treatment of primary biliary cirrhosis including for example, ursodeoxycholic acid (UDCA) and obeticholic acid (OCA).

In some embodiments, the additional therapeutic agent can be an agent for the treatment of primary biliary cholingitis including for example, ursodeoxycholic acid (UDCA) and obeticholic acid (OCA), fibrates (Tricor), and budenoiside.

In some embodiments, the additional therapeutic agent can be an agent for the treatment of ankylosing spondylitis including for example, NSAIDS, COX-2 inhibitors, Etanercept (Enbrel), Infliximab (Remicade), Adalimumab (Humira), Golimumab (Simponi), Certolizumab (Cimzia), and Secukinumab (Cosentyx).

In some embodiments, the additional therapeutic agent can be an agent for the treatment of liver fibrosis including for example, ACE inhibitors such as benazepril, Lisinopril, and ramipril.

In some embodiments, the additional therapeutic agent can be an agent for the treatment of Crohn's disease including for example, Sulfasalazine, Mesalamine, Olsalazine, Balsalazide, Prednisone, Methylprednisolone, Azathioprine, 6-mercaptopurine, Cyclosporine, Tacrolimus, Metronidazole, Ampicillin, Ciprofloxacin, Adalimumab, Certolizumab pegol, Infliximab, Natalizumab, Risankizumab-rzaa, Ustekinumab, Vedolizumab, and Upadacitinib.

In some embodiments, the additional therapeutic agent can be an agent for the treatment of ulcerative colitis including for example, Sulfasalazine, Mesalamine, Olsalazine, Balsalazide, Prednisone, Methylprednisolone, Budesonide, Azathioprine, 6-mercaptopurine, Cyclosporine, Tacrolimus, Ozanimod, Tofacitinib, Upadacitinib, Adalimumab, Golimumab, Infliximab, Ustekinumab, and Vedolizumab.

The methods and compositions of the present disclosure contemplate single antibody or antigen binding fragment thereof, disclosed herein, as well as combinations, or "cocktails," of more than one antibody or antigen binding fragment thereof, disclosed herein. In some embodiments, more than one antibody comprises at least 2, at least 3, at least 4, at least 5, or more antibodies or antigen binding fragments thereof, disclosed herein. In some embodiments, the methods of the present disclosure comprising administering to a subject, a first antibody disclosed herein, or a nucleic acid encoding the first antibody, and subsequently administering an additional antibody disclosed herein, or a nucleic acid encoding the additional antibody, wherein the first antibody and the additional antibody are not the same. In some embodiments, a subject is administered one of the antibodies or antigen-binding fragments herein one or more times. In some embodiments, a subject is administered two of the antibodies or antigen-binding fragments herein one or more times. In some embodiments, a subject is administered three of the antibodies or antigen-binding fragments herein one or more times. In some embodiments, a subject is administered four of the antibodies or antigen-binding fragments herein one or more times. In some embodiments, a subject is administered four or more of the antibodies or antigen-binding fragments herein one or more times. In some embodiments, a subject is administered five of the antibodies or antigen-binding fragments herein one or more times.

In some embodiments, an antibody or an antigen binding fragment thereof disclosed herein, or a composition disclosed herein (e.g., comprising an antibody or antigen binding fragment thereof, or a nucleic acid encoding said antibody or antigen binding fragment thereof described herein) can be administered as a booster dose after an initial dose. The term "booster" refers to an extra administration of an antibody or an antigen binding fragment thereof disclosed herein, or a composition disclosed herein typically provided subsequent to an initial dose of the antibody or an antigen binding fragment thereof, or a composition disclosed herein. In some embodiments, the methods of the present disclosure further comprise administering at least one booster dose to a subject. In some embodiments, the methods disclosed herein comprises administering at least 1, 2, 3, 4, or 5 booster doses. In some embodiments a booster dose is administered at least about 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years, or more than 99 years after administering an initial dose of an antibody, or a composition disclosed herein. In some embodiments, the booster dose comprises a reduced amount of an antibody or antigen binding fragment disclosed herein, or a composition disclosed herein than the initial dose. For example, a booster or subsequent dose of an antibody or antigen binding fragment thereof, or a composition can comprise an amount that is about: 1%, 2%, 3%, 4%, 5%, 7.5%, 10%, 15%, 20%, 25%, 30%, 40%, 50%, 60%, or 75% or less than the initial or preceding dose of the antibody or the antigen binding fragment thereof, or the composition. In some case a therapeutic or prophylactic effect is achieved in absence of a booster dose.

The present disclosure provides methods of reducing the death rate of a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis by administering to a population of subjects in need thereof an antibody or antigen-binding fragment disclosed herein, or a composition disclosed herein. Reduction in death rate can be determined for example by comparing the rate of death of subjects suffering from a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis between the population of subjects that receives an antibody or antigen binding fragment thereof, or a composition and a corresponding population of subjects that does not receive the antibody or antigen binding fragment thereof, or the composition, or are untreated. Death rate can be determined, for example, by determining the number of infected subjects of a population wherein a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis results in death. In some cases, the death rate can be reduced by at least 5%, at least 10%, at least 20%, at least 30%, at least 40%, at least 50%, at least 60%, at least 70%, at least 80%, or at least 90%.

In some embodiments of the methods herein, said administering to a subject of an antibody or antigen binding fragment thereof, or a composition disclosed herein comprising the antibody or antigen binding fragment thereof, or a nucleic acid encoding the antibody or antigen binding fragment thereof results in inhibition of binding of a TL1A with a receptor (e.g., DR3) on a cell in the subject. In some embodiments, the inhibition of binding is by at least about 1%, 2%, 3%, 4%, 5%, 6%, 7%, 8%, 9%, 10%, 15%, 20%, 30%, 40%, 50%, 60%, 70%, 80%, 90%, or more or more compared to that in a subject not treated with the antibody or antigen-binding fragment thereof disclosed herein, or the composition disclosed herein or compared to an untreated subject.

In some embodiments of the methods herein, said administering to a subject of an antibody or antigen binding fragment thereof, or a composition disclosed herein comprising the antibody or antigen binding fragment thereof, or a nucleic acid encoding the antibody or antigen binding fragment thereof results in a decrease in one or more symptoms or conditions resulting from a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis in the subject for any period of time (e.g., for a day, a week, a month, 6 months, a year, or for the remainder of the subject's life).

In some embodiments of the methods herein, said administering to a subject of an antibody or antigen binding fragment thereof, or a composition disclosed herein comprising the antibody or antigen binding fragment thereof, or a nucleic acid encoding the antibody or antigen binding fragment thereof results in a decrease in one or more symptoms or conditions resulting from a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis in the subject for any period of time (e.g., for a day, a week, a month, 6 months, a year, or for the remainder of the subject's life).

Inhibition Activity

In some embodiments, the disclosure provides antibodies or antigen binding fragments thereof disclosed herein that are neutralizing antibodies. As used herein a "neutralizing antibody" is an antibody or antigen binding fragment thereof that binds to TL1A and inhibits the ability of TL1A to bind to or otherwise interact with death receptor 3 (DR3) in the subject. Neutralization assays are capable of being performed and measured in different ways. In some embodiments, the antibodies or antigen binding fragments thereof exhibits increased neutralizing activity relative to that by a corresponding control antibody or an antigen binding fragment thereof. In some embodiments, the increased neutralization activity is by at least about 1%, 2%, 3%, 4%, 5%, 6%, 7%, 8%, 9%, 10%, 15%, 20%, 30%, 40%, 50%, 60%, 70%, 80%, 90%, or more compared a corresponding control antibody or an antigen binding fragment thereof.

Dosages

The compositions are to be used for in vivo administration of a subject by any available means, such as parenteral administration. For administration to a subject, a composition or medicament described herein can be sterile, which can readily be accomplished by filtration through sterile filtration membranes, or other methods known to those of skill in the art. In one embodiment, a composition of medicament has been treated to be free of pyrogens or endotoxins. Testing pharmaceutical compositions or medicaments for pyrogens or endotoxins and preparing pharmaceutical compositions or medicaments free of pyrogens or endotoxins or preparing pharmaceutical compositions or medicaments that have endotoxins at a clinically acceptable level, are well understood to one of ordinary skill in the art. Commercial kits are available to test pharmaceutical compositions or medicaments for pyrogens or endotoxins.

The antibodies or antigen binding fragments thereof, described herein, are formulated, dosed, and administered in a fashion consistent with good medical practice. Factors for consideration in this context include the particular disorder being treated, the particular subject being treated, the clinical condition of the individual subject, the cause of the disorder, the site of delivery of the agent, the method of administration, the scheduling of administration, and other factors known to medical practitioners. The "therapeutically effective amount" to be administered will be governed by such considerations, and refers to the minimum amount necessary to ameliorate, treat, or resolve, a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis; or to prevent or protect against a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis.

The dose of antibody may vary depending upon the age and the size of a subject to be administered, target disease, conditions, route of administration, and the like. The preferred dose is typically calculated according to body weight or body surface area. When an antibody or antigen binding fragment thereof disclosed herein is used for treating a condition or disease in an adult patient, it may be advantageous to intravenously administer the antibody of the present disclosure normally at a single dose of about 0.01 to about 20 mg/kg body weight, more preferably about 0.02 to about 7, about 0.03 to about 5, or about 0.05 to about 3 mg/kg, about 5 mg/kg, about 7.5 mg/kg, about 10 mg/kg, or about 15 mg/kg body weight. Depending on the severity of the condition, the frequency and the duration of the treatment can be adjusted. Effective dosages and schedules for administering may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

The administration can be, for example, by one or more separate administrations, or by continuous infusion. However, other dosage regimens can be useful. In one non-limiting example, an antibody or antigen binding fragment thereof, disclosed herein is administered once every week, every two weeks, or every three weeks, at a dose range from about 5 mg/kg to about 15 mg/kg, including but not limited to 5 mg/kg, 7.5 mg/kg, 10 mg/kg, or 15 mg/kg. The duration of a therapy using the methods described herein will continue for as long as medically indicated or until a desired therapeutic effect (e.g., those described herein) is achieved.

Efficacy of Treatment

The efficacy of treatment or prevention of a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis, comprising administering the antibodies or antigen binding fragments thereof, or pharmaceutical compositions of the present disclosure, may be assessed using standard techniques. Other measures may include duration of survival, progression free survival, overall response rate, duration of response, and quality of life.

In some embodiments, an antibody or antigen binding fragment thereof disclosed herein is a neutralizing antibody or an antigen binding fragment thereof.

A subject can be administered an antibody or antigen-binding fragment thereof disclosed herein, or a composition disclosed herein in an amount that achieves at least partially, a partial, or complete reduction of one or more symptoms (e.g., one or more symptoms associated with disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis). Reduction can be, for example, a decrease of one or more symptoms by at least about 1%, 2%, 3%, 4%, 5%, 6%, 7%, 8%, 9%, 10%, 15%, 20%, 30%, 40%, 50%, 60%, 70%, 80%, 90%, or more or more compared to that in a subject not treated with the antibody or antigen-binding fragment thereof disclosed herein, or the composition disclosed herein or compared to an untreated subject. The amount of an antibody necessary to bring about therapeutic treatment of a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis is not fixed per se. The amount of an antibody administered can vary for example with the extensiveness of the disease, the size of the human suffering, and if the subject is suffering from, or is at risk of another comorbidity. Treatment, in one instance, lowers infection rates in a population of subjects for example by at least about 1%, 2%, 3%, 4%, 5%, 6%, 7%, 8%, 9%, 10%, 15%, 20%, 30%, 40%, 50%, 60%, 70%, 80%, 90%, or more or more compared to treatment of a corresponding population of subjects with another treatment for a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis, or compared to a corresponding untreated subject population. Treatment can also result in a shortened recovery time, in fewer symptoms, or in less severe symptoms, or a combination thereof compared to an untreated subject who has a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis.

Modes of Administration

The antibodies or antigen binding fragments thereof, described herein, can be administered to a subject in need thereof by any appropriate route which results in an effective treatment in the subject. In some embodiments, the antibodies or antigen binding fragments thereof, described herein, or compositions comprising the same is administered to a subject with a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis, or seeking to prevent a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis, by any mode of administration that delivers the agent systemically or to a desired surface or target, and can include, but is not limited to, injection, infusion, instillation, inhalation, parenteral, subcutaneous, intraperitoneal, intrapulmonary, oral and intranasal administration. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intracranial, intraspinal, intracerebro spinal, and intrasternal injection and infusion. Parenteral infusions include intramuscular, intravenous, intraarterial, intraperitoneal, or subcutaneous administration.

Fusion Proteins

In one aspect, provided herein is a fusion protein comprising an antibody or an antigen binding fragment, disclosed herein. In some embodiments, fusion protein comprises one or more antibody or antigen binding fragment thereof, disclosed herein, and an immunomodulator or toxin moiety. Methods of making antibody fusion proteins are known. Antibody fusion proteins comprising an interleukin-2 moiety are described by Boleti et al., Ann. Oneal. 6:945 (1995), Nicolet et al., *Cancer Gene Ther.* 2:161 (1995), Becker et al., *Proc. Natl Acad. Sci. USA* 93:7826 (1996), Hank et al., *Clin. Cancer Res.* 2:1951 (1996), and Hu et al., Cancer Res. 56:4998 (1996). In addition, Yang et al., Hum. Antibodies Hybridomas 6:129 (1995), describe a fusion protein that includes an F(ab')2 fragment and a tumor necrosis factor alpha moiety.

Methods of making antibody-toxin fusion proteins in which a recombinant molecule comprises one or more antibody components and a toxin or a therapeutic agent also are known to those of skill in the art. For example, antibody-*Pseudomonas* exotoxin A fusion proteins have been described by Chaudhary et al., Nature 339:394 (1989), Brinkmann et al., *Proc. Nat'l Acad. Sci.* USA 88:8616 (1991), Batra et al., *Proc. Natl Acad. Sci.* USA 89:5867 (1992), Friedman et al., *J. Immunol.* 150:3054 (1993), Weis et al., *Int. J. Can.* 60:137 (1995), Fominaya et al., *J. Biol. Chem.* 271:10560 (1996), Kuan et al., *Biochemistry* 35:2872 (1996), and Schmidt et al., *Int. J. Can.* 65:538 (1996). Antibody-toxin fusion proteins containing a diphtheria toxin moiety have been described by Kreitman et al., *Leukemia* 7:553 (1993), Nicholls et al., *J. Biol. Chem.* 268:5302 (1993), Thompson et al., *J. Biol. Chem.* 270:28037 (1995), and Vallera et al., *Blood* 88:2342 (1996). Deonarain et al., *Tumor Targeting* 1:177 (1995), have described an antibody-toxin fusion protein having an RNase moiety, while Linardou et al., *Cell Biophys.* 24-25:243 (1994), produced an antibody-toxin fusion protein comprising a DNase I component. Gelonin was used as the toxin moiety in the antibody-toxin fusion protein of Wang et al., Abstracts of the 209th ACS National Meeting, Anaheim, Calif., Apr. 2-6, 1995, Part 1, BIOT005. As a further example, Dohlsten et al., *Proc. Natl Acad. Sci*. USA 91:8945 (1994), reported an antibody-toxin fusion protein comprising Staphylococcal enterotoxin-A.

Illustrative of toxins which are suitably employed in the preparation of such conjugates are ricin, abrin, ribonuclease, DNase I, Staphylococcal enterotoxin-A, pokeweed antiviral protein, gelonin, diphtheria toxin, *Pseudomonas* exotoxin, and *Pseudomonas* endotoxin. See, e.g., Pasta et al., *Cell* 47:641 (1986), and Goldenberg, C A-A *Cancer Journal for Clinicians* 44:43 (1994). Other suitable toxins are known to those of skill in the art.

Antibodies or antigen binding fragments thereof, disclosed herein, may also be used in ADEPT by conjugating the antibody to a prodrug-activating enzyme which converts a prodrug (e.g., a peptidyl chemotherapeutic agent, see WO81/01145) to an active anti-cancer drug. See, for example, WO88/07378 and U.S. Pat. No. 4,975,278. The enzyme component of the immunoconjugate useful for ADEPT includes any enzyme capable of acting on a prodrug in such a way so as to convert it into its more active, cytotoxic form.

Enzymes that are useful in the method of this disclosure include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as galactosidase and neuraminidase useful for converting glycosylated prodrugs into free drugs; lactamase useful for converting drugs derivatized with lactams into free drugs; and penicillin amidases, such as penicillin V amidase or penicillin G amidase, useful for converting drugs derivatized at their amine nitrogen's with phenoxyacetyl or phenylacetyl groups, respectively, into free drugs. Alternatively, antibodies with enzymatic activity, also known in the art as abzymes, can be used to convert the prodrugs of the disclosure into free active drugs (see, e.g., Massey, *Nature* 328: 457-58 (1987)). Antibody-abzyme conjugates can be prepared as described herein for delivery of the abzyme to a tumor cell population. The enzymes can be covalently bound to the antibodies by techniques well known in art such as the use of the heterobifunctional crosslinking reagents discussed above. Alternatively, fusion proteins comprising at least the antigen binding region of an antibody of the disclosure linked to at least a functionally active portion of an enzyme can be constructed using recombinant DNA techniques well known in the art (see, e.g., Neuberger et al., *Nature* 312: 604-08 (1984)).

Immunoconjugates

The antibodies or antigen binding fragments thereof, disclosed herein, may be administered in their "naked" or unconjugated form, or may have an additional therapeutic agent conjugated to them. For example, the antibodies or antigen binding fragments of the present disclosure can have a toxin, radioisotope, or a label conjugated to them. In one embodiment, antibodies or antigen binding fragments thereof are used as a radiosensitizer. In such embodiments, the antibodies or antigen binding fragments are conjugated to a radio sensitizing agent. The term "radiosensitizer," as used herein, is defined as a molecule, preferably a low molecular weight molecule, administered to animals in therapeutically effective amounts to increase the sensitivity of the cells to be detected by radiation, or radio sensitized to electromagnetic radiation and/or to promote the treatment of diseases that are treatable with electromagnetic radiation.

The terms "electromagnetic radiation" and "radiation" as used herein include, but are not limited to, radiation having the wavelength of 10-20 to 100 meters. Preferred embodiments of the present disclosure can employ for example, the electro-magnetic radiation of gamma-radiation c10-20 to 10-13 m), X-ray radiation (10-12 to 10-9 m), ultraviolet light (10 nm to 400 nm), visible light (400 nm to 700 nm), infrared radiation (700 nm to 1.0 mm), and microwave radiation (1 mm to 30 cm).

Examples of photodynamic radiosensitizers include the following, but are not limited to: hematoporphyrin derivatives, Photofrin®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same that can be conjugated to the antibodies or antigen binding fragments thereof disclosed herein.

In another embodiment, the antibody may be conjugated to a receptor (such streptavidin), wherein the antibody-receptor conjugate is administered to the patient, followed by removal of unbound conjugate from the circulation using a clearing agent and then administration of a ligand (e.g., avidin) which is conjugated to an additional therapeutic agent (e.g., an anti-viral agent).

The present disclosure further provides the above-described antibodies or antigen binding fragments thereof in detectably labeled form. Antibodies can be detectably labeled using radioisotopes, affinity labels (such as biotin, avidin, etc.), enzymatic labels (such as horseradish peroxidase, alkaline phosphatase, etc.) fluorescent or luminescent or bioluminescent labels (such as FITC or rhodamine, etc.), paramagnetic atoms, and the like. Procedures for accomplishing such labeling are well known in the art; for example, see (Sternberger, L. A. et al., *J. Histochem. Cytochem.* 18:315 (1970); Bayer, E. A. et al., *Meth. Enzym.* 62:308 (1979); Engval, E. et al., *Immunol.* 109:129 (1972); and Goding, J. W. *J. Immunol. Meth.* 13:215 (1976)).

"Label" refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable. Alternatively, the label may not be detectable on its own but may be an element that is bound by another agent that is detectable (e.g., an epitope tag or one of a binding partner pair such as biotin-avidin, etc.). Thus, the antibody may comprise a label or tag that facilitates its isolation, and methods of the disclosure to identify antibodies include a step of isolating the antigen/antibody through interaction with the label or tag.

Exemplary therapeutic immunoconjugates comprise the antibody described herein conjugated to an antiviral agent, or a radioactive isotope (i.e., a radio conjugate). Fusion proteins are described in further detail above.

In some embodiments, antibodies and antigen binding fragments thereof disclosed herein can be conjugated to an additional therapeutic agent described herein. In another embodiment, antibodies and antigen binding fragments thereof disclosed herein are conjugated to a detectable substrate such as, e.g., an enzyme, fluorescent marker, chemiluminescent marker, bioluminescent material, or radioactive material. In some embodiments of the aspects described herein, the antibody and antibody fragments thereof disclosed herein are conjugated to a toxin (e.g., an enzymatically active toxin of bacterial, fungal, plant or animal origin, or fragments thereof), a small molecule, an siRNA, a nanoparticle, a targeting agent (e.g., a microbubble), or a radioactive isotope (i.e., a radio conjugate). Such conjugates are referred to herein as "immunoconjugates". Such immunoconjugates can be used, for example, in diagnostic, theragnostic, or targeting methods.

Enzymatically active toxins and fragments thereof which can be used include diphtheria chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the trichothecenes. A variety of radioisotopes are available to produce radio conjugate antibodies. Examples include, but are not limited to, 212 Bi, 131 I, 131 In, 90Y and 186Re.

Conjugates of the antibodies or antigen binding fragments thereof described herein and a therapeutic agent can be made using any of a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazonium benzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., 238 *Science* 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026.

Techniques for conjugating such therapeutic moiety to antibodies are well known, see, e.g., Amon et al., "*Monoclonal Antibodies For Immunotargeting Of Drugs In Cancer Therapy*", in MONOCLONAL ANTIBODIES AND CANCER THERAPY, Reisfeld et al. (eds.), pp. 243-56 (Alan R. Liss, Inc. 1985); Hellstrom et al., "*Antibodies For Drug Delivery*", in CONTROLLED DRUG DELIVERY (2nd Ed.), Robinson et al. (eds.), pp. 623-53 (Marcel Dekker, Inc. 1987); Thorpe, "Antibody Carriers Of Cytotoxic Agents In Cancer Therapy: A Review", in MONOCLONAL ANTIBODIES '84: BIOLOGICAL AND CLINICAL APPLICATIONS, Pinchera et al. (eds.), pp. 475-506 (1985); "*Analysis, Results, And Future Prospective Of The Therapeutic Use Of Radiolabeled Antibody In Cancer Therapy*", in MONOCLONAL ANTIBODIES FOR CANCER DETECTION AND THERAPY, Baldwin et al. (eds.), pp. 303-16 (Academic Press 1985), and Thorpe et al., "*The Preparation And Cytotoxic Properties Of Antibody-Toxin Conjugates*", *Immunol. Rev.,* 62: 119-58 (1982).

Production of immunoconjugates is described in U.S. Pat. No. 6,306,393. Immunoconjugates can be prepared by indirectly conjugating a therapeutic agent to an antibody component. General techniques are described in Shih et al., *Int. J. Cancer* 41:832-39 (1988); Shih et al., *Int. J. Cancer* 46:1101-06 (1990); and Shih et al., U.S. Pat. No. 5,057,313. The general method involves reacting an antibody component having an oxidized carbohydrate portion with a carrier polymer that has at least one free amine function and that is loaded with a plurality of drug, toxin, chelator, boron compositions or other therapeutic agents. This reaction results in an initial Schiff base (imine) linkage, which can be stabilized by reduction to a secondary amine to form the final conjugate.

Kits

Provided herein are also kits, medicines, compositions, and unit dosage forms for use in any of the methods described herein. Provided herein is a kit comprising an effective amount of at least one of the antibody or antigen binding fragment thereof disclosed herein, or a composition comprising the at least one antibody or antigen binding fragment thereof or a nucleic acid encoding the at least one antibody or antigen binding fragment thereof disclosed herein. In some embodiments, the kit further comprises an additional therapeutic agent described herein. In some embodiments, the antibody or antigen binding fragment thereof disclosed herein, or a composition disclosed herein is an aqueous form or a lyophilized form. In some embodiments, the kit further comprises a diluent or a reconstitution solution.

Kits can include one or more containers comprising an antibody or a composition described herein (or unit dosage forms and/or articles of manufacture). In some embodiments, a unit dosage is provided wherein the unit dosage contains a predetermined amount of an antibody or antigen binding fragment thereof or a composition disclosed herein, with or without one or more additional agents. In some embodiments, such a unit dosage is supplied in single-use prefilled syringe for injection. In some embodiments, the composition can comprise saline, sucrose, or the like; a buffer, such as phosphate, or the like; and/or be formulated within a stable and effective pH range. In some embodiments, an antibody or antigen binding fragment thereof, or a composition of the disclosure can be provided as a lyophilized powder that can be reconstituted upon addition of an appropriate liquid, for example, sterile water. In some embodiments, the composition further comprises one or more substances that inhibit protein aggregation, including, but not limited to, sucrose and arginine. In some embodiments, the composition further comprises heparin and/or a proteoglycan.

In some embodiments, kits further comprise instructions for use in the treatment of a disease, disorder or inflammation including, for example, autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis in accordance with any of the methods described herein. The kit may further comprise a description of selection an individual suitable or treatment. Instructions supplied in the kits are typically written instructions on a label or package insert (for example, a paper sheet included in the kit), but machine-readable instructions (for example, instructions carried on a magnetic or optical storage disk) are also acceptable. In some embodiments, the kit further comprises an additional therapeutic agent described herein.

The kits are in suitable packaging. Suitable packaging includes, but is not limited to, vials, bottles, jars, flexible packaging (for example, sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

Pharmacokinetics

In some embodiments, the present disclosure provides an antibody or antigen-binding fragment thereof that has an improved biodistribution, e.g., relative to commercially available antibodies or relative to other antibodies that bind TL1A. For example, a half-life of about ($t_{1/2}$ days) 5, 6, 7, 8, 9, 10, 11, 12, 13, 14, 15 or more days is provided herein.

EXAMPLES

The following Examples describe the methods and materials for the identification and assessment of antibodies that bind TL1A according to various embodiments of the present disclosure. AI-based affinity maturation and/or incremental de novo antibody design and/or antibody folding techniques were implemented as described herein.

Protein engineering approaches were first employed to graft the reference molecule (referred to herein as antibody Heron2B) CDRs (CDRH1: GFDIQDTY (SEQ ID NO: 4); CDRH2: IDPASGHT (SEQ ID NO: 49); CDRH3: ARSGGLPDV (SEQ ID NO: 147); CDRL1: SSVSY (SEQ ID NO: 12); CDRL2: ATS; CDRL3: QQWEGNPRT (SEQ ID NO: 3) into numerous frameworks and were screened to identify compatible frameworks. Tocilizumab was chosen as the final framework based on performance in the ACE assay. Grafting enabled a significant edit distance away from the reference molecule, meaning the AI-based techniques could be focused on the CDR elements of the overall antibody structure. As described below, in one embodiment, AI-based affinity maturation and/or antibody design and/or antibody folding techniques were used to create a variant of antibody that is diverse in 5 of 6 CDRs (all but LCDR3) and has higher affinity relative to Heron 2B.

Heavy Chain:

De novo models and inverse folding models were first applied, where in the latter the native HCDR3 sequence was used to generate a structure (using Alpha Fold-Multimer and a docking model) and this structure was used to generate HCDR3 variants (using an inverse folding model). The inverse folding was more successful both in terms of hit rate and affinities. HCDR3 designs that were confirmed as binders were advanced to AI-guided lead optimization (e.g., affinity maturation) steps. Multiple tracks were implemented as described herein. Track 1 involved using the highest affinity binder (an 8.6 nM variant) from inverse folding. Track 2 used a "constellation" approach with multiple binders (with affinities ranging from 23-97 nM) including some from inverse folding methods and some from de novo models. Additional tracks are described below. Tracks 1 and 2 produced variants with higher affinity than Heron2B.

Light Chain:

De novo models were used to design LCDR1 and LCDR2 on their own and then variant LCDR1s and LCDR2s that bound were paired and combinatorially cloned together with the top 50 heavy chain variants as well as Heron2B's heavy chain to get a variant with LCDR1 and LCDR2 distinct from the known Heron2B sequences (up to 6 mutations away) and with equal or improved binding affinity. As noted below, LCDR3 is unchanged compared to the reference molecule, while LCDRL1 and LCDR2 were each changed. Significantly, and unlike LCDR3, LCDR1 and LCDR2 are encoded in germline DNA and thus are not the product of somatic rearrangement (LCDR1 and LCDR2 are encoded in the V segment gene; the kappa light chain typically has only 37 V possible genes). In this way, the de novo-designed LCDR1 and LCDR2 described herein are different from any V gene provided by the reference molecule Heron2B.

Inverse folding models+AI-guided lead optimization as described herein was used for the heavy chain and de novo AI models as described herein was used for the light chain.

To summarize:

HCDR1, HCDR2, and HCDR3: Used inverse folding+AI-guided lead optimization (informed by site-saturation mutagenesis knowledge on key paratope contributions and silent mutations)

LCDR1, LCDR2: used de novo AI models

LCDR3: unchanged

Framework regions: Tocilizumab framework was selected using protein engineering approaches (CDRs grafting)

Example 1: Identification and Assessment of Antibodies that Bind TL1A—Hit Generation and Candidate Selection The present Example provides an experimental validation of functional antibodies that are outputs from the inverse folding methods (Stage 1). Since TL1A increases the production and release of IFN-γ through its interaction with DR3 on T-cells, anti-TL1A antibodies that block these interactions would inhibit production and release of IFN-γ. Overall, the assay measures the inhibitory effect of the antibodies on the endogenous TL1A upon blocking its interaction with its receptor on the cells in human blood. The inhibitory activity of two reference molecules, Heron1 and Heron2B, along with our top candidate with at least one donor was demonstrated. The assay showed a correlation between the inhibition of IFN-γ release and the binding affinities as measured by SPR.

As used herein, "Heron1" refers to PF-06480605 (as described in US 2018/0052175 A1), and "Heron2B" refers to PRA023 as described in U.S. Ser. No. 10/689,439.

As shown in FIG. 1, whole blood IFNγ release assay rank order correlates with affinity.

Example 2: Identification and Assessment of Antibodies that Bind TL1A—AI-Guided Lead Optimization The present Example demonstrates AI-guided lead optimization of hits to TL1-A (Stage2).

Information-rich libraries were designed for gaACE screening and model training. Libraries composed of 120,000 and 210,000 amino acid variants with 2× codon versions were generated from sampling the triple mutant space across 20 positions in the heavy chain CDR1, CDR2, and CDR3. qaACE screening was performed to assign ACE scores to these high diversity libraries. A subset of measured variants was also analyzed by SPR, and ACE scores were confirmed to have high correlation with SPR-measured equilibrium constants (KD), with a Pearson R of 0.72.

| AI-guided optimization track #1 | Approach | Library size | Input |
|---|---|---|---|
| 1 | Conservative | 240 k | Single AI-derived parental lead ($K_D$ = 8 nM) |
| 2 | Maximize search Space | 420 k | 10 AI-derived parental leads ($K_D$ = 20-100 nM) |
| 3 | Increase LC diversity | 210 k | Naive LC + 5 AI-derived parental HC leads ($K_D$ = 20-44 nM) |

-continued

| AI-guided optimization track #1 | Approach | Library size | Input |
|---|---|---|---|
| 4 | Maximize mutational load | 107 | 1 AI-derived parental lead ($K_D$ = 23 nM) |

Figure 2B:
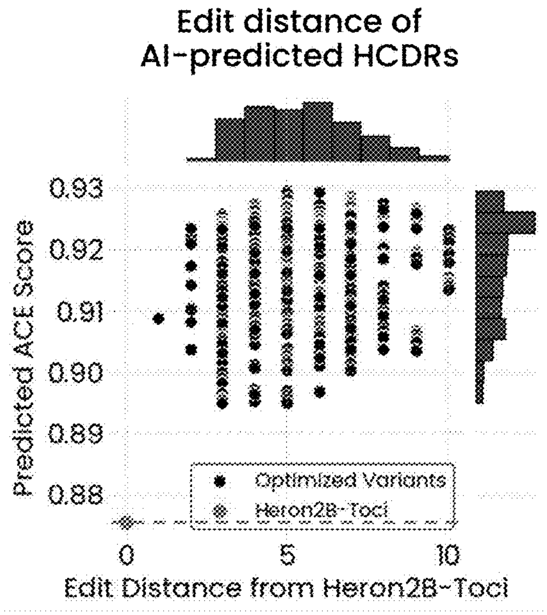

As shown in FIG. 2, models fine-tuned on ACE data were confirmed to accurately predict ACE scores for a holdout set (Pearson R of 0.74). These models were used to predict novel HCDR sequences with improved ACE scores.

Figures 3A, 3B:
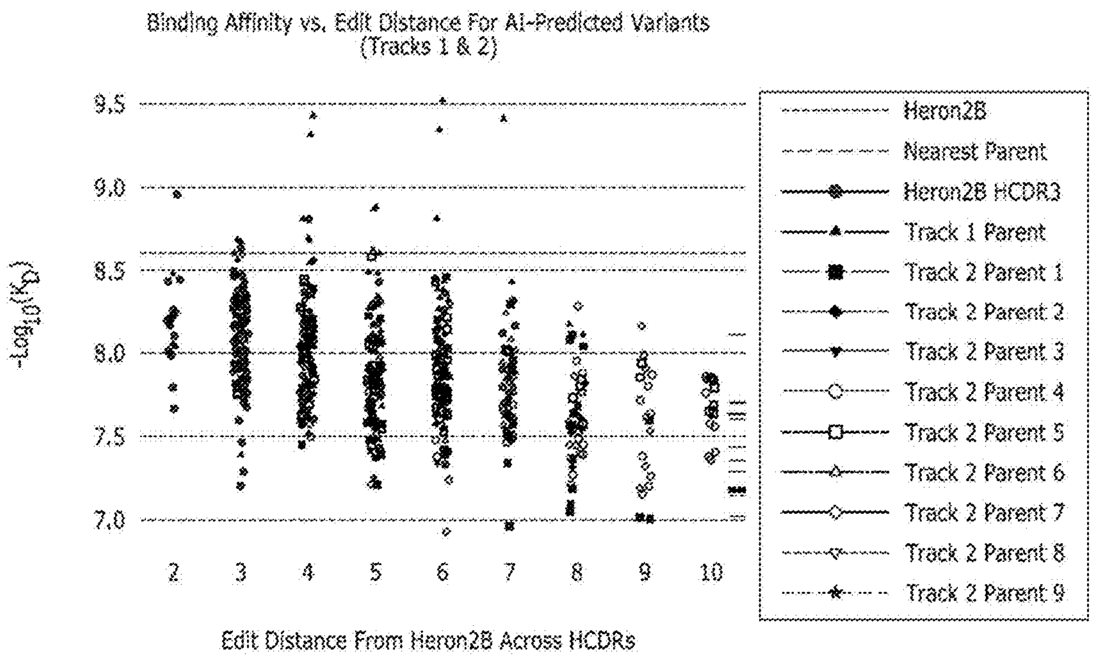
FIGS. 3A-3B depicts SPR binding affinity vs edit distance from Heron2B for novel AI-predicted HCDR sequences.

Sequences with the highest model predicted ACE scores and with 1-7 mutations from the parental were then expressed and binding affinities measured by SPR as shown in FIG. 3.

To summarize, the novel AI-generated and optimized variants have higher affinity than Heron2B:

Six sub-nM binders confirmed from AI-optimization tracks 1 & 2. These tracks generated a total of 22 binders with improved binding over Heron2B.

59 sub-nM binders confirmed from combining track 1 & 2 HC with novel AI-generated de novo LC. A total of 143 binders with affinities higher than Heron2B were identified.

Track 4 AI modelling has been canceled due to lack of high-quality data to train the AI model. 5 sub-nM binders confirmed from a subset of ACE enriched variants screened directly by SPR. A total of 7 binders with affinities higher than Heron2B were identified.

Track 3 did not produce any binders with higher affinity than Heron2B.

Figure 12A:
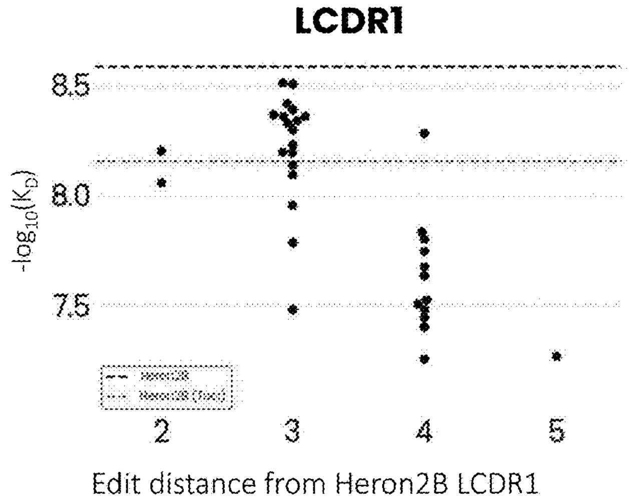
FIG. 12A-12B shows that de novo LCDR modeling generated high affinity variants for LCDR1 and LCDR2.
Figure 12B:
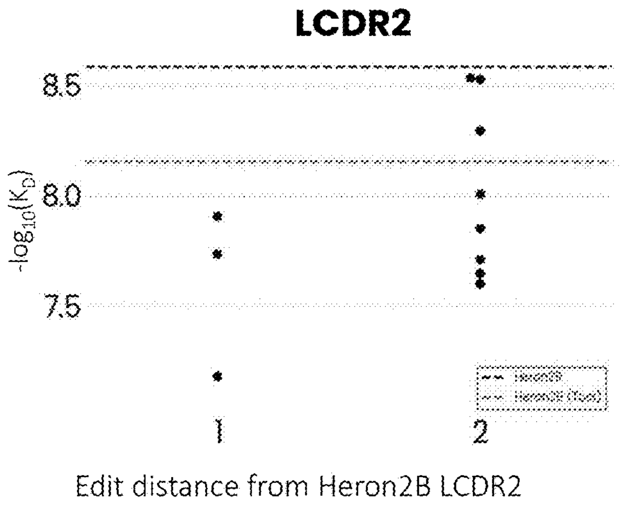

New de novo LCDR modeling generated high affinity variants for LCDR1 and LCDR2 (FIG. 12)

Figure 13:
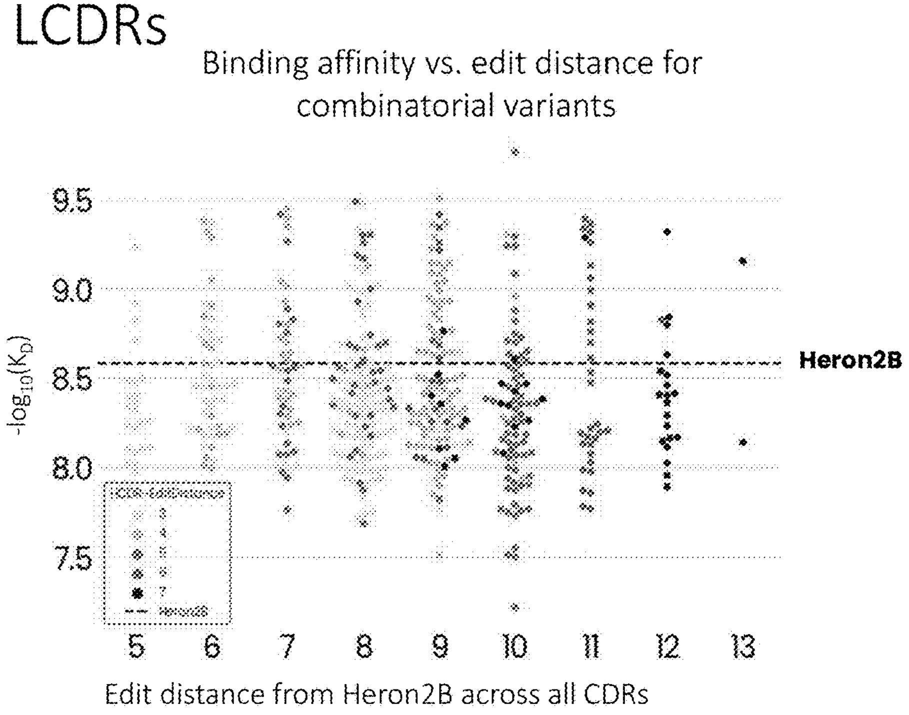
FIG. 13 shows that high affinity and high diversity was obtained by combining AI-optimized HCDRs with de novo AI-generated LCDRs.

High affinity and high diversity obtained by combining AI-optimized HCDRs with de novo AI-generated LCDRs (FIG. 13)

Lead Selection

A total of 100 variants were expressed as mAbs to enable Stage 3 activities. Large scale: high priority 20 variants for developability and functional assessment. Small scale: backup 80 variants for functional assessment. Variants were selected based on the following criteria: SPR binding affinity higher than the reference Heron2B molecule; Maximize CDR edit distance and sequence diversity; Minimize flags on in silico developability and immunogenicity assessments; Cyno TL1A cross-reactivity by SPR.

All 20 high priority AI-optimized leads selected for stage 3 have sub-nM affinity to Human TL1A in Fab format. All 100 AI-optimized leads have affinity higher than Heron2B in Fab format. 20 high-priority leads were risk adjusted to maximize sequence diversity and minimize sequence liabilities. 80 backup leads include 4 high edit distance variants identified from Track 4 with affinities higher than Heron2B but with lower confidence.

The AI-optimized leads retain Cyno TL1A cross reactivity within one log of Human TL1A in Fab format.

Leads were selected to minimize sequence liabilities present in Heron2B. Heron2B has sequence liabilities for fragmentation, Met oxidation, Trp oxidation, and Asp isomerization. Tocilizumab framework used in all 100 leads has one additional Met oxidation liability relative to Heron2B. Sequence liability analysis allowed for exclusion of variants with Asn deamidation or Lys glycation in the top 20. Severe fragmentation liability from Heron2B was removed from 16 of top 20 high priority leads. 12 of top 20 high priority leads have new Met oxidation liabilities.

A summary of the 20 high priority AI-optimized leads described further herein is shown in FIG. 4.

100 novel AI-generated variants with higher affinity than Heron2B were advanced to Stage 3 described below. 20 high priority AI-optimized leads were advanced to large scale production to accelerate final functional characterization and developability assessment. All 20 leads have sub-nM binding affinity to human TL1A (FIG. 14), have cyno TL1A binding affinity within one log, and were selected to maximize edit distance, maximize sequence diversity, and minimize sequence liabilities. 80 back up AI-optimized leads were advanced to small scale production for limited final functional characterization and developability assessment. All 80 leads have higher affinity than Heron2B, have cyno TL1A binding affinity within one log, and were selected to maximize edit distance.

Example 3: Identification and Assessment of Antibodies that Bind TL1A—Functional Characterization and Developability Assessment The present Example describes quality and developability considerations for the described antibodies (Stage 3).

Large Scale Production

Large scale material generation was carried out with the following results:

All 20 high priority leads had >80% purity by NR-CGE and confirmed identities by intact mass as shown in FIG. 5.

19/20 high priority lead mAbs have >97% purity by SEC as shown in FIG. 5.

All 20 high priority lead mabs have acceptable developability metrics by AC-SINS, poly specificity, and HIC assays as shown in FIG. 5.

8/20 high priority lead mAbs had affinity <100 pM to human TL1A by SPR as shown in FIG. 6.

All 20 high priority lead mAbs have cyno cross-reactivity and lack mouse cross-reactivity by SPR as shown in FIG. 7.

$T_{1/2}$ extension mutations increase FcRn affinity at pH 6.0 by ~10-fold relative to Herons by SPR as shown in FIG. 8.

Functional Characterization

The following functional assays are used to measure the neutralization of DR3-dependent activity.

| Assay | Purpose | Outcome | LOD/LOQ* |
|---|---|---|---|
| Surface target expression | Medium-throughput assay | Confirms candidates' binding to the antigen expressed on a mammalian cell membrane | 10-fold over isotype |
| NF-κB signal activation | Medium-throughput function assay | Measures the inhibitory activity of candidate mAbs on antigen-mediated activation of NF-κB signaling | ~3 nm/0.05 nM |
| Apoptosis activation | Medium-throughput functional assay | Measures the inhibitory activity of candidate mAbs on antigen-mediated activation of apoptosis cascade pathway | ~150 nM/ 3.0 nM |

-continued

| Assay | Purpose | Outcome | LOD/LOQ* |
|---|---|---|---|
| ex vivo IFNγ release | Low-throughput confirmatory assay | Measures the neutralizing effect on the mAbs on the endogenous antigen in human and cyno whole blood | 2-fold over Heron2B |

The 20 high priority leads will be assessed by all four functional assays in parallel including both human and cyno whole blood for the IFNγ release assay. The 80 backup leads will be assessed by only surface target expression, NF-kB signal activation, and apoptosis activation assays.

The present example describes functional characterization for the described antibodies by the Surface target expression assay wherein binding of HEK293 cells overexpressing TL1A is measured with cell surface staining using flow cytometry with the following results:

All 20 high priority leads had higher gMFI than a reference antibody (Heron2B).

Figure 9:
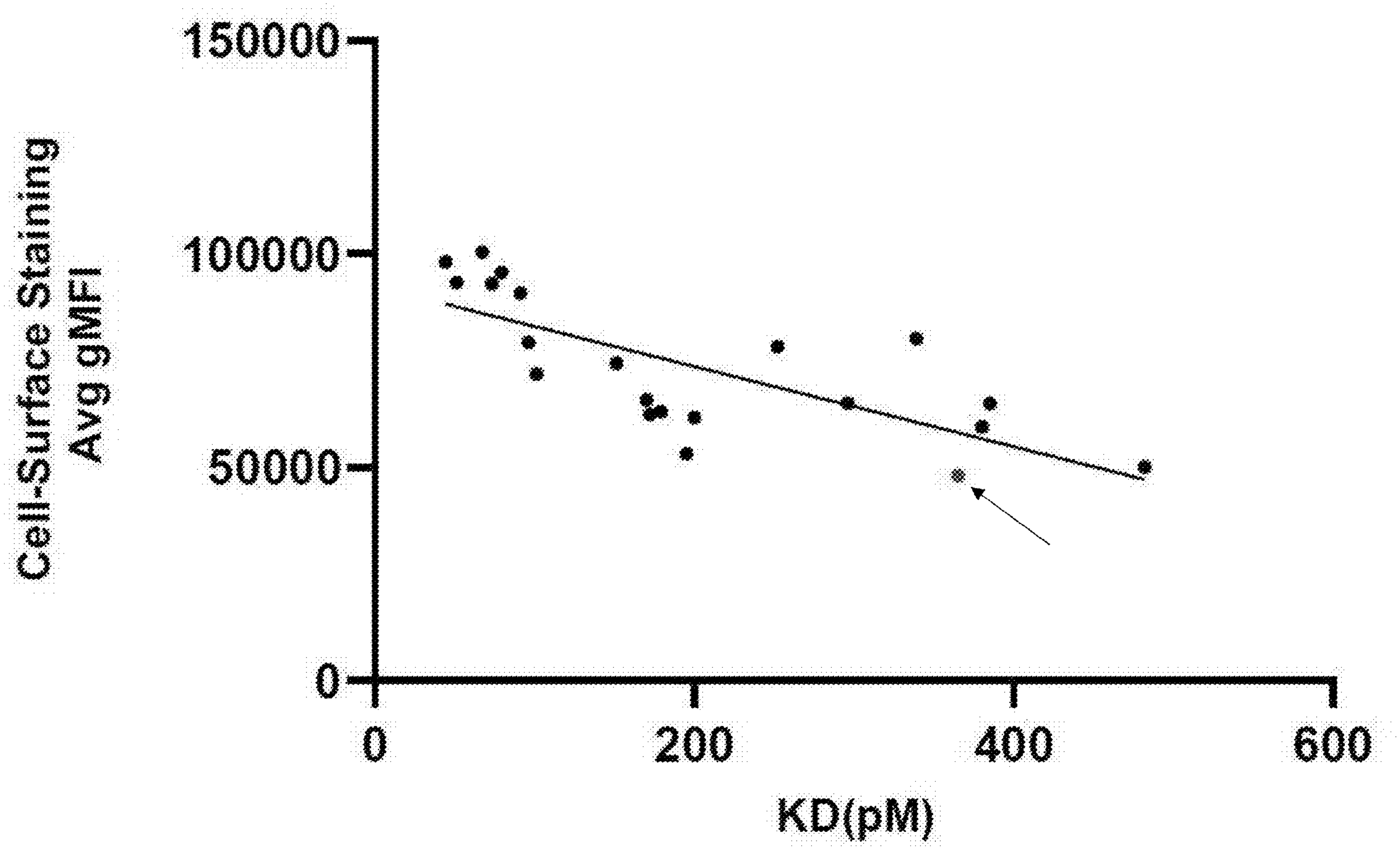
FIG. 9 shows TL1A binding correlation between the surface target expression functional assay and SPR assay.
Figure 10B:
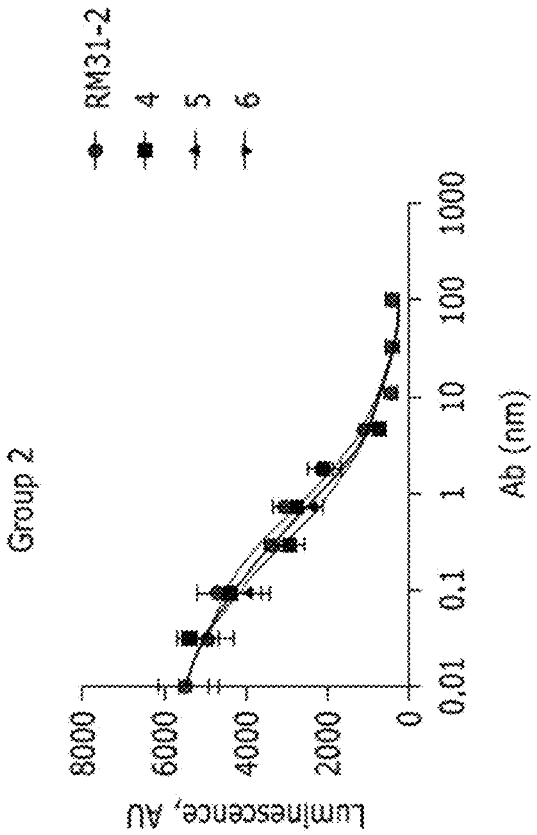
Figure 10A:
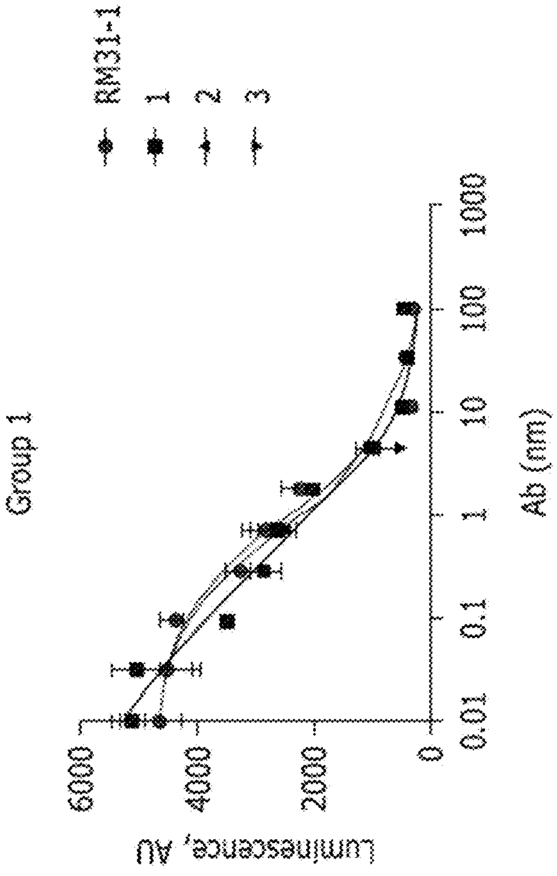
Figure 10C:
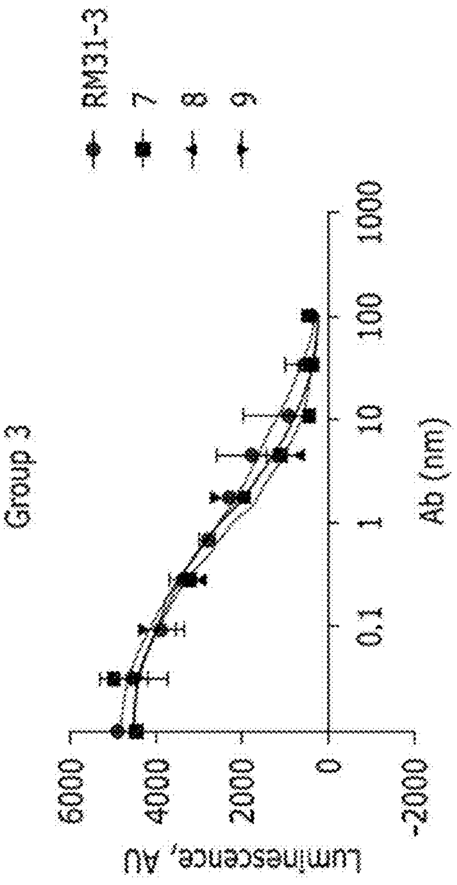
Figure 10D:
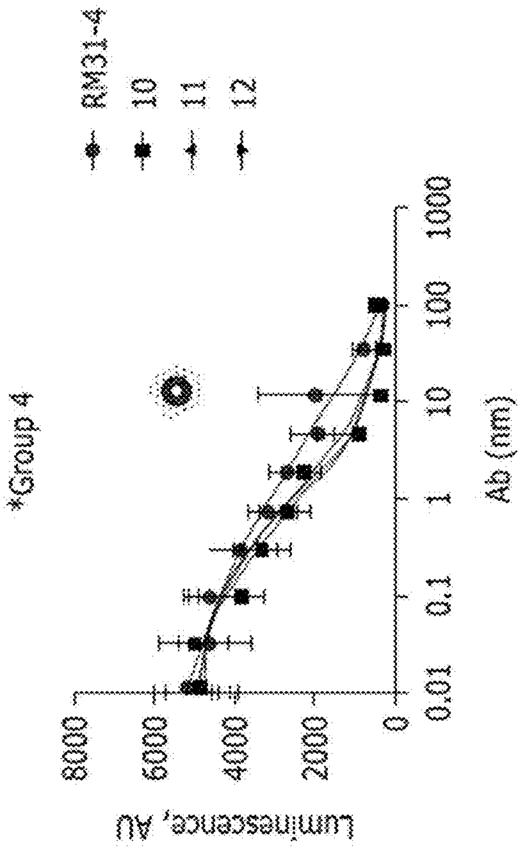
Figure 10E:
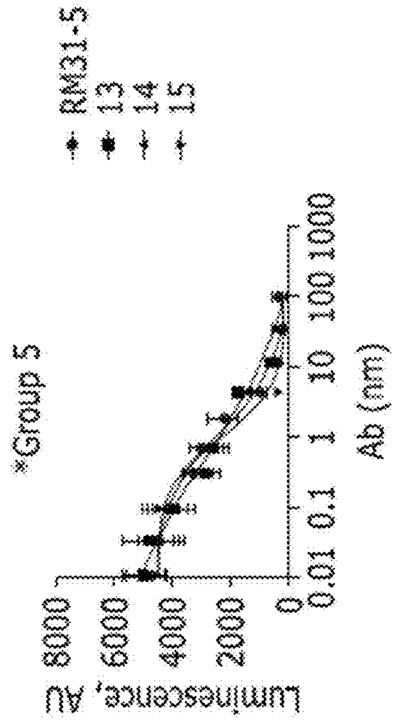
Figure 10F:
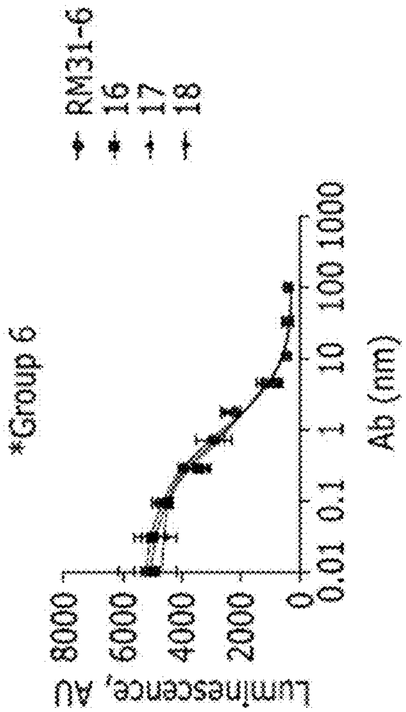
Figure 11A:
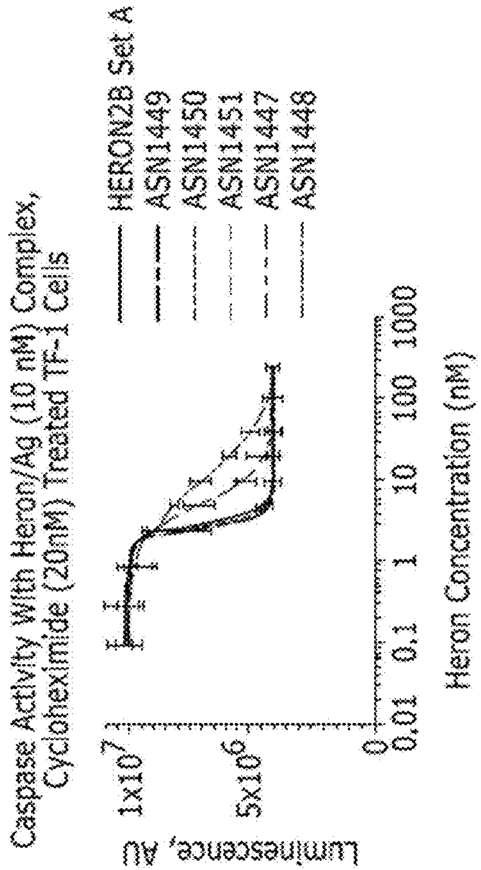
Figure 11B:
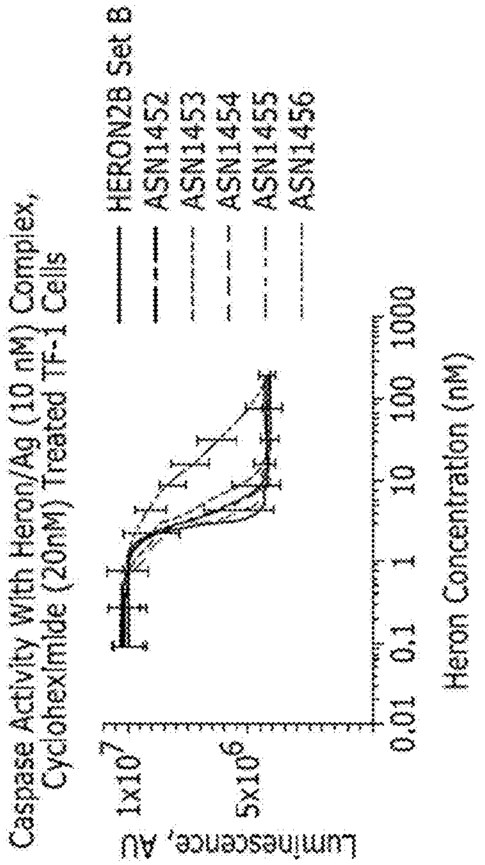
Figure 11C:
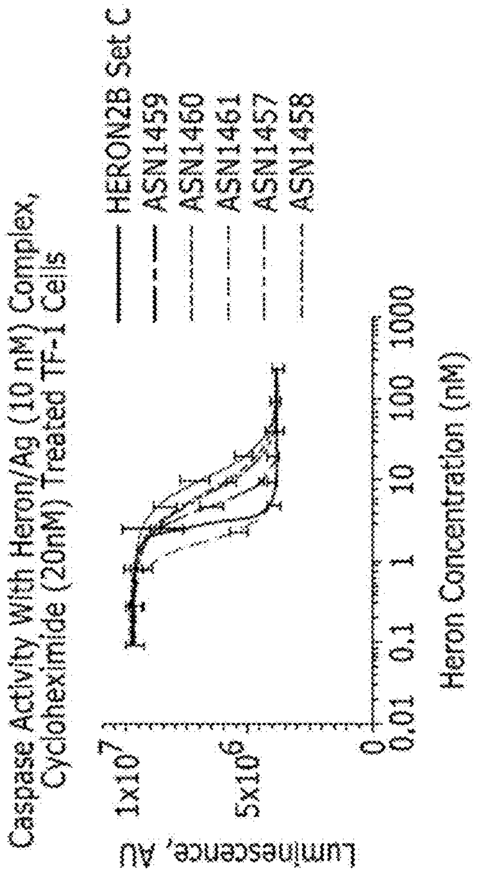
Figure 11D:
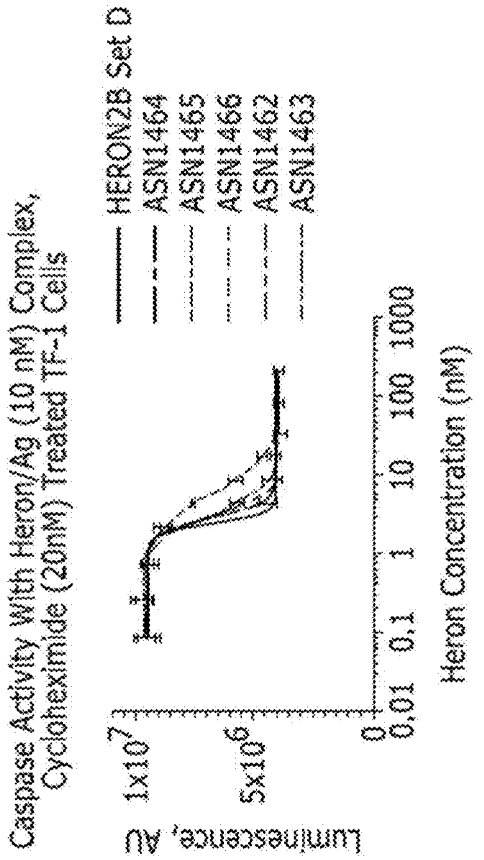

As shown in FIG. 9, cell surface staining Avg gMFI correlates with affinity to TL1A as measured by SPR.

As shown in FIG. 10 and FIG. 11, high priority lead antibodies had similar NFKb, and apoptosis assay results compared to the reference molecule Heron 2B.

In some embodiments, the antibody sequences identified as Lead #1 in the Sequence Table 1 herein is contemplated. In still other embodiments, the above aspects are repeated and contemplated for antibodies numbered 3, 4, 5, 6, 7, 8, 9, 15, and 20 as described herein and provided in Sequence Table 1. Additional antibodies contemplated include the antibodies and sequences in Sequence Table 1 provided herein.

Example 4: Identification and Assessment of Antibodies that Bind TL1A—ABS-101

Using the techniques and assays described herein, monoclonal antibodies that bind TL1A were identified and characterized. FIGS. 15-27 describe the characteristics of ABS-101-A, ABS-101-B, and ABS-101-C.

In some embodiments, the following antibody sequences are contemplated:

```
ABS-101-A-Heavy-Chain
                                                        (SEQ ID NO: 140)
QVQLQESGPGLVRPSQTLSLTCTVSGFDIQDTYMHWVRQRPGRGLEWMGRIEPAGGHT

KYNPSLKSRVTITRDTSKNQVSLRLSSVTAADTAVYYCVRSGGLPDAWGQGSLVTVSSASTKGP

SVFPLAPSSKSTSGGTAALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPEAAGGPSVFLFPPKPKDTLMIS

RTPEVTCVVVSVSHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVLHEALHSHYTQKSLSLSPGK

ABS-101-A-Light-Chain
                                                        (SEQ ID NO: 141)
DIQMTQSPSSLSASVGDRVTITCRASQGVRYMYWYQQKPGKAPKLLIYGASNLASGVPS

RFSGSGSGTDFTFTISSLQPEDIATYYCQQWEGNPRTFGQGTKVEIKRTVAAPSVFIFPPSDEQLK

SGTASVVCLLNNFYPREAKVQWKVDNALQSGNSQESVTEQDSKDSTYSLSSTLTLSKADYEKHK

VYACEVTHQGLSSPVTKSFNRGEC

ABS-101-B-Heavy-Chain
                                                        (SEQ ID NO: 142)
QVQLQESGPGLVRPSQTLSLTCTVSGFDMQDTYMHWVRQRPGRGLEWMGRIEPASGHT

KYNPSLKSRVTITRDTSKNQVSLRLSSVTAADTAVYYCVRSGGLPDVWGQGSLVTVSSASTKGP

SVFPLAPSSKSTSGGTAALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPEAAGGPSVFLFPPKPKDTLMIS

RTPEVTCVVVSVSHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVLHEALHSHYTQKSLSLSPGK

ABS-101-B-Light-Chain
                                                        (SEQ ID NO: 143)
DIQMTQSPSSLSASVGDRVTITCRASQGVMYMYWYQQKPGKAPKLLIYGASNLASGVPS

RFSGSGSGTDFTFTISSLQPEDIATYYCQQWEGNPRTFGQGTKVEIKRTVAAPSVFIFPPSDEQL

KSGTASVVCLLNNFYPREAKVQWKVDNALQSGNSQESVTEQDSKDSTYSLSSTLTLSKADYEKHK

VYACEVTHQGLSSPVTKSFNRGEC
```

-continued

ABS-101-C-Heavy-Chain (SEQ ID NO: 144)

QVQLQESGPGLVRPSQTLSLTCTVSGFDIQDTYMHWVRQRPGRGLEWMGRIEPAGGHT

KYNPSLKSRVTITRDTSKNQVSLRLSSVTAADTAVYYCVRSGGLPDAWGQGSLVTVSSASTKGP

SVFPLAPSSKSTSGGTAALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPEAAGGPSVFLFPPKPKDTLMI

SRTPEVTCVVVSVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVLHEALHSHYTQKSLSLSPGK

ABS-101-C-Light-Chain (SEQ ID NO: 145)

DIQMTQSPSSLSASVGDRVTITCRASQGVGYMYWYQQKPGKAPKLLIYSASNLASGVPS

RFSGSGSGTDFTFTISSLQPEDIATYYCQQWEGNPRTFGQGTKVEIKRTVAAPSVFIFPPSDEQL

KSGTASVVCLLNNFYPREAKVQWKVDNALQSGNSQESVTEQDSKDSTYSLSSTLTLSKADYEKHK

VYACEVTHQGLSSPVTKSFNRGEC

Figure 15A:
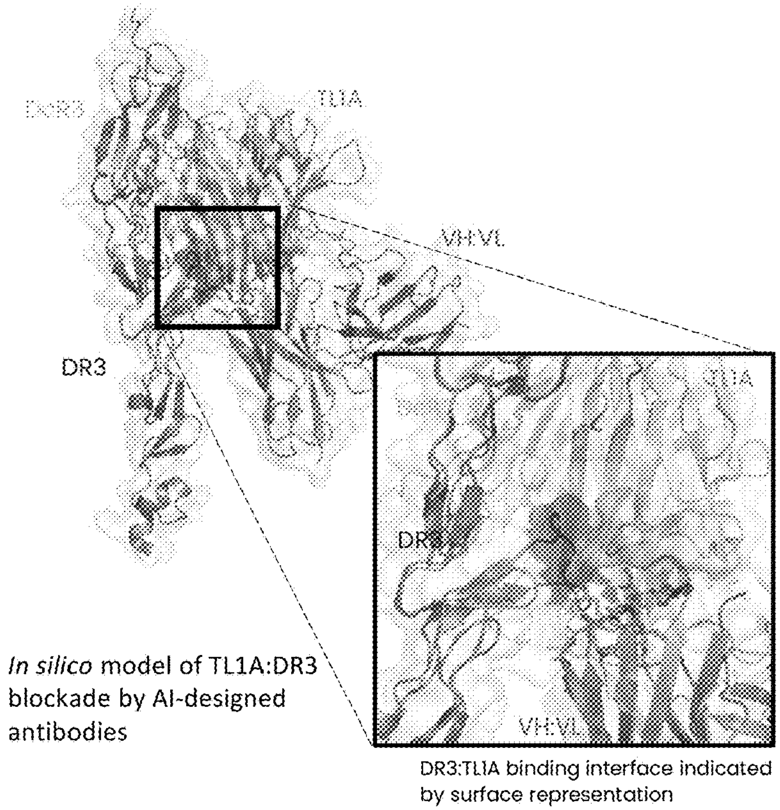
FIGS. 15A-15B shows AI de novo design of initial binders to epitopes of interest.
Figure 15B:
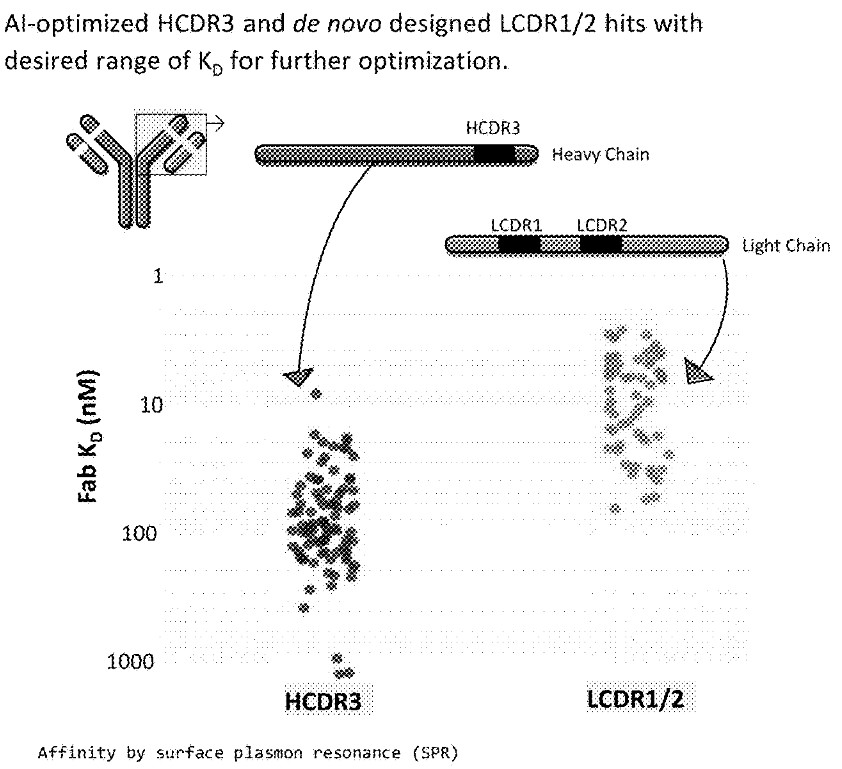

FIG. 15A shows an in silico structural model of TL1A: DR3 blockade by AI-designed antibodies. FIG. 15B shows binding affinity to TL1A of AI-designed HCDR3 and LCDR1/2 hits in Fab format as determined by SPR. Briefly, anti-Fab kappa LC and anti-CHI HC sensor chips were used to immobilize Fab samples via binding to the Fab arms were subsequently probed with a 6-point 2-fold serial dilution of TL1A injected as the analyte. Kinetic parameters $k_{on}$, $k_{off}$, of TL1A binding to the immobilized Fabs were estimated from non-linear regression analysis and dissociation constants ($K_D$) were calculated for each immobilized Fab.

FIG. 16A illustrates an AI-based strategy used to design antibodies. Light chain complementarity determining regions 1 and 2 were designed by de novo AI models described above. The AI-designed light chain was paired with a set of AI-optimized heavy chains followed by experimental validation. The AI models used for generating optimized heavy chains were trained on HTS data generated in house. These models enabled the identification of novel variants with superior binding affinity and diversity.

FIG. 16B shows binding affinity to TL1A of AI optimized variants in Fab format as determined by SPR. Briefly, anti-Fab kappa LC and anti-CHI HC sensor chips were used to immobilize Fab samples via binding to the Fab arms were subsequently probed with a 6-point 2-fold serial dilution of TL1A injected as the analyte. Kinetic parameters $k_{on}$, $k_{off}$, of TL1A binding to the immobilized Fabs were estimated from non-linear regression analysis and dissociation constants ($K_D$) were calculated for each immobilized Fab. Potential developability flags were calculated in silico as described below.

Figure 17:
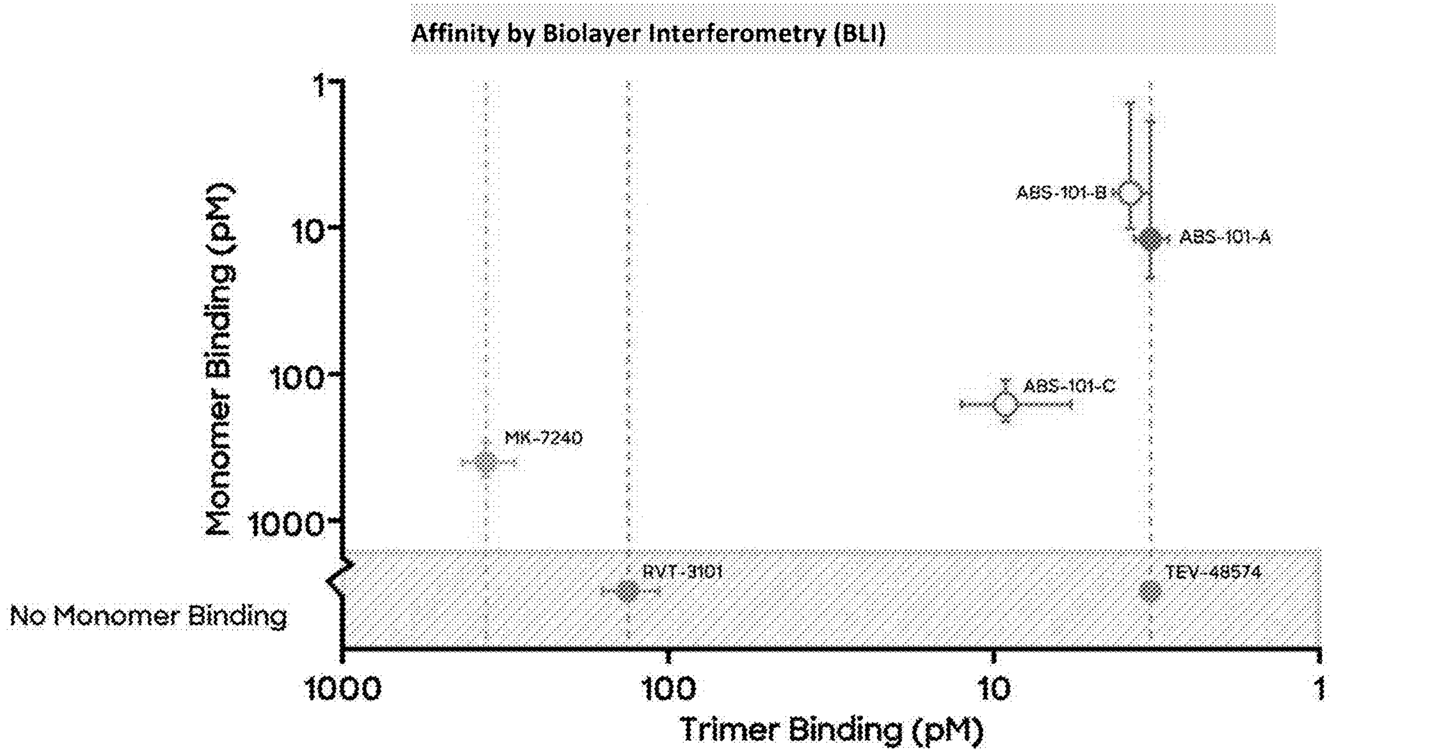
FIG. 17 shows lead candidates bind to both monomeric and trimeric TL1A.

FIG. 17 shows lead mAb candidates bind to monomeric and trimeric TL1A with high affinity by BLI. Briefly, biolayer interferometry (BLI) was used to estimate the kinetic parameters $k_{on}$ and $k_{off}$ of trimeric human TL1A and a monomeric human TL1A isoform to lead mAb and calculate dissociation constants ($K_D$) for each lead candidate.

Figure 18A:
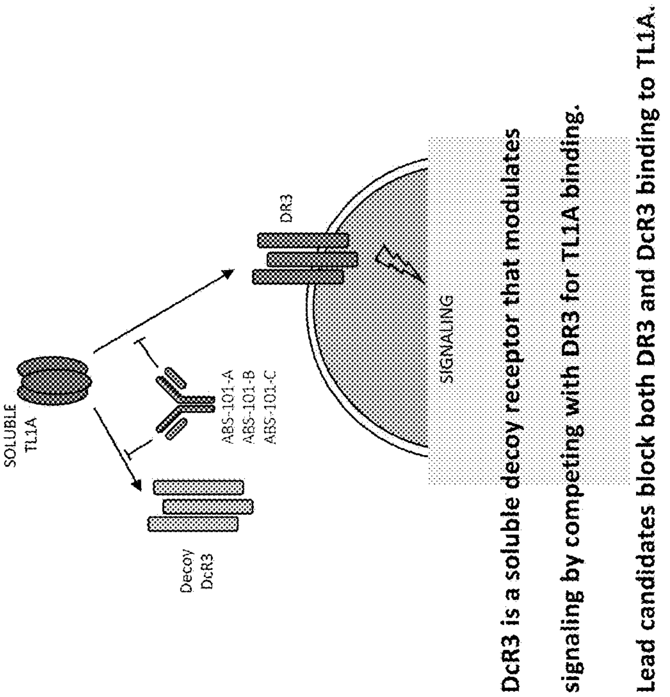
FIGS. 18A-18B shows lead candidates block TL1A binding to DR3 and DcR3.
Figure 18B:
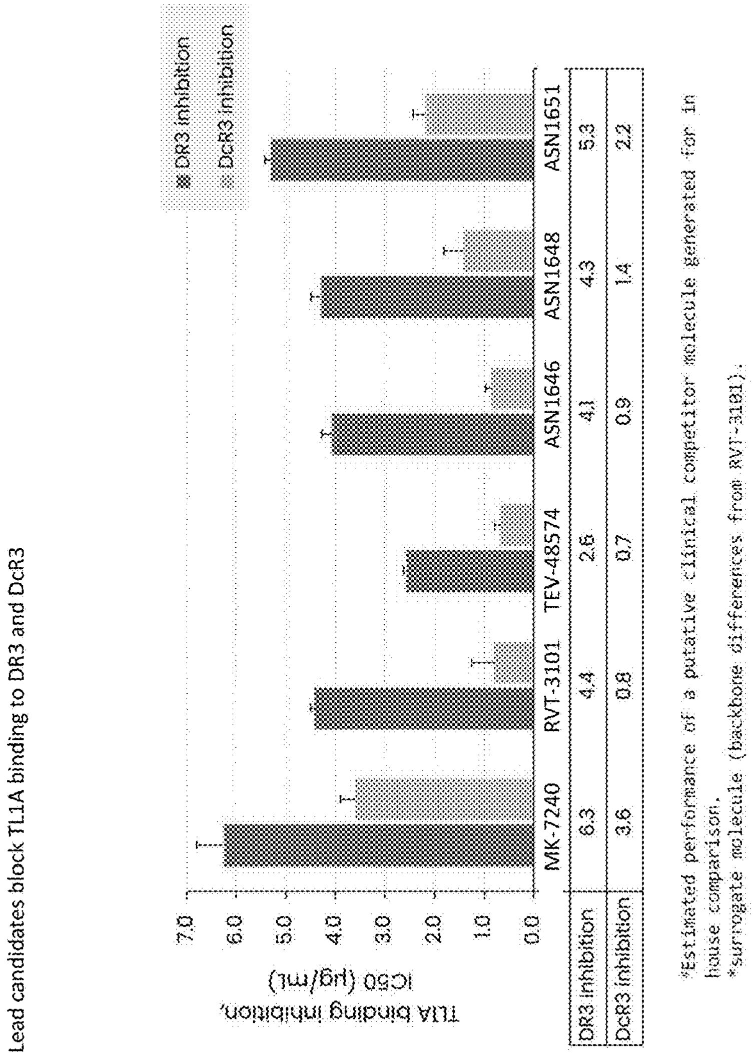

FIG. 18 shows the schematic for (FIG. 18A) and inhibition of TL1A binding to DR3 or DcR3 by lead mAb candidates (FIG. 18B) as determined by selectivity ELISA. Briefly, lead candidates or putative clinical competitor molecules generated for in house comparison at multiple concentrations are incubated with TL1A before being added to plates coated with DR3 or DcR3. A biotinylated anti-TL1A antibody is used to detect any bound TL1A. Then, adequate streptavidin-HRP followed by the chromogenic substrate TMB are used to quantify the amount of bound TL1A. The inhibitory curves are then obtained and IC50s calculated.

Figure 19A:
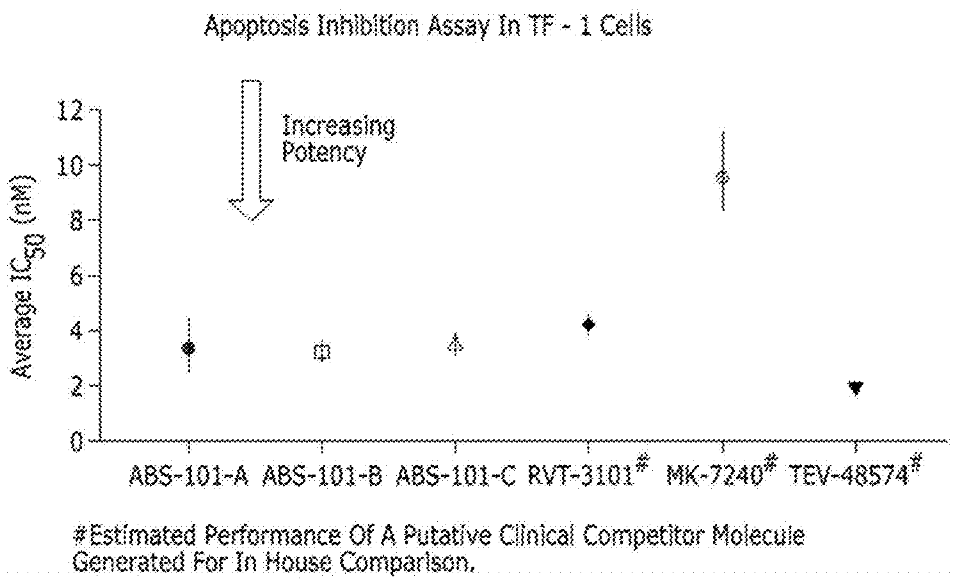
FIGS. 19A-19B shows AI-optimized lead candidates inhibit TL1A:DR3-driven apoptosis.
Figure 19B:
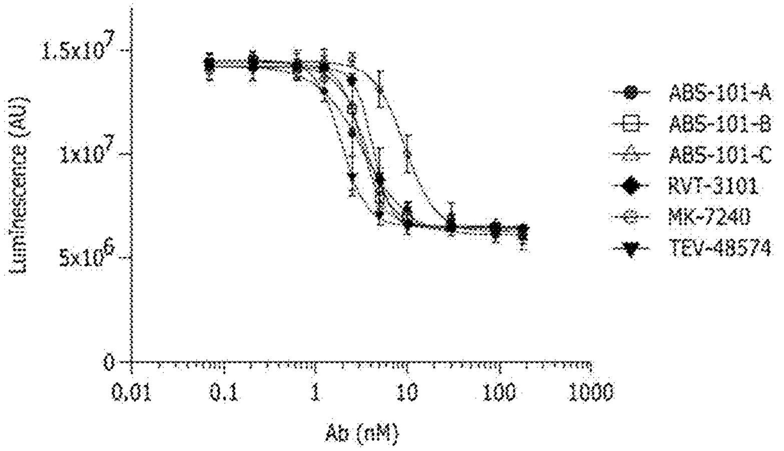

FIG. 19A shows IC50 and 95% confidence interval for apoptosis inhibition assay. Briefly, TF-1 cells treated with cyclohexamide (to induce apoptosis) were co-incubated with TL1A and a lead candidate or clinical benchmark for 5 hours. Caspase activity was then measured using the Promega Caspase-Glo 3/7 kit. FIG. 19B shows antibody titrations plotted against luminescence values. The curves were generated in Prism using a 4-parameter logistic fit model.

Figure 20B:
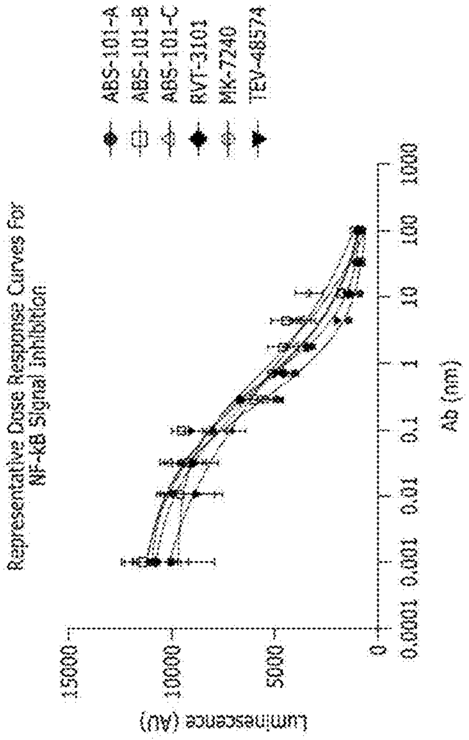
FIGS. 20A-20B shows AI-optimized lead candidates inhibit TL1A:DR3-driven NF-kB activation.
Figure 20A:
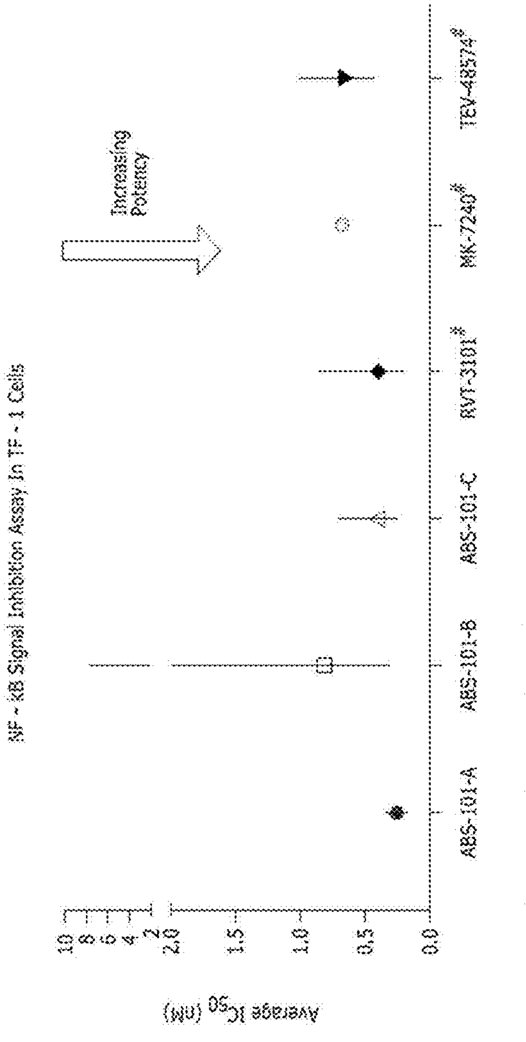

FIG. 20A shows the IC50 and 95% confidence interval of the NF-kB inhibition assay. Briefly, a reporter line was generated by integrating an NF-kB Luciferase reporter gene into TF-1 cells. The cells were maintained in pooled format (as opposed to expanding from single-clones). Early passage cells were stored as frozen stocks and prepared in thaw & use format. TF-1 NF-kB Luciferase reporter cells were stimulated with TL1A in the presence of lead candidate or clinical benchmark for 5 hours. FIG. 20B shows NF-kB induction was measured via luminescence and plotted against antibody titrations.

Figure 21B:
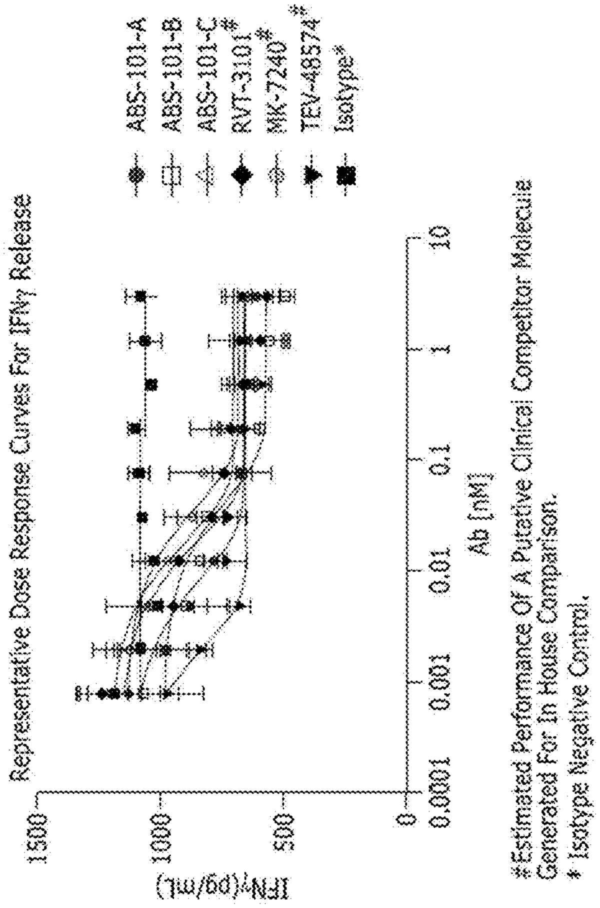
FIGS. 21A-21B shows AI-optimized lead candidates inhibit TL1A:DR3-driven INFγ release.
Figure 21A:
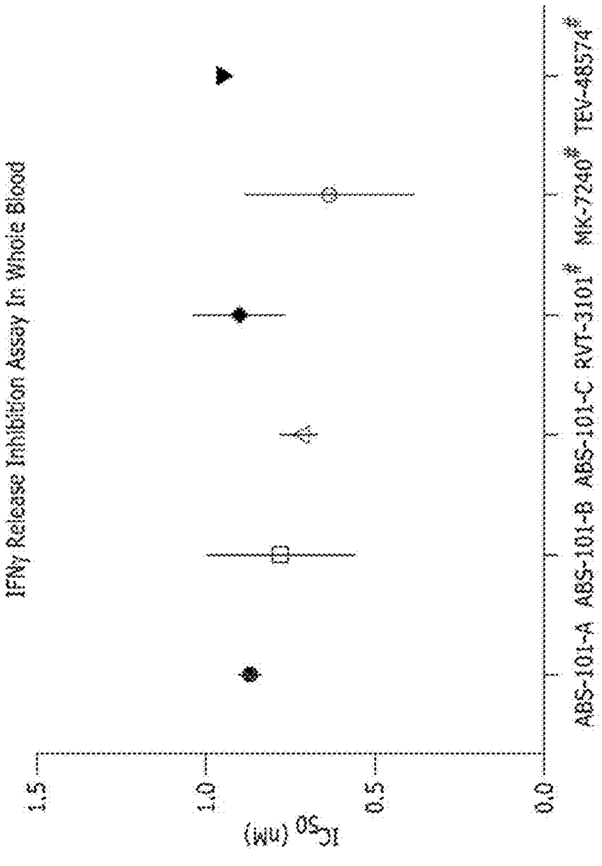

FIG. 21A shows whole blood IFNγ release inhibition assay average IC50 across 3 donors±SD, as determined by nonlinear fit curves. Curves were generated in Prism using a 4-parameter logistic fit model. and FIG. 21B shows whole blood IFNγ release inhibition assay dose response curves with nonlinear fit of curve for Donor 3 for all molecules and dilutions tested. Briefly, to assess the potency of anti-TL1A antibodies in diverse genetic backgrounds and against soluble and membrane bound TL1A, freshly collected human whole blood stimulated with IL-12 and IL-18 on immune complex (IC) coated plates were cultured with either serially diluted lead candidates, controls, or clinical competitor molecules at 37° C. overnight Supernatants were then assessed by IFNg ELISA. Antibody titrations were plotted against IFNγ ELISA concentrations.

FIG. 22 shows confirmation of effector function knockout in an ADCC activation assay for lead mAb candidates. Briefly, the ADCC assay was executed by first incubating titrated concentrations of lead candidates or putative clinical competitor molecules generated for in house comparison with TL1A+293HEK cells. Likewise, SKOV3 cells were incubated with trastuzumab to serve as a positive control. Effector cells were then added, and level of ADCC engagement was measured via their luciferase production.

FIG. 23 shows epitope bins for lead mAb candidates on TL1A determined by an epitope binning assessment conducted by BLI using a tandem epitope binning assay. TL1A was first immobilized on amine reactive probes via a standard amine coupling protocol, followed by association 1 of mAb-1 for 600 seconds then association 2 of mAb-2 for 300 seconds. During association 1, mAb-1 was used to saturate TL1A epitope. During association 2, mAb-2 was assessed for its ability to bind to TL1A in the presence of mAb-1.

FIG. 24 shows the ex vivo immunogenicity assessment. The box plot is the average drug stimulation index (SI) across fourteen HLA-typed donors incubated with lead candidates, clinical competitor molecules, media only, positive controls—protein KLH, or benchmark clinical mAbs with low and high ADA rates where media only has been normalized to 1. Error bars represent max and min values of donors. Briefly, PBMCs for seven HLA supertypes (two from each supertype) were incubated with lead candidates, clinical competitor molecules, media only, the positive control protein KLH (keyhole limpet hemocyanin), or benchmark clinical mAbs (bevacizumab, or bococizumab) with low and high ADA rates, respectively. After stimulation for 72-80 hrs., cells were stained with anti-CD4, CD137, and CD134 antibodies. The SI for each condition was calculated as the fraction of cells positive for either CD137, or CD134, or both in mAb stimulated cells divided by the fraction of cells positive in media only, where the media only SI was normalized to 1. Each condition was run in triplicate and averaged.

Figure 25A:
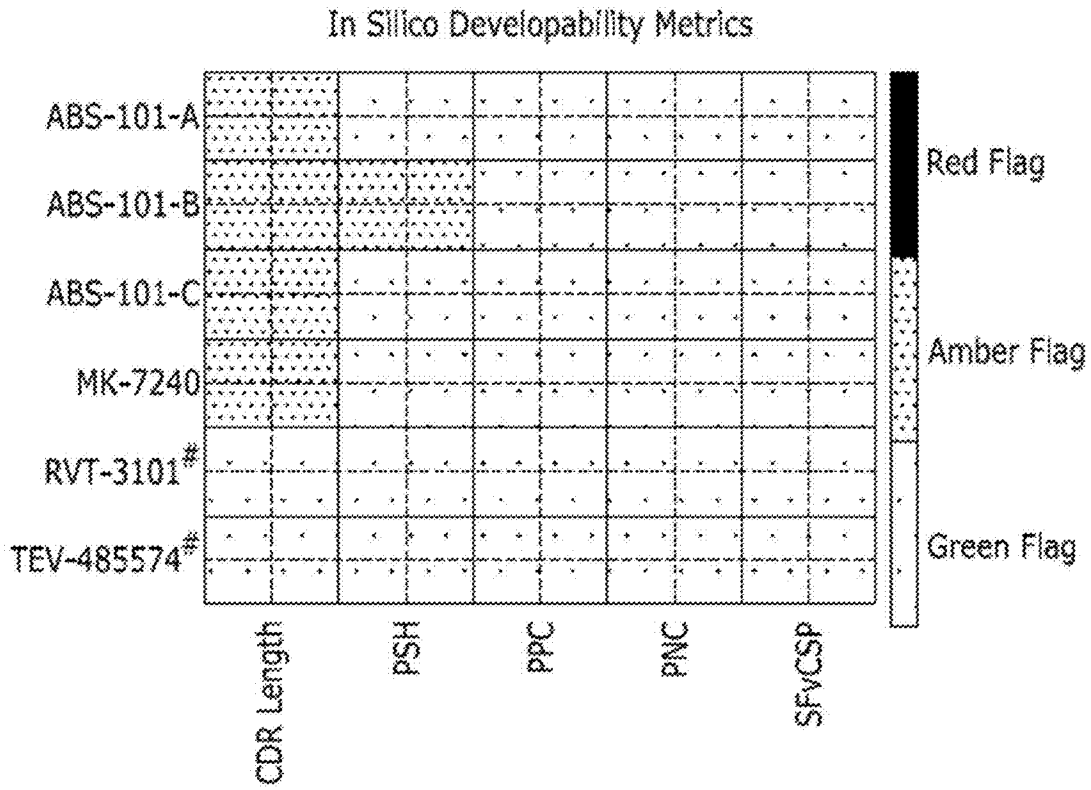
FIGS. 25A-25B shows lead candidates show good in silico developability profile.
Figure 25B:
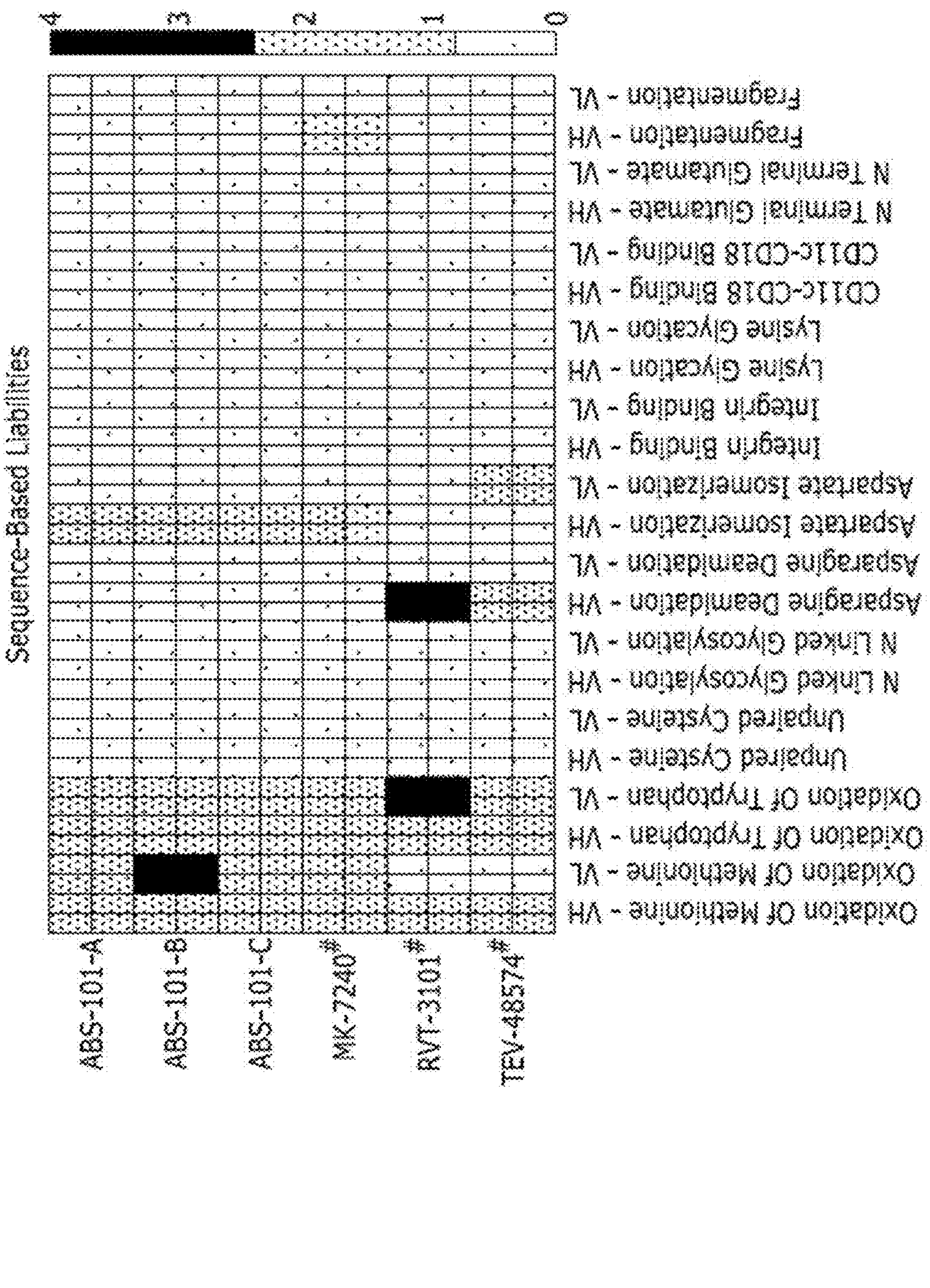

FIG. 25 shows in silico developability metrics (FIG. 25A) and sequence-based liabilities (FIG. 25B) for lead mAb candidates. TAP, an in silico tool developed by Oxford protein informatics group (OPIG), was used to calculate developability metrics for lead candidates or putative clinical competitor molecules generated for in house comparison. For each of these metrics, a reference distribution of values was created based on data from approved clinical-stage therapeutic antibodies and clinical development candidates. In silico assessment of lead candidates or putative clinical competitor molecules generated for in house comparison returned a score that TAP identified as a green, amber, or red flag depending on where it falls within the distribution. Additionally, TAP was used to calculate sequence liabilities across the light or heavy chain of a given test article. ABS-101-A, ABS-101-B, and ABS-101-C did not exhibit any in silico developability red flag.

Figure 26:
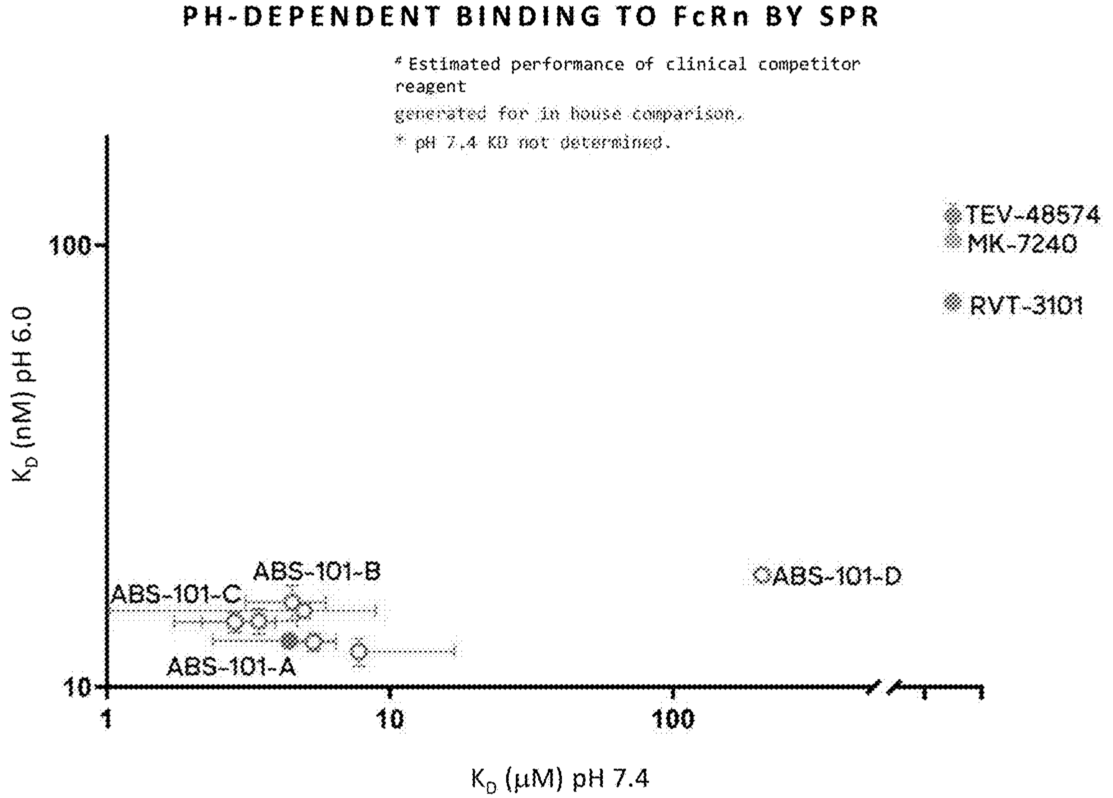
FIG. 26 shows half-life extension mutation to improve antibody pharmacokinetics.

FIG. 26 shows pH-dependent binding to FcRn by lead mAb candidates via SPR. Briefly, for measuring binding kinetics to the Fc region in IgG1 format a biotinylated capture reagent on a streptavidin chip was used to immobilize mAbs via the 2 Fab arms, orienting the Fc region to be subsequently probed with a 6-point 3-fold serial dilution of FcRn injected as the analyte starting at 1000 nM.

Example 5: Formulation and Stability of ABS-101-A

The following Example sets for the results of formulation and stability studies for ABS-101-A.

This study performed using material generated with early pool of clones and staged with 0.8 mL of drug substance in 2R vials. Stability assessment under different stress and storage conditions was measured by changes in the main SEC peak. No significant changes observed by appearance, protein concentration, or sub-visible particles. Changes observed by HIAC, icIEF, reducing and non-reducing CGE were smaller than SEC and are not shown. HIAC sub-visible particles were low after agitation, with final counts lower than 250 and 50, for >10 m and >25 m particles, respectively.

As shown in FIG. 27, antibody ABS-101-A was successfully formulated and developed as a drug substance at concentrations up to approximately 200 mg/mL. Formulations at 200 and 150 mg/mL showed comparable stability, with acceptable performance after 2 weeks at 40° C. and no changes to protein concentration or appearance.

Example 6: Pharmacokinetic Evaluation of Anti-TL1A Antibody

In this Example, studies were conducted to define the pharmacokinetics (PK) of anti-TL1A antibodies (e.g., ABS-101-A) of the present disclosure by comparing to the PK profiles of known anti-TL1A antibodies (e.g, MK-7240 and RVT-3101).

ABS-101 was utilized as the anti-TL1A antibody in these experiments. The known anti-TL1A antibodies utilized for comparisons were MK-7240 and RVT-3101. MK-7240, previously PRA-023 (Prometheus'), is Merck's leading clinical candidate of anti-TL1A humanized monoclonal antibodies. RVT-3101 is Roivant's leading candidate that demonstrated sustained efficacy across a broad dose range.

These studies were conducted in non-human primates (NHP). Antibody amounts in peripheral blood was quantified by ELISA. The results are shown in FIG. 28.

Figure 28A:
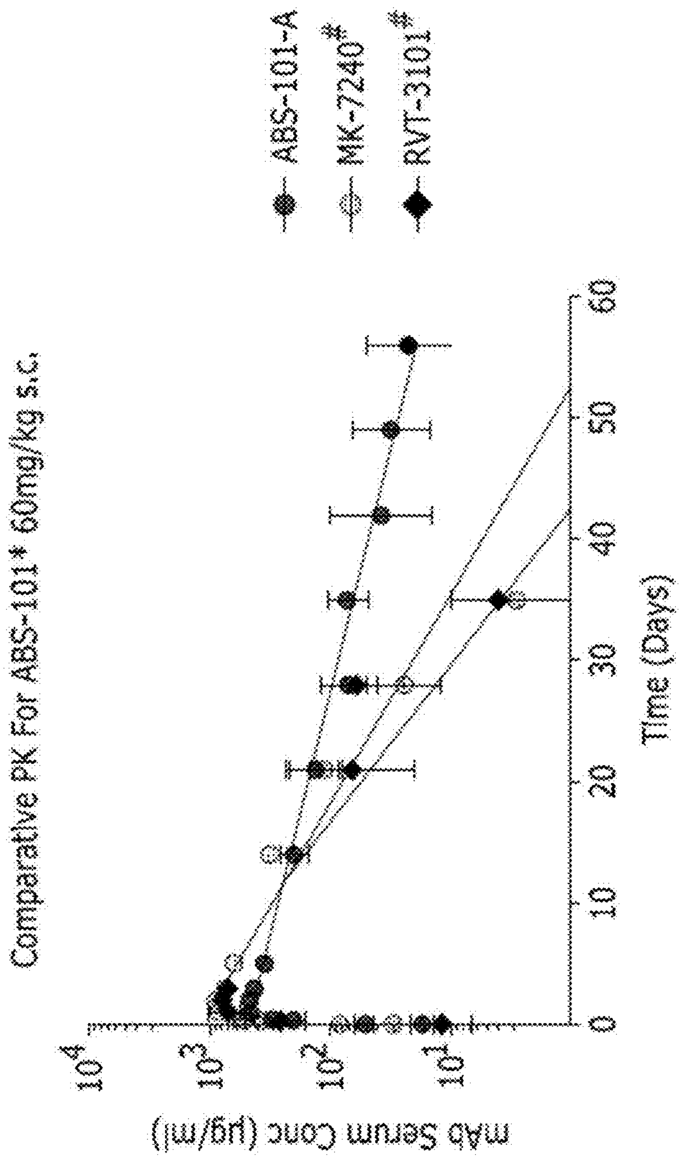

FIG. 28: shows a prolonged half-life profile of ABS-101-A compared to MK-7240 and RVT-3101 based on pharmacokinetics profiles of nonhuman primates (NHP) upon subcutaneous (s.c.) administration.

The results from the experiments indicate that anti-TL1A antibodies of the present disclosure show improved half-life profiles compared to those of MK-7240 and RVT-3101.

ABS-101-A has a higher peripheral partitioning coefficient than RVT-3101 and MK-7240 leading to an overall increased biodistribution. Such an enhanced biodistribution may result in lower Cmax and AUC after subcutaneous administration compared to the competitor molecules, i.e. ABS-101-A is likely to be rapidly sequestered into tissues shortly after entering the systemic circulation, leaving less of the antibody available in the plasma. This rapid and extensive tissue uptake reduces the concentration of the antibody in the bloodstream, leading to a lower Cmax. Additionally, because a substantial portion of the antibody is bound within tissues and may not readily re-enter circulation, the overall exposure of the plasma to the antibody over time (as reflected by AUC) could be reduced. This differs from the competitor antibodies, which, with less potent binding, might remain longer in the plasma, resulting in higher Cmax and AUC values.

Based on in silico modelling using 1) the determined ~2-3× fold improvement of ABS-101-A vs MK-7240 and RVT-3101 and 2) the available human half-life data on MK-7240 and RVT-3101 of t1/2=~19 days, achieving a >Q8W dosing frequency is contemplated herein.

Having described several embodiments of the techniques described herein in detail, various modifications and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 1 | QGVEY (SEQ ID NO: 1) | GAS | QQWEGNPRT (SEQ ID NO: 3) | GFDIQDTY (SEQ ID NO: 4) | IEPAGGHT (SEQ ID NO: 5) | ASSGGMPDL (SEQ ID NO: 6) | DIQMTQSPSSLSASVGDRVTITCRASQGVEYMYWYQQKPGKAPKLLIYGASNLASGVPSRFSGSGSGTDFTFTISSLQPEDIATYYCQQWEGNPRTFGQGTKVEIK (SEQ ID NO: 7) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPAGGHTKYNPSLKSRVTITRDTSKNQVSLRLSSVTAADTAVYYCASSGGMPDLWGQGSLVTVSS (SEQ ID NO: 9) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 2 | SSVSY (SEQ ID NO: 12) | ATS | QQWEGNPRT (SEQ ID NO: 3) | GLDPDDTYMH (SEQ ID NO: 14) | WMGRIEPAGGHTK (SEQ ID NO: 15) | VISGGLPDV (SEQ ID NO: 16) | DIQMTQSPSSLSASVGDRVTITCRASSSVSYMYWYQQKPGKAPKLLIYATSNLASGVPSRFSGSGSGTDFTFTISSLQPEDIATYYCQQWEGNPRTFGQGTKVEIK (SEQ ID NO: 17) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGLDPDDTYMHWVRQRPGRGLEWMGRIEPAGGHTKYNPSLKSRVTITRDTSKNQVSLRLSSVTAADTAVYYCVISGGLPDVWGQGSLVTVSS (SEQ ID NO: 18) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 3 | QGVRY (SEQ ID NO: 19) | GAS | QQWEGNPRT (SEQ ID NO: 3) | GFDIQDTY (SEQ ID NO: 4) | IEPAGGHT (SEQ ID NO: 5) | VRSGGLPDA (SEQ ID NO: 20) | DIQMTQSPSSLSASVGDRVTITCRASQGVRYMYWYQQKPGKAPKLLIYGASNLASGVPSRFSGSGSGTDFTFTISSLQPEDIATYYCQQWEGNPRTFGQGTKVEIK (SEQ ID NO: 21) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPAGGHTKYNPSLKSRVTITRDTSKNQVSLRLSSVTAADTAVYYCVRSGGLPDAWGQGSLVTVSS (SEQ ID NO: 22) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 4 | SSVSY (SEQ ID NO: 12) | GAS | QQWEGNPRT (SEQ ID NO: 3) | GFDMADTY (SEQ ID NO: 23) | IEPAGGHT (SEQ ID NO: 5) | VRSGGLPDM (SEQ ID NO: 24) | DIQMTQSPSSLSASVGDRVTITCRASSSVSYMYWYQQKPGKAPKLLIYGASNLASGVPSRFSGSGSGTDFTFTISSLQPEDIATYYCQQWEGNPRTFGQGTKVEIK (SEQ ID NO: 25) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMADTYMHWVRQRPGRGLEWMGRIEPAGGHTKYNPSLKSRVTITRDTSKNQVSLRLSSVTAADTAVYYCVRSGGLPDMWGQGSLVTVSS (SEQ ID NO: 26) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 5 | QGVMY (SEQ ID NO: 27) | GAS | QQWEGNPRT (SEQ ID NO: 3) | GFDMQDTY (SEQ ID NO: 28) | IEPASGHT (SEQ ID NO: 29) | VRSGGLPDV (SEQ ID NO: 30) | DIQMTQSPSSLSASVGDRVTITCRASQGVMYMYWYQQKPGKAPKLLIYGASNLASGVPSRFSGSGSGTDFTFTISSLQPEDIATYYCQQWEGNPRTFGQGTKVEIK (SEQ ID NO: 31) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMQDTYMHWVRQRPGRGLEWMGRIEPASGHTKYNPSLKSRVTITRDTSKNQVSLRLSSVTAADTAVYYCVRSGGLPDVWGQGSLVTVSS (SEQ ID NO: 32) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 6 | QGVEY (SEQ ID NO: 1) | SAS | QQWEGNPRT (SEQ ID NO: 3) | GFDMADTY (SEQ ID NO: 23) | IEPAGGHT (SEQ ID NO: 5) | VRSGGLPDM (SEQ ID NO: 24) | DIQMTQSPSSLSASVGDRVTITCRASQGVEYMYWYQQKPGKAPKLLIYSASNLASGVPSRFSGSGSGTDETFTISSLQPEDIATYYCQQWEGNPRTFGQGTKVEIK (SEQ ID NO: 34) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMADTYMHWVRQRPGRGLEWMGRIEPAGGHTKYNPSLKSRVTITRDTSKNQVSLRLSSVTAADTAVYYCVRSGGLPDMWGQGSLVTVSS (SEQ ID NO: 26) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 7 | QGVEY (SEQ ID NO: 1) | GAS | QQWEGNPRT (SEQ ID NO: 3) | GFDMGDTY (SEQ ID NO: 35) | IEPAAGHT (SEQ ID NO: 36) | VRSGGLPDI (SEQ ID NO: 37) | DIQMTQSPSSLSASVGDRVTITCRASQGVEYMYWYQQKPGKAPKLLIYGASNLASGVPSRFSGSGSGTDFTFTISSLQPEDIATYYCQQWEGNPRTFGQGTKVEIK (SEQ ID NO: 7) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIEPAAGHTKYNPSLKSRVTITRDTSKNQVSLRLSSVTAADTAVYYCVRSGGLPDIWGQGSLVTVSS (SEQ ID NO: 38) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 8 | SSVSY (SEQ ID NO: 12) | GAS | QQWEGNPRT (SEQ ID NO: 3) | GFDMQSTY (SEQ ID NO: 39) | IEPAGGHT (SEQ ID NO: 5) | VRSGGLPDV (SEQ ID NO: 30) | DIQMTQSPSSLSASVGDRVTITCRASSSVSYMYWYQQKPGKAPKLLIYGASNLASGVPSRFSGSGSGTDFTFTISSLQPEDIATYYCQQWEGNPRTFGQGTKVEIK (SEQ ID NO: 25) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMQSTYMHWVRQRPGRGLEWMGRIEPAGGHTKYNPSLKSRVTITRDTSKNQVSLRLSSVTAADTAVYYCVRSGGLPDVWGQGSLVTVSS (SEQ ID NO: 40) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 9 | QGVGY (SEQ ID NO: 41) | SAS | QQWEGNPRT (SEQ ID NO: 3) | GFDIQDTY (SEQ ID NO: 4) | IEPAGGHT (SEQ ID NO: 5) | VRSGGLPDA (SEQ ID NO: 20) | DIQMTQSPSSLSASVGDRVTITCRASQGVGYMYWYQQKPGKAPKLLIYSASNLASGVPSRFSGSGSGTDFTFTISSLQPEDIATYYCQQWEGNPRTFGQGTKVEIK (SEQ ID NO: 42) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPAGGHTKYNPSLKSRVTITRDTSKNQVSLRLSSVTAADTAVYYCVRSGGLPDAWGQGSLVTVSS (SEQ ID NO: 22) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 10 | QGVEY (SEQ ID NO: 1) | GAS | QQWEGNPRT (SEQ ID NO: 3) | GLDPDDTY (SEQ ID NO: 43) | IEPAGGHT (SEQ ID NO: 5) | VISGGLPDV (SEQ ID NO: 16) | DIQMTQSPSSLSASVGDRVTITCRASQGVEYMYWYQQKPGKAPKLLIYGASNLASGVPSRFSGSGSGTDFTFTISSLQPEDIATYYCQQWEGNPRTFGQGTKVEIK (SEQ ID NO: 7) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGLDPDDTYMHWVRQRPGRGLEWMGRIEPAGGHTKYNPSLKSRVTITRDTSKNQVSLRLSSVTAADTAVYYCVISGGLPDVWGQGSLVTVSS (SEQ ID NO: 18) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 11 | QGVEY (SEQ ID NO: 1) | SAS | QQWEGNPRT (SEQ ID NO: 3) | GFDMGDTY (SEQ ID NO: 35) | IEPAGGHT (SEQ ID NO: 5) | VRSGGMPDV (SEQ ID NO: 44) | DIQMTQSPSSLSASVGDRVTITCRASQGVEYMYWYQQKPGKAPKLLIYSASNLASGVPSRFSGSGSGTDFTFTISSLQPEDIATYYCQQWEGNPRTFGQGTKVEIK (SEQ ID NO: 34) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIEPAGGHTKYNPSLKSRVTITRDTSKNQVSLRLSSVTAADTAVYYCVRSGGMPDVWGQGSLVTVSS (SEQ ID NO: 45) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 12 | QGVEY (SEQ ID NO: 1) | SAS | QQWEGNPRT (SEQ ID NO: 3) | GFDITDTY (SEQ ID NO: 46) | IEPAGGHT (SEQ ID NO: 5) | VRSGGLPDV (SEQ ID NO: 30) | DIQMTQSPSSLSASVGDRVTITCRASQGVEYMYWYQQKPGKAPKLLIYSASNLASGVPSRFSGSGSGTDFTFTISSLQPEDIATYYCQQWEGNPRTFGQGTKVEIK (SEQ ID NO: 34) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDITDTYMHWVRQRPGRGLEWMGRIEPAGGHTKYNPSLKSRVTITRDTSKNQVSLRLSSVTAADTAVYYCVRSGGLPDVWGQGSLVTVSS (SEQ ID NO: 47) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 13 | QGVEY (SEQ ID NO: 1) | ATS | QQWEGNPRT (SEQ ID NO: 3) | GFDYQDTY (SEQ ID NO: 48) | IDPASGHT (SEQ ID NO: 49) | AVSGGMPDV (SEQ ID NO: 50) | DIQMTQSPSSLSASVGDRVTITCRASQGVEYMYWYQQKPGKAPKLLIYATSNLASGVPSRFSGSGSGTDFTFTISSLQPEDIATYYCQQWEGNPRTFGQGTKVEIK (SEQ ID NO: 51) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDYQDTYMHWVRQRPGRGLEWMGRIDPASGHTKYNPSLKSRVTITRDTSKNQVSLRLSSVTAADTAVYYCAVSGGMPDVWGQGSLVTVSS (SEQ ID NO: 52) | LAPSSKSTSGASTKGPSVFPGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 14 | QGIYY (SEQ ID NO: 53) | GAS | QQWEGNPRT (SEQ ID NO: 3) | GLDPDDTY (SEQ ID NO: 43) | IEPAGGHT (SEQ ID NO: 5) | VISGGLPDV (SEQ ID NO: 16) | DIQMTQSPSSLSASVGDRVTITCRASQGIYYMYWYQQKPGKAPKLLIYGASNLASGVPSRFSGSGSGTDFTFTISSLQPEDIATYYCQQWEGNPRTFGQGTKVEIK (SEQ ID NO: 54) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGLDPDDTYMHWVRQRPGRGLEWMGRIEPAGGHTKYNPSLKSRVTITRDTSKNQVSLRLSSVTAADTAVYYCVISGGLPDVWGQGSLVTVSS (SEQ ID NO: 18) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 15 | QGIYY (SEQ ID NO: 53) | GAS | QQWEGNPRT (SEQ ID NO: 3) | GFDIQDTY (SEQ ID NO: 4) | IEPAGGHT (SEQ ID NO: 5) | VRSGGLPDA (SEQ ID NO: 20) | DIQMTQSPSSLSASVGDRVTITCRASQGIYYMYWYQQKPGKAPKLLIYGASNLASGVPSRFSGSGSGTDFTFTISSLQPEDIATYYCQQWEGNPRTFGQGTKVEIK (SEQ ID NO: 54) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPAGGHTKYNPSLKSRVTITRDTSKNQVSLRLSSVTAADTAVYYCVRSGGLPDAWGQGSLVTVSS (SEQ ID NO: 22) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 16 | QGVEY (SEQ ID NO: 1) | GAS | QQWEGNPRT (SEQ ID NO: 3) | GFDMQSTY (SEQ ID NO: 39) | IEPAGGHT (SEQ ID NO: 5) | VRSGGLPDV (SEQ ID NO: 30) | DIQMTQSPSSLSASVGDRVTITCRASQGVEYMYWYQQKPGKAPKLLIYGASNLASGVPSRFSGSGSGTDFTFTISSLQPEDIATYYCQQWEGNPRTFGQGTKVEIK (SEQ ID NO: 7) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMQSTYMHWVRQRPGRGLEWMGRIEPAGGHTKYNPSLKSRVTITRDTSKNQVSLRLSSVTAADTAVYYCVRSGGLPDVWGQGSLVTVSS (SEQ ID NO: 40) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 17 | QGVEY (SEQ ID NO: 1) | GAS | QQWEGNPRT (SEQ ID NO: 3) | GFDMGDTY (SEQ ID NO: 35) | IEPAAGHT (SEQ ID NO: 36) | VRSGGLPDV (SEQ ID NO: 30) | DIQMTQSPSSLSASVGDRVTITCRASQGVEYMYWYQQKPGKAPKLLIYGASNLASGVPSRFSGSGSGTDFTFTISSLQPEDIATYYCQQWEGNPRTFGQGTKVEIK (SEQ ID NO: 7) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIEPAAGHTKYNPSLKSRVTITRDTSKNQVSLRLSSVTAADTAVYYCVRSGGLPDVWGQGSLVTVSS (SEQ ID NO: 55) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 18 | SSVSY (SEQ ID NO: 12) | YAS | QQWEGNPRT (SEQ ID NO: 3) | GFDMGDTY (SEQ ID NO: 35) | IEPAGGHT (SEQ ID NO: 5) | VRSGGMPDV (SEQ ID NO: 44) | DIQMTQSPSSLSASVGDRVTITCRASSSVSYMYWYQQKPGKAPKLLIYYASNLASGVPSRFSGSGSGTDFTFTISSLQPEDIATYYCQQWEGNPRTFGQGTKVEIK (SEQ ID NO: 57) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIEPAGGHTKYNPSLKSRVTITRDTSKNQVSLRLSSVTAADTAVYYCVRSGGMPDVWGQGSLVTVSS (SEQ ID NO: 45) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPRQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 19 | QGVEY (SEQ ID NO: 1) | YAS | QQWEGNPRT (SEQ ID NO: 3) | GFDITDTY (SEQ ID NO: 46) | IEPAGGHT (SEQ ID NO: 5) | VRSGGLPDV (SEQ ID NO: 30) | DIQMTQSPSSLSASVGDRVTITCRASQGVEYMYWYQQKPGKAPKLLIYYASNLASGVPSRFSGSGSGTDFTFTISSLQPEDIATYYCQQWEGNPRTFGQGTKVEIK (SEQ ID NO: 58) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDITDTYMHWVRQRPGRGLEWMGRIEPAGGHTKYNPSLKSRVTITRDTSKNQVSLRLSSVTAADTAVYYCVRSGGLPDVWGQGSLVTVSS (SEQ ID NO: 47) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 20 | QGVMY (SEQ ID NO: 27) | GAS | QQWEGNPRT (SEQ ID NO: 3) | GFDIQDTY (SEQ ID NO: 4) | IEPASGHT (SEQ ID NO: 29) | ARSGGMPDM (SEQ ID NO: 59) | DIQMTQSPSSLSASVGDRVTITCRASQGVMYMYWYQQKPGKAPKLLIYGASNLASGVPSRFSGSGSGTDFTFTISSLQPEDIATYYCQQWEGNPRTFGQGTKVEIK (SEQ ID NO: 31) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPASGHTKYNPSLKSRVTITRDTSKNQVSLRLSSVTAADTAVYYCARSGGMPDMWGQGSLVTVSS (SEQ ID NO: 60) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 21 | FSVDY (SEQ ID NO: 61) | WLIYATSNLAS (SEQ ID NO: 62) | QQWEGNPRS (SEQ ID NO: 63) | GYDLQESYMH (SEQ ID NO: 64) | IEPISGHL (SEQ ID NO: 65) | ARSGSGMSEY (SEQ ID NO: 66) | DIQMTQSPSSLSASVGDRVTITCRASFSVDYMYWYQQKPGKAPKWLIYATSNLASGVPSRFSGSGSGTDFTFTISSLQPEDIATYYCQQWEGNPRSFGQGTKVEIK (SEQ ID NO: 67) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGYDLQESYMHWVRQRPGRGLEWMGRIEPISGHLKYNPSLKSRVTITRDTSKNQVSLRLSSVTAADTAVYYCARSGSGMSEYWGQGSLVTVSS (SEQ ID NO: 68) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 22 | FSVTY (SEQ ID NO: 69) | YLIYPSG NLAS (SEQ ID NO: 70) | QQWEGNP RS (SEQ ID NO: 63) | GYDLQES YMH (SEQ ID NO: 64) | IEPISGH L (SEQ ID NO: 65) | ARSGSGM SEY (SEQ ID NO: 66) | DIQMTQSPSS LSASVGDRVT ITCRASFSVT YMYWYQQKPG KAPKYLIYPS GNLASGVPSR FSGSGSGTDF TFTISSLQPE DIATYYCQQW EGNPRSFGQG TKVEIK (SEQ ID NO: 71) | RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC (SEQ ID NO: 8) | QVQLQESGPGL VRP SQTLSLTC TVSGYDLQESY MHWVRQRPGRG LEWMGRIEPIS GHLKYNPSLKS RVTITRDTSKN QVSLRLSSVTA ADTAVYYCARS GSGMSEYWGQG SLVTVSS (SEQ ID NO: 68) | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHT (SEQ ID NO: 10) | CPPCPAPELLGGPSVFL FPPKPKDTLMISRTPEV TCVVVDVSHEDPEVKFN WYVDGVEVHNAKTKPRE EQYASTYRVVSVLTVLH QDWLNGKEYKCKVSNKA LPAPIEKTISKAKGQPR EPQVYTLPPSRDELTKN QVSLTCLVKGFYPSDIA VEWESNGQPENNYKTTP PVLDSDGSFFLYSKLTV DKSRWQQGNVFSCSVLH EALHSHYTQKSLSLSPG K (SEQ ID NO: 11) |
| 23 | FSVDY (SEQ ID NO: 61) | NLIYATS NLAS (SEQ ID NO: 72) | QQWEGNP RS (SEQ ID NO: 63) | GYDLQES YMH (SEQ ID NO: 64) | IEPISGH L (SEQ ID NO: 65) | AHSGGMT DY (SEQ ID NO: 73) | DIQMTQSPSS LSASVGDRVT ITCRASFSVD YMYWYQQKPG KAPKNLIYAT SNLASGVPSR FSGSGSGTDF TFTISSLQPE DIATYYCQQW EGNPRSFGQG TKVEIK (SEQ ID NO: 74) | RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC (SEQ ID NO: 8) | QVQLQESGPGL VRPSQTLSLTC TVSGYDLQESY MHWVRQRPGRG LEWMGRIEPIS GHLKYNPSLKS RVTITRDTSKN QVSLRLSSVTA ADTAVYYCAHS GGMTDYWGQGS LVTVSS (SEQ ID NO: 75) | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHT (SEQ ID NO: 10) | CPPCPAPELLGGPSVFL FPPKPKDTLMISRTPEV TCVVVDVSHEDPEVKEN WYVDGVEVHNAKTKPRE EQYASTYRVVSVLTVLH QDWLNGKEYKCKVSNKA LPAPIEKTISKAKGQPR EPQVYTLPPSRDELTKN QVSLTCLVKGFYPSDIA VEWESNGQPENNYKTTP PVLDSDGSFFLYSKLTV DKSRWQQGNVFSCSVLH EALHSHYTQKSLSLSPG K (SEQ ID NO: 11) |
| 24 | QGVGY (SEQ ID NO: 41) | ATS | QQWEGNP RT (SEQ ID NO: 3) | GFDIQDT Y (SEQ ID NO: 4) | IEPAGGH T (SEQ ID NO: 5) | VRSGGLP DA (SEQ ID NO: 20) | DIQMTQSPSS LSASVGDRVT ITCRASQGVG YMYWYQQKPG KAPKLLIYAT SNLASGVPSR FSGSGSGTDF TFTISSLQPE DIATYYCQQW EGNPRTFGQG TKVEIK (SEQ ID NO: 76) | RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC (SEQ ID NO: 8) | QVQLQESGPGL VRPSQTLSLTC TVSGFDIQDTY MHWVRQRPGRG LEWMGRIEPAG GHTKYNPSLKS RVTITRDTSKN QVSLRLSSVTA ADTAVYYCVRS GGLPDAWGQGS LVTVSS (SEQ ID NO: 22) | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHT (SEQ ID NO: 10) | CPPCPAPELLGGPSVFL FPPKPKDTLMISRTPEV TCVVVDVSHEDPEVKFN WYVDGVEVHNAKTKPRE EQYASTYRVVSVLTVLH QDWLNGKEYKCKVSNKA LPAPIEKTISKAKGQPR EPQVYTLPPSRDELTKN QVSLTCLVKGFYPSDIA VEWESNGQPENNYKTTP PVLDSDGSFFLYSKLTV DKSRWQQGNVFSCSVLH EALHSHYTQKSLSLSPG K (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 25 | FSVDY (SEQ ID NO: 61) | YLIYVTGNLAS (SEQ ID NO: 77) | QQWEGNPRS (SEQ ID NO: 63) | GFDLQDSFIH (SEQ ID NO: 78) | IDPASGHS (SEQ ID NO: 79) | ARSGGMTDY (SEQ ID NO: 80) | DIQMTQSPSSLSASVGDRVTITCRASFSVDYMYWYQQKPGKAPKYLIYVTGNLASGVPSRFSGSGSGTDFTFTISSLQPEDIATYYCQQWEGNPRSFGQGTKVEIK (SEQ ID NO: 81) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDLQDSFIHWVRQRPGRGLEWMGRIDPASGHSKYNPSLKSRVTITRDTSKNQVSLRLSSVTAADTAVYYCARSGGMTDYWGQGSLVTVSS (SEQ ID NO: 82) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 26 | QGVEY (SEQ ID NO: 1) | ATS | QQWEGNPRT (SEQ ID NO: 3) | GFDMADTY (SEQ ID NO: 23) | IEPAGGHT (SEQ ID NO: 5) | VRSGGLPDM (SEQ ID NO: 24) | DIQMTQSPSSLSASVGDRVTITCRASQGVEYMYWYQQKPGKAPKLLIYATSNLASGVPSRFSGSGSGTDFTFTISSLQPEDIATYYCQQWEGNPRTFGQGTKVEIK (SEQ ID NO: 51) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMADTYMHWVRQRPGRGLEWMGRIEPAGGHTKYNPSLKSRVTITRDTSKNQVSLRLSSVTAADTAVYYCVRSGGLPDMWGQGSLVTVSS (SEQ ID NO: 26) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 27 | QGVRY (SEQ ID NO: 19) | ATS | QQWEGNPRT (SEQ ID NO: 3) | GFDIQDTY (SEQ ID NO: 4) | IEPAGGHT (SEQ ID NO: 5) | VRSGGLPDA (SEQ ID NO: 20) | DIQMTQSPSSLSASVGDRVTITCRASQGVRYMYWYQQKPGKAPKLLIYATSNLASGVPSRFSGSGSGTDFTFTISSLQPEDIATYYCQQWEGNPRTFGQGTKVEIK (SEQ ID NO: 83) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPAGGHTKYNPSLKSRVTITRDTSKNQVSLRLSSVTAADTAVYYCVRSGGLPDAWGQGSLVTVSS (SEQ ID NO: 22) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 28 | QGVGY (SEQ ID NO: 41) | SAS | QQWEGNPRT (SEQ ID NO: 3) | GFDMADTY (SEQ ID NO: 23) | IEPAGGHT (SEQ ID NO: 5) | VRSGGLPDM (SEQ ID NO: 24) | DIQMTQSPSSLSASVGDRVTITCRASQGVGYMYWYQQKPGKAPKLLIYSASNLASGVPSRFSGSGSGTDFTFTISSLQPEDIATYYCQQWEGNPRTFGQGTKVEIK (SEQ ID NO: 42) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMADTYMHWVRQRPGRGLEWMGRIEPAGGHTKYNPSLKSRVTITRDTSKNQVSLRLSSVTAADTAVYYCVRSGGLPDMWGQGSLVTVSS (SEQ ID NO: 26) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAPVLDSDGSFFLYSKLTVDKSRWQQGNVFSCSVLHEALHSHYTQKSLSLSPGK (SEQ ID NO: 11) |
| 29 | SSVSY (SEQ ID NO: 12) | ATS | QQWEGNPRT (SEQ ID NO: 3) | GFDMADTYMH (SEQ ID NO: 84) | WMGRIEPAGGHTK (SEQ ID NO: 15) | VRSGGLPDM (SEQ ID NO: 24) | DIQMTQSPSSLSASVGDRVTITCRASSSVSYMYWYQQKPGKAPKLLIYATSNLASGVPSRFSGSGSGTDFTFTISSLQPEDIATYYCQQWEGNPRTFGQGTKVEIK (SEQ ID NO: 17) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMADTYMHWVRQRPGRGLEWMGRIEPAGGHTKYNPSLKSRVTITRDTSKNQVSLRLSSVTAADTAVYYCVRSGGLPDMWGQGSLVTVSS (SEQ ID NO: 26) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 30 | SSVSY (SEQ ID NO: 12) | SAS | QQWEGNPRT (SEQ ID NO: 3) | GFDIQDTY (SEQ ID NO: 4) | IEPAGGHT (SEQ ID NO: 5) | VRSGGLPDA (SEQ ID NO: 20) | DIQMTQSPSSLSASVGDRVTITCRASSSVSYMYWYQQKPGKAPKLLIYSASNLASGVPSRFSGSGSGTDFTFTISSLQPEDIATYYCQQWEGNPRTFGQGTKVEIK (SEQ ID NO: 85) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPAGGHTKYNPSLKSRVTITRDTSKNQVSLRLSSVTAADTAVYYCVRSGGLPDAWGQGSLVTVSS (SEQ ID NO: 22) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 31 | QGVMY (SEQ ID NO: 27) | ATS | QQWEGNPRT (SEQ ID NO: 3) | GFDMGDTY (SEQ ID NO: 35) | IEPAGGHT (SEQ ID NO: 5) | VRSGGMPDV (SEQ ID NO: 44) | DIQMTQSPSSLSASVGDRVTITCRASQGVMYMYWYQQKPGKAPKLLIYATSNLASGVPSRFSGSGSGTDFTFTISSLQPEDIATYYCQQWEGNPRTFGQGTKVEIK (SEQ ID NO: 86) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIEPAGGHTKYNPSLKSRVTITRDTSKNQVSLRLSSVTAADTAVYYCVRSGGMPDVWGQGSLVTVSS (SEQ ID NO: 45) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 32 | FSVDY (SEQ ID NO: 61) | DLIYATSNLAS (SEQ ID NO: 87) | QQWEGNPRS (SEQ ID NO: 63) | GFDLQDTYIH (SEQ ID NO: 88) | IDPASGHL (SEQ ID NO: 89) | ARSGGMTDY (SEQ ID NO: 80) | DIQMTQSPSSLSASVGDRVTITCRASFSVDYMYWYQQKPGKAPKDLIYATSNLASGVPSRFSGSGSGTDFTFTISSLQPEDIATYYCQQWEGNPRSFGQGTKVEIK (SEQ ID NO: 90) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDLQDTYIHWVRQRPGRGLEWMGRIDPASGHLKYNPSLKSRVTITRDTSKNQVSLRLSSVTAADTAVYYCARSGGMTDYWGQGSLVTVSS (SEQ ID NO: 91) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 33 | QGVEY (SEQ ID NO: 1) | ATS | QQWEGNPRT (SEQ ID NO: 3) | GFDIQDTY (SEQ ID NO: 4) | IEPAGGHT (SEQ ID NO: 5) | VRSGGLPDA (SEQ ID NO: 20) | DIQMTQSPSSLSASVGDRVTITCRASQGVEYMYWYQQKPGKAPKLLIYATSNLASGVPSRFSGSGSGTDFTFTISSLQPEDIATYYCQQWEGNPRTFGQGTKVEIK (SEQ ID NO: 51) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPAGGHTKYNPSLKSRVTITRDTSKNQVSLRLSSVTAADTAVYYCVRSGGLPDAWGQGSLVTVSS (SEQ ID NO: 22) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 34 | QGIYY (SEQ ID NO: 53) | ATS | QQWEGNPRT (SEQ ID NO: 3) | GLDPDDTY (SEQ ID NO: 43) | IEPAGGHT (SEQ ID NO: 5) | VISGGLPDV (SEQ ID NO: 16) | DIQMTQSPSSLSASVGDRVTITCRASQGIYYMYWYQQKPGKAPKLLIYATSNLASGVPSRFSGSGSGTDFTFTISSLQPEDIATYYCQQWEGNPRTFGQGTKVEIK (SEQ ID NO: 92) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGLDPDDTYMHWVRQRPGRGLEWMGRIEPAGGHTKYNPSLKSRVTITRDTSKNQVSLRLSSVTAADTAVYYCVISGGLPDVWGQGSLVTVSS (SEQ ID NO: 18) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAPVLDSDGSFFLYSKLTVDKSRWQQGNVFSCSVLHEALHSHYTQKSLSLSPGK (SEQ ID NO: 11) |
| 35 | QGVGY (SEQ ID NO: 41) | GAS | QQWEGNPRT (SEQ ID NO: 3) | GFDMGDTY (SEQ ID NO: 35) | IEPAGGHT (SEQ ID NO: 5) | VRSGGMPDV (SEQ ID NO: 44) | DIQMTQSPSSLSASVGDRVTITCRASQGVGYMYWYQQKPGKAPKLLIYGASNLASGVPSRFSGSGSGTDFTFTISSLQPEDIATYYCQQWEGNPRTFGQGTKVEIK (SEQ ID NO: 93) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIEPAGGHTKYNPSLKSRVTITRDTSKNQVSLRLSSVTAADTAVYYCVRSGGMPDVWGQGSLVTVSS (SEQ ID NO: 45) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 36 | QGVEY (SEQ ID NO: 1) | SAS | QQWEGNPRT (SEQ ID NO: 3) | GFDMQDTY (SEQ ID NO: 28) | IEPASGHT (SEQ ID NO: 29) | VRSGGLPDV (SEQ ID NO: 30) | DIQMTQSPSSLSASVGDRVTITCRASQGVEYMYWYQQKPGKAPKLLIYSASNLASGVPSRFSGSGSGTDFTFTISSLQPEDIATYYCQQWEGNPRTFGQGTKVEIK (SEQ ID NO: 34) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMQDTYMHWVRQRPGRGLEWMGRIEPASGHTKYNPSLKSRVTITRDTSKNQVSLRLSSVTAADTAVYYCVRSGGLPDVWGQGSLVTVSS (SEQ ID NO: 32) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 37 | SSVSY (SEQ ID NO: 12) | GAS | QQWEGNPRT (SEQ ID NO: 3) | GFDMGDTY (SEQ ID NO: 35) | IEPAGGHT (SEQ ID NO: 5) | VRSGGMPDV (SEQ ID NO: 44) | DIQMTQSPSSLSASVGDRVTITCRASSSVSYMYWYQQKPGKAPKLLIYGASNLASGVPSRFSGSGSGTDFTFTISSLQPEDIATYYCQQWEGNPRTFGQGTKVEIK (SEQ ID NO: 25) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIEPAGGHTKYNPSLKSRVTITRDTSKNQVSLRLSSVTAADTAVYYCVRSGGMPDVWGQGSLVTVSS (SEQ ID NO: 45) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 38 | SSVSY (SEQ ID NO: 12) | SAS | QQWEGNPRT (SEQ ID NO: 3) | GFDMGDTY (SEQ ID NO: 35) | IEPAGGHT (SEQ ID NO: 5) | VRSGGMPDV (SEQ ID NO: 44) | DIQMTQSPSSLSASVGDRVTITCRASSSVSYMYWYQQKPGKAPKLLIYSASNLASGVPSRFSGSGSGTDFTFTISSLQPEDIATYYCQQWEGNPRTFGQGTKVEIK (SEQ ID NO: 85) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIEPAGGHTKYNPSLKSRVTITRDTSKNQVSLRLSSVTAADTAVYYCVRSGGMPDVWGQGSLVTVSS (SEQ ID NO: 45) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 39 | SSVSY (SEQ ID NO: 12) | ATS | QQWEGNPRT (SEQ ID NO: 3) | GFDIQDTYMH (SEQ ID NO: 94) | WMGRIEPAGGHTK (SEQ ID NO: 15) | VRSGGLPDA (SEQ ID NO: 20) | DIQMTQSPSSLSASVGDRVTITCRASSSVSYMYWYQQKPGKAPKLLIYATSNLASGVPSRFSGSGSGTDFTFTISSLQPEDIATYYCQQWEGNPRTFGQGTKVEIK (SEQ ID NO: 17) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPAGGHTKYNPSLKSRVTITRDTSKNQVSLRLSSVTAADTAVYYCVRSGGLPDAWGQGSLVTVSS (SEQ ID NO: 22) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 40 | QGVEY (SEQ ID NO: 1) | ATS | QQWEGNPRT (SEQ ID NO: 3) | GFDMGDTY (SEQ ID NO: 35) | IEPAAGHT (SEQ ID NO: 36) | VRSGGLPDI (SEQ ID NO: 37) | DIQMTQSPSSLSASVGDRVTITCRASQGVEYMYWYQQKPGKAPKLLIYATSNLASGVPSRFSGSGSGTDFTFTISSLQPEDIATYYCQQWEGNPRTFGQGTKVEIK (SEQ ID NO: 51) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIEPAAGHTKYNPSLKSRVTITRDTSKNQVSLRLSSVTAADTAVYYCVRSGGLPDIWGQGSLVTVSS (SEQ ID NO: 38) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 41 | SSVSY (SEQ ID NO: 12) | SAS | QQWEGNPRT (SEQ ID NO: 3) | GFDITDTY (SEQ ID NO: 46) | IEPAGGHT (SEQ ID NO: 5) | VRSGGLPDV (SEQ ID NO: 30) | DIQMTQSPSSLSASVGDRVTITCRASSSVSYMYWYQQKPGKAPKLLIYSASNLASGVPSRFSGSGSGTDFTFTISSLQPEDIATYYCQQWEGNPRTFGQGTKVEIK (SEQ ID NO: 85) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDITDTYMHWVRQRPGRGLEWMGRIEPAGGHTKYNPSLKSRVTITRDTSKNQVSLRLSSVTAADTAVYYCVRSGGLPDVWGQGSLVTVSS (SEQ ID NO: 47) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 42 | QGVGY (SEQ ID NO: 41) | GAS | QQWEGNPRT (SEQ ID NO: 3) | GFDITDTY (SEQ ID NO: 46) | IEPAGGHT (SEQ ID NO: 5) | VRSGGLPDV (SEQ ID NO: 30) | DIQMTQSPSSLSASVGDRVTITCRASQGVGYMYWYQQKPGKAPKLLIYGASNLASGVPSRFSGSGSGTDFTFTISSLQPEDIATYYCQQWEGNPRTFGQGTKVEIK (SEQ ID NO: 93) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDITDTYMHWVRQRPGRGLEWMGRIEPAGGHTKYNPSLKSRVTITRDTSKNQVSLRLSSVTAADTAVYYCVRSGGLPDVWGQGSLVTVSS (SEQ ID NO: 47) | ASTKGP SVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 43 | QGVEY (SEQ ID NO: 1) | GAS | QQWEGNPRT (SEQ ID NO: 3) | GFDIQDTY (SEQ ID NO: 4) | IDPASGHT (SEQ ID NO: 49) | GRSGGMMDL (SEQ ID NO: 95) | DIQMTQSPSSLSASVGDRVTITCRASQGVEYMYWYQQKPGKAPKLLIYGASNLASGVPSRFSGSGSGTDFTFTISSLQPEDIATYYCQQWEGNPRTFGQGTKVEIK (SEQ ID NO: 7) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIDPASGHTKYNPSLKSRVTITRDTSKNQVSLRLSSVTAADTAVYYCGRSGGMMDLWGQGSLVTVSS (SEQ ID NO: 96) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 44 | QGVRY (SEQ ID NO: 19) | SAS | QQWEGNPRT (SEQ ID NO: 3) | GFDMGDTY (SEQ ID NO: 35) | IEPAGGHT (SEQ ID NO: 5) | VRSGGMPDV (SEQ ID NO: 44) | DIQMTQSPSSLSASVGDRVTITCRASQGVRYMYWYQQKPGKAPKLLIYSASNLASGVPSRFSGSGSGTDFTFTISSLQPEDIATYYCQQWEGNPRTFGQGTKVEIK (SEQ ID NO: 97) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIEPAGGHTKYNPSLKSRVTITRDTSKNQVSLRLSSVTAADTAVYYCVRSGGMPDVWGQGSLVTVSS (SEQ ID NO: 45) | ASTKGP SVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 45 | SSVSY (SEQ ID NO: 12) | ATS | QQWEGNPRT (SEQ ID NO: 3) | GFDIEDTYMH (SEQ ID NO: 98) | WMGRIEPASGHTK (SEQ ID NO: 99) | AISGGVPDV (SEQ ID NO: 100) | DIQMTQSPSSLSASVGDRVTITCRASSSVSYMYWYQQKPGKAPKLLIYATSNLASGVPSRFSGSGSGTDFTFTISSLQPEDIATYYCQQWEGNPRTFGQGTKVEIK (SEQ ID NO: 17) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIEDTYMHWVRQRPGRGLEWMGRIEPASGHTKYNPSLKSRVTITRDTSKNQVSLRLSSVTAADTAVYYCAISGGVPDVWGQGSLVTVSS (SEQ ID NO: 101) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 46 | QGVGY (SEQ ID NO: 41) | SAS | QQWEGNPRT (SEQ ID NO: 3) | GFDMGDTY (SEQ ID NO: 35) | IEPAGGHT (SEQ ID NO: 5) | VRSGGMPDV (SEQ ID NO: 44) | DIQMTQSPSSLSASVGDRVTITCRASQGVGYMYWYQQKPGKAPKLLIYSASNLASGVPSRFSGSGSGTDFTFTISSLQPEDIATYYCQQWEGNPRTFGQGTKVEIK (SEQ ID NO: 42) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIEPAGGHTKYNPSLKSRVTITRDTSKNQVSLRLSSVTAADTAVYYCVRSGGMPDVWGQGSLVTVSS (SEQ ID NO: 45) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 47 | QGVGY (SEQ ID NO: 41) | SAS | QQWEGNPRT (SEQ ID NO: 3) | GFDMQSTY (SEQ ID NO: 39) | IEPAGGHT (SEQ ID NO: 5) | VRSGGLPDV (SEQ ID NO: 30) | DIQMTQSPSSLSASVGDRVTITCRASQGVGYMYWYQQKPGKAPKLLIYSASNLASGVPSRFSGSGSGTDFTFTISSLQPEDIATYYCQQWEGNPRTFGQGTKVEIK (SEQ ID NO: 42) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMQSTYMHWVRQRPGRGLEWMGRIEPAGGHTKYNPSLKSRVTITRDTSKNQVSLRLSSVTAADTAVYYCVRSGGLPDVWGQGSLVTVSS (SEQ ID NO: 40) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 48 | QGVMY (SEQ ID NO: 27) | GAS | QQWEGNPRT (SEQ ID NO: 3) | GFDIQDTY (SEQ ID NO: 4) | IEPAGGHT (SEQ ID NO: 5) | VRSGGLPDA (SEQ ID NO: 20) | DIQMTQSPSSLSASVGDRVTITCRASQGVMYMYWYQQKPGKAPKLLIYGASNLASGVPSRFSGSGSGTDFTFTISSLQPEDIATYYCQQWEGNPRTFGQGTKVEIK (SEQ ID NO: 31) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPAGGHTKYNPSLKSRVTITRDTSKNQVSLRLSSVTAADTAVYYCVRSGGLPDAWGQGSLVTVSS (SEQ ID NO: 22) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 49 | QGVEY (SEQ ID NO: 1) | ATS | QQWEGNPRT (SEQ ID NO: 3) | GFDMGDTY (SEQ ID NO: 35) | IEPAGGHT (SEQ ID NO: 5) | VRSGGMPDV (SEQ ID NO: 44) | DIQMTQSPSSLSASVGDRVTITCRASQGVEYMYWYQQKPGKAPKLLIYATSNLASGVPSRFSGSGSGTDFTFTISSLQPEDIATYYCQQWEGNPRTFGQGTKVEIK (SEQ ID NO: 51) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIEPAGGHTKYNPSLKSRVTITRDTSKNQVSLRLSSVTAADTAVYYCVRSGGMPDVWGQGSLVTVSS (SEQ ID NO: 45) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 50 | QGVMY (SEQ ID NO: 27) | GAS | QQWEGNPRT (SEQ ID NO: 3) | GFDMGDTY (SEQ ID NO: 35) | IEPAAGHT (SEQ ID NO: 36) | VRSGGLPDI (SEQ ID NO: 37) | DIQMTQSPSSLSASVGDRVTITCRASQGVMYMYWYQQKPGKAPKLLIYGASNLASGVPSRFSGSGSGTDFTFTISSLQPEDIATYYCQQWEGNPRTFGQGTKVEIK (SEQ ID NO: 31) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIEPAAGHTKYNPSLKSRVTITRDTSKNQVSLRLSSVTAADTAVYYCVRSGGLPDIWGQGSLVTVSS (SEQ ID NO: 38) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 51 | QGVEY (SEQ ID NO: 1) | GAS | QQWEGNPRT (SEQ ID NO: 3) | GFDIQDTY (SEQ ID NO: 4) | IEPAGGHT (SEQ ID NO: 5) | VRSGGLPDA (SEQ ID NO: 20) | DIQMTQSPSSLSASVGDRVTITCRASQGVEYMYWYQQKPGKAPKLLIYGASNLASGVPSRFSGSGSGTDFTFTISSLQPEDIATYYCQQWEGNPRTFGQGTKVEIK (SEQ ID NO: 7) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPAGGHTKYNPSLKSRVTITRDTSKNQVSLRLSSVTAADTAVYYCVRSGGLPDAWGQGSLVTVSS (SEQ ID NO: 22) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 52 | QGVGY (SEQ ID NO: 41) | ATS | QQWEGNPRT (SEQ ID NO: 3) | GFDMQSTY (SEQ ID NO: 39) | IEPAGGHT (SEQ ID NO: 5) | VRSGGLPDV (SEQ ID NO: 30) | DIQMTQSPSSLSASVGDRVTITCRASQGVGYMYWYQQKPGKAPKLLIYATSNLASGVPSRFSGSGSGTDFTFTISSLQPEDIATYYCQQWEGNPRTFGQGTKVEIK (SEQ ID NO: 76) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMQSTYMHWVRQRPGRGLEWMGRIEPAGGHTKYNPSLKSRVTITRDTSKNQVSLRLSSVTAADTAVYYCVRSGGLPDVWGQGSLVTVSS (SEQ ID NO: 40) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 53 | QGVRY (SEQ ID NO: 19) | GAS | QQWEGNPRT (SEQ ID NO: 3) | GFDIQDTY (SEQ ID NO: 4) | IEPASGHT (SEQ ID NO: 29) | ARSGGMMDR (SEQ ID NO: 102) | DIQMTQSPSSLSASVGDRVTITCRASQGVRYMYWYQQKPGKAPKLLIYGASNLASGVPSRFSGSGSGTDFTFTISSLQPEDIATYYCQQWEGNPRTFGQGTKVEIK (SEQ ID NO: 21) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPASGHTKYNPSLKSRVTITRDTSKNQVSLRLSSVTAADTAVYYCARSGGMMDRWGQGSLVTVSS (SEQ ID NO: 103) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 54 | QGVEY (SEQ ID NO: 1) | GAS | QQWEGNPRT (SEQ ID NO: 3) | GFDMQDTY (SEQ ID NO: 28) | IDPAGGHT (SEQ ID NO: 104) | VRSGGLPDE (SEQ ID NO: 105) | DIQMTQSPSSLSASVGDRVTITCRASQGVEYMYWYQQKPGKAPKLLIYGASNLASGVPSRFSGSGSGTDFTFTISSLQPEDIATYYCQQWEGNPRTFGQGTKVEIK (SEQ ID NO: 7) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMQDTYMHWVRQRPGRGLEWMGRIDPAGGHTKYNPSLKSRVTITRDTSKNQVSLRLSSVTAADTAVYYCVRSGGLPDEWGQGSLVTVSS (SEQ ID NO: 106) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 55 | SSVSY (SEQ ID NO: 12) | GAS | QQWEGNPRT (SEQ ID NO: 3) | GFDMGDTY (SEQ ID NO: 35) | IEPAAGHT (SEQ ID NO: 36) | VRSGGLPDV (SEQ ID NO: 30) | DIQMTQSPSSLSASVGDRVTITCRASSSVSYMYWYQQKPGKAPKLLIYGASNLASGVPSRFSGSGSGTDFTFTISSLQPEDIATYYCQQWEGNPRTFGQGTKVEIK (SEQ ID NO: 25) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIEPAAGHTKYNPSLKSRVTITRDTSKNQVSLRLSSVTAADTAVYYCVRSGGLPDVWGQGSLVTVSS (SEQ ID NO: 55) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 56 | QGVGY (SEQ ID NO: 41) | GAS | QQWEGNPRT (SEQ ID NO: 3) | GFDIQDTY (SEQ ID NO: 4) | IEPAGGHT (SEQ ID NO: 5) | VRSGGLPDA (SEQ ID NO: 20) | DIQMTQSPSSLSASVGDRVTITCRASQGVGYMYWYQQKPGKAPKLLIYGASNLASGVPSRFSGSGSGTDETFTISSLQPEDIATYYCQQWEGNPRTFGQGTKVEIK (SEQ ID NO: 93) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPAGGHTKYNPSLKSRVTITRDTSKNQVSLRLSSVTAADTAVYYCVRSGGLPDAWGQGSLVTVSS (SEQ ID NO: 22) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 57 | QGVRY (SEQ ID NO: 19) | GAS | QQWEGNPRT (SEQ ID NO: 3) | GFDMGDTY (SEQ ID NO: 35) | IDPASGHT (SEQ ID NO: 49) | VRSGGMPDA (SEQ ID NO: 107) | DIQMTQSPSSLSASVGDRVTITCRASQGVRYMYWYQQKPGKAPKLLIYGASNLASGVPSRFSGSGSGTDFTFTISSLQPEDIATYYCQQWEGNPRTFGQGTKVEIK (SEQ ID NO: 21) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIDPASGHTKYNPSLKSRVTITRDTSKNQVSLRLSSVTAADTAVYYCVRSGGMPDAWGQGSLVTVSS (SEQ ID NO: 108) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 58 | QGVEY (SEQ ID NO: 1) | GAS | QQWEGNPRT (SEQ ID NO: 3) | GLDMQDTY (SEQ ID NO: 109) | IEPASGHT (SEQ ID NO: 29) | AASGGRPDL (SEQ ID NO: 110) | DIQMTQSPSSLSASVGDRVTITCRASQGVEYMYWYQQKPGKAPKLLIYGASNLASGVPSRFSGSGSGTDFTFTISSLQPEDIATYYCQQWEGNPRTFGQGTKVEIK (SEQ ID NO: 7) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGLDMQDTYMHWVRQRPGRGLEWMGRIEPASGHTKYNPSLKSRVTITRDTSKNQVSLRLSSVTAADTAVYYCAASGGRPDLWGQGSLVTVSS (SEQ ID NO: 111) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 59 | SSVSY (SEQ ID NO: 12) | GAS | QQWEGNPRT (SEQ ID NO: 3) | GFDITDTY (SEQ ID NO: 46) | IEPAGGHT (SEQ ID NO: 5) | VRSGGLPDV (SEQ ID NO: 30) | DIQMTQSPSSLSASVGDRVTITCRASSSVSYMYWYQQKPGKAPKLLIYGASNLASGVPSRFSGSGSGTDFTFTISSLQPEDIATYYCQQWEGNPRTFGQGTKVEIK (SEQ ID NO: 25) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDITDTYMHWVRQRPGRGLEWMGRIEPAGGHTKYNPSLKSRVTITRDTSKNQVSLRLSSVTAADTAVYYCVRSGGLPDVWGQGSLVTVSS (SEQ ID NO: 47) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 60 | SSVSY (SEQ ID NO: 12) | ATS | QQWEGNPRT (SEQ ID NO: 3) | GFDITDTYMH (SEQ ID NO: 112) | WMGRIEPAGGHTK (SEQ ID NO: 15) | VRSGGLPDV (SEQ ID NO: 30) | DIQMTQSPSSLSASVGDRVTITCRASSSVSYMYWYQQKPGKAPKLLIYATSNLASGVPSRFSGSGSGTDFTFTISSLQPEDIATYYCQQWEGNPRTFGQGTKVEIK (SEQ ID NO: 17) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDITDTYMHWVRQRPGRGLEWMGRIEPAGGHTKYNPSLKSRVTITRDTSKNQVSLRLSSVTAADTAVYYCVRSGGLPDVWGQGSLVTVSS (SEQ ID NO: 47) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 61 | QGVEY (SEQ ID NO: 1) | GAS | QQWEGNPRT (SEQ ID NO: 3) | GFDIQDTY (SEQ ID NO: 4) | IEPASGHT (SEQ ID NO: 29) | AASGGMPDM (SEQ ID NO: 113) | DIQMTQSPSSLSASVGDRVTITCRASQGVEYMYWYQQKPGKAPKLLIYGASNLASGVPSRFSGSGSGTDFTFTISSLQPEDIATYYCQQWEGNPRTFGQGTKVEIK (SEQ ID NO: 7) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPASGHTKYNPSLKSRVTITRDTSKNQVSLRLSSVTAADTAVYYCAASGGMPDMWGQGSLVTVSS (SEQ ID NO: 114) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 62 | SSVSY (SEQ ID NO: 12) | ATS | QQWEGNPRT (SEQ ID NO: 3) | GFDMGDTYMH (SEQ ID NO: 115) | WMGRIEPAGGHTK (SEQ ID NO: 15) | VRSGGMPDV (SEQ ID NO: 44) | DIQMTQSPSSLSASVGDRVTITCRASSSVSYMYWYQQKPGKAPKLLIYATSNLASGVPSRFSGSGSGTDFTFTISSLQPEDIATYYCQQWEGNPRTFGQGTKVEIK (SEQ ID NO: 17) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIEPAGGHTKYNPSLKSRVTITRDTSKNQVSLRLSSVTAADTAVYYCVRSGGMPDVWGQGSLVTVSS (SEQ ID NO: 45) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 63 | QGVEY (SEQ ID NO: 1) | GAS | QQWEGNPRT (SEQ ID NO: 3) | GFDIQDTY (SEQ ID NO: 4) | IDPASGHT (SEQ ID NO: 49) | VMSGGVPDV (SEQ ID NO: 116) | DIQMTQSPSSLSASVGDRVTITCRASQGVEYMYWYQQKPGKAPKLLIYGASNLASGVPSRFSGSGSGTDFTFTISSLQPEDIATYYCQQWEGNPRTFGQGTKVEIK (SEQ ID NO: 7) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIDPASGHTKYNPSLKSRVTITRDTSKNQVSLRLSSVTAADTAVYYCVMSGGVPDVWGQGSLVTVSS (SEQ ID NO: 117) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 64 | QGVEY (SEQ ID NO: 1) | YAS | QQWEGNPRT (SEQ ID NO: 3) | GFDIQDTY (SEQ ID NO: 4) | IEPAGGHT (SEQ ID NO: 5) | VRSGGLPDA (SEQ ID NO: 20) | DIQMTQSPSSLSASVGDRVTITCRASQGVEYMYWYQQKPGKAPKLLIYYASNLASGVPSRFSGSGSGTDFTFTISSLQPEDIATYYCQQWEGNPRTFGQGTKVEIK (SEQ ID NO: 58) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPAGGHTKYNPSLKSRVTITRDTSKNQVSLRLSSVTAADTAVYYCVRSGGLPDAWGQGSLVTVSS (SEQ ID NO: 22) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 65 | QGVEY (SEQ ID NO: 1) | GAS | QQWEGNPRT (SEQ ID NO: 3) | GLDPEDTY (SEQ ID NO: 118) | IEPAGGHT (SEQ ID NO: 5) | VISGGLPDV (SEQ ID NO: 16) | DIQMTQSPSSLSASVGDRVTITCRASQGVEYMYWYQQKPGKAPKLLIYGASNLASGVPSRFSGSGSGTDFTFTISSLQPEDIATYYCQQWEGNPRTFGQGTKVEIK (SEQ ID NO: 7) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGLDPEDTYMHWVRQRPGRGLEWMGRIEPAGGHTKYNPSLKSRVTITRDTSKNQVSLRLSSVTAADTAVYYCVISGGLPDVWGQGSLVTVSS (SEQ ID NO: 119) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 66 | QGVEY (SEQ ID NO: 1) | SAS | QQWEGNPRT (SEQ ID NO: 3) | GFDIQDTY (SEQ ID NO: 4) | IEPAGGHT (SEQ ID NO: 5) | VRSGGLPDA (SEQ ID NO: 20) | DIQMTQSPSSLSASVGDRVTITCRASQGVEYMYWYQQKPGKAPKLLIYSASNLASGVPSRFSGSGSGTDFTFTISSLQPEDIATYYCQQWEGNPRTFGQGTKVEIK (SEQ ID NO: 34) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPAGGHTKYNPSLKSRVTITRDTSKNQVSLRLSSVTAADTAVYYCVRSGGLPDAWGQGSLVTVSS (SEQ ID NO: 22) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 67 | QGVRY (SEQ ID NO: 19) | GAS | QQWEGNPRT (SEQ ID NO: 3) | GFDMQSTY (SEQ ID NO: 39) | IEPAGGHT (SEQ ID NO: 5) | VRSGGLPDV (SEQ ID NO: 30) | DIQMTQSPSSLSASVGDRVTITCRASQGVRYMYWYQQKPGKAPKLLIYGASNLASGVPSRFSGSGSGTDFTFTISSLQPEDIATYYCQQWEGNPRTFGQGTKVEIK (SEQ ID NO: 21) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMQSTYMHWVRQRPGRGLEWMGRIEPAGGHTKYNPSLKSRVTITRDTSKNQVSLRLSSVTAADTAVYYCVRSGGLPDVWGQGSLVTVSS (SEQ ID NO: 40) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 68 | QGVGY (SEQ ID NO: 41) | GAS | QQWEGNPRT (SEQ ID NO: 3) | GFDMGDTY (SEQ ID NO: 35) | IEPAAGHT (SEQ ID NO: 36) | VRSGGLPDI (SEQ ID NO: 37) | DIQMTQSPSSLSASVGDRVTITCRASQGVGYMYWYQQKPGKAPKLLIYGASNLASGVPSRFSGSGSGTDFTFTISSLQPEDIATYYCQQWEGNPRTFGQGTKVEIK (SEQ ID NO: 93) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIEPAAGHTKYNPSLKSRVTITRDTSKNQVSLRLSSVTAADTAVYYCVRSGGLPDIWGQGSLVTVSS (SEQ ID NO: 38) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 69 | QGIYY (SEQ ID NO: 53) | ATS | QQWEGNPRT (SEQ ID NO: 3) | GFDIQDTY (SEQ ID NO: 4) | IEPAGGHT (SEQ ID NO: 5) | VRSGGLPDA (SEQ ID NO: 20) | DIQMTQSPSSLSASVGDRVTITCRASQGIYYMYWYQQKPGKAPKLLIYATSNLASGVPSRFSGSGSGTDFTFTISSLQPEDIATYYCQQWEGNPRTFGQGTKVEIK (SEQ ID NO: 92) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPAGGHTKYNPSLKSRVTITRDTSKNQVSLRLSSVTAADTAVYYCVRSGGLPDAWGQGSLVTVSS (SEQ ID NO: 22) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 70 | QGVMY (SEQ ID NO: 27) | GAS | QQWEGNPRT (SEQ ID NO: 3) | GFDMGDTY (SEQ ID NO: 35) | IDPASGHT (SEQ ID NO: 49) | VRSGGMPDA (SEQ ID NO: 107) | DIQMTQSPSSLSASVGDRVTITCRASQGVMYMYWYQQKPGKAPKLLIYGASNLASGVPSRFSGSGSGTDFTFTISSLQPEDIATYYCQQWEGNPRTFGQGTKVEIK (SEQ ID NO: 31) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIDPASGHTKYNPSLKSRVTITRDTSKNQVSLRLSSVTAADTAVYYCVRSGGMPDAWGQGSLVTVSS (SEQ ID NO: 108) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 71 | QGVEY (SEQ ID NO: 1) | ATS | QQWEGNPRT (SEQ ID NO: 3) | GFDMQSTY (SEQ ID NO: 39) | IEPAGGHT (SEQ ID NO: 5) | VRSGGLPDV (SEQ ID NO: 30) | DIQMTQSPSSLSASVGDRVTITCRASQGVEYMYWYQQKPGKAPKLLIYATSNLASGVPSRFSGSGSGTDFTFTISSLQPEDIATYYCQQWEGNPRTFGQGTKVEIK (SEQ ID NO: 51) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMQSTYMHWVRQRPGRGLEWMGRIEPAGGHTKYNPSLKSRVTITRDTSKNQVSLRLSSVTAADTAVYYCVRSGGLPDVWGQGSLVTVSS (SEQ ID NO: 40) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 72 | QGVEY (SEQ ID NO: 1) | SAS | QQWEGNPRT (SEQ ID NO: 3) | GLDPDDTY (SEQ ID NO: 43) | IEPAGGHT (SEQ ID NO: 5) | VISGGLPDV (SEQ ID NO: 16) | DIQMTQSPSSLSASVGDRVTITCRASQGVEYMYWYQQKPGKAPKLLIYSASNLASGVPSRFSGSGSGTDFTFTISSLQPEDIATYYCQQWEGNPRTFGQGTKVEIK (SEQ ID NO: 34) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGLDPDDTYMHWVRQRPGRGLEWMGRIEPAGGHTKYNPSLKSRVTITRDTSKNQVSLRLSSVTAADTAVYYCVISGGLPDVWGQGSLVTVSS (SEQ ID NO: 18) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 73 | QGVEY (SEQ ID NO: 1) | SAS | QQWEGNPRT (SEQ ID NO: 3) | GFDIQDTY (SEQ ID NO: 4) | IEPASGHT (SEQ ID NO: 29) | AASGGMPDM (SEQ ID NO: 113) | DIQMTQSPSSLSASVGDRVTITCRASQGVEYMYWYQQKPGKAPKLLIYSASNLASGVPSRFSGSGSGTDFTFTISSLQPEDIATYYCQQWEGNPRTFGQGTKVEIK (SEQ ID NO: 34) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPASGHTKYNPSLKSRVTITRDTSKNQVSLRLSSVTAADTAVYYCAASGGMPDMWGQGSLVTVSS (SEQ ID NO: 114) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 74 | QGVEY (SEQ ID NO: 1) | YAS | QQWEGNPRT (SEQ ID NO: 3) | GFDMVDTY (SEQ ID NO: 120) | IEPASGHT (SEQ ID NO: 29) | VRSGGLPDV (SEQ ID NO: 30) | DIQMTQSPSSLSASVGDRVTITCRASQGVEYMYWYQQKPGKAPKLLIYYASNLASGVPSRFSGSGSGTDFTFTISSLQPEDIATYYCQQWEGNPRTFGQGTKVEIK (SEQ ID NO: 58) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMVDTYMHWVRQRPGRGLEWMGRIEPASGHTKYNPSLKSRVTITRDTSKNQVSLRLSSVTAADTAVYYCVRSGGLPDVWGQGSLVTVSS (SEQ ID NO: 121) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 75 | QGVGY (SEQ ID NO: 41) | GAS | QQWEGNPRT (SEQ ID NO: 3) | GFDMVDTY (SEQ ID NO: 120) | IEPASGHT (SEQ ID NO: 29) | VRSGGLPDV (SEQ ID NO: 30) | DIQMTQSPSSLSASVGDRVTITCRASQGVGYMYWYQQKPGKAPKLLIYGASNLASGVPSRFSGSGSGTDFTFTISSLQPEDIATYYCQQWEGNPRTFGQGTKVEIK (SEQ ID NO: 93) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMVDTYMHWVRQRPGRGLEWMGRIEPASGHTKYNPSLKSRVTITRDTSKNQVSLRLSSVTAADTAVYYCVRSGGLPDVWGQGSLVTVSS (SEQ ID NO: 121) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 76 | QGVMY (SEQ ID NO: 27) | GAS | QQWEGNPRT (SEQ ID NO: 3) | GFDIQDTY (SEQ ID NO: 4) | IDPASGHT (SEQ ID NO: 49) | GRSGGMMDL (SEQ ID NO: 95) | DIQMTQSPSSLSASVGDRVTITCRASQGVMYMYWYQQKPGKAPKLLIYGASNLASGVPSRFSGSGSGTDFTFTISSLQPEDIATYYCQQWEGNPRTFGQGTKVEIK (SEQ ID NO: 31) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIDPASGHTKYNPSLKSRVTITRDTSKNQVSLRLSSVTAADTAVYYCGRSGGMMDLWGQGSLVTVSS (SEQ ID NO: 96) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 77 | QGVMY (SEQ ID NO: 27) | GAS | QQWEGNPRT (SEQ ID NO: 3) | GFDIDDTY (SEQ ID NO: 122) | IDPASGHT (SEQ ID NO: 49) | VMSGGAPDV (SEQ ID NO: 123) | DIQMTQSPSSLSASVGDRVTITCRASQGVMYMYWYQQKPGKAPKLLIYGASNLASGVPSRFSGSGSGTDFTFTISSLQPEDIATYYCQQWEGNPRTFGQGTKVEIK (SEQ ID NO: 31) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIDDTYMHWVRQRPGRGLEWMGRIDPASGHTKYNPSLKSRVTITRDTSKNQVSLRLSSVTAADTAVYYCVMSGGAPDVWGQGSLVTVSS (SEQ ID NO: 124) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 78 | QGIYY (SEQ ID NO: 53) | GAS | QQWEGNPRT (SEQ ID NO: 3) | GFDMRATY (SEQ ID NO: 125) | IEPAGGHT (SEQ ID NO: 5) | VRSGGLPDV (SEQ ID NO: 30) | DIQMTQSPSSLSASVGDRVTITCRASQGIYYMYWYQQKPGKAPKLLIYGASNLASGVPSRFSGSGSGTDFTFTISSLQPEDIATYYCQQWEGNPRTFGQGTKVEIK (SEQ ID NO: 54) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMRATYMHWVRQRPGRGLEWMGRIEPAGGHTKYNPSLKSRVTITRDTSKNQVSLRLSSVTAADTAVYYCVRSGGLPDVWGQGSLVTVSS (SEQ ID NO: 126) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 79 | SSVSY (SEQ ID NO: 12) | GAS | QQWEGNPRT (SEQ ID NO: 3) | GFDIEDTY (SEQ ID NO: 127) | IEPASGHT (SEQ ID NO: 29) | AISGGVPDV (SEQ ID NO: 100) | DIQMTQSPSSLSASVGDRVTITCRASSSVSYMYWYQQKPGKAPKLLIYGASNLASGVPSRFSGSGSGTDFTFTISSLQPEDIATYYCQQWEGNPRTFGQGTKVEIK (SEQ ID NO: 25) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIEDTYMHWVRQRPGRGLEWMGRIEPASGHTKYNPSLKSRVTITRDTSKNQVSLRLSSVTAADTAVYYCAISGGVPDVWGQGSLVTVSS (SEQ ID NO: 101) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 80 | QGVEY (SEQ ID NO: 1) | ATS | QQWEGNPRT (SEQ ID NO: 3) | GFDIQDTY (SEQ ID NO: 4) | IDPASGHT (SEQ ID NO: 49) | ANSGGLFDH (SEQ ID NO: 128) | DIQMTQSPSSLSASVGDRVTITCRASQGVEYMYWYQQKPGKAPKLLIYATSNLASGVPSRFSGSGSGTDFTFTISSLQPEDIATYYCQQWEGNPRTFGQGTKVEIK (SEQ ID NO: 51) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIDPASGHTKYNPSLKSRVTITRDTSKNQVSLRLSSVTAADTAVYYCANSGGLFDHWGQGSLVTVSS (SEQ ID NO: 129) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 81 | QGIYY (SEQ ID NO: 53) | GAS | QQWEGNPRT (SEQ ID NO: 3) | GFDITDTY (SEQ ID NO: 46) | IEPAGGHT (SEQ ID NO: 5) | VRSGGLPDV (SEQ ID NO: 30) | DIQMTQSPSSLSASVGDRVTITCRASQGIYYMYWYQQKPGKAPKLLIYGASNLASGVPSRFSGSGSGTDFTFTISSLQPEDIATYYCQQWEGNPRTFGQGTKVEIK (SEQ ID NO: 54) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDITDTYMHWVRQRPGRGLEWMGRIEPAGGHTKYNPSLKSRVTITRDTSKNQVSLRLSSVTAADTAVYYCVRSGGLPDVWGQGSLVTVSS (SEQ ID NO: 47) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 82 | QGVEY (SEQ ID NO: 1) | YAS | QQWEGNPRT (SEQ ID NO: 3) | GFDMQDTY (SEQ ID NO: 28) | IEPASGHT (SEQ ID NO: 29) | VRSGGLPDV (SEQ ID NO: 30) | DIQMTQSPSSLSASVGDRVTITCRASQGVEYMYWYQQKPGKAPKLLIYYASNLASGVPSRFSGSGSGTDFTFTISSLQPEDIATYYCQQWEGNPRTFGQGTKVEIK (SEQ ID NO: 58) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMQDTYMHWVRQRPGRGLEWMGRIEPASGHTKYNPSLKSRVTITRDTSKNQVSLRLSSVTAADTAVYYCVRSGGLPDVWGQGSLVTVSS (SEQ ID NO: 32) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAPVLDSDGSFFLYSKLTVDKSRWQQGNVFSCSVLHEALHSHYTQKSLSLSPGK (SEQ ID NO: 11) |
| 83 | SSVSY (SEQ ID NO: 12) | GAS | QQWEGNPRT (SEQ ID NO: 3) | GFDFQDTY (SEQ ID NO: 130) | IDPASEHT (SEQ ID NO: 131) | VRSGGLPDV (SEQ ID NO: 30) | DIQMTQSPSSLSASVGDRVTITCRASSSVSYMYWYQQKPGKAPKLLIYGASNLASGVPSRFSGSGSGTDFTFTISSLQPEDIATYYCQQWEGNPRTFGQGTKVEIK (SEQ ID NO: 25) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDFQDTYMHWVRQRPGRGLEWMGRIDPASEHTKYNPSLKSRVTITRDTSKNQVSLRLSSVTAADTAVYYCVRSGGLPDVWGQGSLVTVSS (SEQ ID NO: 132) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 84 | SSVSY (SEQ ID NO: 12) | SAS | QQWEGNPRT (SEQ ID NO: 3) | GFDMADTY (SEQ ID NO: 23) | IEPAGGHT (SEQ ID NO: 5) | VRSGGLPDM (SEQ ID NO: 24) | DIQMTQSPSSLSASVGDRVTITCRASSSVSYMYWYQQKPGKAPKLLIYSASNLASGVPSRFSGSGSGTDFTFTISSLQPEDIATYYCQQWEGNPRTFGQGTKVEIK (SEQ ID NO: 85) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMADTYMHWVRQRPGRGLEWMGRIEPAGGHTKYNPSLKSRVTITRDTSKNQVSLRLSSVTAADTAVYYCVRSGGLPDMWGQGSLVTVSS (SEQ ID NO: 26) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 85 | QGVEY (SEQ ID NO: 1) | GAS | QQWEGNPRT (SEQ ID NO: 3) | GFDIDDTY (SEQ ID NO: 122) | IDPASGHT (SEQ ID NO: 49) | VMSGGAPDV (SEQ ID NO: 123) | DIQMTQSPSSLSASVGDRVTITCRASQGVEYMYWYQQKPGKAPKLLIYGASNLASGVPSRFSGSGSGTDFTFTISSLQPEDIATYYCQQWEGNPRTFGQGTKVEIK (SEQ ID NO: 7) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIDDTYMHWVRQRPGRGLEWMGRIDPASGHTKYNPSLKSRVTITRDTSKNQVSLRLSSVTAADTAVYYCVMSGGAPDVWGQGSLVTVSS (SEQ ID NO: 124) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 86 | SSVSY (SEQ ID NO: 12) | GAS | QQWEGNPRT (SEQ ID NO: 3) | GFDIQDTY (SEQ ID NO: 4) | IEPAGGHT (SEQ ID NO: 5) | ASSGGMPDL (SEQ ID NO: 6) | DIQMTQSPSSLSASVGDRVTITCRASSSVSYMYWYQQKPGKAPKLLIYGASNLASGVPSRFSGSGSGTDFTFTISSLQPEDIATYYCQQWEGNPRTFGQGTKVEIK (SEQ ID NO: 25) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPAGGHTKYNPSLKSRVTITRDTSKNQVSLRLSSVTAADTAVYYCASSGGMPDLWGQGSLVTVSS (SEQ ID NO: 9) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 87 | QGVRY (SEQ ID NO: 19) | GAS | QQWEGNPRT (SEQ ID NO: 3) | GFDMVDTY (SEQ ID NO: 120) | IEPASGHT (SEQ ID NO: 29) | VRSGGLPDV (SEQ ID NO: 30) | DIQMTQSPSSLSASVGDRVTITCRASQGVRYMYWYQQKPGKAPKLLIYGASNLASGVPSRFSGSGSGTDFTFTISSLQPEDIATYYCQQWEGNPRTFGQGTKVEIK (SEQ ID NO: 21) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMVDTYMHWVRQRPGRGLEWMGRIEPASGHTKYNPSLKSRVTITRDTSKNQVSLRLSSVTAADTAVYYCVRSGGLPDVWGQGSLVTVSS (SEQ ID NO: 121) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 88 | FSVDY (SEQ ID NO: 61) | DLIYATSNLAS (SEQ ID NO: 87) | QQWEGNPRS (SEQ ID NO: 63) | GFDLQDTYIH (SEQ ID NO: 88) | IDPASGHV (SEQ ID NO: 133) | ARSGGMTDY (SEQ ID NO: 80) | DIQMTQSPSSLSASVGDRVTITCRASFSVDYMYWYQQKPGKAPKDLIYATSNLASGVPSRFSGSGSGTDFTFTISSLQPEDIATYYCQQWEGNPRSFGQGTKVEIK (SEQ ID NO: 90) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDLQDTYIHWVRQRPGRGLEWMGRIDPASGHVKYNPSLKSRVTITRDTSKNQVSLRLSSVTAADTAVYYCARSGGMTDYWGQGSLVTVSS (SEQ ID NO: 134) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 89 | SSVSY (SEQ ID NO: 12) | GAS | QQWEGNPRT (SEQ ID NO: 3) | GFDIQDTY (SEQ ID NO: 4) | IEPASGHT (SEQ ID NO: 29) | AASGGMPDM (SEQ ID NO: 113) | DIQMTQSPSSLSASVGDRVTITCRASSSVSYMYWYQQKPGKAPKLLIYGASNLASGVPSRFSGSGSGTDFTFTISSLQPEDIATYYCQQWEGNPRTFGQGTKVEIK (SEQ ID NO: 25) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPASGHTKYNPSLKSRVTITRDTSKNQVSLRLSSVTAADTAVYYCAASGGMPDMWGQGSLVTVSS (SEQ ID NO: 114) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 90 | QGVRY (SEQ ID NO: 19) | GAS | QQWEGNPRT (SEQ ID NO: 3) | GFDFQDTY (SEQ ID NO: 130) | IDPASEHT (SEQ ID NO: 131) | VRSGGLPDV (SEQ ID NO: 30) | DIQMTQSPSSLSASVGDRVTITCRASQGVRYMYWYQQKPGKAPKLLIYGASNLASGVPSRFSGSGSGTDFTFTISSLQPEDIATYYCQQWEGNPRTFGQGTKVEIK (SEQ ID NO: 21) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDFQDTYMHWVRQRPGRGLEWMGRIDPASEHTKYNPSLKSRVTITRDTSKNQVSLRLSSVTAADTAVYYCVRSGGLPDVWGQGSLVTVSS (SEQ ID NO: 132) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 91 | QGVRY (SEQ ID NO: 19) | GAS | QQWEGNPRT (SEQ ID NO: 3) | GFDMQDTY (SEQ ID NO: 28) | IEPASGHT (SEQ ID NO: 29) | VRSGGLPDV (SEQ ID NO: 30) | DIQMTQSPSSLSASVGDRVTITCRASQGVRYMYWYQQKPGKAPKLLIYGASNLASGVPSRFSGSGSGTDFTFTISSLQPEDIATYYCQQWEGNPRTFGQGTKVEIK (SEQ ID NO: 21) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMQDTYMHWVRQRPGRGLEWMGRIEPASGHTKYNPSLKSRVTITRDTSKNQVSLRLSSVTAADTAVYYCVRSGGLPDVWGQGSLVTVSS (SEQ ID NO: 32) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 92 | QGVEY (SEQ ID NO: 1) | GAS | QQWEGNPRT (SEQ ID NO: 3) | GFDMVDTY (SEQ ID NO: 120) | IEPASGHT (SEQ ID NO: 29) | VRSGGLPDV (SEQ ID NO: 30) | DIQMTQSPSSLSASVGDRVTITCRASQGVEYMYWYQQKPGKAPKLLIYGASNLASGVPSRFSGSGSGTDFTFTISSLQPEDIATYYCQQWEGNPRTFGQGTKVEIK (SEQ ID NO: 7) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMVDTYMHWVRQRPGRGLEWMGRIEPASGHTKYNPSLKSRVTITRDTSKNQVSLRLSSVTAADTAVYYCVRSGGLPDVWGQGSLVTVSS (SEQ ID NO: 121) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 93 | QGVEY (SEQ ID NO: 1) | ATS | QQWEGNPRT (SEQ ID NO: 3) | GFDMGDTY (SEQ ID NO: 35) | IEPAAGHT (SEQ ID NO: 36) | VRSGGLPDV (SEQ ID NO: 30) | DIQMTQSPSSLSASVGDRVTITCRASQGVEYMYWYQQKPGKAPKLLIYATSNLASGVPSRFSGSGSGTDFTFTISSLQPEDIATYYCQQWEGNPRTFGQGTKVEIK (SEQ ID NO: 51) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIEPAAGHTKYNPSLKSRVTITRDTSKNQVSLRLSSVTAADTAVYYCVRSGGLPDVWGQGSLVTVSS (SEQ ID NO: 55) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 94 | SSVSY (SEQ ID NO: 12) | GAS | QQWEGNPRT (SEQ ID NO: 3) | GFDIQDTY (SEQ ID NO: 4) | IDPASGHT (SEQ ID NO: 49) | GRSGGMMDL (SEQ ID NO: 95) | DIQMTQSPSSLSASVGDRVTITCRASSSVSYMYWYQQKPGKAPKLLIYGASNLASGVPSRFSGSGSGTDFTFTISSLQPEDIATYYCQQWEGNPRTFGQGTKVEIK (SEQ ID NO: 25) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIDPASGHTKYNPSLKSRVTITRDTSKNQVSLRLSSVTAADTAVYYCGRSGGMMDLWGQGSLVTVSS (SEQ ID NO: 96) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 95 | QGVMY (SEQ ID NO: 27) | GAS | QQWEGNPRT (SEQ ID NO: 3) | GFDITDTY (SEQ ID NO: 46) | IEPAGGHT (SEQ ID NO: 5) | VRSGGLPDV (SEQ ID NO: 30) | DIQMTQSPSSLSASVGDRVTITCRASQGVMYMYWYQQKPGKAPKLLIYGASNLASGVPSRFSGSGSGTDFTFTISSLQPEDIATYYCQQWEGNPRTFGQGTKVEIK (SEQ ID NO: 31) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDITDTYMHWVRQRPGRGLEWMGRIEPAGGHTKYNPSLKSRVTITRDTSKNQVSLRLSSVTAADTAVYYCVRSGGLPDVWGQGSLVTVSS (SEQ ID NO: 47) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 96 | QGVGY (SEQ ID NO: 41) | ATS | QQWEGNPRT (SEQ ID NO: 3) | GFDITDTY (SEQ ID NO: 46) | IEPAGGHT (SEQ ID NO: 5) | VRSGGLPDV (SEQ ID NO: 30) | DIQMTQSPSSLSASVGDRVTITCRASQGVGYMYWYQQKPGKAPKLLIYATSNLASGVPSRFSGSGSGTDFTFTISSLQPEDIATYYCQQWEGNPRTFGQGTKVEIK (SEQ ID NO: 76) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDITDTYMHWVRQRPGRGLEWMGRIEPAGGHTKYNPSLKSRVTITRDTSKNQVSLRLSSVTAADTAVYYCVRSGGLPDVWGQGSLVTVSS (SEQ ID NO: 47) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 97 | QGVEY (SEQ ID NO: 1) | GAS | QQWEGNPRT (SEQ ID NO: 3) | GFDMQDTY (SEQ ID NO: 28) | IDPASGHT (SEQ ID NO: 49) | VRSGGLPDY (SEQ ID NO: 135) | DIQMTQSPSSLSASVGDRVTITCRASQGVEYMYWYQQKPGKAPKLLIYGASNLASGVPSRFSGSGSGTDFTFTISSLQPEDIATYYCQQWEGNPRTFGQGTKVEIK (SEQ ID NO: 7) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMQDTYMHWVRQRPGRGLEWMGRIDPASGHTKYNPSLKSRVTITRDTSKNQVSLRLSSVTAADTAVYYCVRSGGLPDYWGQGSLVTVSS (SEQ ID NO: 136) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 98 | QGVEY (SEQ ID NO: 1) | GAS | QQWEGNPRT (SEQ ID NO: 3) | GFDFDDTY (SEQ ID NO: 137) | IDPASGHT (SEQ ID NO: 49) | VRSGGLPDV (SEQ ID NO: 30) | DIQMTQSPSSLSASVGDRVTITCRASQGVEYMYWYQQKPGKAPKLLIYGASNLASGVPSRFSGSGSGTDFTFTISSLQPEDIATYYCQQWEGNPRTFGQGTKVEIK (SEQ ID NO: 7) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDFDDTYMHWVRQRPGRGLEWMGRIDPASGHTKYNPSLKSRVTITRDTSKNQVSLRLSSVTAADTAVYYCVRSGGLPDVWGQGSLVTVSS (SEQ ID NO: 138) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 99 | QGVEY (SEQ ID NO: 1) | YAS | QQWEGNPRT (SEQ ID NO: 3) | GFDMGDTY (SEQ ID NO: 35) | IEPAGGHT (SEQ ID NO: 5) | VRSGGMPDV (SEQ ID NO: 44) | DIQMTQSPSSLSASVGDRVTITCRASQGVEYMYWYQQKPGKAPKLLIYYASNLASGVPSRFSGSGSGTDFTFTISSLQPEDIATYYCQQWEGNPRTFGQGTKVEIK (SEQ ID NO: 58) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMGDTYMHWVRQRPGRGLEWMGRIEPAGGHTKYNPSLKSRVTITRDTSKNQVSLRLSSVTAADTAVYYCVRSGGMPDVWGQGSLVTVSS (SEQ ID NO: 45) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 100 | QGVEY (SEQ ID NO: 1) | ATS | QQWEGNPRT (SEQ ID NO: 3) | GFDITDTY (SEQ ID NO: 46) | IEPAGGHT (SEQ ID NO: 5) | VRSGGLPDV (SEQ ID NO: 30) | DIQMTQSPSSLSASVGDRVTITCRASQGVEYMYWYQQKPGKAPKLLIYATSNLASGVPSRFSGSGSGTDFTFTISSLQPEDIATYYCQQWEGNPRTFGQGTKVEIK (SEQ ID NO: 51) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDITDTYMHWVRQRPGRGLEWMGRIEPAGGHTKYNPSLKSRVTITRDTSKNQVSLRLSSVTAADTAVYYCVRSGGLPDVWGQGSLVTVSS (SEQ ID NO: 47) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPELLGGPSVFLFPPKPKDTLMISRTPEVTCVVVDVSHEDPEVKENWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 11) |
| 101 ABS-101-A | QGVRY (SEQ ID NO: 19) | GAS | QQWEGNPRT (SEQ ID NO: 3) | GFDIQDTY (SEQ ID NO: 4) | IEPAGGHT (SEQ ID NO: 5) | VRSGGLPDA (SEQ ID NO: 20) | DIQMTQSPSSLSASVGDRVTITCRASQGVRYMYWYQQKPGKAPKLLIYGASNLASGVPSRFSGSGSGTDFTFTISSLQPEDIATYYCQQWEGNPRTFGQGTKVEIK (SEQ ID NO: 21) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPAGGHTKYNPSLKSRVTITRDTSKNQVSLRLSSVTAADTAVYYCVRSGGLPDAWGQGSLVTVSS (SEQ ID NO: 22) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPEAAGGPSVFLFPPKPKDTLMISRTPEVTCVVVSVSHEDPEVKENWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 139) |
| 102 ABS-101-B | QGVMY (SEQ ID NO: 27) | GAS | QQWEGNPRT (SEQ ID NO: 3) | GFDMQDTY (SEQ ID NO: 28) | IEPASGHT (SEQ ID NO: 29) | VRSGGLPDV (SEQ ID NO: 30) | DIQMTQSPSSLSASVGDRVTITCRASQGVMYMYWYQQKPGKAPKLLIYGASNLASGVPSRFSGSGSGTDFTFTISSLQPEDIATYYCQQWEGNPRTFGQGTKVEIK (SEQ ID NO: 31) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDMQDTYMHWVRQRPGRGLEWMGRIEPASGHTKYNPSLKSRVTITRDTSKNQVSLRLSSVTAADTAVYYCVRSGGLPDVWGQGSLVTVSS (SEQ ID NO: 32) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPEAAGGPSVFLFPPKPKDTLMISRTPEVTCVVVSVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 139) |

-continued

Sequence Table 1

| Antibody # | LCDR1 | LCDR2 | LCDR3 | HCDR1 | HCDR2 | HCDR3 | VL domain | CL domain | VH domain | CH domain | Fc |
|---|---|---|---|---|---|---|---|---|---|---|---|
| 103 ABS-101-C | QGVGY (SEQ ID NO: 41) | SAS | QQWEGNPRT (SEQ ID NO: 3) | GFDIQDTY (SEQ ID NO: 4) | IEPAGGHT (SEQ ID NO: 5) | VRSGGLPDA (SEQ ID NO: 20) | DIQMTQSPSSLSASVGDRVTITCRASQGVGYMYWYQQKPGKAPKLLIYSASNLASGVPSRFSGSGSGTDFTFTISSLQPEDIATYYCQQWEGNPRTFGQGTKVEIK (SEQ ID NO: 42) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 8) | QVQLQESGPGLVRPSQTLSLTCTVSGFDIQDTYMHWVRQRPGRGLEWMGRIEPAGGHTKYNPSLKSRVTITRDTSKNQVSLRLSSVTAADTAVYYCVRSGGLPDAWGQGSLVTVSS (SEQ ID NO: 22) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 10) | CPPCPAPEAAGGPSVFLFPPKPKDTLMISRTPEVTCVVVSVSHEDPEVKENWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK (SEQ ID NO: 139) |

What is claimed is:

1. An antibody or antigen-binding fragment thereof, comprising:
   - (a) a variable heavy chain complementarity-determining region CDR-H1, CDR-H2 and CDR-H3, wherein:
     - i. CDR-H1 comprise the polypeptide sequence of SEQ ID NO: 4,
     - ii. CDR-H2 comprises the polypeptide sequence of SEQ ID NO: 5,
     - iii. CDR-H3 comprises the polypeptide sequence of SEQ ID NO: 20; and
   - (b) a variable light chain complementarity-determining region CDR-L1, CDR-L2 and CDR-L3, wherein
     - i. CDR-L1 comprises the polypeptide sequence of SEQ ID NO: 19,
     - ii. CDR-L2 comprises the polypeptide sequence of GAS, and
     - iii. CDR-L3 comprises the polypeptide sequence of SEQ ID NO: 3.

2. An antibody or antigen-binding fragment thereof, comprising:
   - (a) a variable heavy chain complementarity-determining region CDR-H1, CDR-H2 and CDR-H3, wherein:
     - i. CDR-H1 comprise the polypeptide sequence of SEQ ID NO: 28,
     - ii. CDR-H2 comprises the polypeptide sequence of SEQ ID NO: 29,
     - iii. CDR-H3 comprises the polypeptide sequence of SEQ ID NO: 30; and
   - (b) a variable light chain complementarity-determining region CDR-L1, CDR-L2 and CDR-L3, wherein
     - i. CDR-L1 comprises the polypeptide sequence of SEQ ID NO: 27,
     - ii. CDR-L2 comprises the polypeptide sequence of GAS, and
     - iii. CDR-L3 comprises the polypeptide sequence of SEQ ID NO: 3.

3. An antibody or antigen-binding fragment thereof, comprising:

(a) a variable heavy chain complementarity-determining region CDR-H1, CDR-H2 and CDR-H3, wherein:

i. CDR-H1 comprise the polypeptide sequence of SEQ ID NO: 4, ii. CDR-H2 comprises the polypeptide sequence of SEQ ID NO: 5, iii. CDR-H3 comprises the polypeptide sequence of SEQ ID NO: 20; and (b) a variable light chain complementarity-determining region CDR-L1, CDR-L2 and CDR-L3, wherein i. CDR-L1 comprises the polypeptide sequence of SEQ ID NO: 41, ii. CDR-L2 comprises the polypeptide sequence of SAS, and iii. CDR-L3 comprises the polypeptide sequence of SEQ ID NO: 3.

4. An antibody or antigen-binding fragment thereof according to any one of claims 1-3 comprising at least one of:

(a) a variable heavy chain, wherein the variable heavy chain comprises a polypeptide sequence having at least 99% sequence identity to the amino acid sequence of SEQ ID NO: 22; and (b) a variable light chain, wherein the variable light chain comprises a polypeptide sequence having at least 99% sequence identity to the amino acid sequence of SEQ ID NO: 21.

5. The antibody or antigen-binding fragment thereof according to claim 1, wherein the antibody is capable of binding human TL1A.

6. The antibody or antigen-binding fragment thereof of claim 5, wherein the antibody comprises an IgG, IgA, IgM, or IgE antibody.

7. The antibody or antigen-binding fragment thereof of claim 6, wherein the IgG comprises IgG1, IgG2, IgG3, IgG4, IgGA1, or IgGA2.

8. The antibody or antigen-binding fragment thereof of claim 5, wherein the antibody comprises a bispecific antibody, a multispecific antibody, a multivalent antibody, a chimeric antibody, a human antibody, humanized antibody, a monoclonal antibody, a deimmunized antibody, or a combination thereof.

9. The antibody or antigen-binding fragment thereof of claim 8, wherein the antibody is a human antibody.

10. The antibody or antigen-binding fragment thereof of claim 5, wherein the antigen-binding fragment comprises a Fab, Fab', Fab'-SH, Fv, scFv, F $(ab')_2$, a diabody, a linear antibody, or a multi-specific antibody formed from antibody fragments.

11. The antibody or antigen-binding fragment thereof of claim 5, wherein the antibody or antigen-binding fragment thereof is recombinant or synthetic.

12. The antibody or antigen-binding fragment thereof of claim 5, wherein the antibody or antigen-binding fragment thereof further comprise an enzyme, a substrate, cofactor, a fluorescent marker, a chemiluminescent marker, a peptide tag, a magnetic particle, a drug, a toxin, or a combination thereof.

13. The antibody or antigen-binding fragment thereof of claim 5, wherein the antibody or antigen-binding fragment thereof inhibits inflammation.

14. The antibody or antigen-binding fragment thereof of claim 5, wherein the antibody or antigen-binding fragment thereof inhibits binding of TL1A to DR3 on a host cell.

15. The antibody or antigen-binding fragment thereof of claim 5, wherein the antibody or antigen-binding fragment is capable of binding to human TL1A or human FcRn with an affinity at least up to 1, 2, 3, 4, 5, 6, 7, 8, 9 or 10-fold higher compared to a reference antibody.

16. A pharmaceutical composition or a medicament that comprises:

the antibody or antigen-binding fragment thereof of claim 5; and a pharmaceutically acceptable carrier, excipient, or diluent.

17. The pharmaceutical composition or medicament of claim 16, wherein the pharmaceutical composition or medicament is formulated for administration through subcutaneous, intravenous, intradermal, intraperitoneal, intramuscular, intracerebroventricular, intracranial, intracelial, or intracerebellar administration means.

18. The pharmaceutical composition or medicament of claim 16, comprising an additional therapeutic agent.

19. The pharmaceutical composition or medicament of claim 18, wherein the additional therapeutic agent is a nonsteroidal anti-inflammatory drug, a corticosteroid, a dietary supplement such as an antioxidant, a small molecule, a therapeutic vaccine, an immunomodulator, an anti-viral agent, acetaminophen, an anti-cancer agent, a chemotherapy, or an additional anti-TL1A antibody.

20. A method for treating a disease, disorder or inflammation in a subject in need thereof, the method comprising administering to the subject, (a) an antibody or antigen-binding fragment thereof according to claim 5; or (b) a pharmaceutical composition or medicament comprising an antibody of (a) and a pharmaceutically acceptable carrier, excipient, or diluent.

21. The method of claim 20, wherein the disease, disorder, or inflammation is selected from the group consisting of: autoimmune diseases including rheumatoid arthritis, inflammatory bowel disease, atopic dermatitis, systemic lupus erythematosus, asthma, ulcerative colitis, Crohn's disease, psoriasis, primary biliary cirrhosis, primary biliary cholangitis, ankylosing spondylitis, and fibrosis including intestinal fibrosis, pulmonary fibrosis, and liver fibrosis.

22. The method of claim 20, wherein the antibody or antigen-binding fragment thereof binds to TL1A and/or inhibits binding of TL1A to DR3 on a host cell.

23. The method of claim 20, wherein the antibody or antigen binding fragment thereof is administered to the subject with an additional therapeutic agent, wherein the additional therapeutic agent is one or more of an aminosalicylate, balsalazide, olsalazine, prednisone, azathioprine, 6-Mercaptopurine methotrexate; infliximab, adalimumab, certolizumab pegol, natalizumab, a nonsteroidal anti-inflammatory drug, a corticosteroid, a dietary supplement such as an antioxidant, a small molecule, a therapeutic vaccine, an immunomodulator, an anti-viral agent, acetaminophen, an anti-cancer agent, a chemotherapy, or an additional anti-TL1A antibody.

* * * * *

SEQUENCE LISTING

```
Sequence total quantity: 145
SEQ ID NO: 1            moltype = AA  length = 5
FEATURE                 Location/Qualifiers
source                  1..5
                        mol_type = protein
                        organism = synthetic construct
SEQUENCE: 1
QGVEY                                                                5

SEQ ID NO: 2            moltype =   length =
SEQUENCE: 2
000

SEQ ID NO: 3            moltype = AA  length = 9
FEATURE                 Location/Qualifiers
source                  1..9
                        mol_type = protein
                        organism = synthetic construct
SEQUENCE: 3
QQWEGNPRT                                                            9

SEQ ID NO: 4            moltype = AA  length = 8
FEATURE                 Location/Qualifiers
source                  1..8
                        mol_type = protein
                        organism = synthetic construct
SEQUENCE: 4
GFDIQDTY                                                             8

SEQ ID NO: 5            moltype = AA  length = 8
FEATURE                 Location/Qualifiers
source                  1..8
                        mol_type = protein
                        organism = synthetic construct
SEQUENCE: 5
IEPAGGHT                                                             8

SEQ ID NO: 6            moltype = AA  length = 9
FEATURE                 Location/Qualifiers
source                  1..9
                        mol_type = protein
                        organism = synthetic construct
SEQUENCE: 6
ASSGGMPDL                                                            9

SEQ ID NO: 7            moltype = AA  length = 106
FEATURE                 Location/Qualifiers
source                  1..106
                        mol_type = protein
                        organism = synthetic construct
SEQUENCE: 7
DIQMTQSPSS LSASVGDRVT ITCRASQGVE YMYWYQQKPG KAPKLLIYGA SNLASGVPSR  60
FSGSGSGTDF TFTISSLQPE DIATYYCQQW EGNPRTFGQG TKVEIK                 106

SEQ ID NO: 8            moltype = AA  length = 107
FEATURE                 Location/Qualifiers
source                  1..107
                        mol_type = protein
                        organism = synthetic construct
SEQUENCE: 8
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 9            moltype = AA  length = 116
FEATURE                 Location/Qualifiers
source                  1..116
                        mol_type = protein
                        organism = synthetic construct
SEQUENCE: 9
QVQLQESGPG LVRPSQTLSL TCTVSGFDIQ DTYMHWVRQR PGRGLEWMGR IEPAGGHTKY  60
NPSLKSRVTI TRDTSKNQVS LRLSSVTAAD TAVYYCASSG GMPDLWGQGS LVTVSS      116

SEQ ID NO: 10           moltype = AA  length = 108
FEATURE                 Location/Qualifiers
source                  1..108
                        mol_type = protein
                        organism = synthetic construct
SEQUENCE: 10
```

```
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHT              108

SEQ ID NO: 11          moltype = AA  length = 222
FEATURE                Location/Qualifiers
source                 1..222
                       mol_type = protein
                       organism = synthetic construct
SEQUENCE: 11
CPPCPAPELL GGPSVFLFPP KPKDTLMISR TPEVTCVVVD VSHEDPEVKF NWYVDGVEVH  60
NAKTKPREEQ YASTYRVVSV LTVLHQDWLN GKEYKCKVSN KALPAPIEKT ISKAKGQPRE  120
PQVYTLPPSR DELTKNQVSL TCLVKGFYPS DIAVEWESNG QPENNYKTTP PVLDSDGSFF  180
LYSKLTVDKS RWQQGNVFSC SVLHEALHSH YTQKSLSLSP GK                    222

SEQ ID NO: 12          moltype = AA  length = 5
FEATURE                Location/Qualifiers
source                 1..5
                       mol_type = protein
                       organism = synthetic construct
SEQUENCE: 12
SSVSY                                                             5

SEQ ID NO: 13          moltype =   length =
SEQUENCE: 13
000

SEQ ID NO: 14          moltype = AA  length = 10
FEATURE                Location/Qualifiers
source                 1..10
                       mol_type = protein
                       organism = synthetic construct
SEQUENCE: 14
GLDPDDTYMH                                                        10

SEQ ID NO: 15          moltype = AA  length = 13
FEATURE                Location/Qualifiers
source                 1..13
                       mol_type = protein
                       organism = synthetic construct
SEQUENCE: 15
WMGRIEPAGG HTK                                                    13

SEQ ID NO: 16          moltype = AA  length = 9
FEATURE                Location/Qualifiers
source                 1..9
                       mol_type = protein
                       organism = synthetic construct
SEQUENCE: 16
VISGGLPDV                                                         9

SEQ ID NO: 17          moltype = AA  length = 106
FEATURE                Location/Qualifiers
source                 1..106
                       mol_type = protein
                       organism = synthetic construct
SEQUENCE: 17
DIQMTQSPSS LSASVGDRVT ITCRASSSVS YMYWYQQKPG KAPKLLIYAT SNLASGVPSR  60
FSGSGSGTDF TFTISSLQPE DIATYYCQQW EGNPRTFGQG TKVEIK                106

SEQ ID NO: 18          moltype = AA  length = 116
FEATURE                Location/Qualifiers
source                 1..116
                       mol_type = protein
                       organism = synthetic construct
SEQUENCE: 18
QVQLQESGPG LVRPSQTLSL TCTVSGLDPD DTYMHWVRQR PGRGLEWMGR IEPAGGHTKY  60
NPSLKSRVTI TRDTSKNQVS LRLSSVTAAD TAVYYCVISG GLPDVWGQGS LVTVSS      116

SEQ ID NO: 19          moltype = AA  length = 5
FEATURE                Location/Qualifiers
source                 1..5
                       mol_type = protein
                       organism = synthetic construct
SEQUENCE: 19
QGVRY                                                             5

SEQ ID NO: 20          moltype = AA  length = 9
FEATURE                Location/Qualifiers
source                 1..9
```

```
                         mol_type = protein
                         organism = synthetic construct
SEQUENCE: 20
VRSGGLPDA                                                               9

SEQ ID NO: 21            moltype = AA  length = 106
FEATURE                  Location/Qualifiers
source                   1..106
                         mol_type = protein
                         organism = synthetic construct
SEQUENCE: 21
DIQMTQSPSS LSASVGDRVT ITCRASQGVR YMYWYQQKPG KAPKLLIYGA SNLASGVPSR  60
FSGSGSGTDF TFTISSLQPE DIATYYCQQW EGNPRTFGQG TKVEIK                 106

SEQ ID NO: 22            moltype = AA  length = 116
FEATURE                  Location/Qualifiers
source                   1..116
                         mol_type = protein
                         organism = synthetic construct
SEQUENCE: 22
QVQLQESGPG LVRPSQTLSL TCTVSGFDIQ DTYMHWVRQR PGRGLEWMGR IEPAGGHTKY  60
NPSLKSRVTI TRDTSKNQVS LRLSSVTAAD TAVYYCVRSG GLPDAWGQGS LVTVSS      116

SEQ ID NO: 23            moltype = AA  length = 8
FEATURE                  Location/Qualifiers
source                   1..8
                         mol_type = protein
                         organism = synthetic construct
SEQUENCE: 23
GFDMADTY                                                                8

SEQ ID NO: 24            moltype = AA  length = 9
FEATURE                  Location/Qualifiers
source                   1..9
                         mol_type = protein
                         organism = synthetic construct
SEQUENCE: 24
VRSGGLPDM                                                               9

SEQ ID NO: 25            moltype = AA  length = 106
FEATURE                  Location/Qualifiers
source                   1..106
                         mol_type = protein
                         organism = synthetic construct
SEQUENCE: 25
DIQMTQSPSS LSASVGDRVT ITCRASSSVS YMYWYQQKPG KAPKLLIYGA SNLASGVPSR  60
FSGSGSGTDF TFTISSLQPE DIATYYCQQW EGNPRTFGQG TKVEIK                 106

SEQ ID NO: 26            moltype = AA  length = 116
FEATURE                  Location/Qualifiers
source                   1..116
                         mol_type = protein
                         organism = synthetic construct
SEQUENCE: 26
QVQLQESGPG LVRPSQTLSL TCTVSGFDMA DTYMHWVRQR PGRGLEWMGR IEPAGGHTKY  60
NPSLKSRVTI TRDTSKNQVS LRLSSVTAAD TAVYYCVRSG GLPDMWGQGS LVTVSS      116

SEQ ID NO: 27            moltype = AA  length = 5
FEATURE                  Location/Qualifiers
source                   1..5
                         mol_type = protein
                         organism = synthetic construct
SEQUENCE: 27
QGVMY                                                                   5

SEQ ID NO: 28            moltype = AA  length = 8
FEATURE                  Location/Qualifiers
source                   1..8
                         mol_type = protein
                         organism = synthetic construct
SEQUENCE: 28
GFDMQDTY                                                                8

SEQ ID NO: 29            moltype = AA  length = 8
FEATURE                  Location/Qualifiers
source                   1..8
                         mol_type = protein
                         organism = synthetic construct
SEQUENCE: 29
```

```
IEPASGHT                                                   8

SEQ ID NO: 30          moltype = AA  length = 9
FEATURE                Location/Qualifiers
source                 1..9
                       mol_type = protein
                       organism = synthetic construct
SEQUENCE: 30
VRSGGLPDV                                                  9

SEQ ID NO: 31          moltype = AA  length = 106
FEATURE                Location/Qualifiers
source                 1..106
                       mol_type = protein
                       organism = synthetic construct
SEQUENCE: 31
DIQMTQSPSS LSASVGDRVT ITCRASQGVM YMYWYQQKPG KAPKLLIYGA SNLASGVPSR  60
FSGSGSGTDF TFTISSLQPE DIATYYCQQW EGNPRTFGQG TKVEIK                 106

SEQ ID NO: 32          moltype = AA  length = 116
FEATURE                Location/Qualifiers
source                 1..116
                       mol_type = protein
                       organism = synthetic construct
SEQUENCE: 32
QVQLQESGPG LVRPSQTLSL TCTVSGFDMQ DTYMHWVRQR PGRGLEWMGR IEPASGHTKY  60
NPSLKSRVTI TRDTSKNQVS LRLSSVTAAD TAVYYCVRSG GLPDVWGQGS LVTVSS      116

SEQ ID NO: 33          moltype =   length =
SEQUENCE: 33
000

SEQ ID NO: 34          moltype = AA  length = 106
FEATURE                Location/Qualifiers
source                 1..106
                       mol_type = protein
                       organism = synthetic construct
SEQUENCE: 34
DIQMTQSPSS LSASVGDRVT ITCRASQGVE YMYWYQQKPG KAPKLLIYSA SNLASGVPSR  60
FSGSGSGTDF TFTISSLQPE DIATYYCQQW EGNPRTFGQG TKVEIK                 106

SEQ ID NO: 35          moltype = AA  length = 8
FEATURE                Location/Qualifiers
source                 1..8
                       mol_type = protein
                       organism = synthetic construct
SEQUENCE: 35
GFDMGDTY                                                   8

SEQ ID NO: 36          moltype = AA  length = 8
FEATURE                Location/Qualifiers
source                 1..8
                       mol_type = protein
                       organism = synthetic construct
SEQUENCE: 36
IEPAAGHT                                                   8

SEQ ID NO: 37          moltype = AA  length = 9
FEATURE                Location/Qualifiers
source                 1..9
                       mol_type = protein
                       organism = synthetic construct
SEQUENCE: 37
VRSGGLPDI                                                  9

SEQ ID NO: 38          moltype = AA  length = 116
FEATURE                Location/Qualifiers
source                 1..116
                       mol_type = protein
                       organism = synthetic construct
SEQUENCE: 38
QVQLQESGPG LVRPSQTLSL TCTVSGFDMG DTYMHWVRQR PGRGLEWMGR IEPAAGHTKY  60
NPSLKSRVTI TRDTSKNQVS LRLSSVTAAD TAVYYCVRSG GLPDIWGQGS LVTVSS      116

SEQ ID NO: 39          moltype = AA  length = 8
FEATURE                Location/Qualifiers
source                 1..8
                       mol_type = protein
                       organism = synthetic construct
```

```
SEQUENCE: 39
GFDMQSTY                                                      8

SEQ ID NO: 40          moltype = AA  length = 116
FEATURE                Location/Qualifiers
source                 1..116
                       mol_type = protein
                       organism = synthetic construct
SEQUENCE: 40
QVQLQESGPG LVRPSQTLSL TCTVSGFDMQ STYMHWVRQR PGRGLEWMGR IEPAGGHTKY  60
NPSLKSRVTI TRDTSKNQVS LRLSSVTAAD TAVYYCVRSG GLPDVWGQGS LVTVSS      116

SEQ ID NO: 41          moltype = AA  length = 5
FEATURE                Location/Qualifiers
source                 1..5
                       mol_type = protein
                       organism = synthetic construct
SEQUENCE: 41
QGVGY                                                         5

SEQ ID NO: 42          moltype = AA  length = 106
FEATURE                Location/Qualifiers
source                 1..106
                       mol_type = protein
                       organism = synthetic construct
SEQUENCE: 42
DIQMTQSPSS LSASVGDRVT ITCRASQGVG YMYWYQQKPG KAPKLLIYSA SNLASGVPSR  60
FSGSGSGTDF TFTISSLQPE DIATYYCQQW EGNPRTFGQG TKVEIK              106

SEQ ID NO: 43          moltype = AA  length = 8
FEATURE                Location/Qualifiers
source                 1..8
                       mol_type = protein
                       organism = synthetic construct
SEQUENCE: 43
GLDPDDTY                                                      8

SEQ ID NO: 44          moltype = AA  length = 9
FEATURE                Location/Qualifiers
source                 1..9
                       mol_type = protein
                       organism = synthetic construct
SEQUENCE: 44
VRSGGMPDV                                                     9

SEQ ID NO: 45          moltype = AA  length = 116
FEATURE                Location/Qualifiers
source                 1..116
                       mol_type = protein
                       organism = synthetic construct
SEQUENCE: 45
QVQLQESGPG LVRPSQTLSL TCTVSGFDMG DTYMHWVRQR PGRGLEWMGR IEPAGGHTKY  60
NPSLKSRVTI TRDTSKNQVS LRLSSVTAAD TAVYYCVRSG GMPDVWGQGS LVTVSS      116

SEQ ID NO: 46          moltype = AA  length = 8
FEATURE                Location/Qualifiers
source                 1..8
                       mol_type = protein
                       organism = synthetic construct
SEQUENCE: 46
GFDITDTY                                                      8

SEQ ID NO: 47          moltype = AA  length = 116
FEATURE                Location/Qualifiers
source                 1..116
                       mol_type = protein
                       organism = synthetic construct
SEQUENCE: 47
QVQLQESGPG LVRPSQTLSL TCTVSGFDIT DTYMHWVRQR PGRGLEWMGR IEPAGGHTKY  60
NPSLKSRVTI TRDTSKNQVS LRLSSVTAAD TAVYYCVRSG GLPDVWGQGS LVTVSS      116

SEQ ID NO: 48          moltype = AA  length = 8
FEATURE                Location/Qualifiers
source                 1..8
                       mol_type = protein
                       organism = synthetic construct
SEQUENCE: 48
GFDYQDTY                                                      8
```

```
SEQ ID NO: 49          moltype = AA  length = 8
FEATURE                Location/Qualifiers
source                 1..8
                       mol_type = protein
                       organism = synthetic construct
SEQUENCE: 49
IDPASGHT                                                          8

SEQ ID NO: 50          moltype = AA  length = 9
FEATURE                Location/Qualifiers
source                 1..9
                       mol_type = protein
                       organism = synthetic construct
SEQUENCE: 50
AVSGGMPDV                                                         9

SEQ ID NO: 51          moltype = AA  length = 106
FEATURE                Location/Qualifiers
source                 1..106
                       mol_type = protein
                       organism = synthetic construct
SEQUENCE: 51
DIQMTQSPSS LSASVGDRVT ITCRASQGVE YMYWYQQKPG KAPKLLIYAT SNLASGVPSR  60
FSGSGSGTDF TFTISSLQPE DIATYYCQQW EGNPRTFGQG TKVEIK                106

SEQ ID NO: 52          moltype = AA  length = 116
FEATURE                Location/Qualifiers
source                 1..116
                       mol_type = protein
                       organism = synthetic construct
SEQUENCE: 52
QVQLQESGPG LVRPSQTLSL TCTVSGFDYQ DTYMHWVRQR PGRGLEWMGR IDPASGHTKY  60
NPSLKSRVTI TRDTSKNQVS LRLSSVTAAD TAVYYCAVSG GMPDVWGQGS LVTVSS      116

SEQ ID NO: 53          moltype = AA  length = 5
FEATURE                Location/Qualifiers
source                 1..5
                       mol_type = protein
                       organism = synthetic construct
SEQUENCE: 53
QGIYY                                                             5

SEQ ID NO: 54          moltype = AA  length = 106
FEATURE                Location/Qualifiers
source                 1..106
                       mol_type = protein
                       organism = synthetic construct
SEQUENCE: 54
DIQMTQSPSS LSASVGDRVT ITCRASQGIY YMYWYQQKPG KAPKLLIYGA SNLASGVPSR  60
FSGSGSGTDF TFTISSLQPE DIATYYCQQW EGNPRTFGQG TKVEIK                106

SEQ ID NO: 55          moltype = AA  length = 116
FEATURE                Location/Qualifiers
source                 1..116
                       mol_type = protein
                       organism = synthetic construct
SEQUENCE: 55
QVQLQESGPG LVRPSQTLSL TCTVSGFDMG DTYMHWVRQR PGRGLEWMGR IEPAAGHTKY  60
NPSLKSRVTI TRDTSKNQVS LRLSSVTAAD TAVYYCVRSG GLPDVWGQGS LVTVSS      116

SEQ ID NO: 56          moltype =   length =
SEQUENCE: 56
000

SEQ ID NO: 57          moltype = AA  length = 106
FEATURE                Location/Qualifiers
source                 1..106
                       mol_type = protein
                       organism = synthetic construct
SEQUENCE: 57
DIQMTQSPSS LSASVGDRVT ITCRASSSVS YMYWYQQKPG KAPKLLIYYA SNLASGVPSR  60
FSGSGSGTDF TFTISSLQPE DIATYYCQQW EGNPRTFGQG TKVEIK                106

SEQ ID NO: 58          moltype = AA  length = 106
FEATURE                Location/Qualifiers
source                 1..106
                       mol_type = protein
                       organism = synthetic construct
SEQUENCE: 58
```

```
DIQMTQSPSS LSASVGDRVT ITCRASQGVE YMYWYQQKPG KAPKLLIYYA SNLASGVPSR  60
FSGSGSGTDF TFTISSLQPE DIATYYCQQW EGNPRTFGQG TKVEIK                106

SEQ ID NO: 59          moltype = AA  length = 9
FEATURE                Location/Qualifiers
source                 1..9
                       mol_type = protein
                       organism = synthetic construct
SEQUENCE: 59
ARSGGMPDM                                                         9

SEQ ID NO: 60          moltype = AA  length = 116
FEATURE                Location/Qualifiers
source                 1..116
                       mol_type = protein
                       organism = synthetic construct
SEQUENCE: 60
QVQLQESGPG LVRPSQTLSL TCTVSGFDIQ DTYMHWVRQR PGRGLEWMGR IEPASGHTKY  60
NPSLKSRVTI TRDTSKNQVS LRLSSVTAAD TAVYYCARSG GMPDMWGQGS LVTVSS     116

SEQ ID NO: 61          moltype = AA  length = 5
FEATURE                Location/Qualifiers
source                 1..5
                       mol_type = protein
                       organism = synthetic construct
SEQUENCE: 61
FSVDY                                                             5

SEQ ID NO: 62          moltype = AA  length = 11
FEATURE                Location/Qualifiers
source                 1..11
                       mol_type = protein
                       organism = synthetic construct
SEQUENCE: 62
WLIYATSNLA S                                                      11

SEQ ID NO: 63          moltype = AA  length = 9
FEATURE                Location/Qualifiers
source                 1..9
                       mol_type = protein
                       organism = synthetic construct
SEQUENCE: 63
QQWEGNPRS                                                         9

SEQ ID NO: 64          moltype = AA  length = 10
FEATURE                Location/Qualifiers
source                 1..10
                       mol_type = protein
                       organism = synthetic construct
SEQUENCE: 64
GYDLQESYMH                                                        10

SEQ ID NO: 65          moltype = AA  length = 8
FEATURE                Location/Qualifiers
source                 1..8
                       mol_type = protein
                       organism = synthetic construct
SEQUENCE: 65
IEPISGHL                                                          8

SEQ ID NO: 66          moltype = AA  length = 10
FEATURE                Location/Qualifiers
source                 1..10
                       mol_type = protein
                       organism = synthetic construct
SEQUENCE: 66
ARSGSGMSEY                                                        10

SEQ ID NO: 67          moltype = AA  length = 106
FEATURE                Location/Qualifiers
source                 1..106
                       mol_type = protein
                       organism = synthetic construct
SEQUENCE: 67
DIQMTQSPSS LSASVGDRVT ITCRASFSVD YMYWYQQKPG KAPKWLIYAT SNLASGVPSR  60
FSGSGSGTDF TFTISSLQPE DIATYYCQQW EGNPRSFGQG TKVEIK                106

SEQ ID NO: 68          moltype = AA  length = 117
FEATURE                Location/Qualifiers
```

```
source                  1..117
                        mol_type = protein
                        organism = synthetic construct
SEQUENCE: 68
QVQLQESGPG LVRPSQTLSL TCTVSGYDLQ ESYMHWVRQR PGRGLEWMGR IEPISGHLKY  60
NPSLKSRVTI TRDTSKNQVS LRLSSVTAAD TAVYYCARSG SGMSEYWGQG SLVTVSS     117

SEQ ID NO: 69           moltype = AA  length = 5
FEATURE                 Location/Qualifiers
source                  1..5
                        mol_type = protein
                        organism = synthetic construct
SEQUENCE: 69
FSVTY                                                              5

SEQ ID NO: 70           moltype = AA  length = 11
FEATURE                 Location/Qualifiers
source                  1..11
                        mol_type = protein
                        organism = synthetic construct
SEQUENCE: 70
YLIYPSGNLA S                                                       11

SEQ ID NO: 71           moltype = AA  length = 106
FEATURE                 Location/Qualifiers
source                  1..106
                        mol_type = protein
                        organism = synthetic construct
SEQUENCE: 71
DIQMTQSPSS LSASVGDRVT ITCRASFSVT YMYWYQQKPG KAPKYLIYPS GNLASGVPSR  60
FSGSGSGTDF TFTISSLQPE DIATYYCQQW EGNPRSFGQG TKVEIK                 106

SEQ ID NO: 72           moltype = AA  length = 11
FEATURE                 Location/Qualifiers
source                  1..11
                        mol_type = protein
                        organism = synthetic construct
SEQUENCE: 72
NLIYATSNLA S                                                       11

SEQ ID NO: 73           moltype = AA  length = 9
FEATURE                 Location/Qualifiers
source                  1..9
                        mol_type = protein
                        organism = synthetic construct
SEQUENCE: 73
AHSGGMTDY                                                          9

SEQ ID NO: 74           moltype = AA  length = 106
FEATURE                 Location/Qualifiers
source                  1..106
                        mol_type = protein
                        organism = synthetic construct
SEQUENCE: 74
DIQMTQSPSS LSASVGDRVT ITCRASFSVD YMYWYQQKPG KAPKNLIYAT SNLASGVPSR  60
FSGSGSGTDF TFTISSLQPE DIATYYCQQW EGNPRSFGQG TKVEIK                 106

SEQ ID NO: 75           moltype = AA  length = 116
FEATURE                 Location/Qualifiers
source                  1..116
                        mol_type = protein
                        organism = synthetic construct
SEQUENCE: 75
QVQLQESGPG LVRPSQTLSL TCTVSGYDLQ ESYMHWVRQR PGRGLEWMGR IEPISGHLKY  60
NPSLKSRVTI TRDTSKNQVS LRLSSVTAAD TAVYYCAHSG GMTDYWGQGS LVTVSS      116

SEQ ID NO: 76           moltype = AA  length = 106
FEATURE                 Location/Qualifiers
source                  1..106
                        mol_type = protein
                        organism = synthetic construct
SEQUENCE: 76
DIQMTQSPSS LSASVGDRVT ITCRASQGVG YMYWYQQKPG KAPKLLIYAT SNLASGVPSR  60
FSGSGSGTDF TFTISSLQPE DIATYYCQQW EGNPRTFGQG TKVEIK                 106

SEQ ID NO: 77           moltype = AA  length = 11
FEATURE                 Location/Qualifiers
source                  1..11
                        mol_type = protein
```

```
                         organism = synthetic construct
SEQUENCE: 77
YLIYVTGNLA S                                                  11

SEQ ID NO: 78            moltype = AA  length = 10
FEATURE                  Location/Qualifiers
source                   1..10
                         mol_type = protein
                         organism = synthetic construct
SEQUENCE: 78
GFDLQDSFIH                                                    10

SEQ ID NO: 79            moltype = AA  length = 8
FEATURE                  Location/Qualifiers
source                   1..8
                         mol_type = protein
                         organism = synthetic construct
SEQUENCE: 79
IDPASGHS                                                      8

SEQ ID NO: 80            moltype = AA  length = 9
FEATURE                  Location/Qualifiers
source                   1..9
                         mol_type = protein
                         organism = synthetic construct
SEQUENCE: 80
ARSGGMTDY                                                     9

SEQ ID NO: 81            moltype = AA  length = 106
FEATURE                  Location/Qualifiers
source                   1..106
                         mol_type = protein
                         organism = synthetic construct
SEQUENCE: 81
DIQMTQSPSS LSASVGDRVT ITCRASFSVD YMYWYQQKPG KAPKYLIYVT GNLASGVPSR  60
FSGSGSGTDF TFTISSLQPE DIATYYCQQW EGNPRSFGQG TKVEIK                106

SEQ ID NO: 82            moltype = AA  length = 116
FEATURE                  Location/Qualifiers
source                   1..116
                         mol_type = protein
                         organism = synthetic construct
SEQUENCE: 82
QVQLQESGPG LVRPSQTLSL TCTVSGFDLQ DSFIHWVRQR PGRGLEWMGR IDPASGHSKY  60
NPSLKSRVTI TRDTSKNQVS LRLSSVTAAD TAVYYCARSG GMTDYWGQGS LVTVSS      116

SEQ ID NO: 83            moltype = AA  length = 106
FEATURE                  Location/Qualifiers
source                   1..106
                         mol_type = protein
                         organism = synthetic construct
SEQUENCE: 83
DIQMTQSPSS LSASVGDRVT ITCRASQGVR YMYWYQQKPG KAPKLLIYAT SNLASGVPSR  60
FSGSGSGTDF TFTISSLQPE DIATYYCQQW EGNPRTFGQG TKVEIK                106

SEQ ID NO: 84            moltype = AA  length = 10
FEATURE                  Location/Qualifiers
source                   1..10
                         mol_type = protein
                         organism = synthetic construct
SEQUENCE: 84
GFDMADTYMH                                                    10

SEQ ID NO: 85            moltype = AA  length = 106
FEATURE                  Location/Qualifiers
source                   1..106
                         mol_type = protein
                         organism = synthetic construct
SEQUENCE: 85
DIQMTQSPSS LSASVGDRVT ITCRASSSVS YMYWYQQKPG KAPKLLIYSA SNLASGVPSR  60
FSGSGSGTDF TFTISSLQPE DIATYYCQQW EGNPRTFGQG TKVEIK                106

SEQ ID NO: 86            moltype = AA  length = 106
FEATURE                  Location/Qualifiers
source                   1..106
                         mol_type = protein
                         organism = synthetic construct
SEQUENCE: 86
DIQMTQSPSS LSASVGDRVT ITCRASQGVM YMYWYQQKPG KAPKLLIYAT SNLASGVPSR  60
```

```
FSGSGSGTDF TFTISSLQPE DIATYYCQQW EGNPRTFGQG TKVEIK                106

SEQ ID NO: 87           moltype = AA  length = 11
FEATURE                 Location/Qualifiers
source                  1..11
                        mol_type = protein
                        organism = synthetic construct
SEQUENCE: 87
DLIYATSNLA S                                                      11

SEQ ID NO: 88           moltype = AA  length = 10
FEATURE                 Location/Qualifiers
source                  1..10
                        mol_type = protein
                        organism = synthetic construct
SEQUENCE: 88
GFDLQDTYIH                                                        10

SEQ ID NO: 89           moltype = AA  length = 8
FEATURE                 Location/Qualifiers
source                  1..8
                        mol_type = protein
                        organism = synthetic construct
SEQUENCE: 89
IDPASGHL                                                          8

SEQ ID NO: 90           moltype = AA  length = 106
FEATURE                 Location/Qualifiers
source                  1..106
                        mol_type = protein
                        organism = synthetic construct
SEQUENCE: 90
DIQMTQSPSS LSASVGDRVT ITCRASFSVD YMYWYQQKPG KAPKDLIYAT SNLASGVPSR  60
FSGSGSGTDF TFTISSLQPE DIATYYCQQW EGNPRSFGQG TKVEIK                106

SEQ ID NO: 91           moltype = AA  length = 116
FEATURE                 Location/Qualifiers
source                  1..116
                        mol_type = protein
                        organism = synthetic construct
SEQUENCE: 91
QVQLQESGPG LVRPSQTLSL TCTVSGFDLQ DTYIHWVRQR PGRGLEWMGR IDPASGHLKY  60
NPSLKSRVTI TRDTSKNQVS LRLSSVTAAD TAVYYCARSG GMTDYWGQGS LVTVSS      116

SEQ ID NO: 92           moltype = AA  length = 106
FEATURE                 Location/Qualifiers
source                  1..106
                        mol_type = protein
                        organism = synthetic construct
SEQUENCE: 92
DIQMTQSPSS LSASVGDRVT ITCRASQGIY YMYWYQQKPG KAPKLLIYAT SNLASGVPSR  60
FSGSGSGTDF TFTISSLQPE DIATYYCQQW EGNPRTFGQG TKVEIK                106

SEQ ID NO: 93           moltype = AA  length = 106
FEATURE                 Location/Qualifiers
source                  1..106
                        mol_type = protein
                        organism = synthetic construct
SEQUENCE: 93
DIQMTQSPSS LSASVGDRVT ITCRASQGVG YMYWYQQKPG KAPKLLIYGA SNLASGVPSR  60
FSGSGSGTDF TFTISSLQPE DIATYYCQQW EGNPRTFGQG TKVEIK                106

SEQ ID NO: 94           moltype = AA  length = 10
FEATURE                 Location/Qualifiers
source                  1..10
                        mol_type = protein
                        organism = synthetic construct
SEQUENCE: 94
GFDIQDTYMH                                                        10

SEQ ID NO: 95           moltype = AA  length = 9
FEATURE                 Location/Qualifiers
source                  1..9
                        mol_type = protein
                        organism = synthetic construct
SEQUENCE: 95
GRSGGMMDL                                                         9

SEQ ID NO: 96           moltype = AA  length = 116
```

```
FEATURE                Location/Qualifiers
source                 1..116
                       mol_type = protein
                       organism = synthetic construct
SEQUENCE: 96
QVQLQESGPG LVRPSQTLSL TCTVSGFDIQ DTYMHWVRQR PGRGLEWMGR IDPASGHTKY  60
NPSLKSRVTI TRDTSKNQVS LRLSSVTAAD TAVYYCGRSG GMMDLWGQGS LVTVSS      116

SEQ ID NO: 97          moltype = AA  length = 106
FEATURE                Location/Qualifiers
source                 1..106
                       mol_type = protein
                       organism = synthetic construct
SEQUENCE: 97
DIQMTQSPSS LSASVGDRVT ITCRASQGVR YMYWYQQKPG KAPKLLIYSA SNLASGVPSR  60
FSGSGSGTDF TFTISSLQPE DIATYYCQQW EGNPRTFGQG TKVEIK                 106

SEQ ID NO: 98          moltype = AA  length = 10
FEATURE                Location/Qualifiers
source                 1..10
                       mol_type = protein
                       organism = synthetic construct
SEQUENCE: 98
GFDIEDTYMH                                                         10

SEQ ID NO: 99          moltype = AA  length = 13
FEATURE                Location/Qualifiers
source                 1..13
                       mol_type = protein
                       organism = synthetic construct
SEQUENCE: 99
WMGRIEPASG HTK                                                     13

SEQ ID NO: 100         moltype = AA  length = 9
FEATURE                Location/Qualifiers
source                 1..9
                       mol_type = protein
                       organism = synthetic construct
SEQUENCE: 100
AISGGVPDV                                                          9

SEQ ID NO: 101         moltype = AA  length = 116
FEATURE                Location/Qualifiers
source                 1..116
                       mol_type = protein
                       organism = synthetic construct
SEQUENCE: 101
QVQLQESGPG LVRPSQTLSL TCTVSGFDIE DTYMHWVRQR PGRGLEWMGR IEPASGHTKY  60
NPSLKSRVTI TRDTSKNQVS LRLSSVTAAD TAVYYCAISG GVPDVWGQGS LVTVSS      116

SEQ ID NO: 102         moltype = AA  length = 9
FEATURE                Location/Qualifiers
source                 1..9
                       mol_type = protein
                       organism = synthetic construct
SEQUENCE: 102
ARSGGMMDR                                                          9

SEQ ID NO: 103         moltype = AA  length = 116
FEATURE                Location/Qualifiers
source                 1..116
                       mol_type = protein
                       organism = synthetic construct
SEQUENCE: 103
QVQLQESGPG LVRPSQTLSL TCTVSGFDIQ DTYMHWVRQR PGRGLEWMGR IEPASGHTKY  60
NPSLKSRVTI TRDTSKNQVS LRLSSVTAAD TAVYYCARSG GMMDRWGQGS LVTVSS      116

SEQ ID NO: 104         moltype = AA  length = 8
FEATURE                Location/Qualifiers
source                 1..8
                       mol_type = protein
                       organism = synthetic construct
SEQUENCE: 104
IDPAGGHT                                                           8

SEQ ID NO: 105         moltype = AA  length = 9
FEATURE                Location/Qualifiers
source                 1..9
                       mol_type = protein
```

```
                        organism = synthetic construct
SEQUENCE: 105
VRSGGLPDE                                                         9

SEQ ID NO: 106          moltype = AA  length = 116
FEATURE                 Location/Qualifiers
source                  1..116
                        mol_type = protein
                        organism = synthetic construct
SEQUENCE: 106
QVQLQESGPG LVRPSQTLSL TCTVSGFDMQ DTYMHWVRQR PGRGLEWMGR IDPAGGHTKY  60
NPSLKSRVTI TRDTSKNQVS LRLSSVTAAD TAVYYCVRSG GLPDEWGQGS LVTVSS      116

SEQ ID NO: 107          moltype = AA  length = 9
FEATURE                 Location/Qualifiers
source                  1..9
                        mol_type = protein
                        organism = synthetic construct
SEQUENCE: 107
VRSGGMPDA                                                         9

SEQ ID NO: 108          moltype = AA  length = 116
FEATURE                 Location/Qualifiers
source                  1..116
                        mol_type = protein
                        organism = synthetic construct
SEQUENCE: 108
QVQLQESGPG LVRPSQTLSL TCTVSGFDMG DTYMHWVRQR PGRGLEWMGR IDPASGHTKY  60
NPSLKSRVTI TRDTSKNQVS LRLSSVTAAD TAVYYCVRSG GMPDAWGQGS LVTVSS      116

SEQ ID NO: 109          moltype = AA  length = 8
FEATURE                 Location/Qualifiers
source                  1..8
                        mol_type = protein
                        organism = synthetic construct
SEQUENCE: 109
GLDMQDTY                                                          8

SEQ ID NO: 110          moltype = AA  length = 9
FEATURE                 Location/Qualifiers
source                  1..9
                        mol_type = protein
                        organism = synthetic construct
SEQUENCE: 110
AASGGRPDL                                                         9

SEQ ID NO: 111          moltype = AA  length = 116
FEATURE                 Location/Qualifiers
source                  1..116
                        mol_type = protein
                        organism = synthetic construct
SEQUENCE: 111
QVQLQESGPG LVRPSQTLSL TCTVSGLDMQ DTYMHWVRQR PGRGLEWMGR IEPASGHTKY  60
NPSLKSRVTI TRDTSKNQVS LRLSSVTAAD TAVYYCAASG GRPDLWGQGS LVTVSS      116

SEQ ID NO: 112          moltype = AA  length = 10
FEATURE                 Location/Qualifiers
source                  1..10
                        mol_type = protein
                        organism = synthetic construct
SEQUENCE: 112
GFDITDTYMH                                                        10

SEQ ID NO: 113          moltype = AA  length = 9
FEATURE                 Location/Qualifiers
source                  1..9
                        mol_type = protein
                        organism = synthetic construct
SEQUENCE: 113
AASGGMPDM                                                         9

SEQ ID NO: 114          moltype = AA  length = 116
FEATURE                 Location/Qualifiers
source                  1..116
                        mol_type = protein
                        organism = synthetic construct
SEQUENCE: 114
QVQLQESGPG LVRPSQTLSL TCTVSGFDIQ DTYMHWVRQR PGRGLEWMGR IEPASGHTKY  60
NPSLKSRVTI TRDTSKNQVS LRLSSVTAAD TAVYYCAASG GMPDMWGQGS LVTVSS      116
```

```
SEQ ID NO: 115          moltype = AA  length = 10
FEATURE                 Location/Qualifiers
source                  1..10
                        mol_type = protein
                        organism = synthetic construct
SEQUENCE: 115
GFDMGDTYMH                                                           10

SEQ ID NO: 116          moltype = AA  length = 9
FEATURE                 Location/Qualifiers
source                  1..9
                        mol_type = protein
                        organism = synthetic construct
SEQUENCE: 116
VMSGGVPDV                                                            9

SEQ ID NO: 117          moltype = AA  length = 116
FEATURE                 Location/Qualifiers
source                  1..116
                        mol_type = protein
                        organism = synthetic construct
SEQUENCE: 117
QVQLQESGPG LVRPSQTLSL TCTVSGFDIQ DTYMHWVRQR PGRGLEWMGR IDPASGHTKY  60
NPSLKSRVTI TRDTSKNQVS LRLSSVTAAD TAVYYCVMSG GVPDVWGQGS LVTVSS      116

SEQ ID NO: 118          moltype = AA  length = 8
FEATURE                 Location/Qualifiers
source                  1..8
                        mol_type = protein
                        organism = synthetic construct
SEQUENCE: 118
GLDPEDTY                                                             8

SEQ ID NO: 119          moltype = AA  length = 116
FEATURE                 Location/Qualifiers
source                  1..116
                        mol_type = protein
                        organism = synthetic construct
SEQUENCE: 119
QVQLQESGPG LVRPSQTLSL TCTVSGLDPE DTYMHWVRQR PGRGLEWMGR IEPAGGHTKY  60
NPSLKSRVTI TRDTSKNQVS LRLSSVTAAD TAVYYCVISG GLPDVWGQGS LVTVSS      116

SEQ ID NO: 120          moltype = AA  length = 8
FEATURE                 Location/Qualifiers
source                  1..8
                        mol_type = protein
                        organism = synthetic construct
SEQUENCE: 120
GFDMVDTY                                                             8

SEQ ID NO: 121          moltype = AA  length = 116
FEATURE                 Location/Qualifiers
source                  1..116
                        mol_type = protein
                        organism = synthetic construct
SEQUENCE: 121
QVQLQESGPG LVRPSQTLSL TCTVSGFDMV DTYMHWVRQR PGRGLEWMGR IEPASGHTKY  60
NPSLKSRVTI TRDTSKNQVS LRLSSVTAAD TAVYYCVRSG GLPDVWGQGS LVTVSS      116

SEQ ID NO: 122          moltype = AA  length = 8
FEATURE                 Location/Qualifiers
source                  1..8
                        mol_type = protein
                        organism = synthetic construct
SEQUENCE: 122
GFDIDDTY                                                             8

SEQ ID NO: 123          moltype = AA  length = 9
FEATURE                 Location/Qualifiers
source                  1..9
                        mol_type = protein
                        organism = synthetic construct
SEQUENCE: 123
VMSGGAPDV                                                            9

SEQ ID NO: 124          moltype = AA  length = 116
FEATURE                 Location/Qualifiers
source                  1..116
```

```
                        mol_type = protein
                        organism = synthetic construct
SEQUENCE: 124
QVQLQESGPG LVRPSQTLSL TCTVSGFDID DTYMHWVRQR PGRGLEWMGR IDPASGHTKY  60
NPSLKSRVTI TRDTSKNQVS LRLSSVTAAD TAVYYCVMSG GAPDVWGQGS LVTVSS      116

SEQ ID NO: 125          moltype = AA  length = 8
FEATURE                 Location/Qualifiers
source                  1..8
                        mol_type = protein
                        organism = synthetic construct
SEQUENCE: 125
GFDMRATY                                                           8

SEQ ID NO: 126          moltype = AA  length = 116
FEATURE                 Location/Qualifiers
source                  1..116
                        mol_type = protein
                        organism = synthetic construct
SEQUENCE: 126
QVQLQESGPG LVRPSQTLSL TCTVSGFDMR ATYMHWVRQR PGRGLEWMGR IEPAGGHTKY  60
NPSLKSRVTI TRDTSKNQVS LRLSSVTAAD TAVYYCVRSG GLPDVWGQGS LVTVSS      116

SEQ ID NO: 127          moltype = AA  length = 8
FEATURE                 Location/Qualifiers
source                  1..8
                        mol_type = protein
                        organism = synthetic construct
SEQUENCE: 127
GFDIEDTY                                                           8

SEQ ID NO: 128          moltype = AA  length = 9
FEATURE                 Location/Qualifiers
source                  1..9
                        mol_type = protein
                        organism = synthetic construct
SEQUENCE: 128
ANSGGLFDH                                                          9

SEQ ID NO: 129          moltype = AA  length = 116
FEATURE                 Location/Qualifiers
source                  1..116
                        mol_type = protein
                        organism = synthetic construct
SEQUENCE: 129
QVQLQESGPG LVRPSQTLSL TCTVSGFDIQ DTYMHWVRQR PGRGLEWMGR IDPASGHTKY  60
NPSLKSRVTI TRDTSKNQVS LRLSSVTAAD TAVYYCANSG GLFDHWGQGS LVTVSS      116

SEQ ID NO: 130          moltype = AA  length = 8
FEATURE                 Location/Qualifiers
source                  1..8
                        mol_type = protein
                        organism = synthetic construct
SEQUENCE: 130
GFDFQDTY                                                           8

SEQ ID NO: 131          moltype = AA  length = 8
FEATURE                 Location/Qualifiers
source                  1..8
                        mol_type = protein
                        organism = synthetic construct
SEQUENCE: 131
IDPASEHT                                                           8

SEQ ID NO: 132          moltype = AA  length = 116
FEATURE                 Location/Qualifiers
source                  1..116
                        mol_type = protein
                        organism = synthetic construct
SEQUENCE: 132
QVQLQESGPG LVRPSQTLSL TCTVSGFDFQ DTYMHWVRQR PGRGLEWMGR IDPASEHTKY  60
NPSLKSRVTI TRDTSKNQVS LRLSSVTAAD TAVYYCVRSG GLPDVWGQGS LVTVSS      116

SEQ ID NO: 133          moltype = AA  length = 8
FEATURE                 Location/Qualifiers
source                  1..8
                        mol_type = protein
                        organism = synthetic construct
SEQUENCE: 133
```

```
IDPASGHV                                                          8

SEQ ID NO: 134          moltype = AA  length = 116
FEATURE                 Location/Qualifiers
source                  1..116
                        mol_type = protein
                        organism = synthetic construct
SEQUENCE: 134
QVQLQESGPG LVRPSQTLSL TCTVSGFDLQ DTYIHWVRQR PGRGLEWMGR IDPASGHVKY  60
NPSLKSRVTI TRDTSKNQVS LRLSSVTAAD TAVYYCARSG GMTDYWGQGS LVTVSS      116

SEQ ID NO: 135          moltype = AA  length = 9
FEATURE                 Location/Qualifiers
source                  1..9
                        mol_type = protein
                        organism = synthetic construct
SEQUENCE: 135
VRSGGLPDY                                                         9

SEQ ID NO: 136          moltype = AA  length = 116
FEATURE                 Location/Qualifiers
source                  1..116
                        mol_type = protein
                        organism = synthetic construct
SEQUENCE: 136
QVQLQESGPG LVRPSQTLSL TCTVSGFDMQ DTYMHWVRQR PGRGLEWMGR IDPASGHTKY  60
NPSLKSRVTI TRDTSKNQVS LRLSSVTAAD TAVYYCVRSG GLPDYWGQGS LVTVSS      116

SEQ ID NO: 137          moltype = AA  length = 8
FEATURE                 Location/Qualifiers
source                  1..8
                        mol_type = protein
                        organism = synthetic construct
SEQUENCE: 137
GFDFDDTY                                                          8

SEQ ID NO: 138          moltype = AA  length = 116
FEATURE                 Location/Qualifiers
source                  1..116
                        mol_type = protein
                        organism = synthetic construct
SEQUENCE: 138
QVQLQESGPG LVRPSQTLSL TCTVSGFDFD DTYMHWVRQR PGRGLEWMGR IDPASGHTKY  60
NPSLKSRVTI TRDTSKNQVS LRLSSVTAAD TAVYYCVRSG GLPDVWGQGS LVTVSS      116

SEQ ID NO: 139          moltype = AA  length = 222
FEATURE                 Location/Qualifiers
source                  1..222
                        mol_type = protein
                        organism = synthetic construct
SEQUENCE: 139
CPPCPAPEAA GGPSVFLFPP KPKDTLMISR TPEVTCVVVS VSHEDPEVKF NWYVDGVEVH  60
NAKTKPREEQ YNSTYRVVSV LTVLHQDWLN GKEYKCKVSN KALPAPIEKT ISKAKGQPRE  120
PQVYTLPPSR DELTKNQVSL TCLVKGFYPS DIAVEWESNG QPENNYKTTP PVLDSDGSFF  180
LYSKLTVDKS RWQQGNVFSC SVLHEALHSH YTQKSLSLSP GK                    222

SEQ ID NO: 140          moltype = AA  length = 446
FEATURE                 Location/Qualifiers
source                  1..446
                        mol_type = protein
                        organism = synthetic construct
SEQUENCE: 140
QVQLQESGPG LVRPSQTLSL TCTVSGFDIQ DTYMHWVRQR PGRGLEWMGR IEPAGGHTKY  60
NPSLKSRVTI TRDTSKNQVS LRLSSVTAAD TAVYYCVRSG GLPDAWGQGS LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGGPSVF  240
LFPPKPKDTL MISRTPEVTC VVVSVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVLHEA LHSHYTQKSL SLSPGK                                      446

SEQ ID NO: 141          moltype = AA  length = 213
FEATURE                 Location/Qualifiers
source                  1..213
                        mol_type = protein
                        organism = synthetic construct
SEQUENCE: 141
DIQMTQSPSS LSASVGDRVT ITCRASQGVR YMYWYQQKPG KAPKLLIYGA SNLASGVPSR  60
FSGSGSGTDF TFTISSLQPE DIATYYCQQW EGNPRTFGQG TKVEIKRTVA APSVFIFPPS  120
```

```
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 142         moltype = AA  length = 446
FEATURE                Location/Qualifiers
source                 1..446
                       mol_type = protein
                       organism = synthetic construct
SEQUENCE: 142
QVQLQESGPG LVRPSQTLSL TCTVSGFDMQ DTYMHWVRQR PGRGLEWMGR IEPASGHTKY  60
NPSLKSRVTI TRDTSKNQVS LRLSSVTAAD TAVYYCVRSG GLPDVWGQGS LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGGPSVF  240
LFPPKPKDTL MISRTPEVTC VVVSVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVLHEA LHSHYTQKSL SLSPGK                                       446

SEQ ID NO: 143         moltype = AA  length = 213
FEATURE                Location/Qualifiers
source                 1..213
                       mol_type = protein
                       organism = synthetic construct
SEQUENCE: 143
DIQMTQSPSS LSASVGDRVT ITCRASQGVM YMYWYQQKPG KAPKLLIYGA SNLASGVPSR  60
FSGSGSGTDF TFTISSLQPE DIATYYCQQW EGNPRTFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 144         moltype = AA  length = 446
FEATURE                Location/Qualifiers
source                 1..446
                       mol_type = protein
                       organism = synthetic construct
SEQUENCE: 144
QVQLQESGPG LVRPSQTLSL TCTVSGFDIQ DTYMHWVRQR PGRGLEWMGR IEPAGGHTKY  60
NPSLKSRVTI TRDTSKNQVS LRLSSVTAAD TAVYYCVRSG GLPDAWGQGS LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGGPSVF  240
LFPPKPKDTL MISRTPEVTC VVVSVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVLHEA LHSHYTQKSL SLSPGK                                       446

SEQ ID NO: 145         moltype = AA  length = 213
FEATURE                Location/Qualifiers
source                 1..213
                       mol_type = protein
                       organism = synthetic construct
SEQUENCE: 145
DIQMTQSPSS LSASVGDRVT ITCRASQGVG YMYWYQQKPG KAPKLLIYSA SNLASGVPSR  60
FSGSGSGTDF TFTISSLQPE DIATYYCQQW EGNPRTFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213
```